US007115627B2

United States Patent
Pinto et al.

(10) Patent No.: US 7,115,627 B2
(45) Date of Patent: Oct. 3, 2006

(54) GLYCINAMIDES AS FACTOR XA INHIBITORS

(75) Inventors: Donald J. P. Pinto, Kennett Square, PA (US); Wei Han, Newark, DE (US); Zilun Hu, Thornton, PA (US); Jennifer Qiao, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 609 days.

(21) Appl. No.: 10/304,070

(22) Filed: Nov. 25, 2002

(65) Prior Publication Data

US 2003/0232804 A1 Dec. 18, 2003

Related U.S. Application Data

(60) Provisional application No. 60/336,994, filed on Dec. 4, 2001.

(51) Int. Cl.
C07D 405/10 (2006.01)
C07D 471/04 (2006.01)
A61K 31/423 (2006.01)
A61P 7/02 (2006.01)

(52) U.S. Cl. .................. 514/303; 546/119; 546/120
(58) Field of Classification Search ............... 546/119, 546/120; 514/303
See application file for complete search history.

(56) References Cited

U.S. PATENT DOCUMENTS

| 3,340,269 | A | 9/1967 | Blatter |
|---|---|---|---|
| 3,365,459 | A | 1/1968 | Blatter |
| 3,423,414 | A | 1/1969 | Blatter |
| 5,342,851 | A | 8/1994 | Sanfilippo et al. |
| 5,998,424 | A | 12/1999 | Galemmo, Jr. et al. |
| 6,020,357 | A | 2/2000 | Pinto et al. |
| 6,060,491 | A | 5/2000 | Pruitt et al. |
| 6,191,159 | B1 | 2/2001 | Pinto |
| 6,271,237 | B1 | 8/2001 | Galemmo, Jr. et al. |

FOREIGN PATENT DOCUMENTS

| WO | WO 98/28269 | 7/1998 |
|---|---|---|
| WO | WO 98/28282 | 7/1998 |
| WO | WO 98/57934 | 12/1998 |
| WO | WO 98/57951 | 12/1998 |
| WO | WO 99/32454 | 7/1999 |
| WO | WO 99/50255 | 10/1999 |
| WO | WO 00/39108 | 7/2000 |
| WO | WO 00/39131 | 7/2000 |
| WO | WO 00/59902 | 10/2000 |
| WO | WO 01/05784 | 1/2001 |
| WO | WO 01/19798 | 3/2001 |
| WO | WO 01/32628 | 5/2001 |

OTHER PUBLICATIONS

Wee, A.G. et al., "The Nafion-H Catalysed Cyclization of α-Carbomethoxy-α-Diazoacetanilides. Synthesis of 3-Unsubstituted-2-Indolinones", Tetrahedron, vol. 50, No. 3, pp. 609-626 (1994).

*Primary Examiner*—Bruck Kifle
(74) *Attorney, Agent, or Firm*—Jing G. Sun; David H. Vance

(57) ABSTRACT

The present application describes glycinamidic compounds and derivatives thereof, or pharmaceutically acceptable salt forms thereof, which are useful as inhibitors of factor Xa.

11 Claims, No Drawings

GLYCINAMIDES AS FACTOR XA INHIBITORS

CROSS-REFERENCE TO REALTED APPLICATIONS

The present application claims the priority benefit of U.S. Provisional Application No. 60/336,994, filed Dec. 4, 2001, the disclosure of which is incorporated herein by reference in its entirety.

FIELD OF THE INVENTION

This invention relates generally to glycinamidic compounds, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

U.S. Pat. Nos. 3,365,459, 3,340,269, and 3,423,414 illustrate anti-inflammatory inhibitors of the following formula:

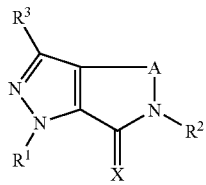

wherein A is 2–3 carbon atoms, X can be O, and $R^1$ and $R^3$ can be substituted or unsubstituted aromatic groups. None of these patents, however, exemplify or suggest compounds of the present invention.

U.S. Pat. No. 5,342,851 depicts thiazole platelet aggregation inhibitors including those of the following formula:

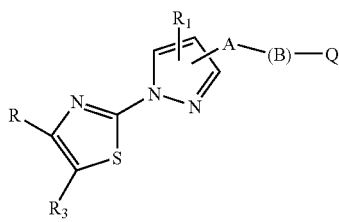

wherein A is a linker, B can be a linker or a ring, Q is a ring or an amino group, R, $R_1$, and $R_3$ are a variety of groups. This patent, however, does not exemplify or suggest compounds of the present invention.

WO00/39131 describes heterobicyclic Factor Xa inhibitors of which the following is an example formula:

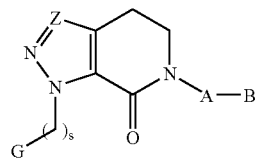

wherein Z is C or N, G is a mono- or bicyclic group, A is a cyclic moiety and B is a basic group or a cyclic moiety. Compounds specifically described in WO00/39131 are not considered to be part of the present invention.

WO98/28269, WO98/28282, WO99/32454, U.S. Pat. No. 6,020,357, and U.S. Pat. No. 6,271,237 describe Factor Xa inhibitors of the following formula:

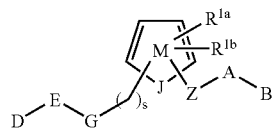

wherein ring M is a heterocycle, Z is a linker, A is a ring, B is a basic or cylic group, D is a basic moiety, and E is a ring. Compounds specifically described in WO98/28269, WO98/28282, WO99/32454, U.S. Pat. No. 6,020,357, and U.S. Pat. No. 6,271,237 are not considered to be part of the present invention.

WO98/57951 describes Factor Xa inhibitors of the following formula:

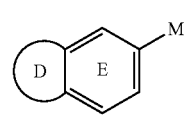

wherein ring M can be a variety of heterocycles and rings D-E represent a heterobicyclic group. Compounds specifically described in WO98/57951 are not considered to be part of the present invention.

WO98/57934 and U.S. Pat. No. 6,060,491 describe Factor Xa inhibitors of the following formula:

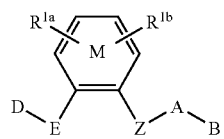

wherein ring M is a 6-membered heteroaryl, Z is a linker, A is a ring, B is a basic or cylic group, D is a basic moiety, and E is a ring. Compounds specifically described in WO98/57934 and U.S. Pat. No. 6,060,491 are not considered to be part of the present invention.

WO98/57937 and U.S. Pat. No. 5,998,424 describe Factor Xa inhibitors of the following formula:

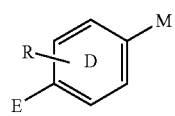

wherein ring M is a variety of rings, ring D is an aromatic ring, and R and E are non-basic groups. Compounds specifically described in WO98/57937 and U.S. Pat. No. 5,998,424 are not considered to be part of the present invention.

WO99/50255 and U.S. Pat. No. 6,191,159 describe pyrazoline and triazoline Factor Xa inhibitors of the following formulas:

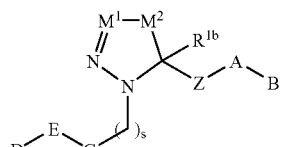

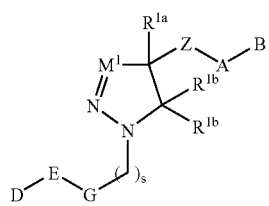

Compounds specifically described in WO99/50255 and U.S. Pat. No. 6,191,159 are not considered to be part of the present invention.

WO00/59902 describes Factor Xa inhibitors of the following formula:

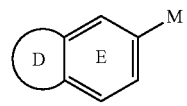

wherein ring M can be a variety of rings all of which are substituted with Z-A-B, Z is a linker, A is a ring, B is a sulfonyl-containing heterobicycle, and rings D-E represent a heterobicyclic group or a 6-membered ring. Compounds specifically described in WO00/59902 are not considered to be part of the present invention.

WO01/32628 describes cyano-pyrroles, cyano-imidazoles, cyano-pyrazoles, and cyano-triazoles that are Factor Xa inhibitors. Compounds specifically described in WO01/32628 are not considered to be part of the present invention.

WO01/05784 describes Factor Xa inhibitors of the following formulas:

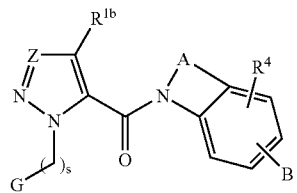

-continued

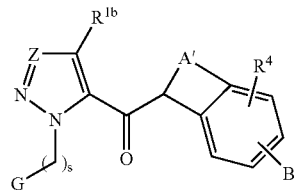

wherein Z is C or N, G is a mono- or bicyclic ring M, A is a linker, B is a basic or cyclic group. Compounds specifically described in WO01/05784 are not considered to be part of the present invention.

WO00/39108 describes Factor Xa inhibitors of the following formula:

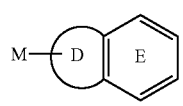

wherein ring M can be a variety of heterocycles and rings D-E represent a heterobicyclic group. Compounds specifically described in WO00/39108 are not considered to be part of the present invention.

WO01/19798 describes factor Xa inhibitors of the following formula:

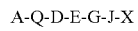

A-Q-D-E-G-J-X wherein A, D, G, and X can be phenyl or heterocycle. However, none of the presently claimed compounds are exemplified or suggested in WO01/19798.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories: (a) pharmaceutical properties (e.g., solubility, permeability, and amenability to sustained release formulations); (b) dosage requirements (e.g., lower dosages and/or once-daily dosing); (c) factors which decrease blood concentration peak-to-trough characteristics (e.g., clearance and/or volume of distribution); (d) factors that increase the concentration of active drug at the receptor (e.g., protein binding, volume of distribution); (e) factors that decrease the liability for clinical drug-drug interactions (e.g., cytochrome P450 enzyme inhibition or induction); (f) factors that decrease the potential for adverse side-effects (e.g., pharmacological selectivity beyond serine proteases, potential chemical or metabolic reactivity, and limited CNS penetration); and, (g) factors that improve manufacturing costs or feasibility (e.g., difficulty of synthesis, number of chiral centers, chemical stability, and ease of handling).

SUMMARY OF THE INVENTION

Accordingly, the present invention provides novel glycinamidic compounds that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a host in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt form thereof in an amount effective to treat a thromboembolic disorder The present invention provides a novel method, comprising: administering a compound of the present invention or a pharmaceutically acceptable salt form thereof in an amount effective to treat a thromboembolic disorder.

The present invention provides novel compounds for use in therapy.

The present invention provides the use of novel compounds for the manufacture of a medicament for the treatment of a thromboembolic disorder.

These and other objects, which will become apparent during the following detailed description, have been achieved by the inventors' discovery that the presently claimed compounds, or pharmaceutically acceptable salt or prodrug forms thereof, are effective factor Xa inhibitors.

DETAILED DESCRIPTION OF PREFERRED EMBODIMENTS

[1] In an embodiment, the present invention provides a novel compound of formula I:

$$P_4\text{—}P\text{-}M\text{-}M_4 \qquad I$$

or a stereoisomer or pharmaceutically acceptable salt thereof, wherein;

M is a 3–10 membered carbocycle or a 4–10 membered heterocycle, consisting of: carbon atoms and 1–3 heteroatoms selected from O, $S(O)_p$, N, and $NZ^2$;

ring M is substituted with 0–3 $R^{1a}$ and 0–2 carbonyl groups, and there are 0–3 ring double bonds;

P is fused onto ring M and is a 5, 6, or 7 membered carbocycle or a 5, 6, or 7 membered heterocycle, consisting of: carbon atoms and 1–3 heteroatoms selected from O, $S(O)_p$, and N;

ring P is substituted with 0–3 $R^{1a}$ and 0–2 carbonyl groups, and there are 0–3 ring double bonds;

alternatively, ring P is absent and $P_4$ is directly attached to ring M;

one of $P_4$ and $M_4$ is -Z-A-B and the other -$G_1$-G, provided that $P_4$ and $M_4$ are attached to different rings when ring P is present;

G is a group of formula IIa or IIb:

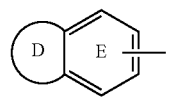

IIa

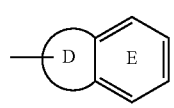

IIb ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–2 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–1 carbonyls and 1–2 R and has 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, C($=NR^8$)$NR^7R^9$, NHC($=NR^8$)$NR^7R^9$, ONHC($=NR^8$)$NR^7R^9$, $NR^8CH(=NR^7)$, $NH_2$, $NH(C_{1-3}$ alkyl), $N(C_{1-3}$ alkyl)$_2$, C($=NH$)$NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), $CH_2CH_2N(C_{1-3}$ alkyl)$_2$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rNR^7C(O)R^7$, $(CR^8R^9)_rOR^3$, $(CR^8R^9)_rS(O)_pNR^7R^8$, $(CR^8R^9)_rNR^7S(O)_pR^7$, $(CR^8R^9)_rSR^3$, $(CR^8R^9)_rS(O)R^3$, $(CR^8R^9)_rS(O)_2R^3$, and $OCF_3$;

alternatively, when 2 R groups are attached to adjacent atoms, they combine to form methylenedioxy or ethylenedioxy;

A is selected from: $C_{3-10}$ carbocycle substituted with 0–2 $R^4$, and 5–12 membered heterocycle consisting of: carbon atoms and 1–4 heteroatoms selected from the group consisting of N, O, and $S(O)_p$ and substituted with 0–2 $R^4$;

B is selected from N(B¹)C(O)C(R³R³ᵍ)R³, N(B¹)C(O)C(R³R³ᵍ)OR³, N(B¹)C(O)C(R³R³ᵍ)NB²B³, N(B¹)C(O)C(R³R³ᵍ)C(R³R³ᵍ)NB²B³, N(B¹)C(O)C(R³R³ᵍ)C(R³R³ᵍ)C(R³R³ᵍ)NB²B³, and N(B¹)C(O)C(R³R³ᵍ)C(R³R³ᵍ)C(R³R³ᵍ)C(R³R³ᵍ)NB²B³, provided that Z and B are attached to different atoms on A;

B¹ is selected from H, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, —(CH₂)₀₋₂—C₃₋₇ carbocycle substituted with 0–2 R⁴ᵇ, and —(CH₂)₀₋₂-5–6 membered heterocycle consisting of: carbon atoms and 1–4 heteroatoms selected from the group consisting of N, O, and S(O)ₚ and substituted with 0–2 R⁴ᵇ;

B² is selected from H, C₁₋₆ alkyl substituted with 0–2 R⁴ᶜ, C(O)R²ᵉ, C(O)OR²ᵈ, C(O)NR²ᵈR²ᵈ, C(O)NH(CH₂)₂NR²ᵈR²ᵈ, SO₂NR²ᵈR²ᵈ, C(O)NHSO₂—C₁₋₄ alkyl, and S(O)ₚR⁵ᵃ;

B³ is selected from H, C₁₋₆ alkyl substituted with 0–1 R⁴ᶜ, —(CH₂)₀₋₁-3–8 membered carbocycle substituted with 0–2 R⁵, and a —(CH₂)₀₋₁-3–8 membered heterocycle consisting of: carbon atoms and 1–4 heteroatoms selected from the group consisting of N, O, and S(O)ₚ and substituted with 0–2 R⁵;

alternatively, NB²B³ is a 3–8 membered heterocycle consisting of: the shown N, carbon atoms, and 0–3 additional heteroatoms selected from the group consisting of N, O, and S(O)ₚ and substituted with 0–2 R⁵;

G₁ is absent or is selected from (CR³R³ᵃ)₁₋₅, (CR³R³ᵃ)₀₋₂CR³=CR³(CR³R³ᵃ)₀₋₂, (CR³R³ᵃ)₀₋₂C≡C(CR³R³ᵃ)₀₋₂, (CR³R³ᵃ)ᵤC(O)(CR³R³ᵃ)ᵥᵥ, (CR³R³ᵃ)ᵤC(O)O(CR³R³ᵃ)ᵥᵥ, (CR³R³ᵃ)ᵤOC(O)(CR³R³ᵃ)ᵥᵥ, (CR³R³ᵃ)ᵤO(CR³R³ᵃ)ᵥᵥ, (CR³R³ᵃ)ᵤN³ᵇ(CR³R³ᵃ)ᵥᵥ, (CR³R³ᵃ)ᵤC(O)N³ᵇ(R³R³ᵃ)ᵥᵥ, (CR³R³ᵃ)ᵤN³ᵇC(O)(CR³R³ᵃ)ᵥᵥ, (CR³R³ᵃ)ᵤOC(O)N³ᵇ(CR³R³ᵃ)ᵥᵥ, (CR³R³ᵃ)ᵤN³ᵇC(O)(CR³R³ᵃ)ᵥᵥ, (CR³R³ᵃ)ᵤN³ᵇC(O)N³ᵇ(CR³R³ᵃ)ᵥᵥ, (CR³R³ᵃ)ᵤN³ᵇC(S)N³ᵇ(CR³R³ᵃ)ᵥᵥ, (CR³R³ᵃ)ᵤS(CR³R³ᵃ)ᵥᵥ, (CR³R³ᵃ)ᵤS(O)(CR³R³ᵃ)ᵥᵥ, (CR³R³ᵃ)ᵤS(O)₂(CR³R³ᵃ)ᵥᵥ, (CR³R³ᵃ)ᵤS(O)N³ᵇ(CR³R³ᵃ)ᵥᵥ, (CR³R³ᵃ)ᵤN³ᵇS(O)₂(CR³R³ᵃ)ᵥᵥ, (CR³R³ᵃ)ᵤ S(O)₂N³ᵇ(CR³R³ᵃ)ᵥᵥ, (CR³R³ᵃ)ᵤN³ᵇS(O)₂N³ᵇ(CR³R³ᵃ)ᵥᵥ, (CR³R³ᵃ)ᵤ NR³ᵉ (CR³R³ᵃ)ᵥᵥ, (CR³R³ᵃ)ᵤC(O)(CR³R³ᵃ)ᵤC(O)(CR³R³ᵃ)ᵥᵥ, (CR³R³ᵃ)ᵤNR³ᵇC(CR³R³ᵃ)ᵤC(O)NR³ᵇ(CR³R³ᵃ)ᵥᵥ, (CR³R³ᵃ)ᵤNR³ᵇC(O)(CR³R³ᵃ)ᵤC(O)(CR³R³ᵃ)ᵥᵥ, (CR³R³ᵃ)ᵤC(O)(CR³R³ᵃ)ᵤC(O)NR³ᵇ(CR³R³ᵃ)ᵥᵥ, (CR³R³ᵃ)ᵤNR³ᵇC(O)(CR³R³ᵃ)ᵤC(O)NR³ᵇ(CR³R³ᵃ)ᵥᵥ, (CR³R³ᵃ)ᵤS(O)NR³ᵇC(O)(CR³R³ᵃ)ᵥᵥ, (CR³R³ᵃ)ᵤC(O)NR³ᵇS(O)₂(CR³R³ᵃ)ᵥᵥ, and (CR³R³ᵃ)ᵤS(O)₂NR³ᵇC(O)NR³ᵇCR³R³ᵃ)ᵥᵥ, wherein u+w total 0, 1, 2, 3, or 4, provided that G₁ does not form a N—S, NCH₂N, NCH₂O, or NCH₂S bond with either group to which it is attached;

Z is selected from a bond, —(CR³R³ᵉ)₁₋₄—, (CR³R³ᵉ)ᵩO(CR³R³ᵉ)q1, (CR³R³ᵉ)ᵩNR³ᵇ(CR³R³ᵉ)q1, (CR³R³ᵉ)ᵩC(O)(CR³R³ᵉ)q1, (CR³R³ᵉ)ᵩC(O)O(CR³R³ᵉ)q1, (CR³R³ᵉ)ᵩOC(O)(CR³R³ᵉ)q1, (CR³R³ᵉ)ᵩC(O)NR³ᵇ(CR³R³ᵉ)q1, (CR³R³ᵉ)ᵩNR³ᵇC(O)(CR³R³ᵉ)q1, (CR³R³ᵉ)ᵩOC(O)O(CR³R³ᵉ)q1, (CR³R³ᵉ)ᵩOC(O)NR³ᵇ(CR³R³ᵉ)q1, (CR³R³ᵉ)ᵩNR³ᵇC(O)O(CR³R³ᵉ)q1, (CR³R³ᵉ)ᵩNR³ᵇC(O)NR³ᵇ(CR³R³ᵉ)q1, (CR³R³ᵉ)ᵩC(O)(CR³R³ᵉ)ᵩC(O)(CR³R³ᵉ)q1, (CR³R³ᵉ)ᵩNR³ᵇ(CR³R³ᵉ)ᵩC(O)NR³ᵇ(CR³R³ᵉ)q1, (CR³R³ᵉ)ᵩNR³ᵇC(O)(CR³R³ᵉ)ᵩC(O)(CR³R³ᵉ)q1, (CR³R³ᵉ)ᵩC(O)(CR³R³ᵉ)ᵩC(O)NR³ᵇ(CR³R³ᵉ)q1, (CR³R³ᵉ)ᵩNR³ᵇC(O)(CR³R³ᵉ)ᵩC(O)NR³ᵇ(CR³R³ᵉ)q1, (CR³R³ᵉ)ᵩS(CR³R³ᵉ)q1, (CR³R³ᵉ)ᵩS(O)(CR³R³ᵉ)q1, (CR³R³ᵉ)ᵩS(O)₂(CR³R³ᵉ)q1, (CR³R³ᵉ)ᵩSO₂NR³ᵇ(CR³R³ᵉ)q1, (CR³R³ᵉ)ᵩNR³ᵇSO₂(CR³R³ᵉ)q1, (CR³R³ᵉ)ᵩS(O)NR³ᵇC(O)(CR³R³ᵉ)q1, (CR³R³ᵉ)ᵩC(O)NR³ᵇS(O)₂(CR³R³ᵉ)q1, and (CR³R³ᵉ)ᵩNR³ᵇSO₂NR³ᵇ(CR³R³ᵉ)q1, wherein q+q1 total 0, 1, 2, 3, or 4, provided that Z does not form a N—S, NCH₂N, NCH₂O, or NCH₂S bond with either group to which it is attached;

Z² is selected from H, S(O)₂NHR³ᵇ, C(O)R³ᵇ, C(O)NHR³ᵇ, C(O)OR³ᶠ, S(O)R³ᶠ, S(O)₂R³ᶠ, C₁₋₆ alkyl substituted with 0–2 R¹ᵃ, C₂₋₆ alkenyl substituted with 0–2 R¹ᵃ, C₂₋₆ alkynyl substituted with 0–2 R¹ᵃ, —(C₀₋₄ alkyl)-cycloalkyl substituted with 0–3 R¹ᵃ, —(C₀₋₄ alkyl)-heterocycle substituted with 0–3 R¹ᵃ, —(C₀₋₄ alkyl)-aryl substituted with 0–3 R¹ᵃ, and, —(C₀₋₄ alkyl)-heteroaryl substituted with 0–3 R¹ᵃ;

R¹ᵃ, at each occurrence, is selected from H, —(CR³R³ᵃ)ᵣ—R¹ᵇ, —(CR³R³ᵃ)ᵣ—CR³R¹ᵇR¹ᵇ, —(CR³R³ᵃ)ᵣ—O—(CR³R³ᵃ)ᵣ—R¹ᵇ, —(CR³R³ᵃ)ᵣ—NR²—(CR³R³ᵃ)ᵣ—R¹ᵇ, —(CR³R³ᵃ)ᵣ—S(O)ₚ—(CR³R³ᵃ)ᵣ—R¹ᵇ, —(CR³R³ᵃ)ᵣ—CO₂—(CR³R³ᵃ)ᵣ—R¹ᵇ, —(CR³R³ᵃ)ᵣ—C(O)NR²—(CR³R³ᵃ)ᵣ—R¹ᵇ, —(CR³R³ᵃ)ᵣ—C(O)—(CR³R³ᵃ)ᵣ—R¹ᵇ, —C₂₋₆ alkenylene-R¹ᵇ, —C₂₋₆ alkynylene-R¹ᵇ, and —(CR³R³ᵃ)ᵣ—C(=NR¹ᵇ)NR³R¹ᵇ, provided that R¹ᵃ forms other than an N-halo, N—S, O—O, or N—CN bond;

alternatively, when two R¹ᵃ groups are attached to adjacent atoms or to the same carbon atom, together with the atoms to which they are attached, they form a 5–7 membered ring consisting of: carbon atoms and 0–2 heteroatoms selected from the group consisting of N, O, and S(O)ₚ, this ring being substituted with 0–2 R⁴ᵇ and comprising: 0–3 double bonds;

R¹ᵇ is selected from H, C₁₋₃ alkyl, F, Cl, Br, I, —CN, —NO₂, —CHO, (CF₂)ᵣCF₃, (CR³R³ᵃ)ᵣOR², NR²R²ᵃ, C(O)R²ᵇ, CO₂R²ᵇ, OC(O)R², CH(CH₂OR²)₂, (CF₂)ᵣCO₂R²ᵃ, S(O)ₚR²ᵇ, NR²(CH₂)ᵣOR², C(=NR²ᶜ)NR²R²ᵃ, NR²C(O)R²ᵇ, NR²C(O)NR²R²ᵃ, NR²C(O)₂R²ᵃ, OC(O)NR²R²ᵃ, C(O)NR²R²ᵃ, C(O)NR²(CH₂)ᵣOR², SO₂NR²R²ᵃ, NR²SO₂R², C(O)NR²SO₂R², C₃₋₆ carbocycle substituted with 0–2 R⁴ᵇ, and 5–10 membered heterocycle substituted with 0–2 R⁴ᵇ and consisting of carbon atoms and from 1–4 heteroatoms selected from the group consisting of N, O, and S(O)ₚ, provided that R¹ᵇ forms other than an O—O, N-halo, N—S, or N—CN bond and provided that S(O)ₚR² forms other than S(O)₂H or S(O)H;

R², at each occurrence, is selected from H, CF₃, C₁₋₆ alkyl, benzyl, —(CH₂)ᵣ—C₃₋₁₀ carbocycle substituted with 0–2 R⁴ᵇ, and —(CH₂)ᵣ-5–10 membered heterocycle consisting of: carbon atoms and 1–4 heteroatoms selected from the group consisting of N, O, and S(O)ₚ and substituted with 0–2 R⁴ᵇ;

R²ᵃ, at each occurrence, is selected from H, CF₃, C₁₋₆ alkyl, benzyl, —(CH₂)ᵣ—C₃₋₁₀ carbocycle substituted with 0–2 R⁴ᵇ, and —(CH₂)ᵣ-5–10 membered heterocycle consisting of: carbon atoms and 1–4 heteroatoms selected from the group consisting of N, O, and S(O)ₚ and substituted with 0–2 R⁴ᵇ;

alternatively, R² and R²ᵃ, together with the atom to which they are attached, combine to form a 5 or 6 membered saturated, partially saturated or unsaturated ring substituted with 0–2 R⁴ᵇ and consisting of: 0–1 additional heteroatoms selected from the group consisting of N, O, and S(O)ₚ;

R²ᵇ, at each occurrence, is selected from CF₃, C₁₋₄ alkoxy, C₁₋₆ alkyl substituted with 0–2 R⁴ᵇ, —(CH₂)ᵣ—C₃₋₁₀ carbocycle substituted with 0–2 R⁴ᵇ, and —(CH₂)ᵣ-5–10 membered heterocycle consisting of: carbon atoms and 1–4 heteroatoms selected from the group consisting of N, O, and S(O)ₚ and substituted with 0–2 R⁴ᵇ;

$R^{2c}$, at each occurrence, is selected from $CF_3$, OH, $C_{1-4}$ alkoxy, $C_{1-6}$ alkyl, $-(CH_2)_r-C_{3-10}$ carbocycle substituted with 0–2 $R^{4b}$, and $-(CH_2)_r$-5–10 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-6}$ alkyl substituted with 0–2 $R^{4c}$, $-(CR^3R^{3a})_r-C_{3-10}$ carbocycle substituted with 0–2 $R^{4c}$, and $-(CR^3R^{3a})_r$-5–10 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-6}$ alkyl substituted with 0–2 $R^{4c}$, $-(CR^3R^{3a})_r-C_{3-10}$ carbocycle substituted with 0–2 $R^{4c}$, and $-(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from $CF_3$, $C_{1-4}$ alkoxy substituted with 0–2 $R^{4b}$, $C_{1-6}$ alkyl substituted with 0–2 $R^{4b}$, $-(CH_2)_r-C_{3-10}$ carbocycle substituted with 0–2 $R^{4b}$, and $-(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $-(C_{0-4}$ alkyl)-5–10 membered carbocycle substituted with 0–3 $R^{1a}$, and $-(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, $-(C_{0-4}$ alkyl)-5–10 membered carbocycle substituted with 0–3 $R^{1a}$, and $-(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3g}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $-(CH_2)_r$-3–6 membered carbocycle, and $-(CH_2)_r$-5–6 membered heterocycle consisting of: carbon atoms and 1–4 heteroatoms selected from the group consisting of N, O, and $S(O)_p$;

alternatively, when $R^3$ and $R^{3g}$ are attached to the same carbon atom, they combine with the attached carbon atom to form a cyclopropyl group;

$R^4$, at each occurrence, is selected from H, =O, $(CR^3R^{3a})_r$OR$^2$, F, Cl, Br, I, $C_{1-4}$ alkyl, $(CR^3R^{3a})_r$CN, $(CR^3R^{3a})_r$NO$_2$, $(CR^3R^{3a})_r$NR$^2$R$^{2a}$, $(CR^3R^{3a})_r$C(O)R$^{2c}$, $(CR^3R^{3a})_r$NR$^2$C(O)R$^{2b}$, $(CR^3R^{3a})_r$C(O)NR$^2$R$^{2a}$, $(CR^3R^{3a})_r$NR$^2$C(O)NR$^2$R$^{2a}$, $(CR^3R^{3a})_r$C(=NR$^2$)NR$^2$R$^{2a}$, $(CR^3R^{3a})_r$C(=NS(O)_2R$^{5a}$)NR$^2$R$^{2a}$, $(CR^3R^{3a})_r$NHC(=NR$^2$)NR$^2$R$^{2a}$, $(CR^3R^{3a})_r$C(O)NHC(=NR$^2$)NR$^2$R$^{2a}$, $(CR^3R^{3a})_r$SO$_2$NR$^2$R$^{2a}$, $(CR^3R^{3a})_r$NR$^2$SO$_2$NR$^2$R$^{2a}$, $(CR^3R^{3a})_r$NR$^2$SO$_2$—$C_{1-4}$ alkyl, $(CR^3R^{3a})_r$NR$^2$SO$_2$R$^{5a}$, $(CR^3R^{3a})_r$S(O)$_p$R$^{5a}$, $(CR^3R^{3a})_r$(CF$_2$)_rCF$_3$, NHCH$_2$R$^{1b}$, OCH$_2$R$^{1b}$, SCH$_2$R$^{1b}$, N(CH$_2$)_2(CH$_2$)_rR$^{1b}$, O(CH$_2$)_2(CH$_2$)_rR$^{1b}$, S(CH$_2$)_2(CH$_2$)_rR$^{1b}$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4b}$, at each occurrence, is selected from H, =O, $(CH_2)_r$OR$^3$, $(CH_2)_r$F, $(CH_2)_r$Cl, $(CH_2)_r$Br, $(CH_2)_r$I, $C_{1-4}$ alkyl, $(CH_2)_r$CN, $(CH_2)_r$NO$_2$, $(CH_2)_r$NR$^3$R$^{3a}$, $(CH_2)_r$C(O)R$^3$, $(CH_2)_r$C(O)OR$^{3c}$, $(CH_2)_r$NR$^3$C(O)R$^{3a}$, $(CH_2)_r$—C(O)NR$^3$R$^{3a}$, $(CH_2)_r$NR$^3$C(O)NR$^3$R$^{3a}$, $(CH_2)_r$—C(=NR$^3$)NR$^3$R$^{3a}$, $(CH_2)_r$NR$^3$C(=NR$^3$)NR$^3$R$^{3a}$, $(CH_2)_r$SO$_2$NR$^3$R$^{3a}$, $(CH_2)_r$NR$^3$SO$_2$NR$^3$R$^{3a}$, $(CH_2)_r$NR$^3$SO$_2$—$C_{1-4}$ alkyl, $(CH_2)_r$NR$^3$SO$_2$CF$_3$, $(CH_2)_r$NR$^3$SO$_2$-phenyl, $(CH_2)_r$S(O)$_p$CF$_3$, $(CH_2)_r$S(O)$_p$—$C_{1-14}$ alkyl, $(CH_2)_r$S(O)$_p$-phenyl, and $(CH_2)_r$(CF$_2$)_rCF$_3$;

$R^{4c}$, at each occurrence, is selected from =O, $(CR^3R^{3a})_r$OR$^2$, $(CR^3R^{3a})_r$F, $(CR^3R^{3a})_r$Br, $(CR^3R^{3a})_r$Cl, $(CR^3R^{3a})_r$CF$_3$, $C_{1-4}$ alkyl, $(CR^3R^{3a})_r$CN, $(CR^3R^{3a})_r$NO$_2$, $(CR^3R^{3a})_r$NR$^2$R$^{2a}$, $(CR^3R^{3a})_r$N(→O)R$^2$R$^{2a}$, $(CR^3R^{3a})_r$C(O)R$^{2c}$, $(CR^3R^{3a})_r$NR$^2$C(O)R$^{2b}$, $(CR^3R^{3a})_r$C(O)NR$^2$R$^{2a}$, $(CR^3R^{3a})_r$N=CHOR$^3$, $(CR^3R^{3a})_r$C(O)NH(CR$^3$R$^{3a}$)_2NR$^2$R$^{2a}$, $(CR^3R^{3a})_r$NR$^2$C(O)NR$^2$R$^{2a}$, $(CR^3R^{3a})_r$C(=NR$^2$)NR$^2$R$^{2a}$, $(CR^3R^{3a})_r$NHC(=NR$^2$)NR$^2$R$^{2a}$, $(CR^3R^{3a})_r$SO$_2$NR$^2$R$^{2a}$, $(CR^3R^{3a})_r$NR$^2$SO$_2$NR$^2$R$^{2a}$, $(CR^3R^{3a})_r$C(O)NHSO$_2$—$C_{1-4}$ alkyl, $(CR^3R^{3a})_r$NR$^2$SO$_2$R$^{5a}$, $(CR^3R^{3a})_r$S(O)$_p$R$^{5a}$, $(CF_2)_r$CF$_3$, $(CR^3R^{3a})_r$C$_{3-10}$ carbocycle substituted with 0–2 $R^{4b}$, and $(CR^3R^{3a})_r$5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, $C_{1-6}$ alkyl, =O, $(CH_2)_r$OR$^3$, F, Cl, Br, I, —CN, NO$_2$, $(CH_2)_r$NR$^3$R$^{3a}$, $(CH_2)_r$C(O)R$^3$, $(CH_2)_r$C(O)OR$^{3c}$, $(CH_2)_r$NR$^3$C(O)R$^{3a}$, $(CH_2)_r$C(O)NR$^3$R$^{3a}$, $(CH_2)_r$NR$^3$C(O)NR$^3$R$^{3a}$, $(CH_2)_r$CH(=NOR$^{3d}$), $(CH_2)_r$C(=NR$^3$)NR$^3$R$^{3a}$, $(CH_2)_r$NR$^3$C(=NR$^3$)NR$^3$R$^{3a}$, $(CH_2)_r$SO$_2$NR$^3$R$^{3a}$, $(CH_2)_r$NR$^3$SO$_2$NR$^3$R$^{3a}$, $(CH_2)_r$NR$^3$SO$_2$—$C_{1-4}$ alkyl, $(CH_2)_r$NR$^3$SO$_2$CF$_3$, $(CH_2)_r$NR$^3$SO$_2$-phenyl, $(CH_2)_r$S(O)$_p$CF$_3$, $(CH_2)_r$S(O)$_p$—$C_{1-4}$ alkyl, $(CH_2)_r$S(O)$_p$-phenyl, $(CF_2)_r$CF$_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_r$OR$^3$, $(CH_2)_r$NR$^3$R$^{3a}$, $(CH_2)_r$C(O)R$^3$, $(CH_2)_r$C(O)OR$^{3c}$, $(CH_2)_r$NR$^3$C(O)R$^{3a}$, $(CH_2)_r$C(O)NR$^3$R$^{3a}$, $(CF_2)_r$CF$_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond;

R⁶, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

R⁷, at each occurrence, is selected from H, OH, $C_{1-6}$ alkyl, $C_{1-6}$ alkyl-C(O)—, $C_{1-6}$ alkyl-O—, $(CH_2)_n$-phenyl, $C_{1-4}$ alkyl-OC(O)—, $C_{6-10}$ aryl-O—, $C_{6-10}$ aryl-OC(O)—, $C_{6-10}$ aryl-$CH_2$—C(O)—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-$NH_2$—C(O)—, phenyl-$NH_2$—C(O)—, and phenyl $C_{1-4}$ alkyl-C(O)—;

R⁸, at each occurrence, is selected from H, $C_{1-6}$ alkyl, and $(CH_2)_n$-phenyl;

alternatively, R⁷ and R⁸, when attached to the same nitrogen, combine to form a 5–10 membered heterocyclic ring consisting of carbon atoms and 0–2 additional heteroatoms selected from the group consisting of N, O, and $S(O)_p$;

R⁹, at each occurrence, is selected from H, $C_{1-6}$ alkyl, and $(CH_2)_n$-phenyl;

n, at each occurrence, is selected from 0, 1, 2, and 3;
p, at each occurrence, is selected from 0, 1, and 2;
r, at each occurrence, is selected from 0, 1, 2, 3, 4, 5, and 6;
t, at each occurrence, is selected from 0, 1, 2, and 3; and,
provided that when ring M is phenyl and is substituted 1, 2 by $M_4$ and $P_4$ and $G_1$ is present, then Z-A is other than NHC(O)-thienyl, $NHCH_2$-thienyl, NHC(O)-benzothienyl, and $NHCH_2$-benzothienyl.

[2] In a preferred embodiment, the present invention provides a novel compound of Formula II:

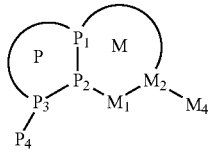

II or a stereoisomer or pharmaceutically acceptable salt thereof, wherein;

ring M, including $P_1$, $P_2$, $M_1$, and $M_2$, is a 5, 6, or 7 membered carbocycle or a 5, 6, or 7 membered heterocycle, consisting of: carbon atoms and 1–3 heteroatoms selected from O, $S(O)_p$, N, and $NZ^2$;

ring M is substituted with 0–2 $R^{1a}$ and 0–2 carbonyl groups, and there are 0–3 ring double bonds;

ring P, including $P_1$, $P_2$, and $P_3$, is a 5 or 6 membered aromatic heterocycle, consisting of: carbon atoms and 1–3 heteroatoms selected from O, $S(O)_p$, and N;

alternatively, ring P, including $P_1$, $P_2$, and $P_3$, is a 5 or 6 membered dihydro-aromatic heterocycle, consisting of: carbon atoms and 1–3 heteroatoms selected from O, $S(O)_p$, and N;

ring P is substituted with 0–2 $R^{1a}$;

one of $P_4$ and $M_4$ is -Z-A-B and the other $-G_1$-G;

G is a group of formula IIa or IIb:

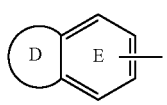

IIa

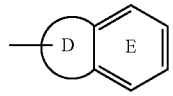

IIb ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with 1 R and with a 5 membered heterocycle consisting of: carbon atoms and 1–4 heteroatoms selected from the group consisting of N, O, and $S(O)_p$, wherein the 5 membered heterocycle is substituted with 0–1 carbonyls and 1–2 R and there are 0–3 ring double bonds;

R is selected from H, $C_{1-4}$ alkyl, F, Cl, OH, $OCH_3$, $OCH_2CH_3$, $OCH(CH_3)_2$, CN, $C(=NH)NH_2$, $C(=NH)NHOH$, $C(=NH)NHOCH_3$, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $(CR^8R^9)_rNR^7R^8$, $C(O)NR^7R^8$, $CH_2C(O)NR^7R^8$, $S(O)_2R^3$, $S(O)_pNR^7R^8$, $CH_2S(O)_pNR^7R^8$, and $OCF_3$;

alternatively, when 2 R groups are attached to adjacent atoms, they combine to form methylenedioxy or ethylenedioxy;

A is selected from: $C_{5-10}$ carbocycle substituted with 0–2 R⁴, and 5–10 membered heterocycle consisting of: carbon atoms and 1–4 heteroatoms selected from the group consisting of N, O, and $S(O)_p$ and substituted with 0–2 R⁴;

B is selected from $N(B^1)C(O)C(R^3R^{3g})R^3$, $N(B^1)C(O)C(R^3R^{3g})NB^2B^3$, and $N(B^1)C(O)C(R^3R^{3g})C(R^3R^{3g})NB^2B^3$, provided that Z and B are attached to different atoms on A;

B¹ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $—(CH_2)_{0-1}$-$C_{3-7}$ carbocycle substituted with 0–2 $R^{4b}$, and $—(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

B² is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2$—$NR^{2d}R^{2d}$, $CH_2CH_2$—$NR^{2d}R^{2d}$, $C(O)R^{2e}$, $C(O)NR^{2d}R^{2d}$, $SO_2NR^{2d}R^{2d}$, and $S(O)_pR^{5a}$;

B³ is selected from H, $C_{1-6}$ alkyl substituted with 0–1 $R^{4c}$, $—(CH_2)_{0-1}$-3–6 membered carbocycle substituted with 0–2 R⁵, and a $—(CH_2)_{0-1}$-4–7 membered heterocycle consisting of: carbon atoms and 1–4 heteroatoms selected from the group consisting of N, O, and $S(O)_p$ and substituted with 0–2 R⁵;

alternatively, $NB^2B^3$ is a 4–7 membered heterocycle consisting of: the shown N, carbon atoms, and 0–3 additional heteroatoms selected from the group consisting of N, O, and $S(O)_p$ and substituted with 0–2 R⁵;

Z is selected from a bond, $CH_2$, $CH_2CH_2$, $CH_2O$, $OCH_2$, $C(O)$, NH, $CH_2NH$, $NHCH_2$, $CH_2C(O)$, $C(O)CH_2$, $C(O)NH$, NHC(O), $NHC(O)CH_2C(O)NH$, $S(O)_2$, $CH_2S(O)_2$, $S(O)_2(CH_2)$, $SO_2NH$, and $NHSO_2$, provided that Z does not form a N—S, $NCH_2N$, $NCH_2O$, or $NCH_2S$ bond with either group to which it is attached;

$Z^2$ is selected from H, $C_{1-4}$ alkyl, phenyl, benzyl, $C(O)R^{3b}$, $S(O)R^{3f}$, and $S(O)_2R^{3f}$;

$R^{1a}$ is selected from H, $-(CH_2)_r-R^{1b}$, $-(CH(CH_3))_r-R^{1b}$, $-(C(CH_3)_2)_r-R^{1b}$, $NHCH_2R^{1b}$, $OCH_2R^{1b}$, $SCH_2R^{1b}$, $NH(CH_2)_2(CH_2)_rR^{1b}$, and $O(CH_2)_2(CH_2)_rR^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C_{5-6}$ carbocycle substituted with 0–2 $R^{4b}$, and 5–6 membered heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, a $C_{5-6}$ carbocyclic-$CH_2$-group substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, $-(CR^3R^{3a})_r-C_{3-6}$ carbocycle substituted with 0–2 $R^{4c}$, and $-(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $-(CR^3R^{3a})_r-C_{3-6}$ carbocycle substituted with 0–2 $R^{4c}$, and $-(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^{3g}$, at each occurrence, is selected from H, $CH_3$, $CH_2CH_3$, $CH_2CH_2CH_3$, $CH(CH_3)_2$, cyclopropyl, cyclopropyl-methyl, benzyl, and phenyl;

alternatively, when $R^3$ and $R^{3g}$ are attached to the same carbon atom, they combine with the attached carbon atom to form a cyclopropyl group;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$ and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2-C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2-C_{1-4}$ alkyl, $CH_2NR^3SO_2-C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)-C_{1-4}$ alkyl, $CH_2S(O)_p-C_{1-4}$ alkyl, $S(O)_p$-phenyl, $CH_2S(O)_p$-phenyl, $CF_3$, and $CH_2—CF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl; and, r, at each occurrence, is selected from 0, 1, and 2.

[3] In another preferred embodiment, the present invention provides a novel compound, wherein:

ring M is substituted with 0–2 $R^{1a}$ and is selected from the group:

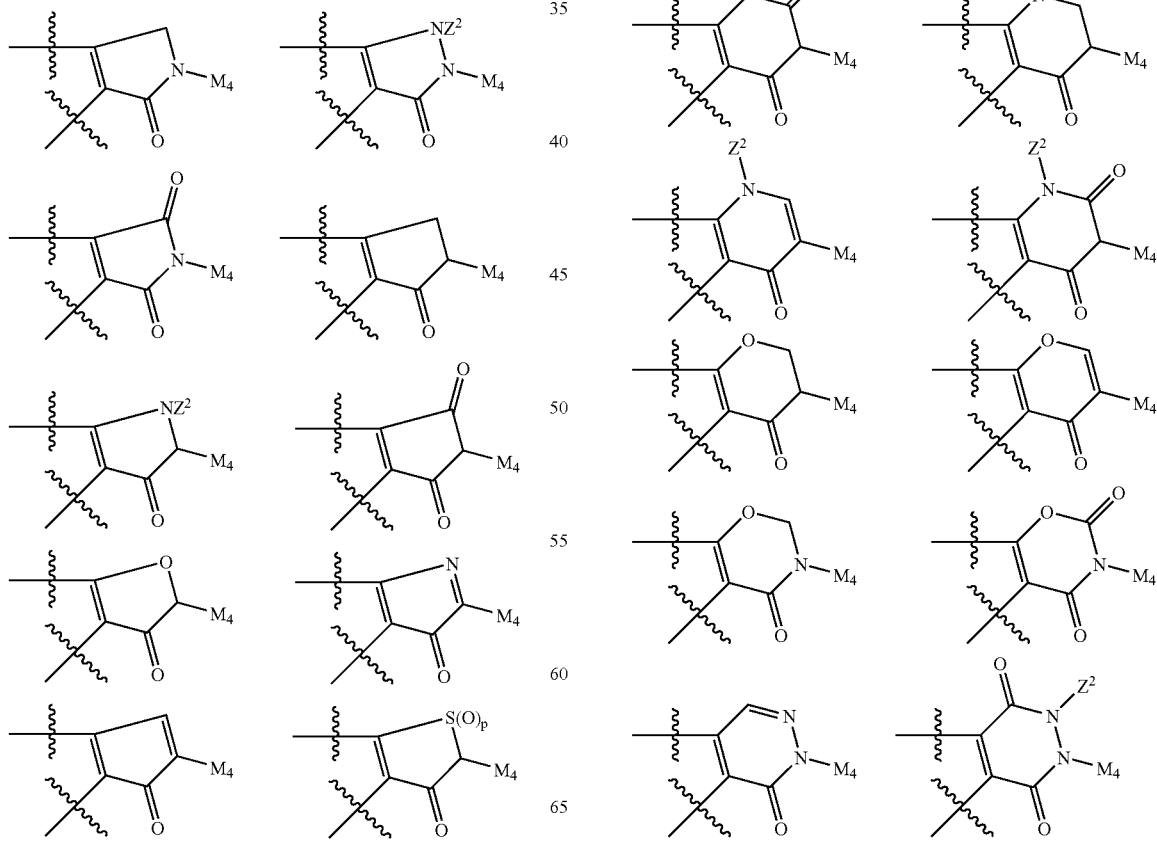

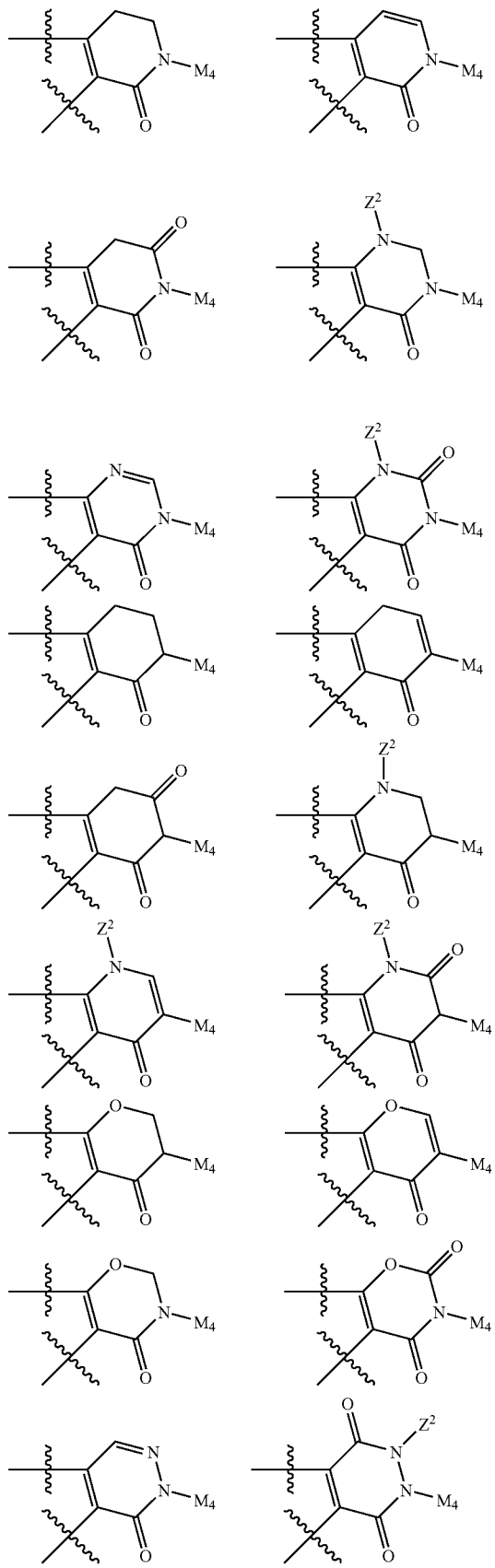

-continued
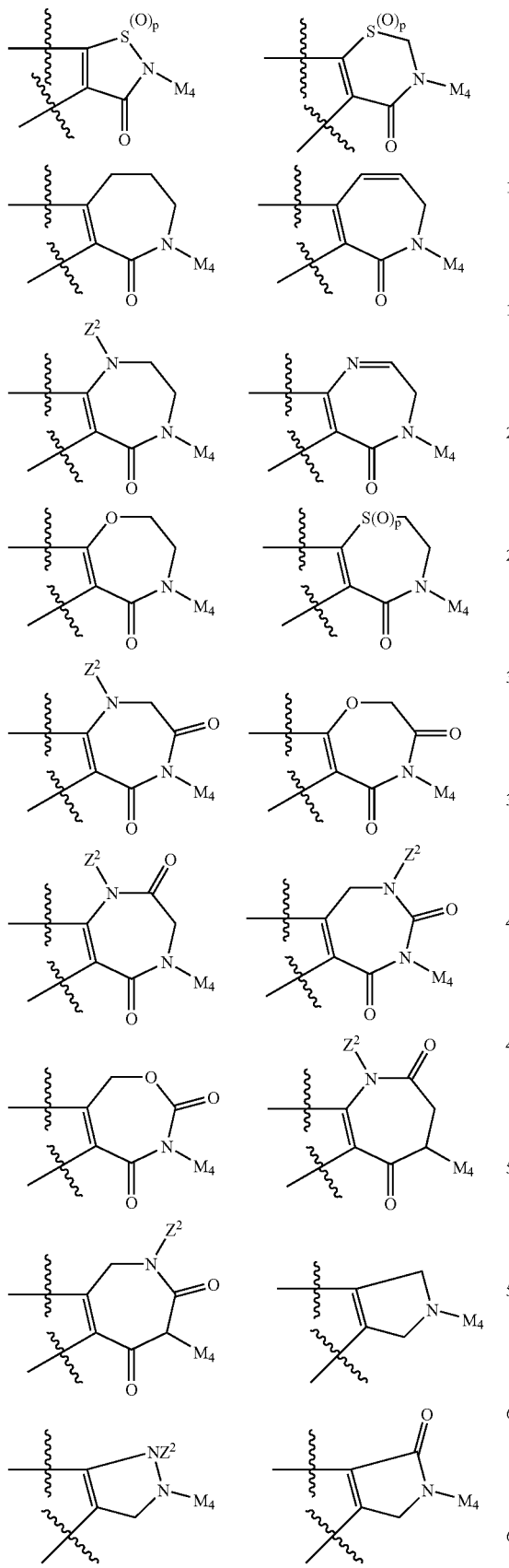
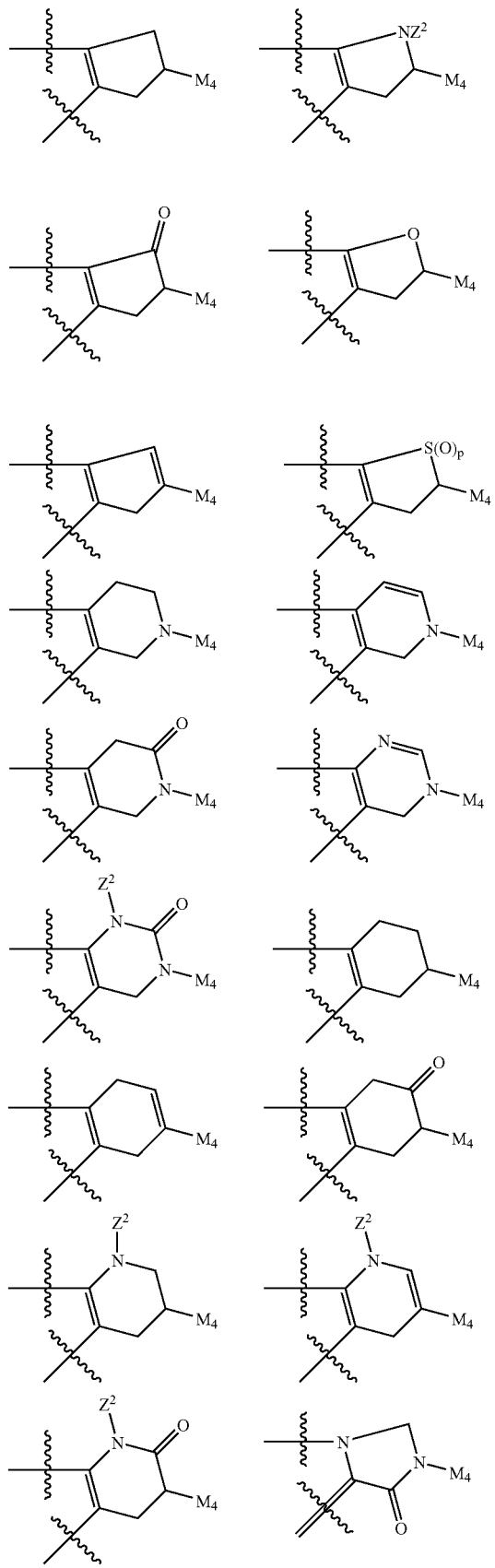

-continued

-continued ring P, including $P_1$, $P_2$, $P_3$, $P_4$ is selected from group:

-continued
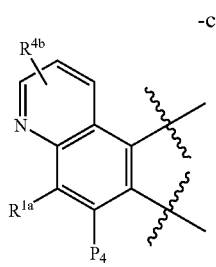 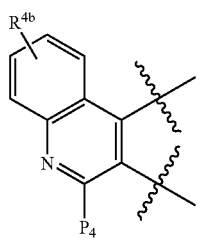 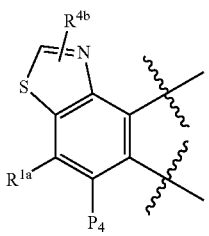 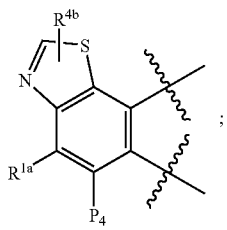
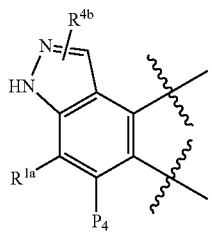 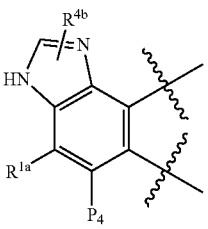
one of $P_4$ and $M_4$ is -Z-A-B and the other -$G_1$-G;
G is selected from the group:
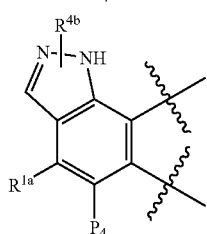 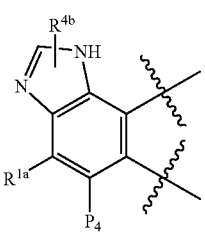
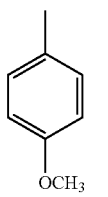 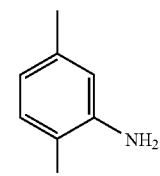 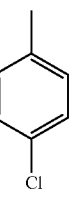
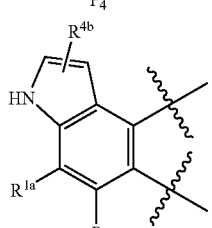 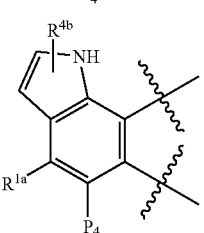
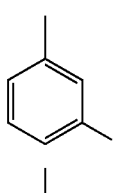 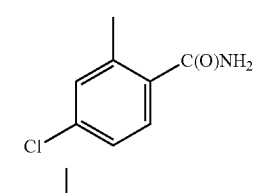
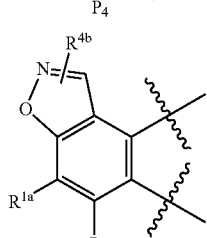 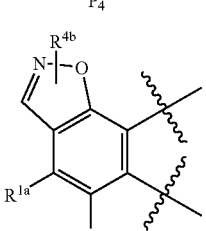
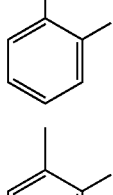 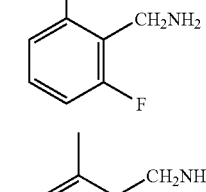
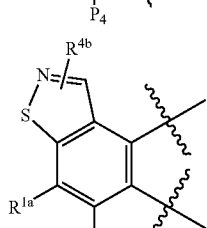 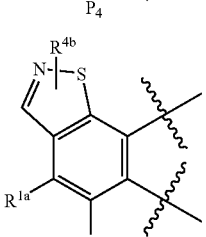
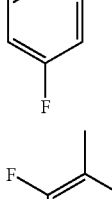 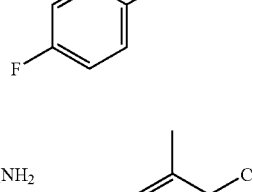
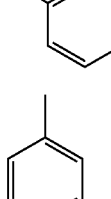 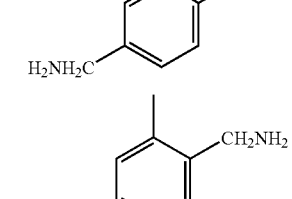
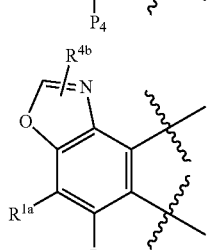 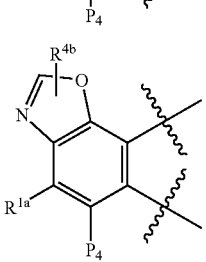
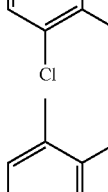 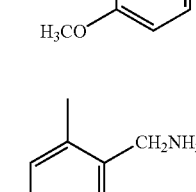
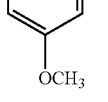 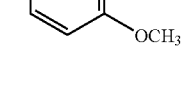

-continued
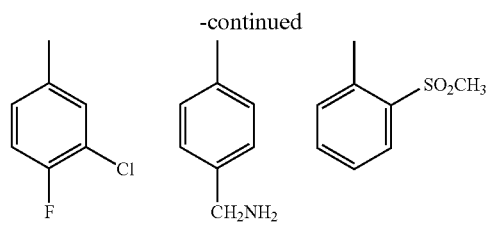
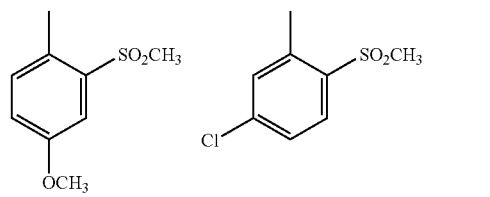
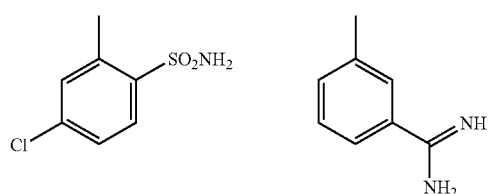
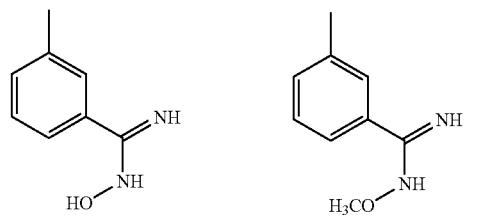
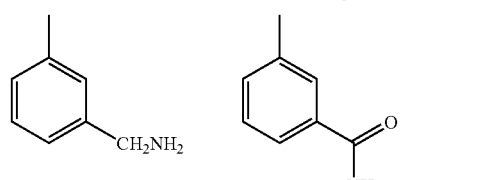
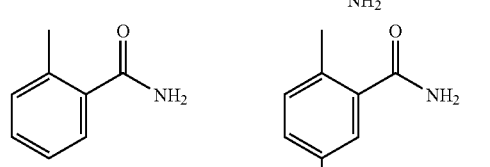
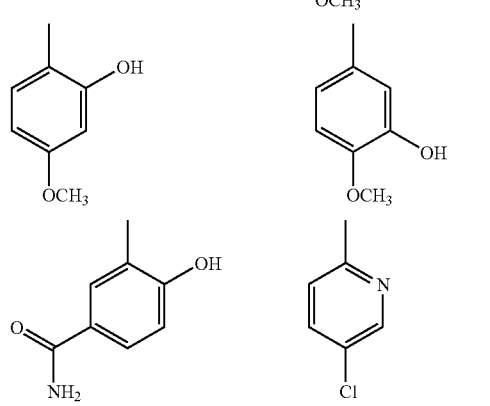
-continued
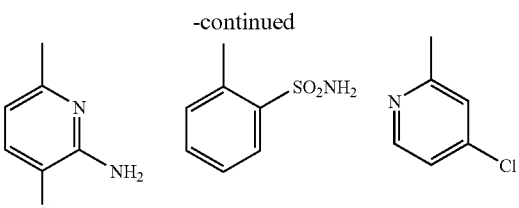
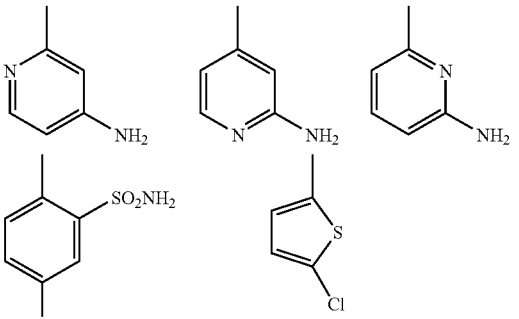
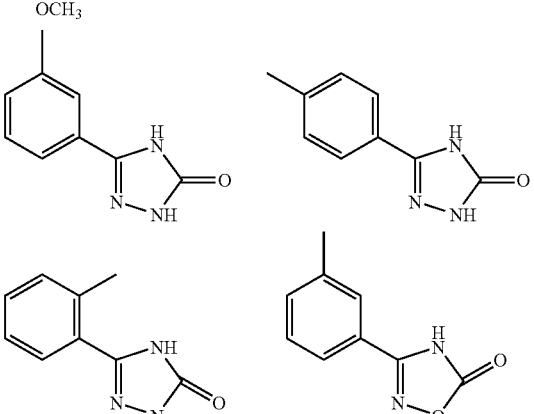
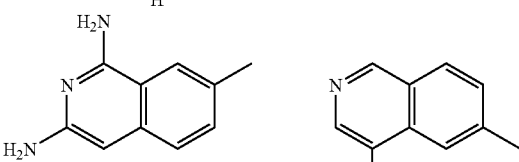
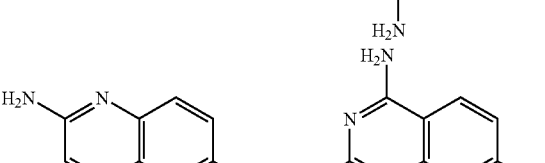
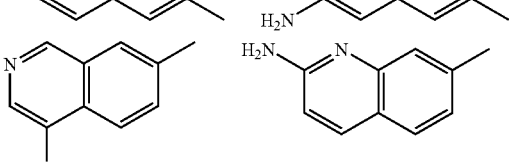
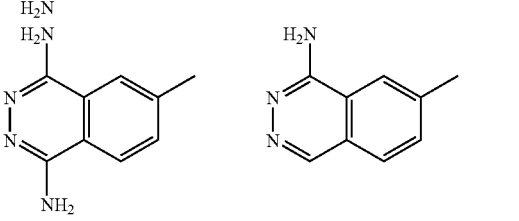

-continued
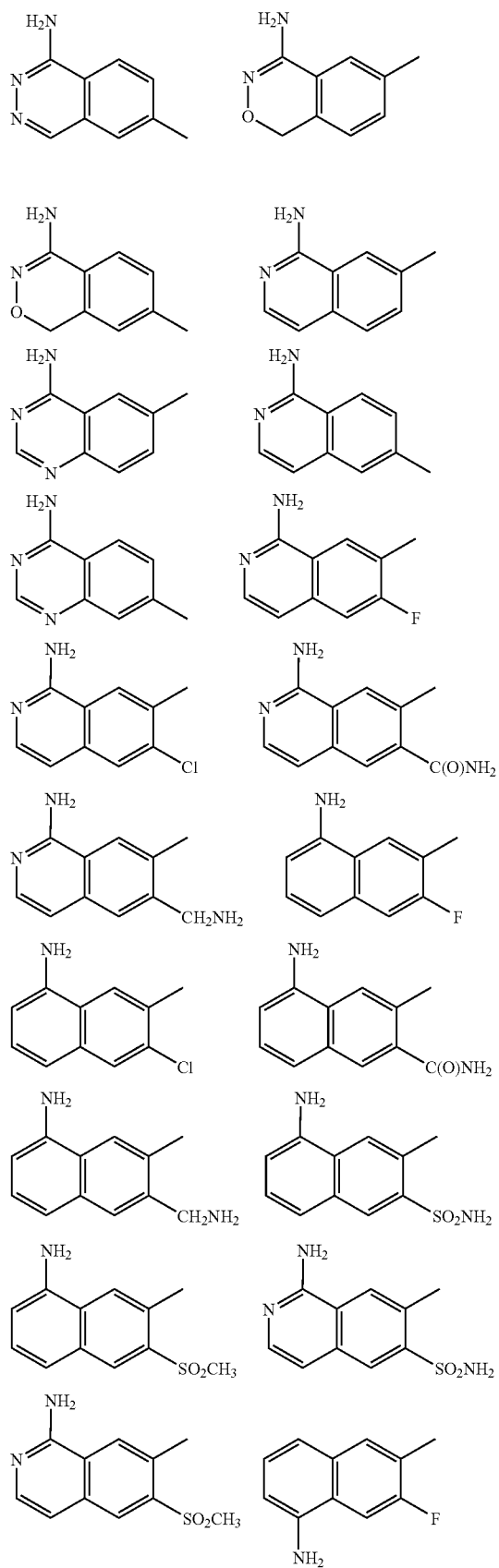
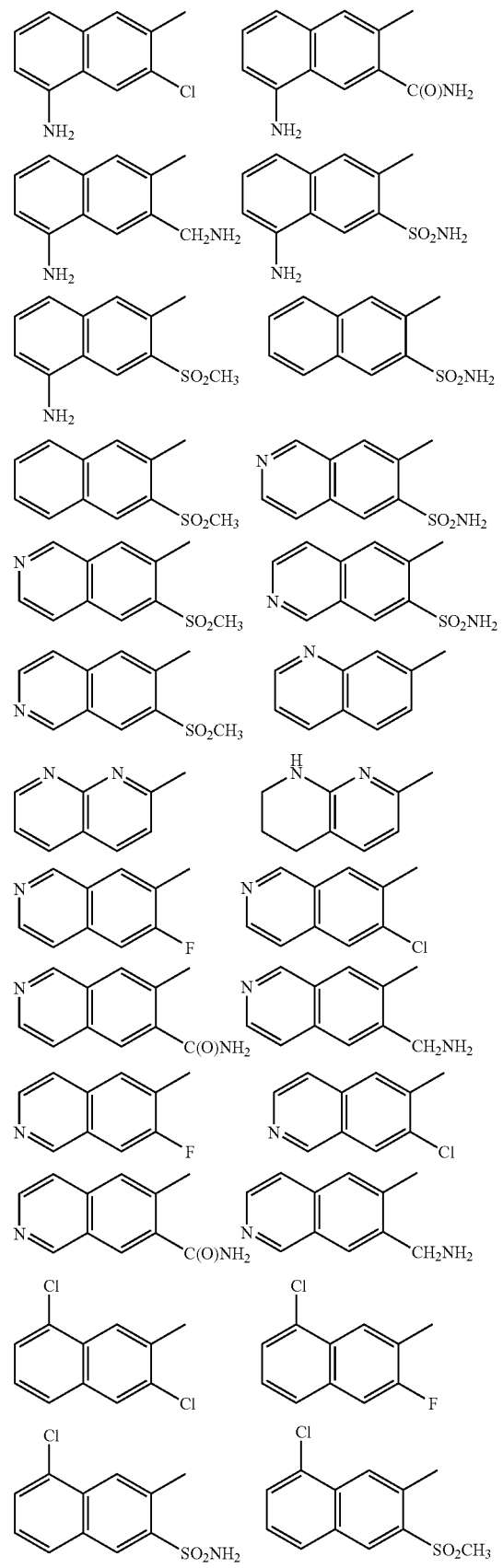

-continued
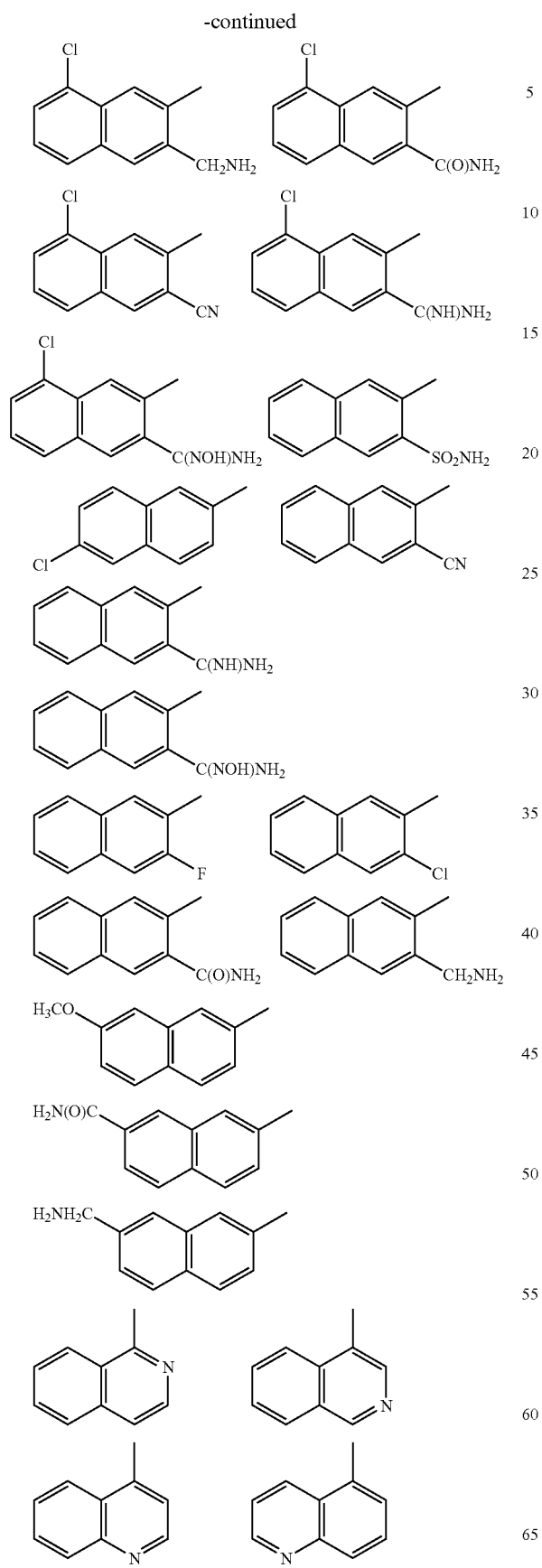
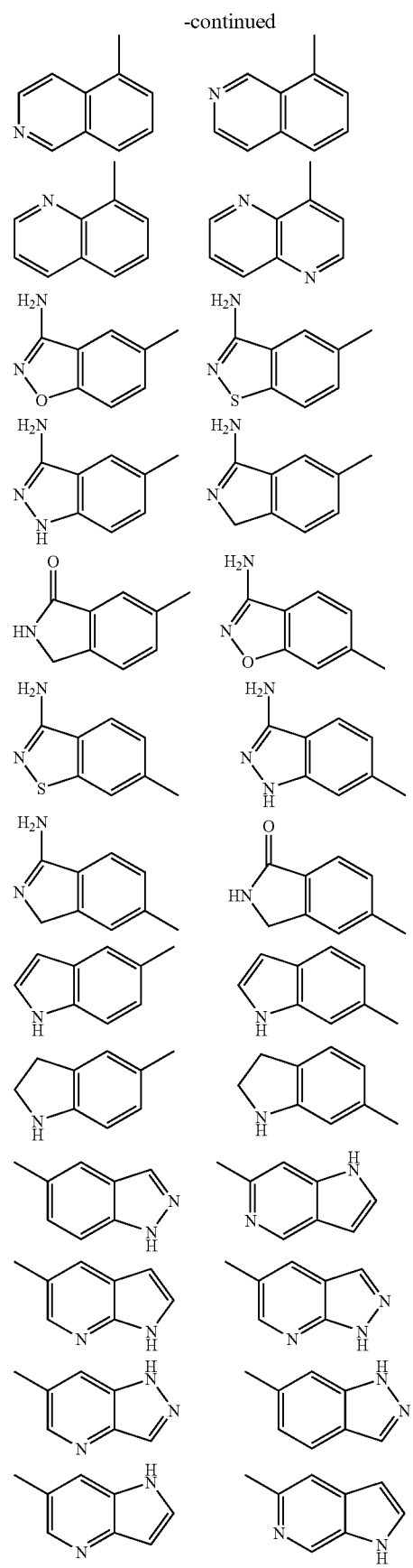

-continued

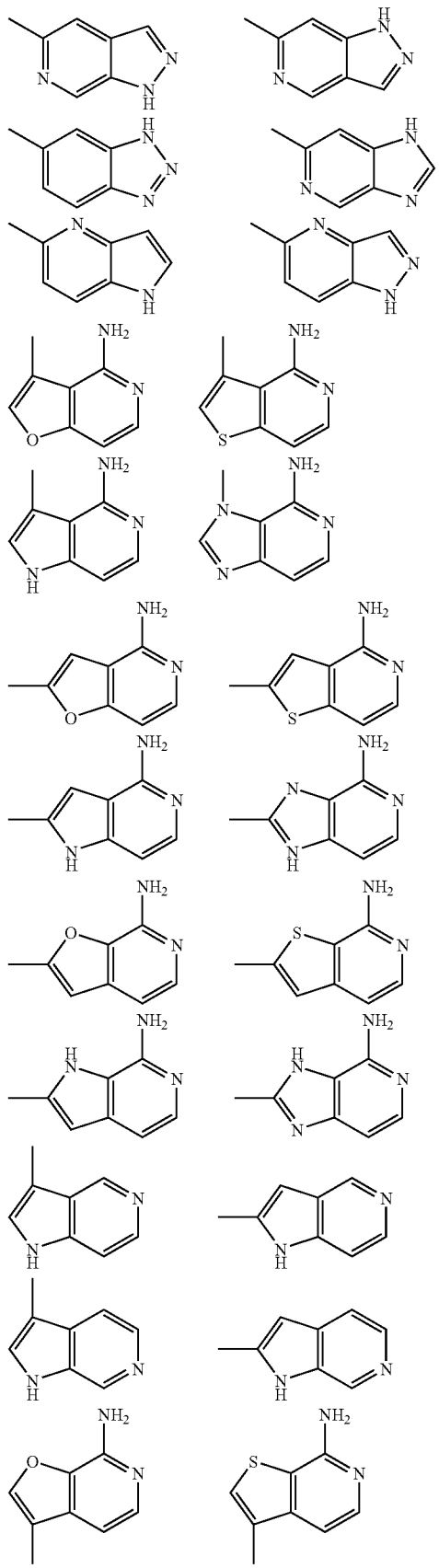

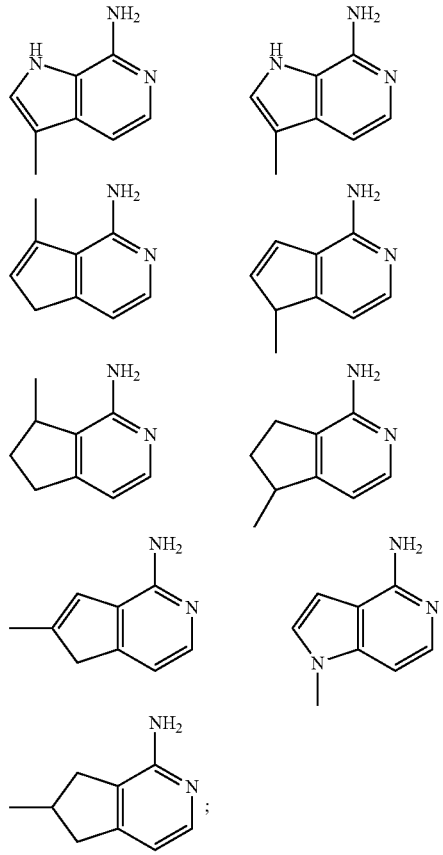

G$_1$ is absent or is selected from (CR$^3$R$^{3a}$)$_{1-3}$, (CR$^3$R$^{3a}$)$_u$C(O)(CR$^3$R$^{3a}$)$_w$, (CR$^3$R$^{3a}$)$_u$O(CR$^3$R$^{3a}$)$_w$, (CR$^3$R$^{3a}$)$_u$NR$^{3b}$(CR$^3$R$^{3a}$)$_w$, (CR$^3$R$^{3a}$)$_u$C(O)NR$^{3b}$(CR$^3$R$^{3a}$)$_w$, (CR$^3$R$^{3a}$)$_u$NR$^{3b}$C(O)(CR$^3$R$^{3a}$)$_w$, (CR$^3$R$^{3a}$)$_u$NR$^{3b}$C(O)(CR$^3$R$^{3a}$)$_u$C(O)NR$^{3b}$(CR$^3$R$^{3a}$)$_w$, (CR$^3$R$^{3a}$)$_u$S(CR$^3$R$^{3a}$)$_w$, (CR$^3$R$^{3a}$)$_u$S(O)(CR$^3$R$^{3a}$)$_w$, (CR$^3$R$^{3a}$)$_u$S(O)$_2$(CR$^3$R$^{3a}$)$_w$, (CR$^3$R$^{3a}$)$_u$S(O)NR$^{3b}$(CR$^3$R$^{3a}$)$_w$, (CR$^3$R$^{3a}$)$_u$NR$^{3b}$S(O)$_2$(CR$^3$R$^{3a}$)$_w$, and (CR$^3$R$^{3a}$)$_u$S(O)$_2$NR$^{3b}$(CR$^3$R$^{3a}$)$_w$, wherein u+w total 0, 1, or 2, provided that G$_1$ does not form a N—S, NCH$_2$N, NCH$_2$O, or NCH$_2$S bond with either group to which it is attached;

R$^{1a}$ is selected from H, R$^{1b}$, CH(CH$_3$)R$^{1b}$, C(CH$_3$)$_2$R$^{1b}$, CH$_2$R$^{1b}$, and CH$_2$CH$_2$R$^{1b}$, provided that R$^{1a}$ forms other than an N-halo, N—S, or N—CN bond;

alternatively, when two R$^{1a}$ groups are attached to adjacent atoms, together with the atoms to which they are attached they form a 5–6 membered ring consisting of: carbon atoms and 0–2 heteroatoms selected from the group consisting of N, O, and S(O)$_p$, this ring being substituted with 0–2 R$^{4b}$ and 0–3 ring double bonds;

R$^{1b}$ is selected from H, CH$_3$, CH$_2$CH$_3$, F, Cl, Br, —CN, —CHO, CF$_3$, OR$^2$, NR$^2$R$^{2a}$, C(O)R$^{2b}$, CO$_2$R$^{2b}$, OC(O)R$^2$, CO$_2$R$^{2a}$, S(O)$_p$R$^2$, NR$^2$(CH$_2$)$_r$OR$^2$, NR$^2$C(O)R$^{2b}$, C(O)NR$^2$R$^{2a}$, SO$_2$NR$^2$R$^{2a}$, NR$^2$SO$_2$R$^2$, phenyl substituted with 0–2 R$^{4b}$, and 5–6 membered aromatic heterocycle consisting of carbon atoms and from 1–4 heteroatoms selected from the group consisting of N, O, and S(O)$_p$ and substituted with 0–2 R$^{4b}$, provided that R$^{1b}$ forms other than an O—O, N-halo, N—S, or N—CN bond;

A is selected from one of the following carbocyclic and heterocyclic groups which are substituted with 0–2 $R^4$; phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

$B^1$ is selected from H, $CH_3$, $CH_2CH_3$, $CH_2CH_2CH_3$, $CH(CH_3)_2$, $—(CH_2)_{0-1}—C_{5-6}$ carbocycle substituted with 0–2 $R^{4b}$, and $—(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, $—(CH_2)_{0-1}$-3–6 membered carbocycle substituted with 0–1 $R^5$, and a $—(CH_2)_{0-1}$-5–6 membered heterocycle consisting of: carbon atoms and 1–4 heteroatoms selected from the group consisting of N, O, and $S(O)_p$ and substituted with 0–1 $R^5$;

alternatively, $NB^2B^3$ is a 4–7 membered heterocycle consisting of: the shown N, carbon atoms, and 0–3 additional heteroatoms selected from the group consisting of N, O, and $S(O)_p$ and substituted with 0–1 $R^5$;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $—(CR^3R^{3a})—C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and $—(CR^3R^{3a})$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—S $(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $—(CR^3R^{3a})—C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and $—(CR^3R^{3a})$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^4$, at each occurrence, is selected from H, $(CH_2)_2OR^2$, $CH_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2—C(O)R^3$, $C(O)OR^{3c}$, $CH_2—C(O)OR^{3c}$, $NR^3C(O)R^{3a}$, $CH_2NR^3C(O)R^{3a}$, $C(O)NR^3R^{3a}$, $CH_2—C(O)NR^3R^{3a}$, $SO_2NR^3R^{3a}$, $CH_2SO_2NR^3R^{3a}$, $NR^3SO_2—C_{1-4}$ alkyl, $CH_2NR^3SO_2—C_{1-4}$ alkyl, $NR^3SO_2$-phenyl, $CH_2NR^3SO_2$-phenyl, $S(O)_pCF_3$, $CH_2S(O)_pCF_3$, $S(O)_p—C_{1-4}$ alkyl, $CH_2S(O)_p—C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})F$, Br, $(CR^3R^{3a})Br$, Cl, $(CR^3R^{3a})Cl$, $CF_3$, $(CR^3R^{3a})CF_3$, $C_{1-4}$ alkyl, —CN, $(CR^3R^{3a})CN$, $NO_2$, $(CR^3R^{3a})NO_2$, $NR^2R^{2a}$, $(CR^3R^{3a})NR^2R^{2a}$, $N(→O)R^2R^{2a}$, $(CR^3R^{3a})N(→O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$-5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2—C_{1-4}$ alkyl, $NR^3SO_2CF_3$, $NR^3SO_2$-phenyl, $S(O)_pCF_3$, $S(O)_p—C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

[4] In another preferred embodiment, the present invention provides a novel compound, wherein:
ring M is substituted with 0–2 $R^{1a}$ and is selected from the group:
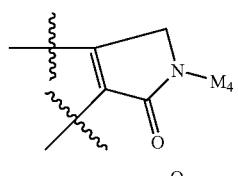 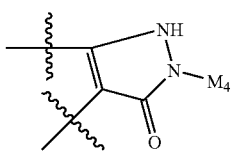
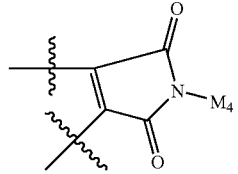 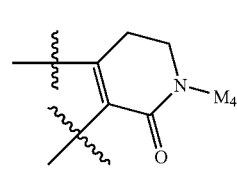
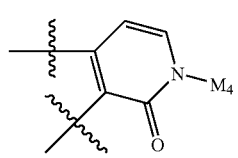 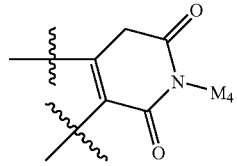
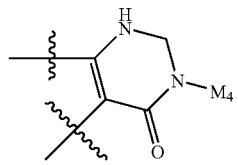 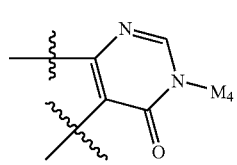
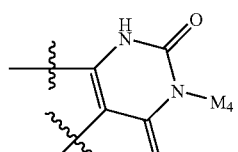 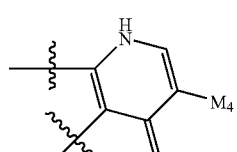
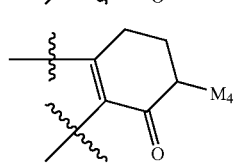 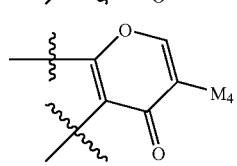
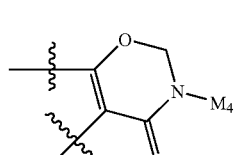 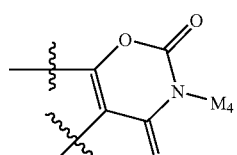
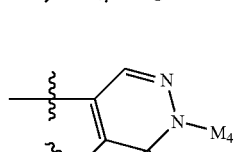 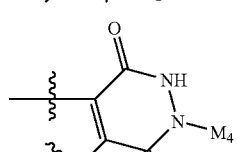
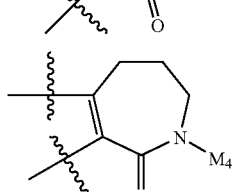 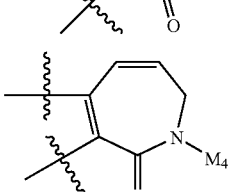
-continued
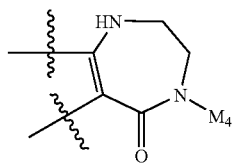 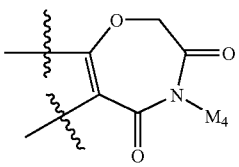
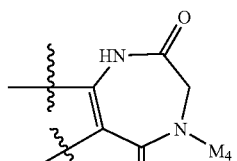 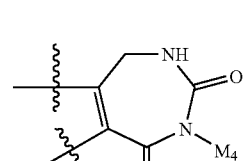
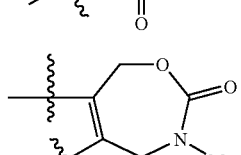 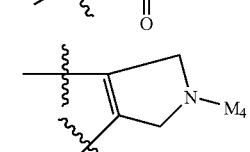
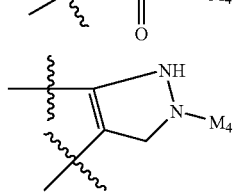 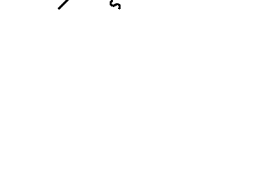
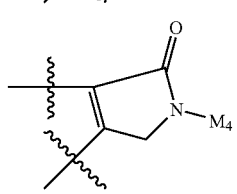 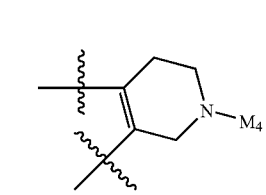
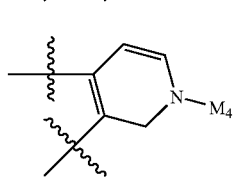 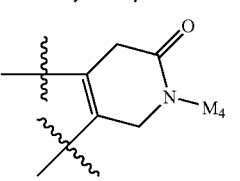
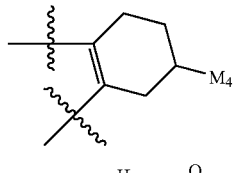 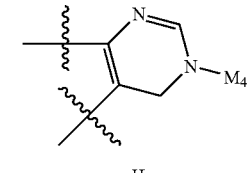
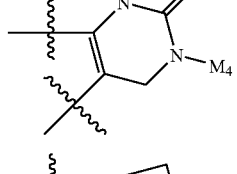 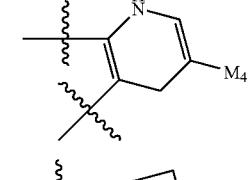
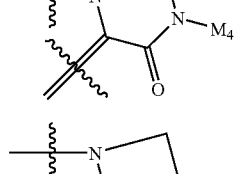 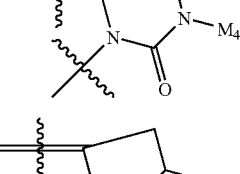
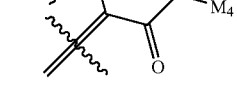 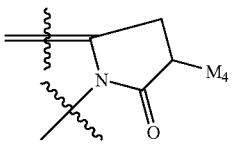

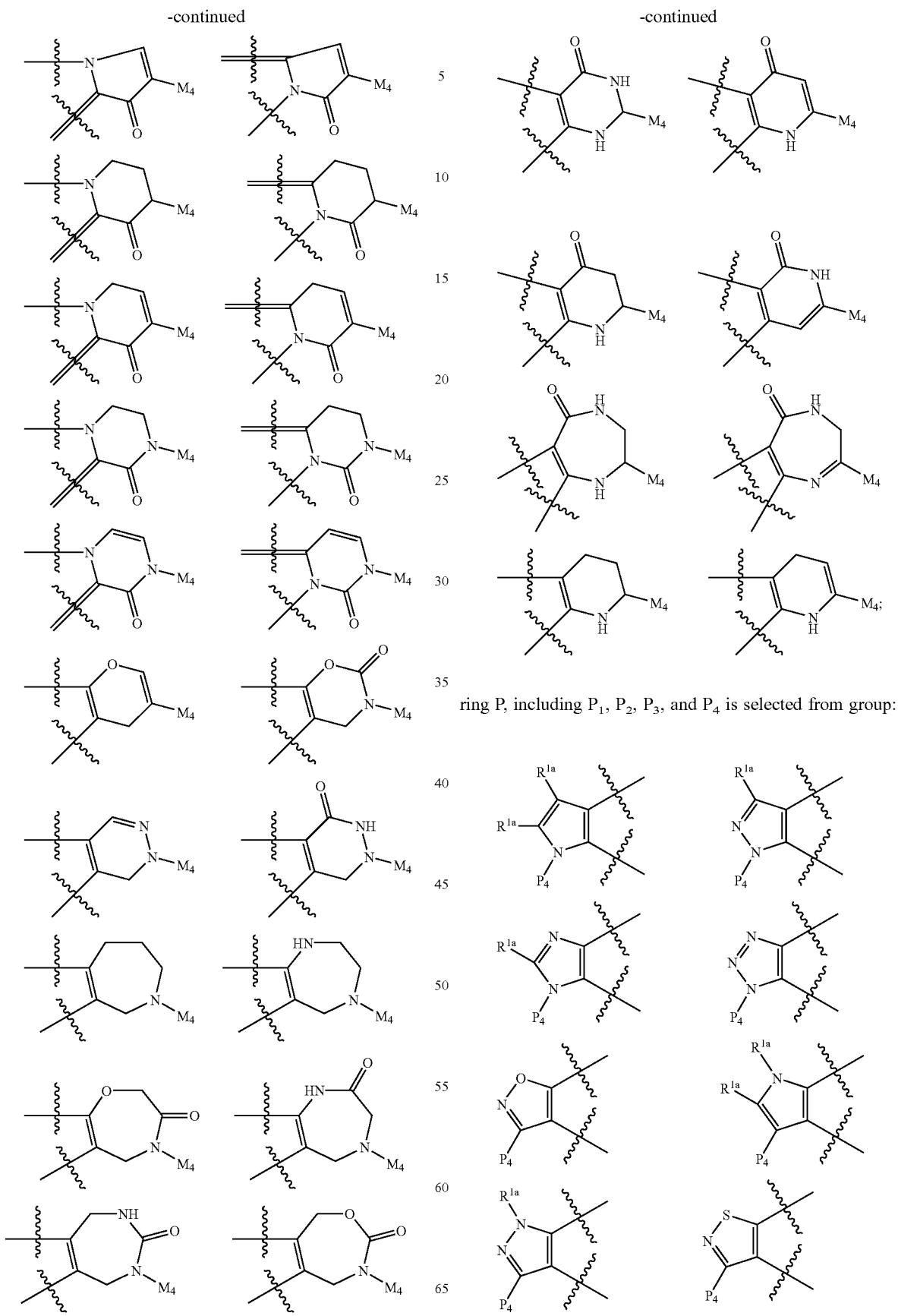
ring P, including $P_1$, $P_2$, $P_3$, and $P_4$ is selected from group:

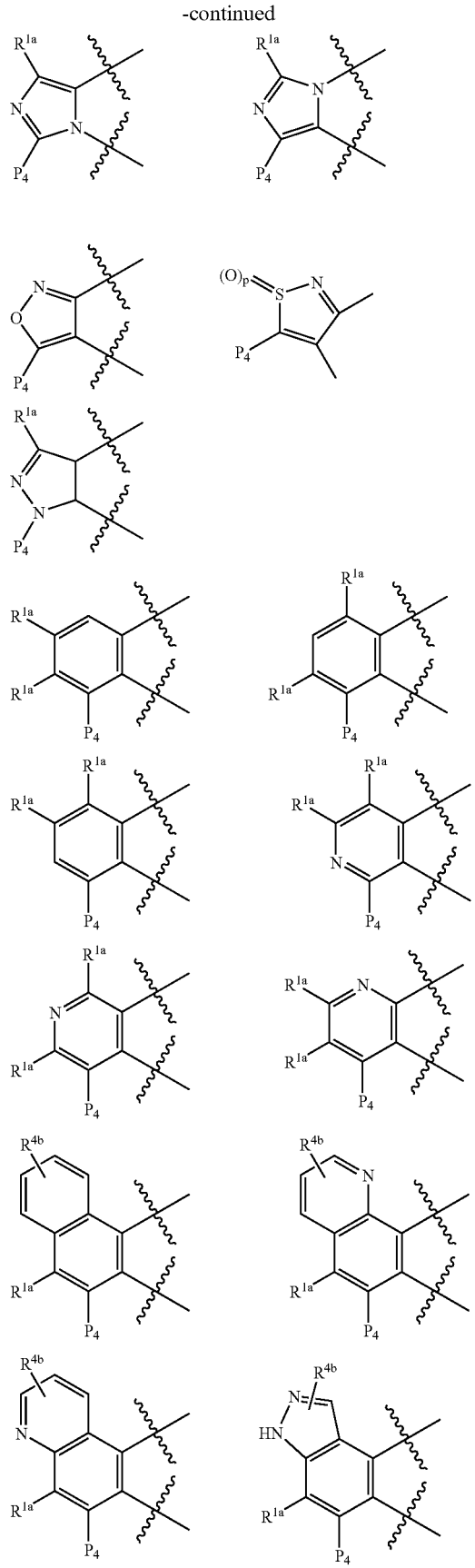
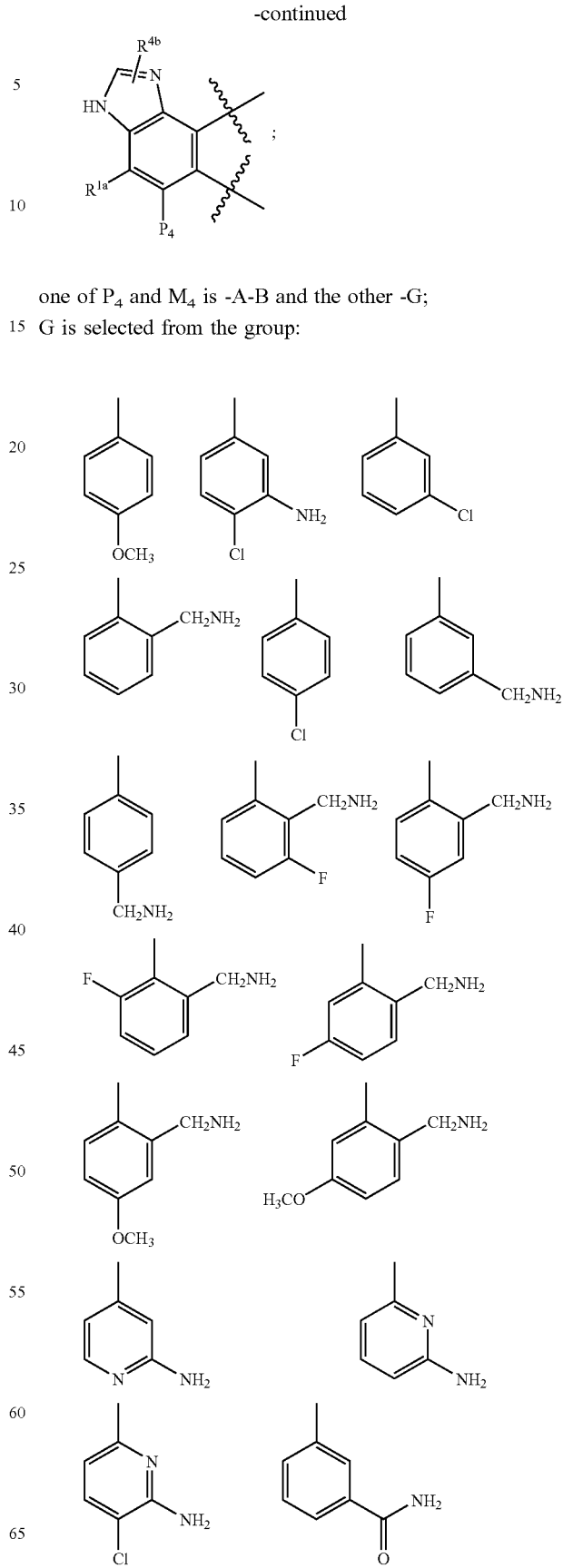
one of $P_4$ and $M_4$ is -A-B and the other -G;
G is selected from the group:

-continued
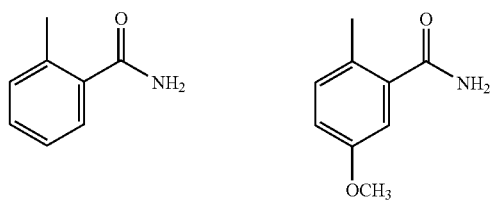
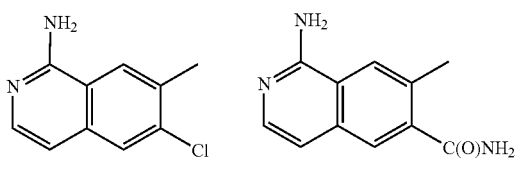
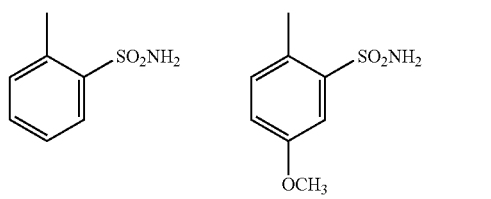
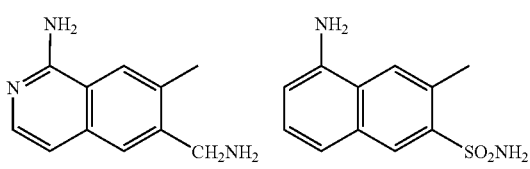
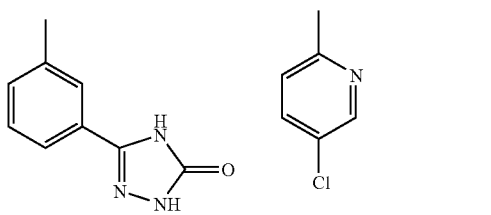
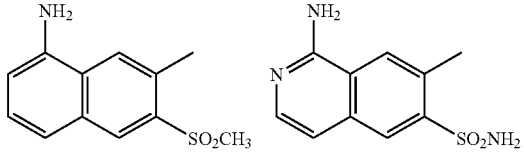
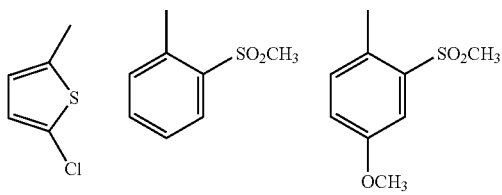
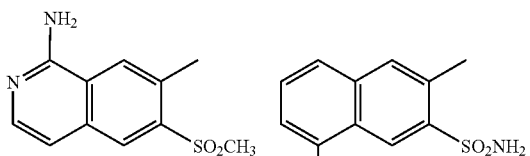
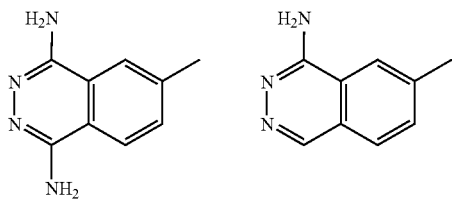
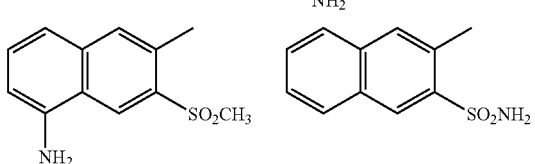
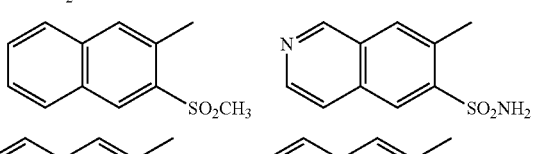
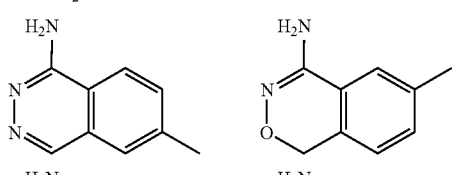
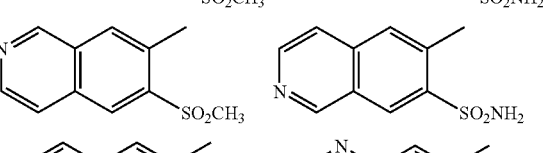
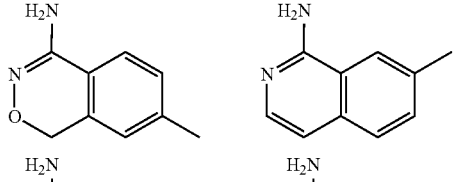
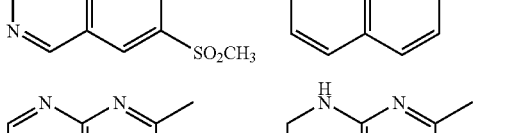
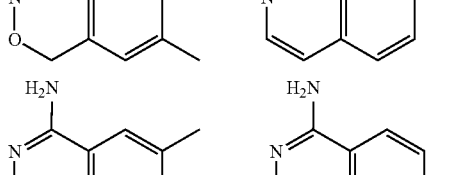
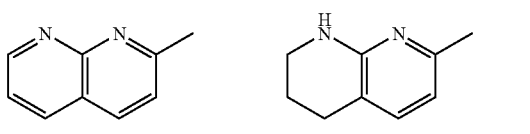
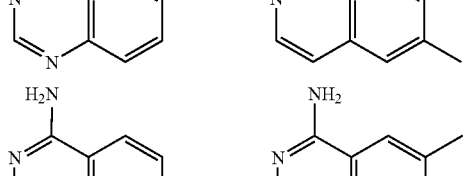
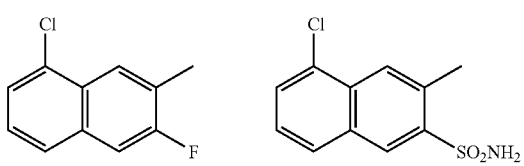

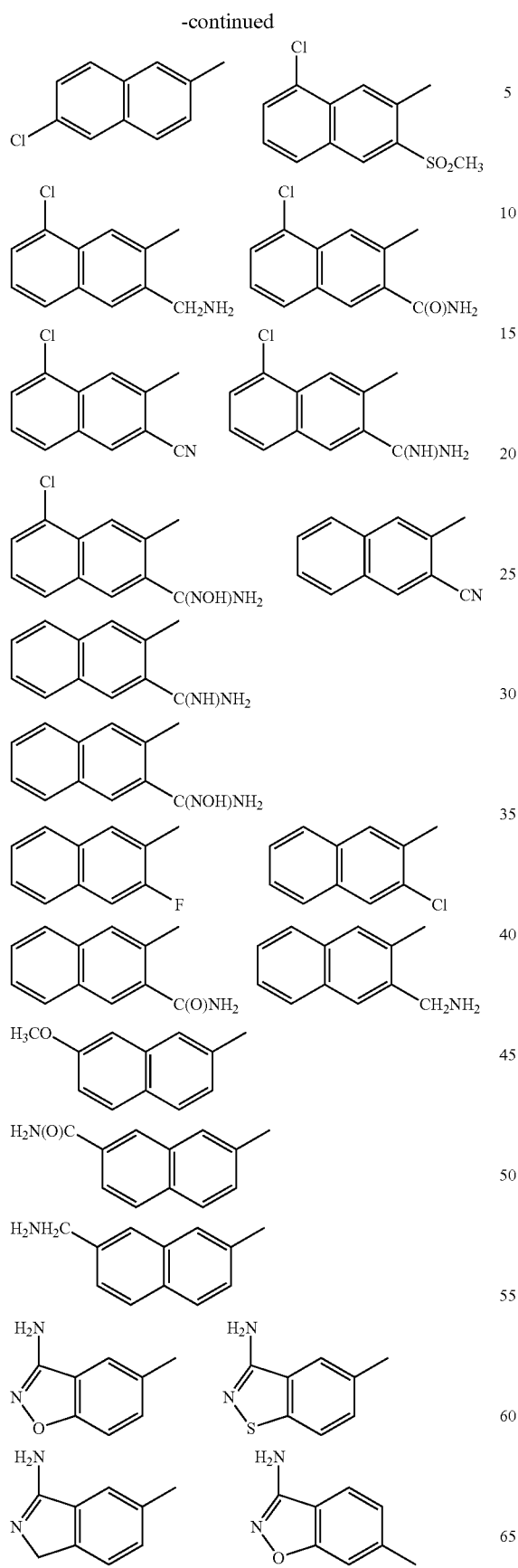
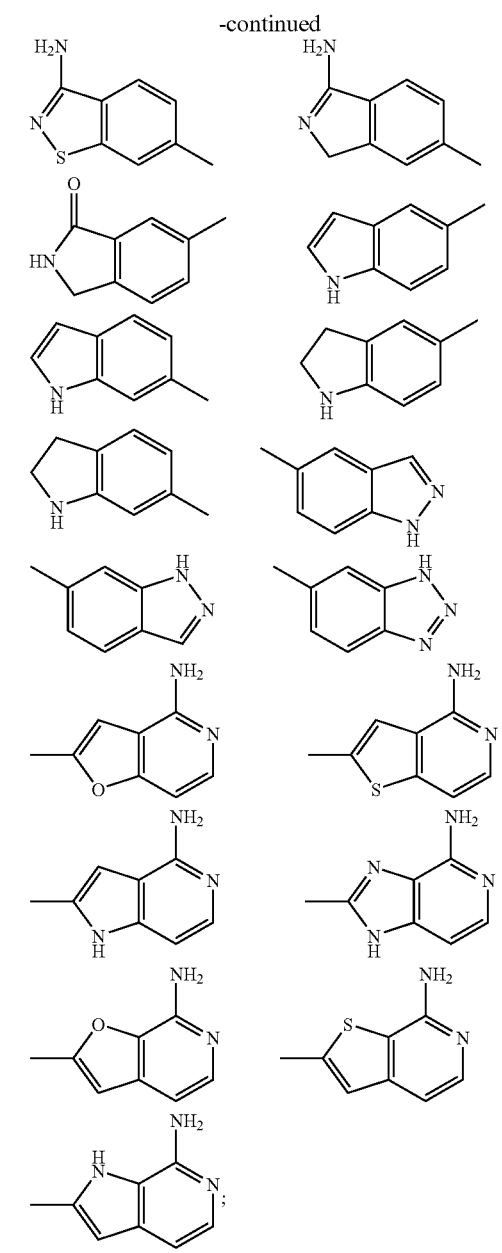

G$_1$ is absent or is selected from CH$_2$, CH$_2$CH$_2$, CH$_2$O, OCH$_2$, NH, CH$_2$NH, NHCH$_2$, CH$_2$C(O), C(O)CH$_2$, C(O)NH, NHC(O), CH$_2$S(O)$_2$, S(O)$_2$(CH$_2$), SO$_2$NH, and NHSO$_2$, provided that G$_1$ does not form a N—S, NCH$_2$N, NCH$_2$O, or NCH$_2$S bond with either group to which it is attached;

A is selected from phenyl, pyridyl, and pyrimidyl, and is substituted with 0–2 R$^4$;

B is N(B$^1$)C(O)C(R$^3$R$^{3a}$)NB$^2$B$^3$, provided that Z and B are attached to different atoms on A;

B$^1$ is selected from H, CH$_3$, CH$_2$CH$_3$, CH$_2$CH$_2$CH$_3$, and CH(CH$_3$)$_2$;

B$^2$ is selected from H, CH$_3$, CH$_2$CH$_3$, CH$_2$CH$_2$CH$_3$, and CH(CH$_3$)$_2$;

B$^3$ is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, C$_{2-5}$ alkyl substituted with 1 R$^{4c}$, —(CH$_2$)$_{0-1}$-3–6 membered carbocycle substituted with 0–1 R$^5$, and a —(CH$_2$)$_{0-1}$-5–6 membered heterocycle consisting of: carbon atoms and 1–4 heteroatoms selected from the group consisting of N, O, and S(O)$_p$ and substituted with 0–1 R$^5$;

alternatively, NB$^2$B$^3$ is a 5–6 membered heterocycle consisting of: the shown N, carbon atoms, and 0–2 additional heteroatoms selected from the group consisting of N, O, and S(O)$_p$ and substituted with 0–1 R$^5$;

R$^{1a}$ is selected from H, R$^{1b}$, C(CH$_3$)$_2$R$^{1b}$, and CH$_2$R$^{1b}$, provided that R$^{1a}$ forms other than an N-halo, N—S, or N—CN bond;

R$^{1b}$ is selected from CH$_3$, CH$_2$CH$_3$, F, Cl, Br, —CN, CF$_3$, OR$^2$, NR$^2$R$^{2a}$, C(O)R$^{2b}$, CO$_2$R$^{2b}$, CO$_2$R$^{2a}$, S(O)$_p$R$^2$, C(O)NR$^2$R$^{2a}$, SO$_2$NR$^2$R$^{2a}$, NR$^2$SO$_2$R$^2$, and 5–6 membered aromatic heterocycle consisting of carbon atoms and from 1–4 heteroatoms selected from the group consisting of N, O, and S(O)$_p$ and substituted with 0–2 R$^{4b}$, provided that R$^{1b}$ forms other than an O—O, N-halo, N—S, or N—CN bond;

R$^2$, at each occurrence, is selected from H, CH$_3$, CH$_2$CH$_3$, CH$_2$CH$_2$CH$_3$, CH(CH$_3$)$_2$, phenyl substituted with 0–1 R$^{4b}$, benzyl substituted with 0–1 R$^{4b}$, and 5–6 membered aromatic heterocycle consisting of: carbon atoms and 1–4 heteroatoms selected from the group consisting of N, O, and S(O)$_p$ and substituted with 0–1 R$^{4b}$;

R$^{2a}$, at each occurrence, is selected from H, CH$_3$, CH$_2$CH$_3$, CH$_2$CH$_2$CH$_3$, CH(CH$_3$)$_2$, benzyl, phenyl substituted with 0–1 R$^{4b}$, and 5–6 membered aromatic heterocycle consisting of: carbon atoms and 1–4 heteroatoms selected from the group consisting of N, O, and S(O)$_p$ and substituted with 0–1 R$^{4b}$;

alternatively, R$^2$ and R$^{2a}$, together with the atom to which they are attached, combine to form a 5 or 6 membered saturated, partially saturated or unsaturated ring substituted with 0–1 R$^{4b}$ and consisting of: 0–1 additional heteroatoms selected from the group consisting of N, O, and S(O)$_p$;

R$^{2b}$, at each occurrence, is selected from OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl, phenyl substituted with 0–1 R$^{4b}$, and 5–6 membered aromatic heterocycle consisting of: carbon atoms and 1–4 heteroatoms selected from the group consisting of N, O, and S(O)$_p$ and substituted with 0–1 R$^{4b}$;

R$^{2c}$, at each occurrence, is selected from OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl, phenyl substituted with 0–1 R$^{4b}$, and 5–6 membered aromatic heterocycle containing from 1–4 heteroatoms selected from the group consisting of N, O, and S(O)$_p$ and substituted with 0–1 R$^{4b}$;

R$^{2d}$, at each occurrence, is selected from H, R$^{4c}$, C$_{1-4}$ alkyl substituted with 0–2 R$^{4c}$, C$_{3-6}$ carbocycle substituted with 0–2 R$^{4c}$, —(CH$_2$)—C$_{3-6}$ carbocycle substituted with 0–2 R$^{4c}$, 5–6 membered heterocycle consisting of: carbon atoms and 1–4 heteroatoms selected from the group consisting of N, O, and S(O)$_p$ and substituted with 0–2 R$^{4c}$, and —(CH$_2$)-5–6 membered heterocycle consisting of: carbon atoms and 1–4 heteroatoms selected from the group consisting of N, O, and S(O)$_p$ and substituted with 0–2 R$^{4c}$, provided that R$^{2d}$ forms other than a N-halo, N—C-halo, S(O)$_p$-halo, O-halo, N—S, S—N, S(O)$_p$—S (O)$_p$, S—O, O—N, O—S, or O—O moiety;

R$^{2e}$, at each occurrence, is selected from H, R$^{4c}$, C$_{1-4}$ alkyl substituted with 0–2 R$^{4c}$, C$_{3-6}$ carbocycle substituted with 0–2 R$^{4c}$, —(CH$_2$)—C$_{3-6}$ carbocycle substituted with 0–2 R$^{4c}$, 5–6 membered heterocycle consisting of: carbon atoms and 1–4 heteroatoms selected from the group consisting of N, O, and S(O)$_p$ and substituted with 0–2 R$^{4c}$, and —(CH$_2$)-5–6 membered heterocycle consisting of: carbon atoms and 1–4 heteroatoms selected from the group consisting of N, O, and S(O)$_p$ and substituted with 0–2 R$^{4c}$, provided that R$^{2e}$ forms other than a C(O)-halo or C(O)—S(O)$_p$ moiety;

R$^4$, at each occurrence, is selected from OH, OR$^2$, CH$_2$OR$^2$, (CH$_2$)$_2$OR$^2$, F, Br, Cl, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^2$R$^{2a}$, CH$_2$NR$^2$R$^{2a}$, (CH$_2$)$_2$NR$^2$R$^{2a}$, CF$_3$, and CF$_2$CF$_3$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, and CF$_3$;

R$^{4c}$, at each occurrence, is selected from =O, OR$^2$, CH$_2$OR$^2$, F, Br, Cl, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$) CH$_2$CH$_3$, C(CH$_3$)$_3$, —CN, NO$_2$, NR$^2$R$^{2a}$, CH$_2$NR$^2$R$^{2a}$, N(→O)R$^2$R$^{2a}$, CH$_2$N(→O)R$^2$R$^{2a}$, C(O)R$^{2c}$, CH$_2$C(O) R$^{2c}$, NR$^2$C(O)R$^{2b}$, CH$_2$NR$^2$C(O)R$^{2b}$, C(O)NR$^2$R$^{2a}$, CH$_2$C(O)NR$^2$R$^{2a}$, SO$_2$NR$^2$R$^{2a}$, CH$_2$SO$_2$NR$^2$R$^{2a}$, NR$^2$SO$_2$R$^{5a}$, CH$_2$NR$^2$SO$_2$R$^{5a}$, S(O)$_p$R$^{5a}$, CH$_2$S(O)$_p$R$^{5a}$, CF$_3$, CF$_2$CF$_3$, C$_{3-6}$ carbocycle substituted with 0–2 R$^{4b}$, (CH$_2$)C$_{3-6}$ carbocycle substituted with 0–2 R$^{4b}$, 5–6 membered heterocycle consisting of carbon atoms and from 1–4 heteroatoms selected from the group consisting of N, O, and S(O)$_p$ and substituted with 0–2 R$^{4b}$, and (CH$_2$)-5–6 membered heterocycle consisting of carbon atoms and from 1–4 heteroatoms selected from the group consisting of N, O, and S(O)$_p$ and substituted with 0–2 R$^{4b}$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl, NR$^3$SO$_2$-phenyl, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and, R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O) R$^{2b}$, and SO$_2$NR$^2$R$^{2a}$.

[5] In another preferred embodiment, the present invention provides a novel compound, wherein:

ring M is substituted with 0–1 R$^{1a}$ and is selected from the group:

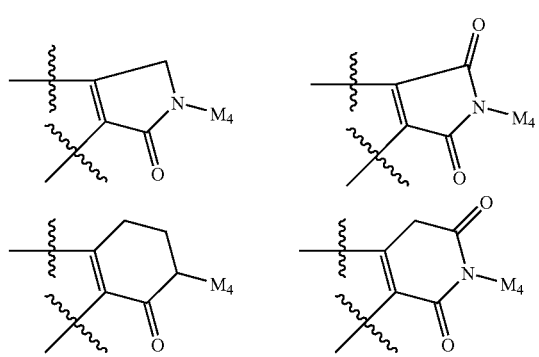

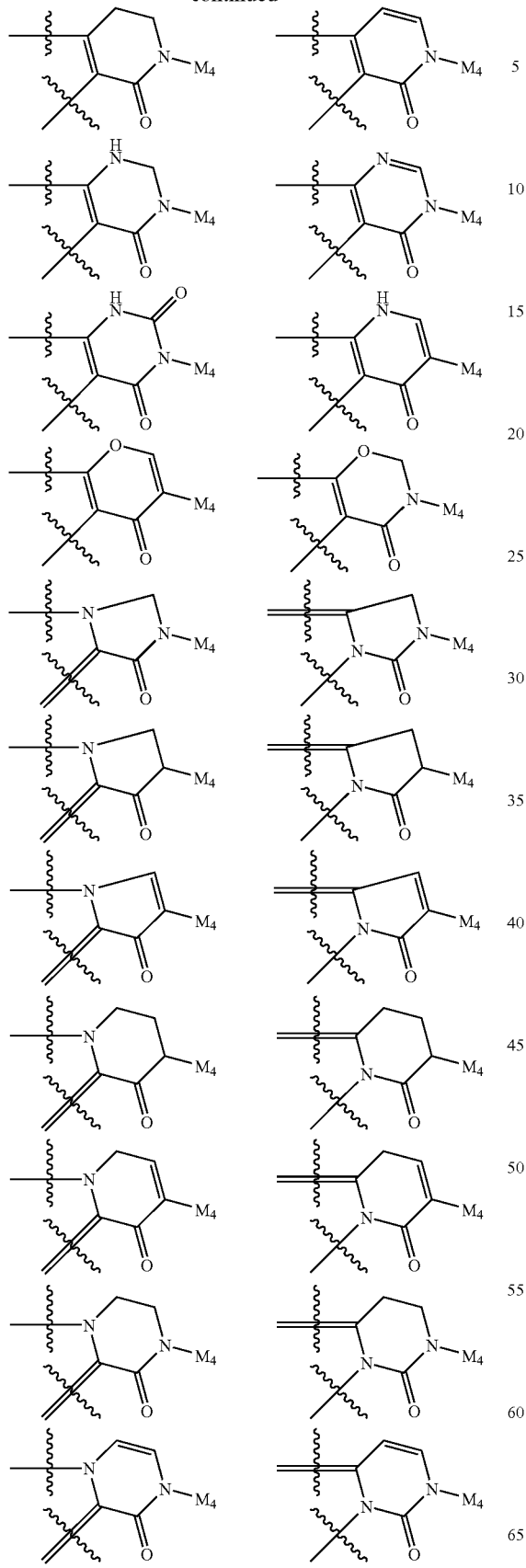
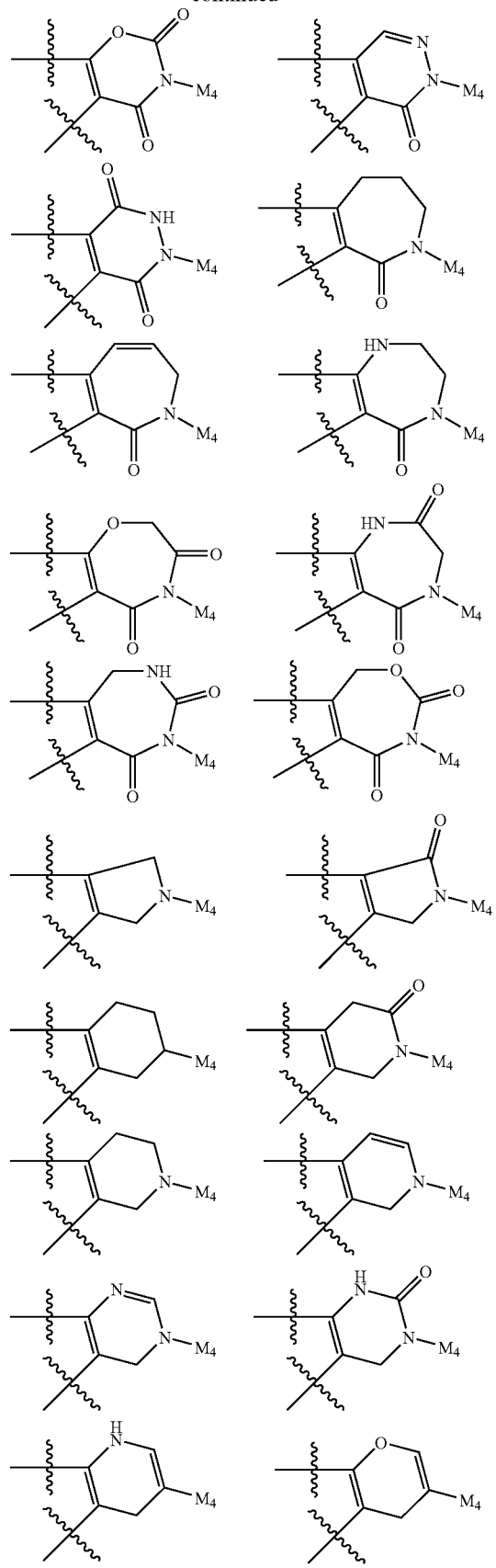

-continued
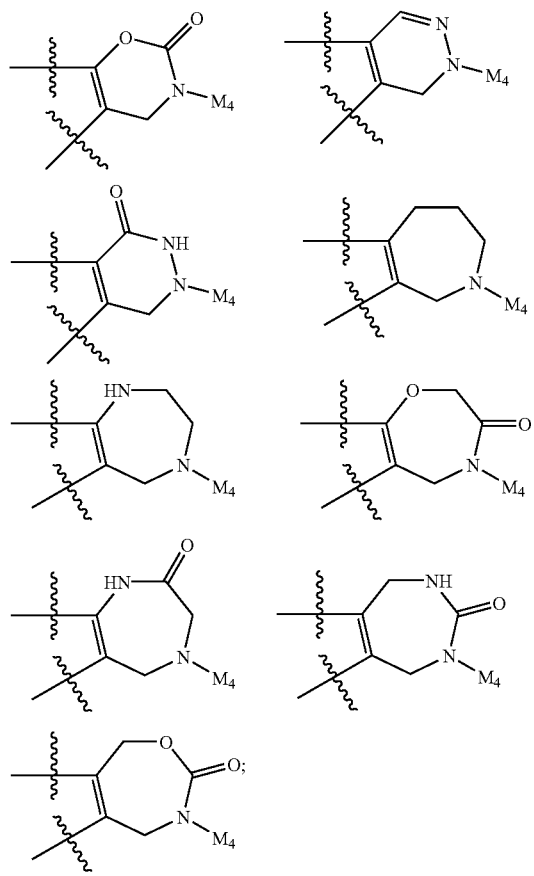
ring P, including $P_1$, $P_2$, $P_3$, and $P_4$ is selected from group:
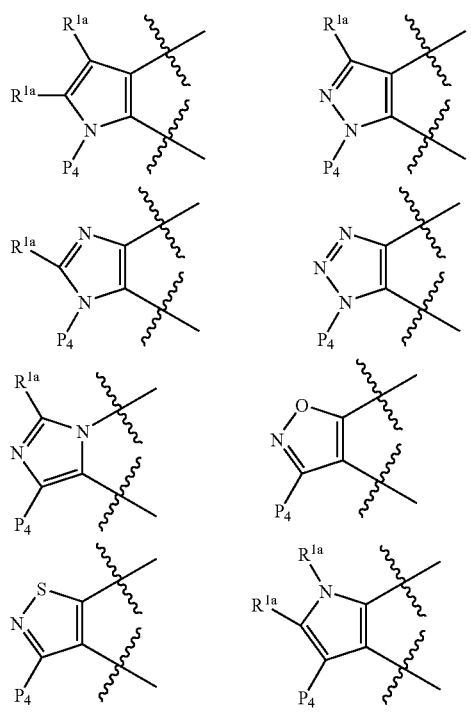
-continued
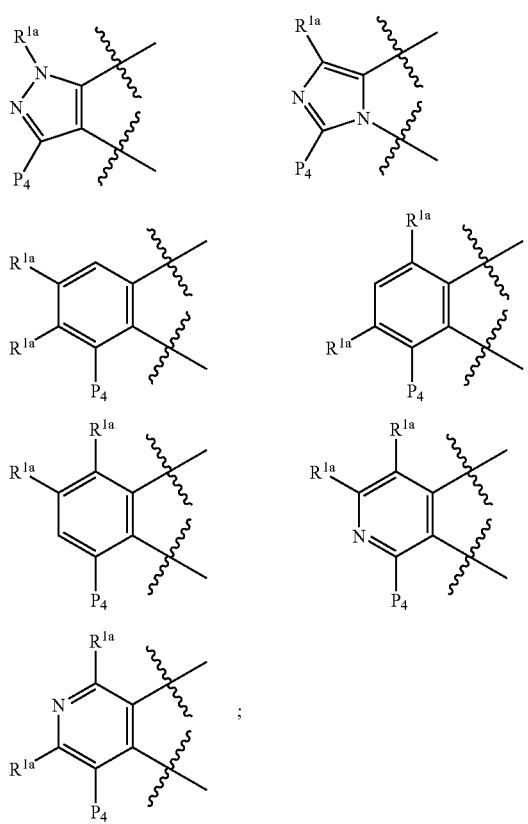
one of $P_4$ and $M_4$ is -A-B and the other -G;
G is selected from:
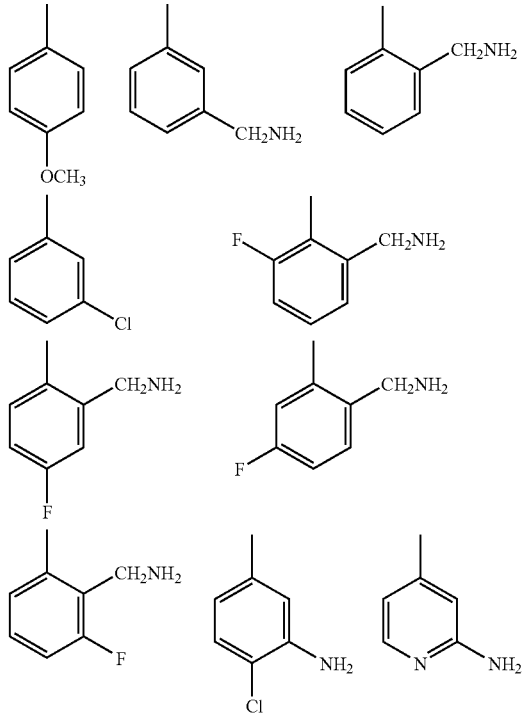

-continued
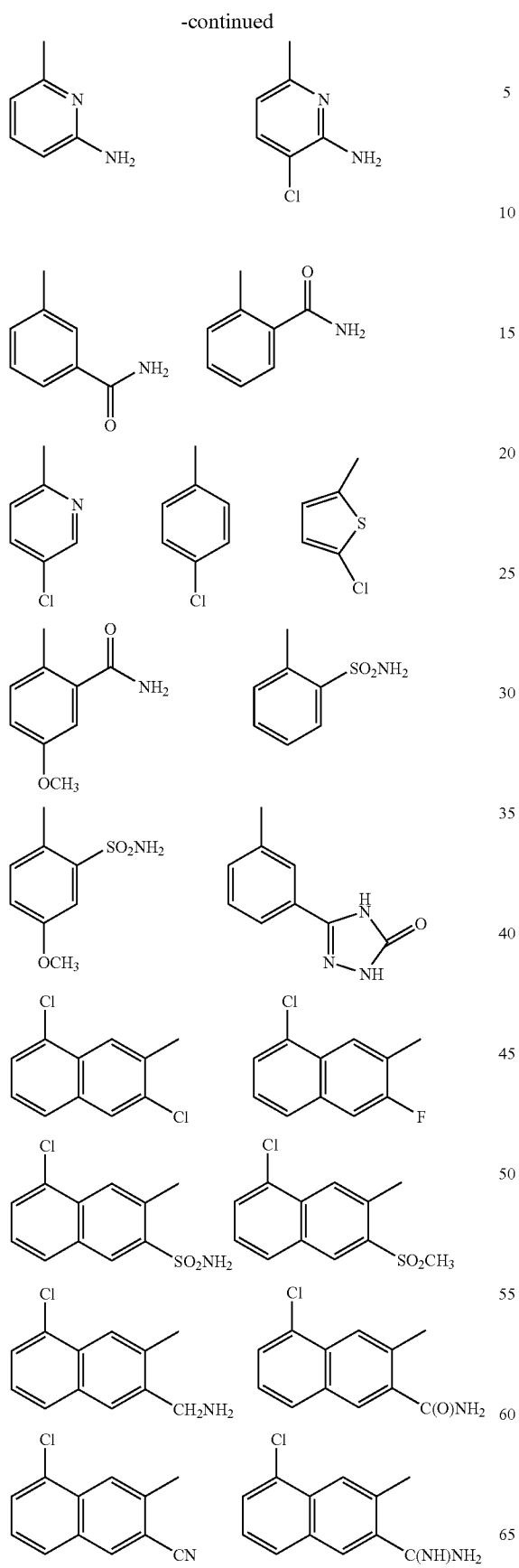
-continued
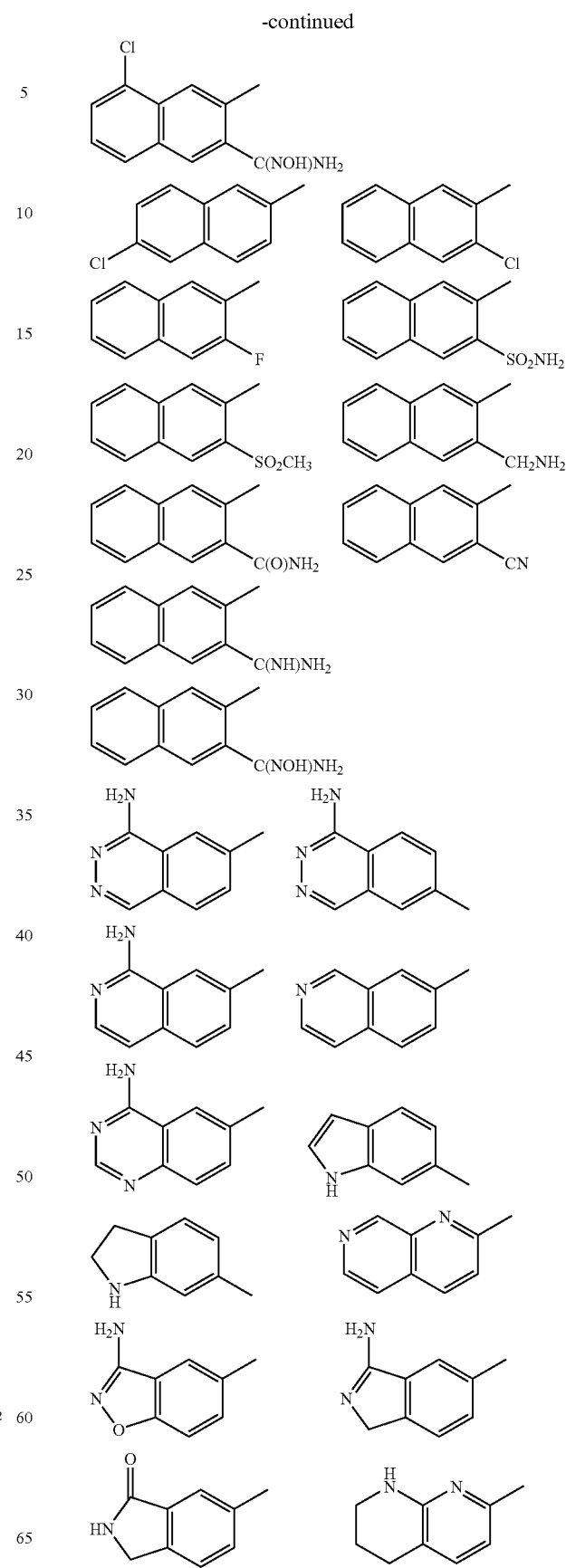

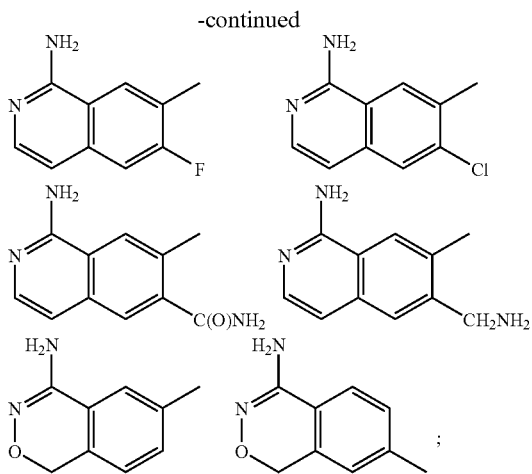

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

$B^1$ is selected from H, $CH_3$, $CH_2CH_3$, and $CH_2CH_2CH_3$;

$B^2$ is selected from H, $CH_3$, and $CH_2CH_3$;

$B^3$ is selected from $CH_3$, $CH_2CH_3$, $CH_2CH_2CH_3$, $CH(CH_3)_2$, $CH_2CH_2CH_2CH_3$, $C(CH_3)_3$, $CH(CH_3)CH_2CH(CH_3)_2$, $CH_2CH_2OH$, $CH(CH_3)CH_2OH$, $CH(phenyl)CH_2CH_3$, cyclopropyl, cyclobutyl, cyclopentyl, and $CH_2$-cyclopropyl;

alternatively, $NB^2B^3$ is a ring selected from pyrrolidinyl, piperidinyl, and morpholinyl;

$R^{1a}$ is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from OH, $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(→O)R^2R^{2a}$, $CH_2N(→O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, cyclopropyl substituted with 0–1 $R^{4b}$, cyclobutyl substituted with 0–1 $R^{4b}$, cyclopentyl substituted with 0–1 $R^{4b}$, phenyl substituted with 0–1 $R^{4b}$, —$CH_2$-cyclopropyl substituted with 0–1 $R^{4b}$, —$CH_2$-cyclobutyl substituted with 0–1 $R^{4b}$, —$CH_2$-cyclopentyl substituted with 0–1 $R^{4b}$, benzyl substituted with 0–2 $R^{4b}$, 5–6 membered aromatic heterocycle consisting of carbon atoms and from 1–4 heteroatoms selected from the group consisting of N, O, and $S(O)_p$ and substituted with 0–2 $R^{4b}$, and $(CH_2)$-5–6 membered aromatic heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[6] In another preferred embodiment, the present invention provides a novel compound, wherein the compound is selected from:

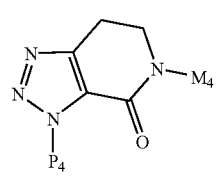 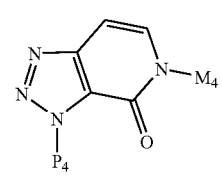

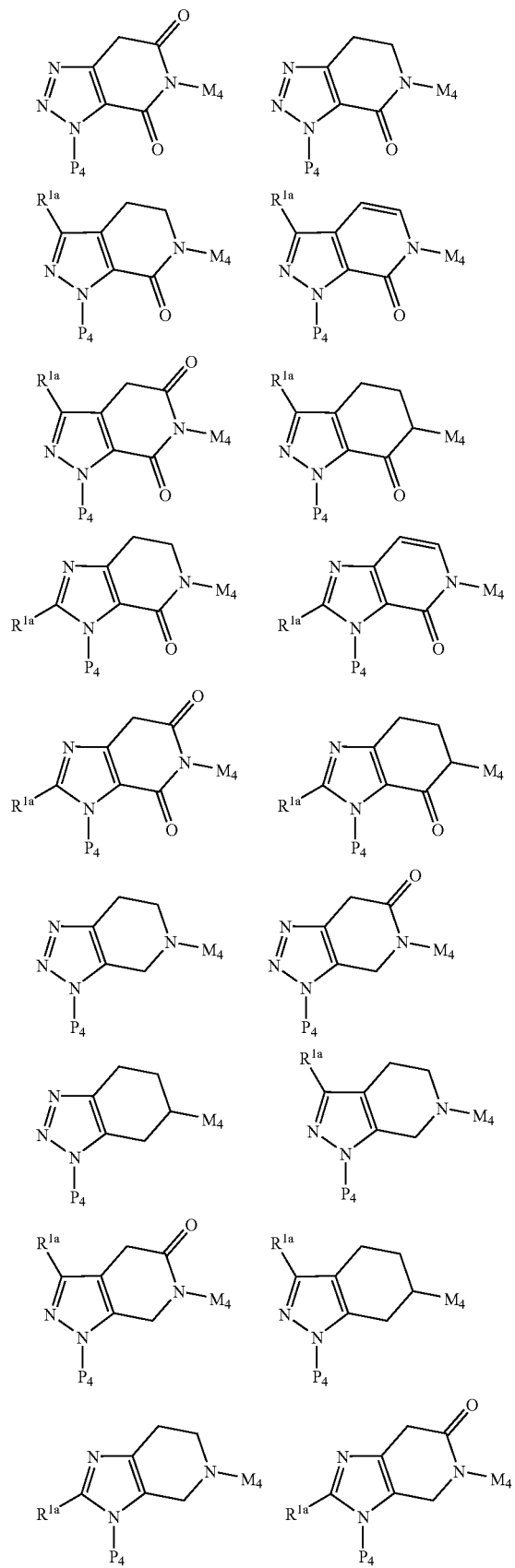
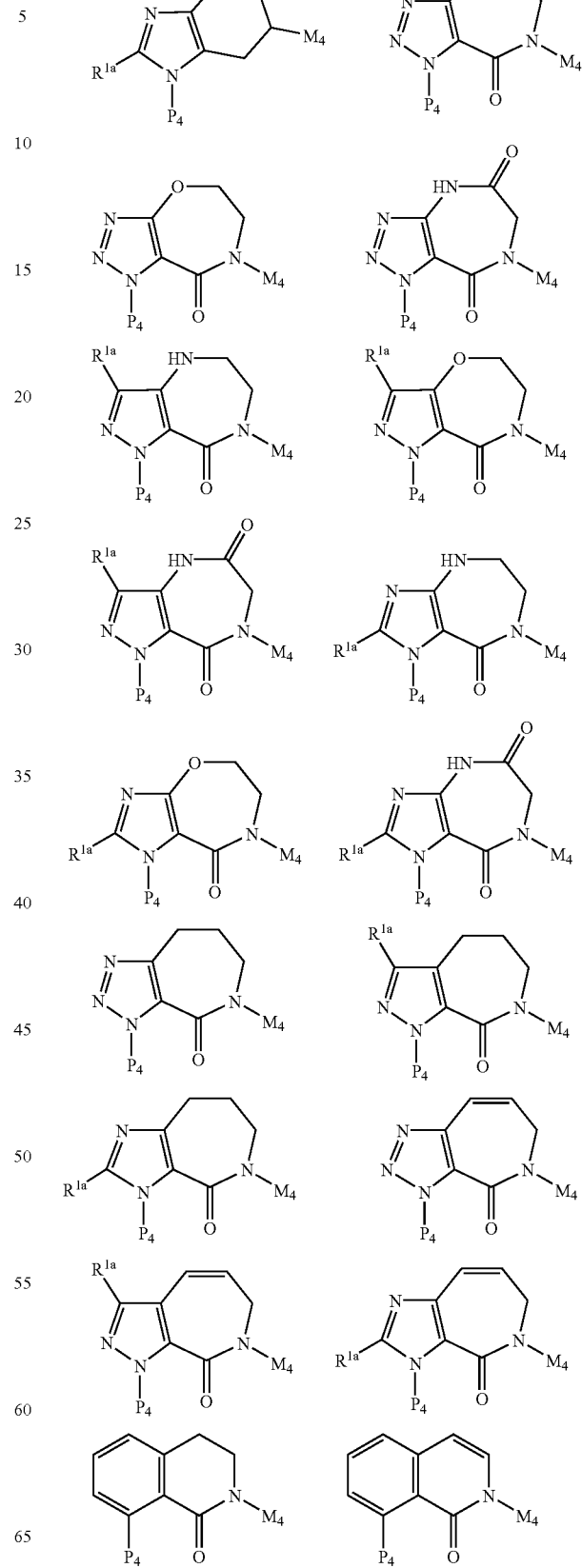

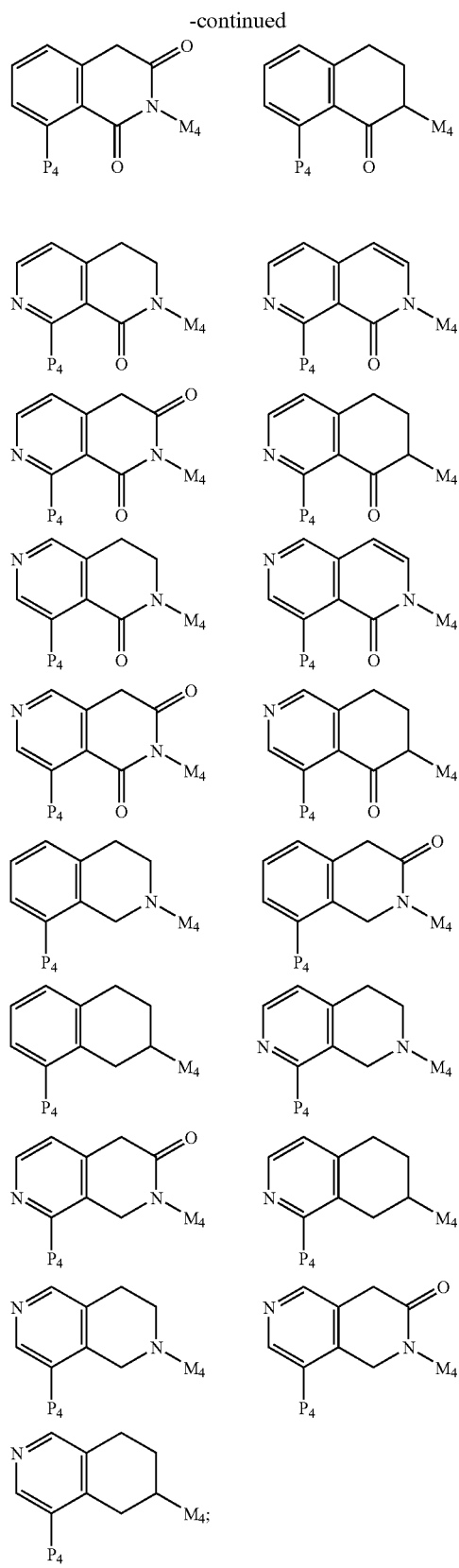
P4 is -G;
M4 is —A—B;
M4 is -A-B;
G is selected from:
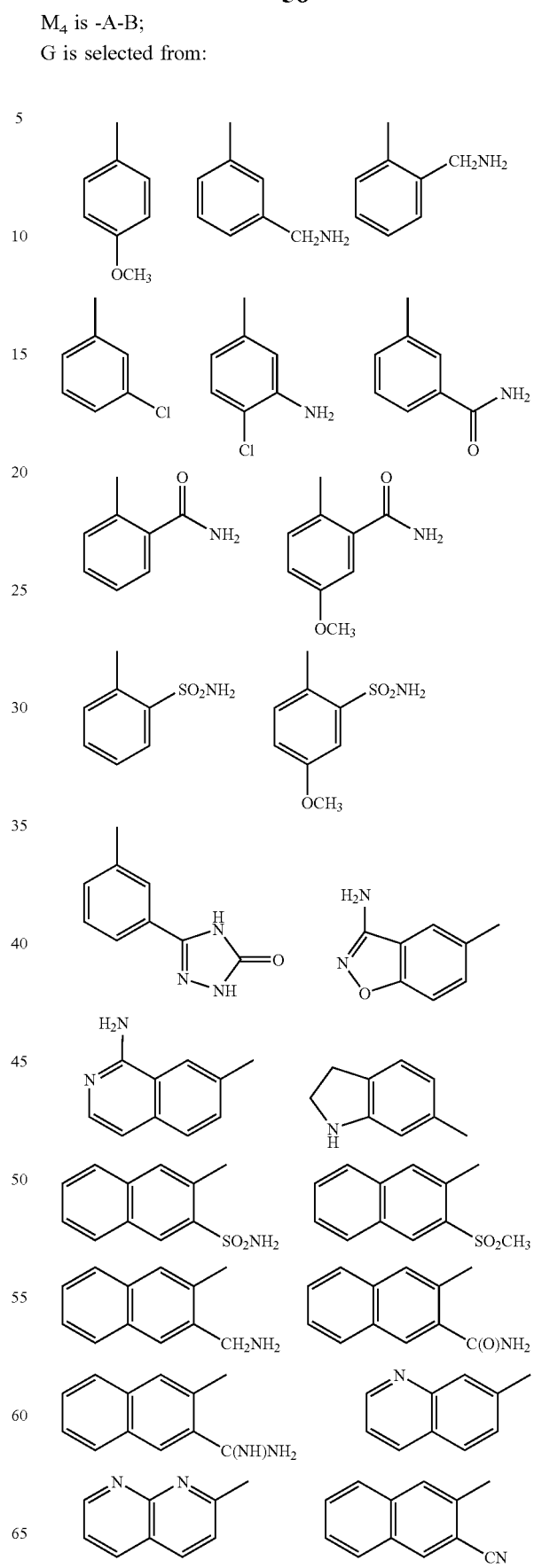

-continued
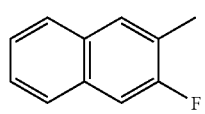
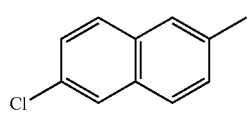
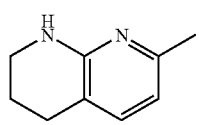
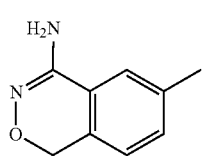
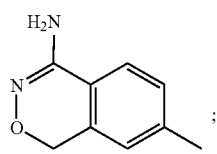
A-B is selected from:
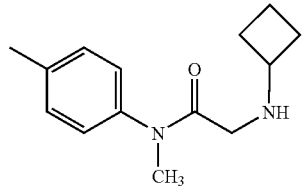
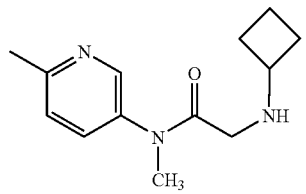
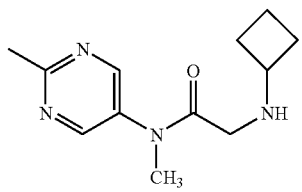
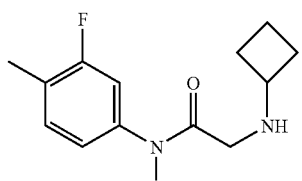
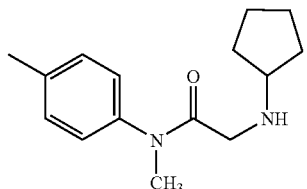
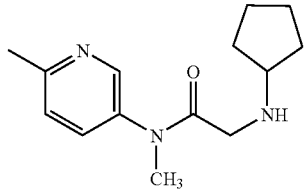
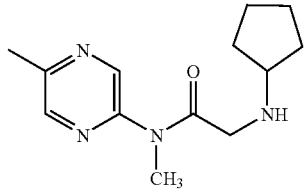
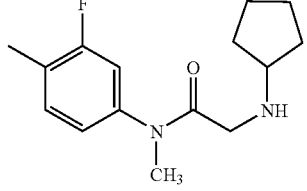

-continued
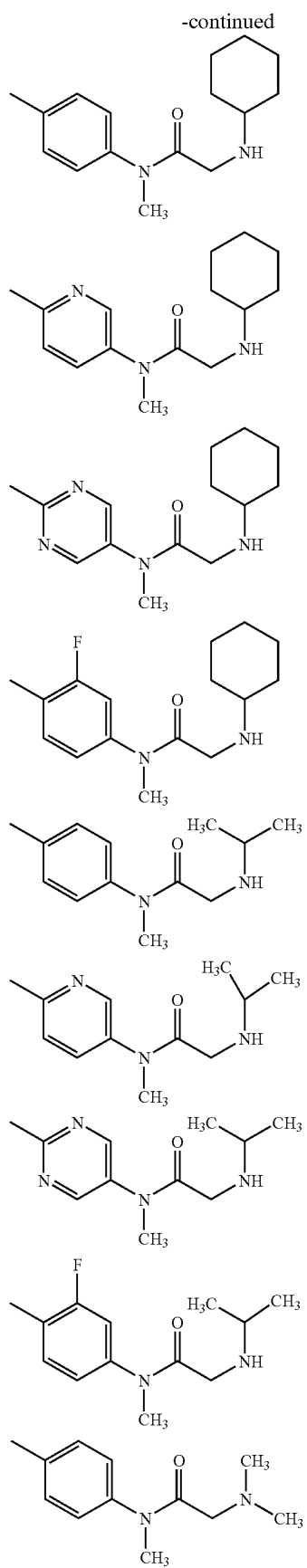
-continued
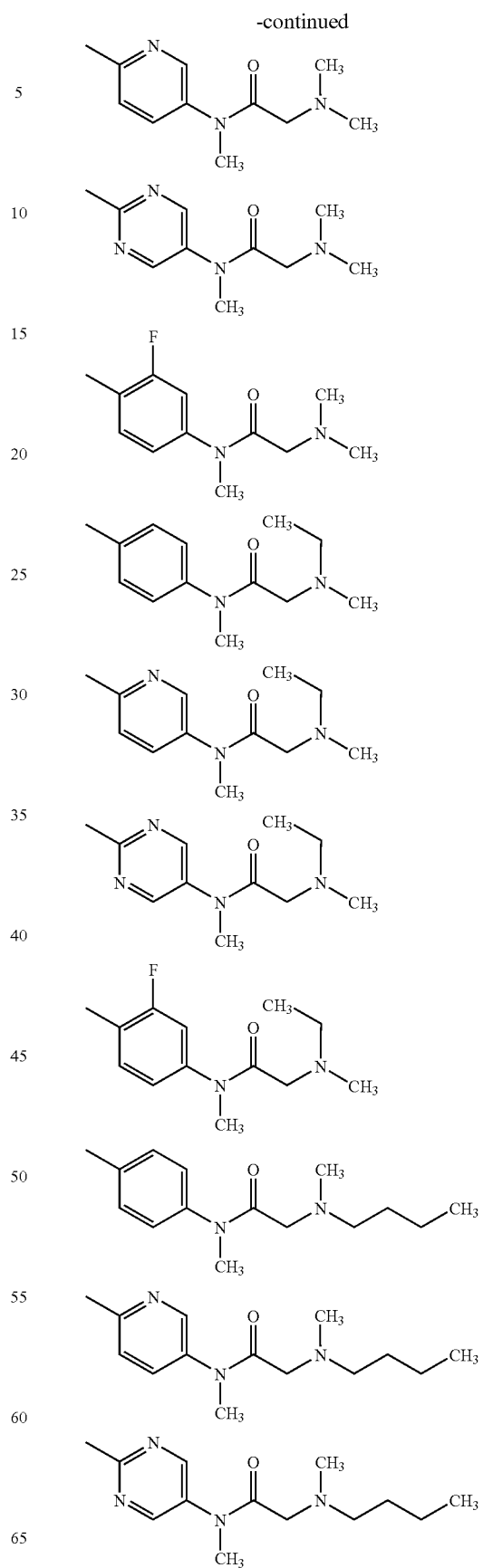

-continued

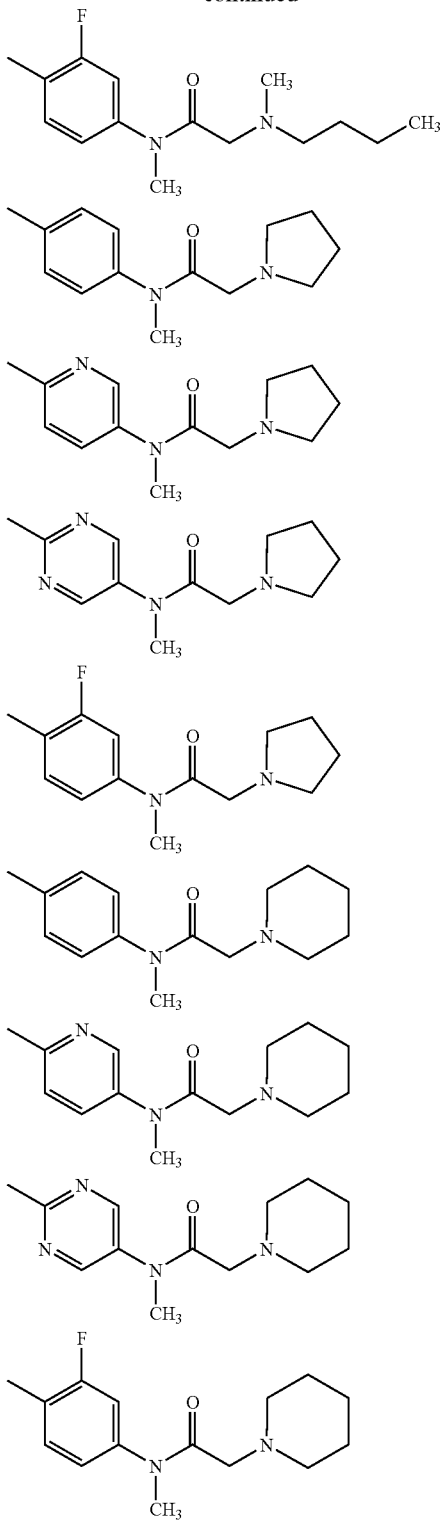

$R^{2d}$, at each occurrence, is selected from H, $R^{4c}$, $C_{1-4}$ alkyl substituted with 0–1 $R^{4c}$, cyclopropyl, cyclobutyl, cyclopentyl, cyclohexyl, phenyl, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—S$(O)_p$, S—O, O—N, O—S, or O—O moiety;

$R^{2e}$, at each occurrence, is selected from H, $R^{4c}$, $C_{1-4}$ alkyl substituted with 0–1 $R^{4c}$, cyclopropyl, cyclobutyl, cyclopentyl, cyclohexyl, phenyl, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety.

[7] In another preferred embodiment, the present invention provides a novel compound, wherein the compound is of the formula:

$P_4$ is -G; and

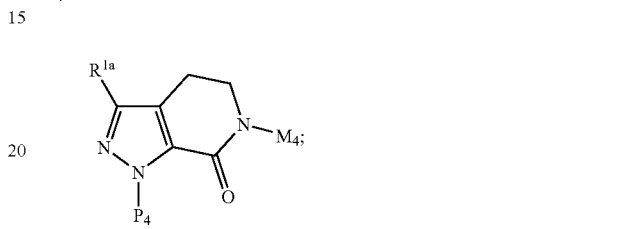

$M_4$ is -A-B.

[8] In another preferred embodiment, the present invention provides a novel compound, wherein the compound is selected from the group:

3-[6-{4-[(N,N-dimethylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[(N-ethyl-N-methylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[methyl(N-methylglycyl)amino]phenyl}-7-oxo-3-(trifluoromethyl)-4,5,6,7-tetrahydro-1H-pyrazolo[3,4-c]pyridin-1-yl]benzamide;

3-[6-{4-[(N-ethyl-N-propylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[(N-isopropylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[(N-butyl-N-methylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[[N-(2-hydroxyethyl)glycyl](methyl)amino]phenyl}-7-oxo-3-(trifluoromethyl)-4,5,6,7-tetrahydro-1H-pyrazolo[3,4-c]pyridin-1-yl]benzamide;

$N^1$-{4-[3-methoxy-1-(4-methoxyphenyl)-7-oxo-1,4,5,7-tetrahydro-6H-pyrazolo[3,4-c]pyridin-6-yl]phenyl}-$N^1$,$N^2$,$N^2$-trimethylglycinamide;

$N^2$-ethyl-$N^1$-{4-[3-methoxy-1-(4-methoxyphenyl)-7-oxo-1,4,5,7-tetrahydro-6H-pyrazolo[3,4-c]pyridin-6-yl]phenyl}-$N^1$,$N^2$-dimethylglycinamide;

$N^2$-isopropyl-$N^1$-{4-[3-methoxy-1-(4-methoxyphenyl)-7-oxo-1,4,5,7-tetrahydro-6H-pyrazolo[3,4-c]pyridin-6-yl]phenyl}-$N^1$-methylglycinamide;

$N^2$-butyl-$N^1$-{4-[3-methoxy-1-(4-methoxyphenyl)-7-oxo-1,4,5,7-tetrahydro-6H-pyrazolo[3,4-c]pyridin-6-yl]phenyl}-$N^1$,$N^2$-dimethylglycinamide;

$N^1$-{4-[1-(4-methoxyphenyl)-7-oxo-3-(trifluoromethyl)-1,4,5,7-tetrahydro-6H-pyrazolo[3,4-c]pyridin-6-yl]phenyl}-$N^1$,$N^2$,$N^2$-trimethylglycinamide;

N²-(tert-butyl)-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide;

N²-cyclobutyl-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide;

N²-(cyclopropylmethyl)-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide;

N²-cyclopentyl-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide;

N²-((R)-2-hydroxyl-1-methylethyl)-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide;

6-{4-[(N,N-dimethylglycyl)(methyl)amino]phenyl}-1-(4-methoxyphenyl)-7-oxo-4,5,6,7-tetrahydro-1H-pyrazolo[3,4-c]pyridine-3-carboxamide;

N¹-{4-[1-(4-methoxyphenyl)-3-(methylsulfonyl)-7-oxo-1,4,5,7-tetrahydro-6H-pyrazolo[3,4-c]pyridin-6-yl]phenyl}-N¹,N²,N²-trimethylgycinamide;

N¹-{4-[1-(4-methoxyphenyl)-3-(methylsulfonyl)-7-oxo-1,4,5,7-tetrahydro-6H-pyrazolo[3,4-c]pyridin-6-yl]phenyl}-N¹,N²-dimethylgycinamide;

3-[6-[4-(ethyl{N-[(1S)-1-phenylpropyl]glycyl}amino)phenyl]-7-oxo-3-(trifluoromethyl)-4,5,6,7-tetrahydro-1H-pyrazolo[3,4-c]pyridin-1-yl]benzamide;

3-[6-{4-[[N-(1,3-dimethylbutyl)glycyl](ethyl)amino]phenyl}-7-oxo-3-(trifluoromethyl)-4,5,6,7-tetrahydro-1H-pyrazolo[3,4-c]pyridin-1-yl]benzamide;

2-Dimethylamino-N-{4-[1-(4-methoxy-phenyl)-3-(4-methyl-oxazol-2-yl)-7-oxo-1,4,5,7-tetrahydro-pyrazolo[3,4-c]pyridin-6-yl]-phenyl}-N-methyl-acetamide;

6-[4-(2-hydroxy-2-methyl-propionylamino)-phenyl]-1-(4-methoxy-phenyl)-7-oxo-4,5,6,7-tetrahydro-1H-pyrazolo[3,4-c]pyridine-3-carboxylic acid amide;

3-[6-{4-[[(3-hydroxy-1-pyrrolidinyl)acetyl](methyl)amino]phenyl}-7-oxo-3-(trifluoromethyl)-4,5,6,7-tetrahydro-1H-pyrazolo[3,4-c]pyridin-1-yl]benzamide;

3-[6-{4-[methyl(1-pyrrolidinylacetyl)amino]phenyl}-7-oxo-3-(trifluoromethyl)-4,5,6,7-tetrahydro-1H-pyrazolo[3,4-c]pyridin-1-yl]benzamide;

3-[6-{4-[[(4-hydroxy-1-piperidinyl)acetyl](methyl)amino]phenyl}-7-oxo-3-(trifluoromethyl)-4,5,6,7-tetrahydro-1H-pyrazolo[3,4-c]pyridin-1-yl]benzamide;

3-[7-oxo-6-{4-[propyl(1-pyrrolidinylacetyl)amino]phenyl}-3-(trifluoromethyl)-4,5,6,7-tetrahydro-1H-pyrazolo[3,4-c]pyridin-1-yl]benzamide;

3-[6-{4-[ethyl(1-pyrrolidinylacetyl)amino]phenyl}-7-oxo-3-(trifluoromethyl)-4,5,6,7-tetrahydro-1H-pyrazolo[3,4-c]pyridin-1-yl]benzamide;

N-{4-[3-methoxy-1-(4-methoxyphenyl)-7-oxo-1,4,5,7-tetrahydro-6H-pyrazolo[3,4-c]pyridin-6-yl]phenyl}-N-methyl-2-(1-pyrrolidinyl)acetamide;

2-(3-hydroxy-1-pyrrolidinyl)-N-{4-[3-methoxy-1-(4-methoxyphenyl)-7-oxo-1,4,5,7-tetrahydro-6H-pyrazolo[3,4-c]pyridin-6-yl]phenyl}-N-methylacetamide;

N-{4-[1-(4-methoxyphenyl)-7-oxo-3-(trifluoromethyl)-1,4,5,7-tetrahydro-6H-pyrazolo[3,4-c]pyridin-6-yl]phenyl}-N-methyl-2-(1-pyrrolidinyl)acetamide;

1-(4-methoxyphenyl)-6-{4-[methyl(1-pyrrolidinylacetyl)amino]phenyl}-7-oxo-4,5,6,7-tetrahydro-1H-pyrazolo[3,4-c]pyridine-3-carboxamide;

N¹-{4-[1-(4-methoxyphenyl)-3-(methylsulfonyl)-7-oxo-1,4,5,7-tetrahydro-6H-pyrazolo[3,4-c]pyridin-6-yl]phenyl}-N-methyl-2-(1-pyrrolidinyl)acetamide;

3-[6-[4-(ethyl{[3-(methylsulfonyl)-1-pyrrolidinyl]acetyl}amino)phenyl]-7-oxo-3-(trifluoromethyl)-4,5,6,7-tetrahydro-1H-pyrazolo[3,4-c]pyridin-1-yl]benzamide;

3-[6-[4-[{[3-(cyclohexylmethyl)-1-piperidinyl]acetyl}(ethyl)amino]phenyl]-7-oxo-3-(trifluoromethyl)-4,5,6,7-tetrahydro-1H-pyrazolo[3,4-c]pyridin-1-yl]benzamide;

N-{4-[1-(3-amino-1,2-benzisoxazol-5-yl)-3-methoxy-7-oxo-1,4,5,7-tetrahydro-6H-pyrazolo[3,4-c]pyridin-6-yl]phenyl}-N-methyl-2-(1-pyrrolidinyl)acetamide;

N-{4-[1-(4-methoxyphenyl)-3-(methylsulfonyl)-7-oxo-1,4,5,7-tetrahydro-6H-pyrazolo[3,4-c]pyridin-6-yl]phenyl}-N-methyl-2-(2-methyl-1H-imidazol-1-yl)acetamide;

N-{4-[1-(4-methoxyphenyl)-3-(trifluoromethyl)-7-oxo-1,4,5,7-tetrahydro-6H-pyrazolo[3,4-c]pyridin-6-yl]phenyl}-N-methyl-2-(2-methyl-1H-imidazol-1-yl)acetamide;

1-(3-Chloro-phenyl)-6-{4-[methyl-(2-pyrrolidin-1-yl-acetyl)-amino]-phenyl}-7-oxo-4,5,6,7-tetrahydro-1H-pyrazolo[3,4-c]pyridine-3-carboxylic acid amide;

N-{4-[1-(4-Methoxy-phenyl)-3-(4-methyl-oxazol-2-yl)-7-oxo-1,4,5,7-tetrahydro-pyrazolo[3,4-c]pyridin-6-yl]-phenyl}-N-methyl-2-pyrrolidin-1-yl-acetamide;

N-{4-[1-(4-Methoxy-phenyl)-3-(4-methyl-oxazol-2-yl)-7-oxo-1,4,5,7-tetrahydro-pyrazolo[3,4-c]pyridin-6-yl]-phenyl}-N-methyl-3-pyrrolidin-1-yl-propionamide;

or a pharmaceutically acceptable salt form thereof.

[9] In another preferred embodiment, the present invention provides a novel compound, wherein the compound is of Formula IIIa, IIIb, or IIIc:

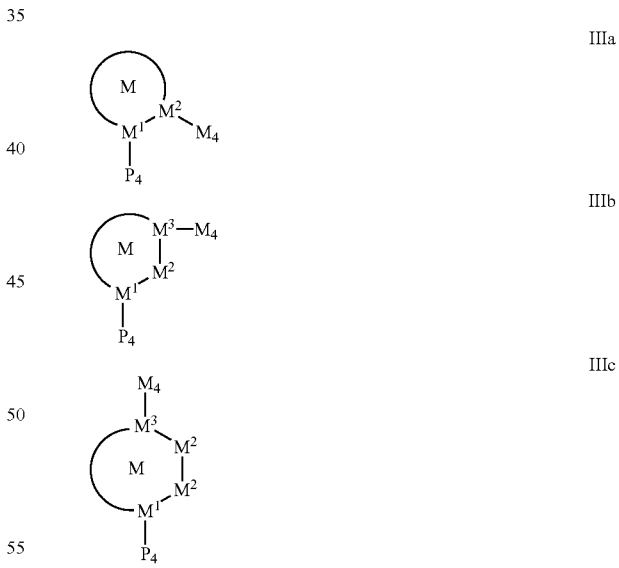

or a stereoisomer or pharmaceutically acceptable salt thereof, wherein;

ring M, including $M_1$, $M_2$, and, if present, $M_3$, is phenyl or a 3–10 membered carbocyclic or 4–10 membered heterocyclic ring consisting of: carbon atoms and 1–4 heteroatoms selected from O, $S(O)_p$, N, and $NZ^2$;

ring M is substituted with 0–3 $R^{1a}$ and 0–2 carbonyl groups, and there are 0–3 ring double bonds;

one of $P_4$ and $M_4$ is -Z-A-B and the other -$G_1$-G;

G is a group of formula IIa or IIb:

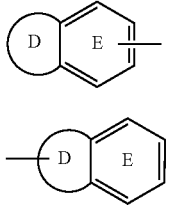

IIa

IIb ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–2 R;

alternatively, ring D is absent, and ring E is selected from phenyl, pyridyl, pyrimidyl, and thienyl, and ring E is substituted with 1–2 R;

alternatively, ring D is absent, ring E is selected from phenyl, pyridyl, and thienyl, and ring E is substituted with 1 R and with a 5 membered heterocycle consisting of: carbon atoms and 1–4 heteroatoms selected from the group consisting of N, O, and $S(O)_p$, wherein the 5 membered heterocycle is substituted with 0–1 carbonyls and 1–2 R and there are 0–3 ring double bonds;

R is selected from H, $C_{1-4}$ alkyl, F, Cl, OH, $OCH_3$, $OCH_2CH_3$, $OCH(CH_3)_2$, CN, C(=NH)$NH_2$, C(=NH)NHOH, C(=NH)$NHOCH_3$, $NH_2$, $NH(C_{1-3}$ alkyl), $N(C_{1-3}$ alkyl)$_2$, C(=NH)$NH_2$, $CH_2NH_2$, $CH_2NH(C_{1-3}$ alkyl), $CH_2N(C_{1-3}$ alkyl)$_2$, $(CR^8R^9)_rNR^7R^8$, C(O)$NR^7R^8$, $CH_2C(O)NR^7R^8$, $S(O)_2R^3$, $S(O)_pNR^7R^8$, $CH_2S(O)_pNR^7R^8$, and $OCF_3$;

alternatively, when 2 R groups are attached to adjacent atoms, they combine to form methylenedioxy or ethylenedioxy;

A is selected from: $C_{5-10}$ carbocycle substituted with 0–2 $R^4$, and 5–10 membered heterocycle consisting of: carbon atoms and 1–4 heteroatoms selected from the group consisting of N, O, and $S(O)_p$ and substituted with 0–2 $R^4$;

B is selected from $N(B^1)C(O)C(R^3R^{3g})R^3$, $N(B^1)C(O)C(R^3R^{3g})NB^2B^3$, and $N(B^1)C(O)C(R^3R^{3g})C(R^3R^{3g})NB^2B^3$, provided that Z and B are attached to different atoms on A;

$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-1}$—$C_{3-7}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2$—$NR^{2d}R^{2d}$, $CH_2CH_2$—$NR^{2d}R^{2d}$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–2 $R^5$, and a —$(CH_2)_{0-1}$-4–7 membered heterocycle consisting of: carbon atoms and 1–4 heteroatoms selected from the group consisting of N, O, and $S(O)_p$ and substituted with 0–2 $R^5$;

alternatively, $NB^2B^3$ is a 4–7 membered heterocycle consisting of: the shown N, carbon atoms, and 0–3 additional heteroatoms selected from the group consisting of N, O, and $S(O)_p$ and substituted with 0–2 $R^5$;

Z is selected from a bond, $CH_2$, $CH_2CH_2$, $CH_2O$, $OCH_2$, C(O), NH, $CH_2NH$, $NHCH_2$, $CH_2C(O)$, C(O)$CH_2$, C(O)NH, NHC(O), NHC(O)NH, NHC(O)$CH_2C(O)NH$, C(O)NHS(O)$_2$, S(O)$_2$, $CH_2S(O)_2$, S(O)$_2(CH_2)$, $SO_2NH$, and $NHSO_2$, provided that Z does not form a N—S, $NCH_2N$, $NCH_2O$, or $NCH_2S$ bond with either group to which it is attached;

$Z^2$ is selected from H, $C_{1-4}$ alkyl, phenyl, benzyl, C(O)$R^{3b}$, $S(O)R^{3f}$, and $S(O)_2R^{3f}$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms or to the same carbon atom, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, C(O)$R^{2b}$, $CO_2R^{2b}$, OC(O)$R^2$, $CO_2R^{2a}$, $S(O)_pR^2$, $NR^2(CH_2)_rOR^2$, $NR^2C(O)R^{2b}$, $NR^2C(O)NHR^2$, $NR^2C(O)_2R^{2a}$, OC(O)$NR^2R^{2a}$, C(O)$NR^2R^{2a}$, C(O)$NR^2(CH_2)_rOR^2$, $SO_2NR^2R^{2a}$, $NR^2SO_2R^2$, $C_{5-6}$ carbocycle substituted with 0–2 $R^{4b}$, and 5–6 membered heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, a $C_{5-6}$ carbocyclic-$CH_2$-group substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, $-(CR^3R^{3a})_r-C_{3-6}$ carbocycle substituted with 0–2 $R^{4c}$, and $-(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $-(CR^3R^{3a})_r-C_{3-6}$ carbocycle substituted with 0–2 $R^{4c}$, and $-(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^{3g}$, at each occurrence, is selected from H, $CH_3$, $CH_2CH_3$, $CH_2CH_2CH_3$, $CH(CH_3)_2$, cyclopropyl, cyclopropyl-methyl, benzyl, and phenyl;

alternatively, when $R^3$ and $R^{3g}$ are attached to the same carbon atom, they combine with the attached carbon atom to form a cyclopropyl group;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$ and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2$—$CF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$;

$R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl; and, r, at each occurrence, is selected from 0, 1, and 2.

[10] In another preferred embodiment, the present invention provides a novel compound, wherein:

ring M, including $M_1$, $M_2$, and, if present, $M_3$, is selected from phenyl, pyrrole, furan, thiophene, pyrazole, imidazole, isoxazole, oxazole, isothiazole, thiazole, 1,2,3-triazole, 1,2,4-triazole, 1,3,4-triazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3,4-tetrazole, 1,2,3,5-tetrazole, pyran, thiopyran, thiopyran=1,1-dioxide, pyridine, pyrimidine, pyridazine, pyrazine, 1,2,3-triazine, 1,2,4-triazine, 1,2,3,4-tetrazine, dihydro-pyrrole, dihydro-furan, dihydro-thiophene, dihydro-pyrazole, dihydro-imidazole, dihydro-isoxazole, dihydro-oxazole, dihydro-isothiazole, dihydro-thiazole, dihydro-1,2,3-triazole, dihydro-1,2,4-triazole, dihydro-1,3,4-triazole, dihydro-1,2,3-oxadiazole, dihydro-1,2,4-oxadiazole, dihydro-1,3,4-oxadiazole, dihydro-1,2,3-thiadiazole, dihydro-1,2,4-thiadiazole, dihydro-1,3,4-thiadiazole, dihydro-1,2,3,4-tetrazole, dihydro-1,2,3,5-tetrazole, dihydro-pyran, dihydro-thiopyran, dihydro-thiopyran=1,1-dioxide, dihydro-pyridine, dihydro-pyrimidine, dihydro-pyridazine, dihydro-pyrazine, dihydro-1,2,3-triazine, dihydro-1,2,4-triazine, dihydro-1,2,3,4-tetrazine, cyclopentene, cyclopentane, cyclohexene, cyclohexane, tetrahydro-pyrrole, tetrahydro-furan, tetrahydro-thiophene, tetrahydro-thiophene-1,1-dioxide, tetrahydro-pyrazole, tetrahydro-imidazole, tetrahydro-isoxazole, tetrahydro-oxazole, tetrahydro-isothiazole, tetrahydro-thiazole, tetrahydro-1,2,3-triazole, tetrahydro-1,2,4-triazole, tetrahydro-1,3,4-triazole, tetrahydro-1,2,3-oxadiazole, tetrahydro-1,2,4-oxadiazole, tetrahydro-1,3,4-oxadiazole, tetrahydro-1,2,3-thiadiazole, tetrahydro-1,2,4-thiadiazole, tetrahydro-1,3,4-thiadiazole, tetrahydro-1,2,3,4-tetrazole, tetrahydro-1,2,3,5-tetrazole, tetrahydro-pyran, tetrahydro-thiopyran, tetrahydro-thiopyran-1,1-dioxide, tetrahydro-pyridine, tetrahydro-pyrimidine, tetrahydro-pyridazine, tetrahydro-pyrazine, tetrahydro-1,2,3-triazine, tetrahydro-1,2,4-triazine, and tetrahydro-1,2,3,4-tetrazine;
ring M is substituted with 0–3 $R^{1a}$ and 0–1 carbonyl group;
G is selected from the group:
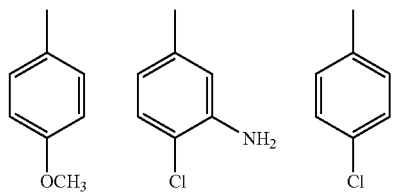
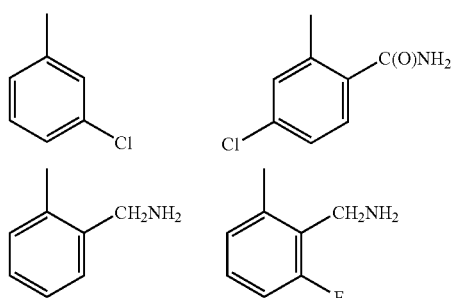
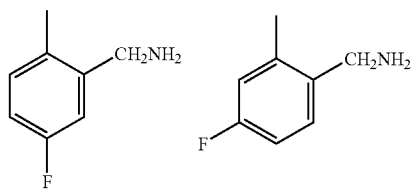
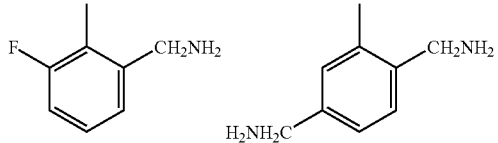
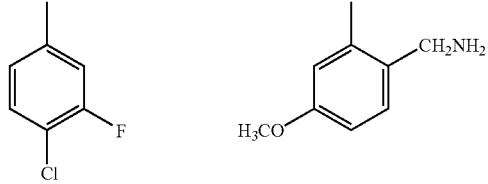
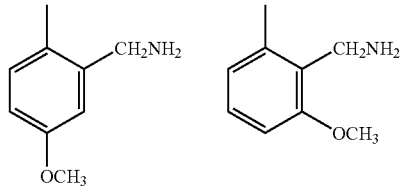
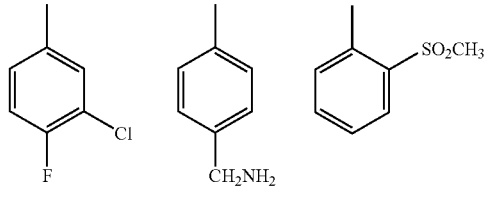
-continued
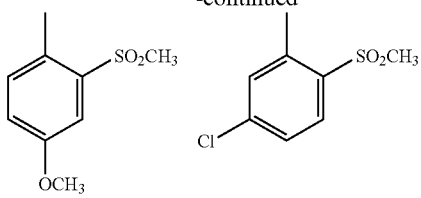
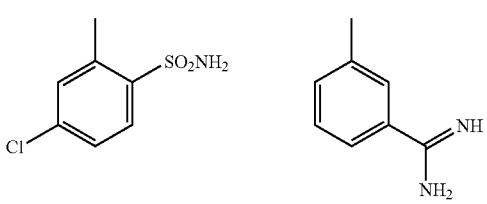
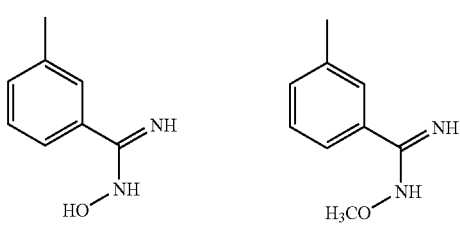
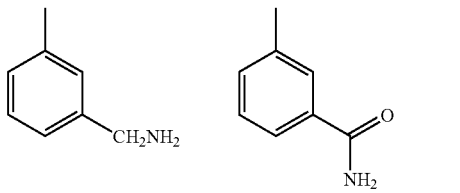
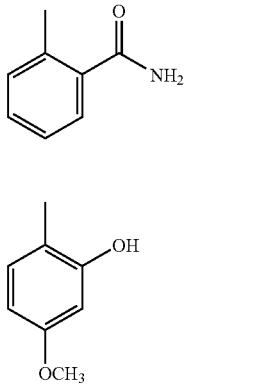
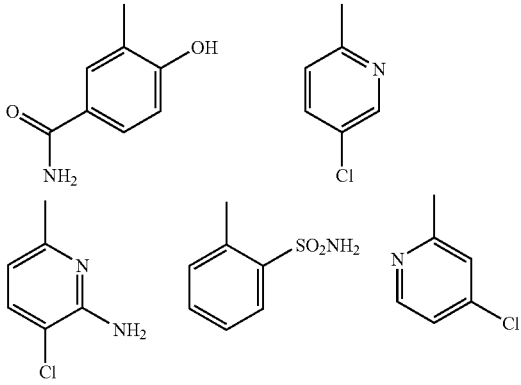

-continued
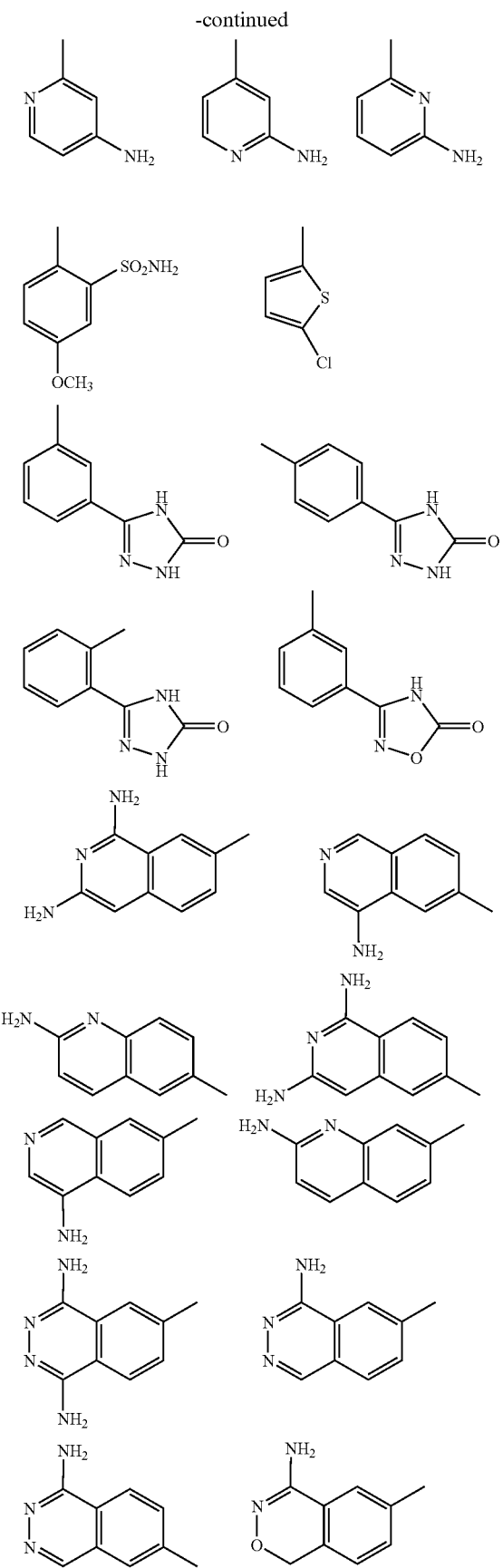
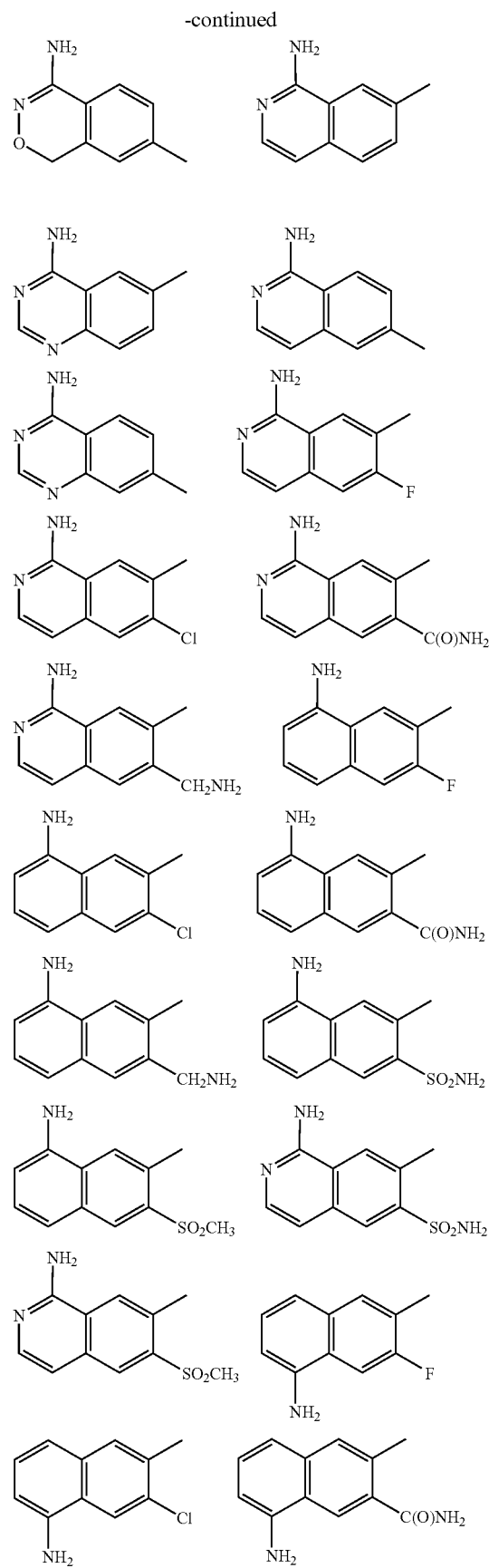

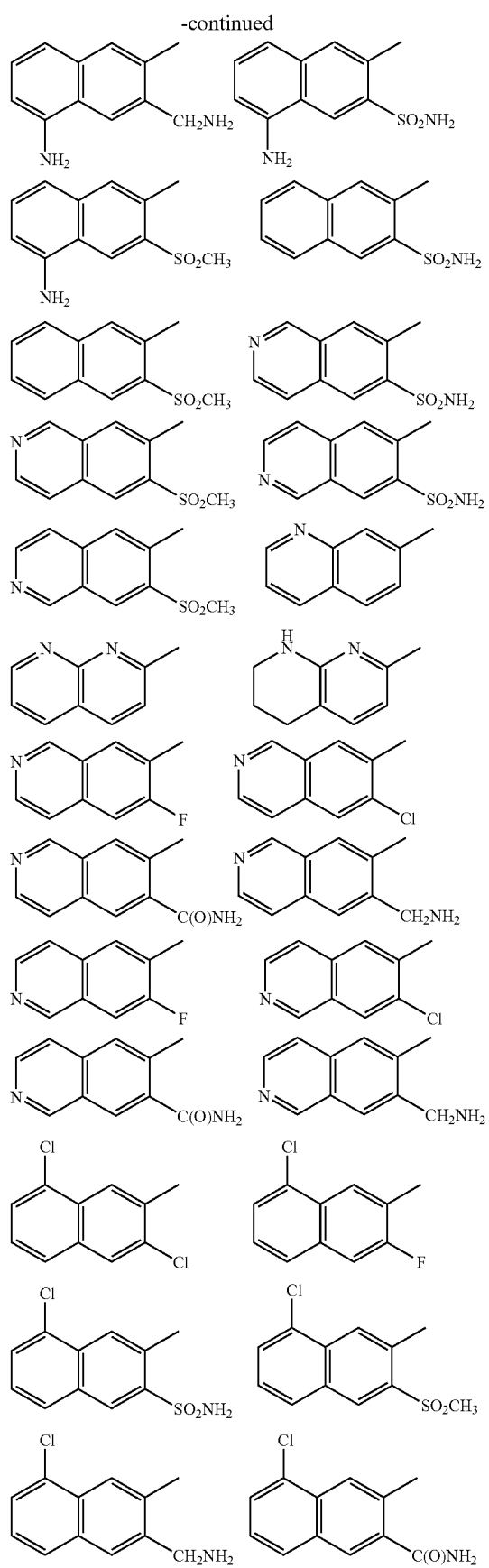

-continued
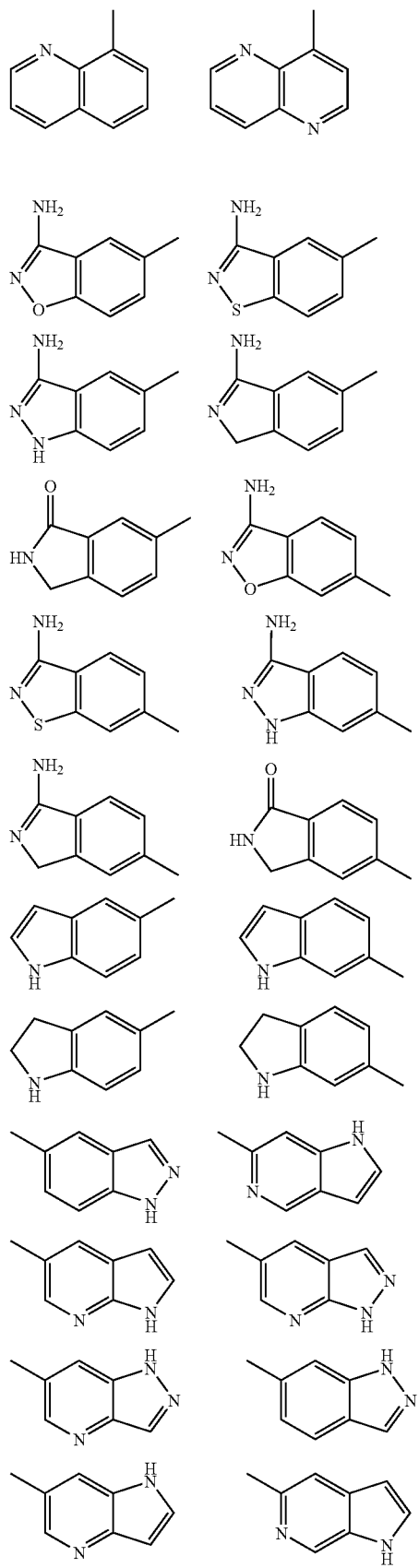
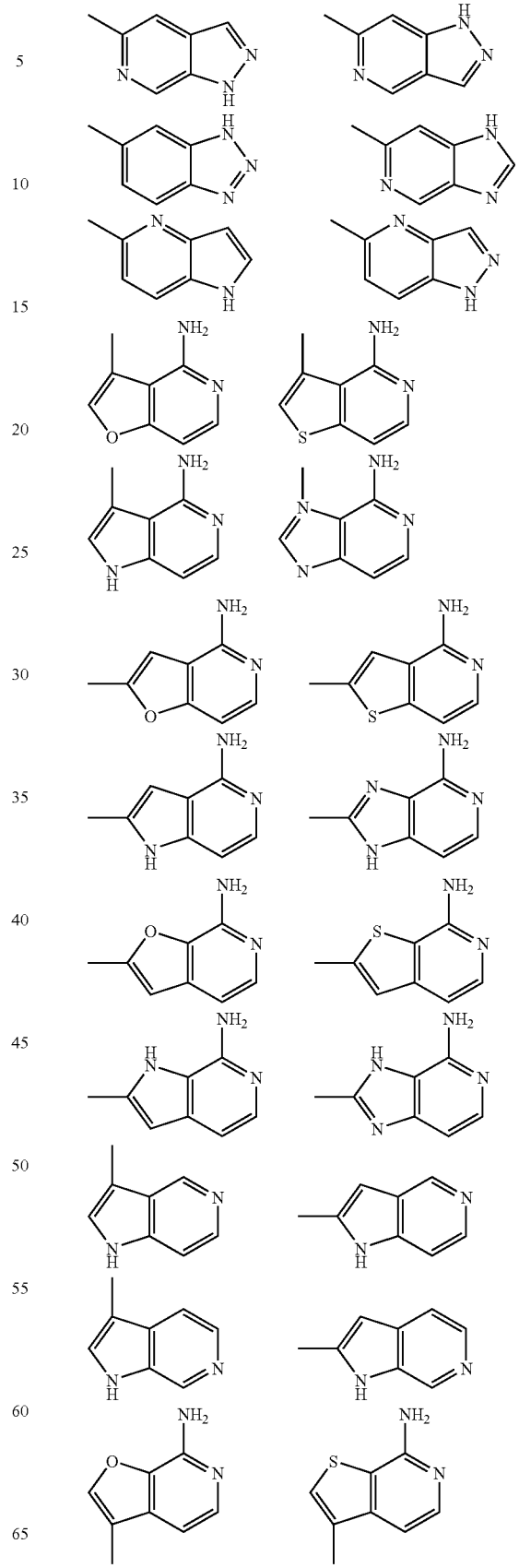

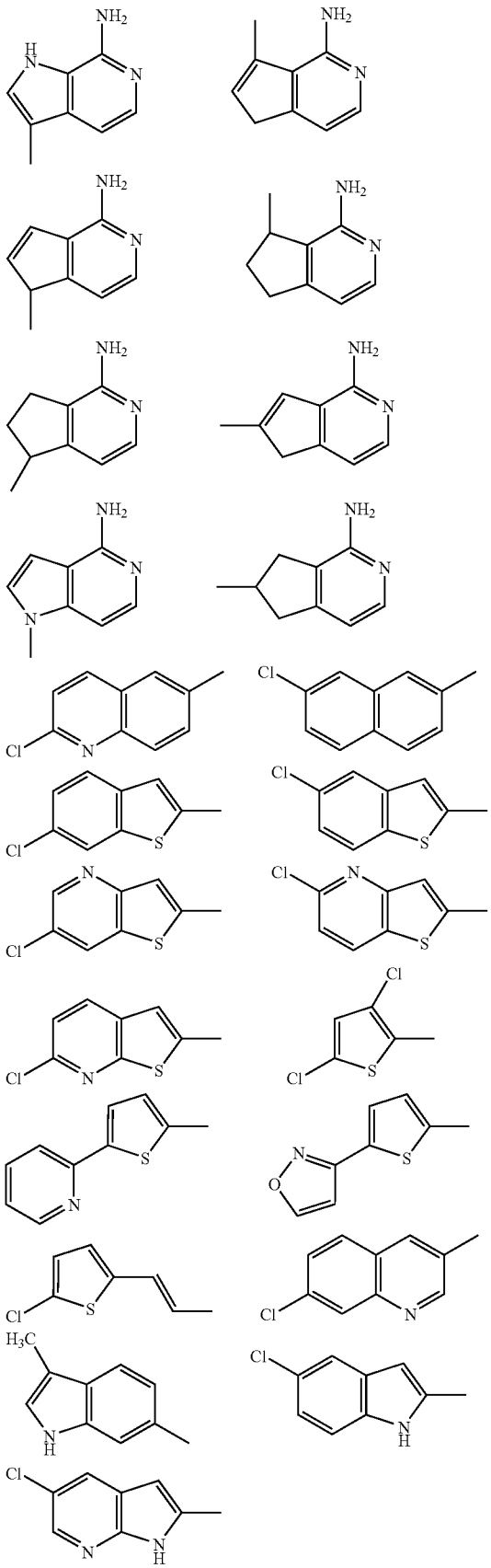

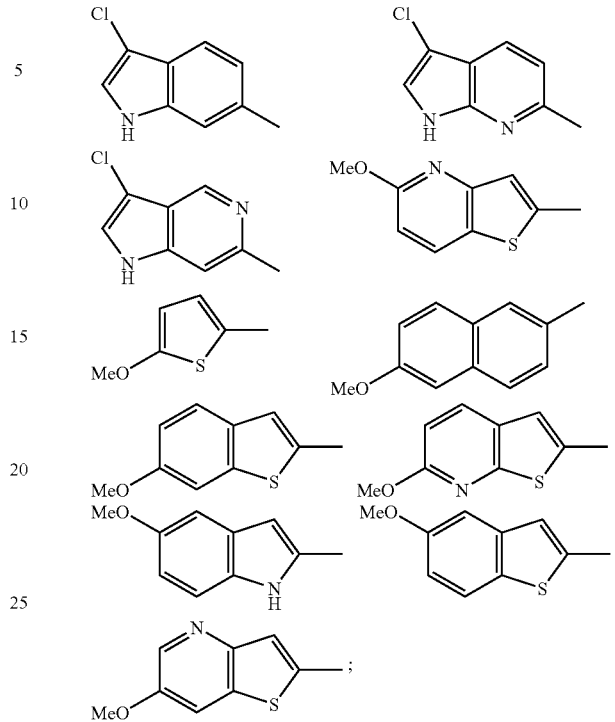

G₁ is absent or is selected from $(CR^3R^{3a})_{1-3}$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)NR^{3b}(CR^3R^{3a})_w$, $(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, and $(CR^3R^{3a})_uC(O)NR^{3b}S(O)_2(CR^3R^{3a})W$, wherein u+w total 0, 1, or 2, provided that G₁ does not form a N—S, NCH₂N, NCH₂O, or NCH₂S bond with either group to which it is attached;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–6 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

A is selected from one of the following carbocyclic and heterocyclic groups which are substituted with 0–2 $R^4$;

phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

$B^1$ is selected from H, $CH_3$, $CH_2CH_3$, $CH_2CH_2CH_3$, $CH(CH_3)_2$, $-(CH_2)_{0-1}-C_{5-6}$ carbocycle substituted with 0–2 $R^{4b}$, and $-(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, $-(CH_2)_{0-1}$-3–6 membered carbocycle substituted with 0–1 $R^5$, and a $-(CH_2)_{0-1}$-5–6 membered heterocycle consisting of: carbon atoms and 1–4 heteroatoms selected from the group consisting of N, O, and $S(O)_p$ and substituted with 0–1 $R^5$;

alternatively, $NB^2B^3$ is a 4–7 membered heterocycle consisting of: the shown N, carbon atoms, and 0–3 additional heteroatoms selected from the group consisting of N, O, and $S(O)_p$ and substituted with 0–1 $R^5$;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $-(CR^3R^{3a})-C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and $-(CR^3R^{3a})$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—S(O)$_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $-(CR^3R^{3a})-C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and $-(CR^3R^{3a})$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^4$, at each occurrence, is selected from H, $(CH_2)_2OR^2$, $CH_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $-CN$, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $-CN$, $NO_2$, $NR^3R^{3a}$, $CH_2NR^3R^{3a}$, $C(O)R^3$, $CH_2-C(O)R^3$, $C(O)OR^{3c}$, $CH_2-C(O)OR^{3c}$, $NR^3C(O)R^{3a}$, $CH_2NR^3C(O)R^{3a}$, $C(O)NR^3R^{3a}$, $CH_2-C(O)NR^3R^{3a}$, $SO_2NR^3R^{3a}$, $CH_2SO_2NR^3R^{3a}$, $NR^3SO_2-C_{1-4}$ alkyl, $CH_2NR^3SO_2-C_{1-4}$ alkyl, $NR^3SO_2$-phenyl, $CH_2NR^3SO_2$-phenyl, $S(O)_pCF_3$, $CH_2S(O)_pCF_3$, $S(O)_p-C_{1-4}$ alkyl, $CH_2S(O)_p-C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})$F, Br, $(CR^3R^{3a})$Br, Cl, $(CR^3R^{3a})$Cl, $CF_3$, $(CR^3R^{3a})CF_3$, $C_{1-4}$ alkyl, $-CN$, $(CR^3R^{3a})$CN, $NO_2$, $(CR^3R^{3a})NO_2$, $NR^2R^{2a}$, $(CR^3R^{3a})NR^2R^{2a}$, $N(\rightarrow O)R^2R^{2a}$, $(CR^3R^{3a})N(\rightarrow O)R^2R^{2a}$, $C(O)R^{2c}$, $(CR^3R^{3a})C(O)R^{2c}$, $NR^2C(O)R^{2b}$, $(CR^3R^{3a})NR^2C(O)R^{2b}$, $C(O)NR^2R^{2a}$, $(CR^3R^{3a})C(O)NR^2R^{2a}$, $NR^2C(O)NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$ 5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, $-CN$, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2-C_{1-4}$ alkyl, $NR^3SO_2CF_3$, $NR^3SO_2$-phenyl, $S(O)_pCF_3$, $S(O)_p-C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, $-CN$, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

[11] In another preferred embodiment, the present invention provides a novel compound, wherein the compound is selected from:
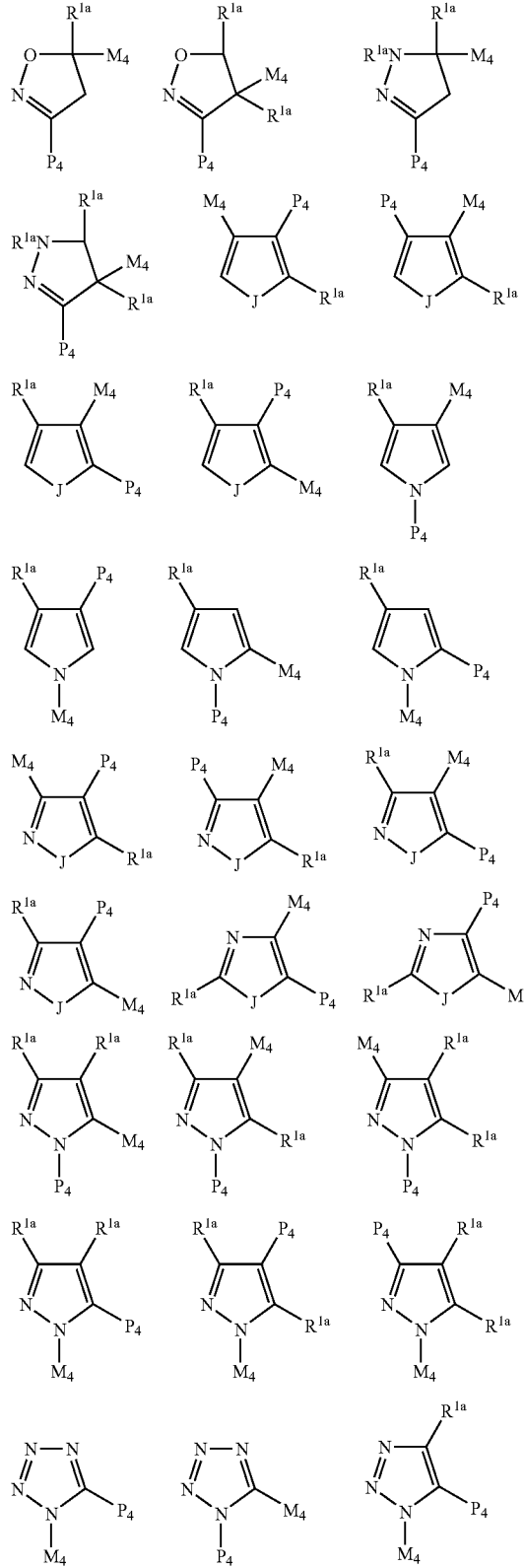
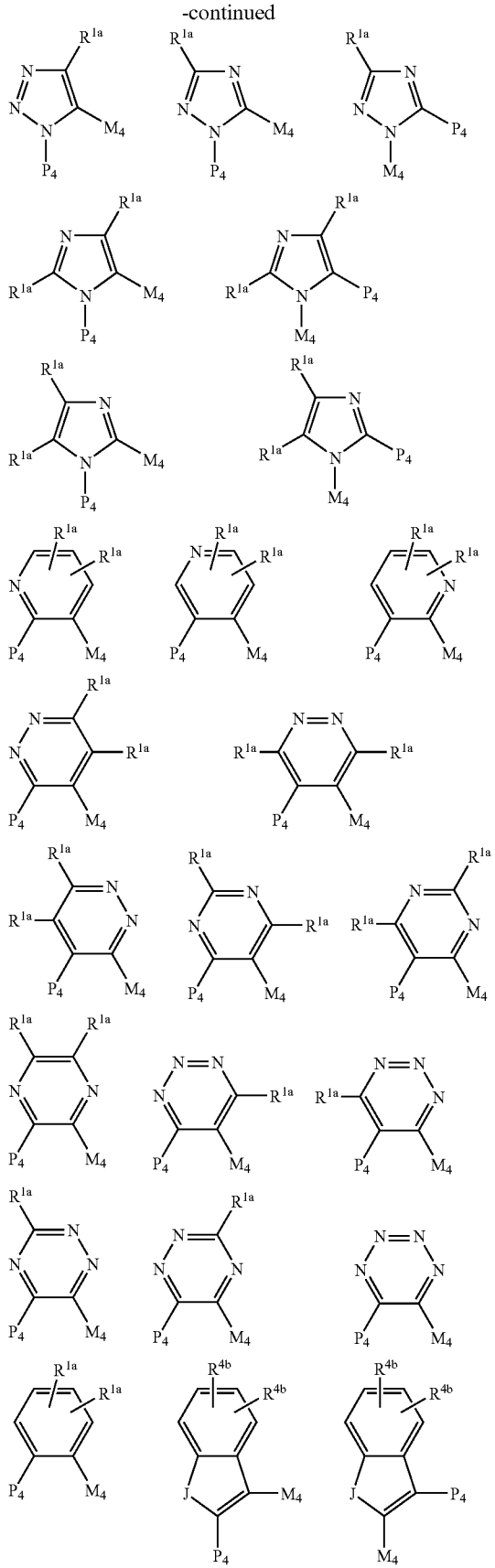

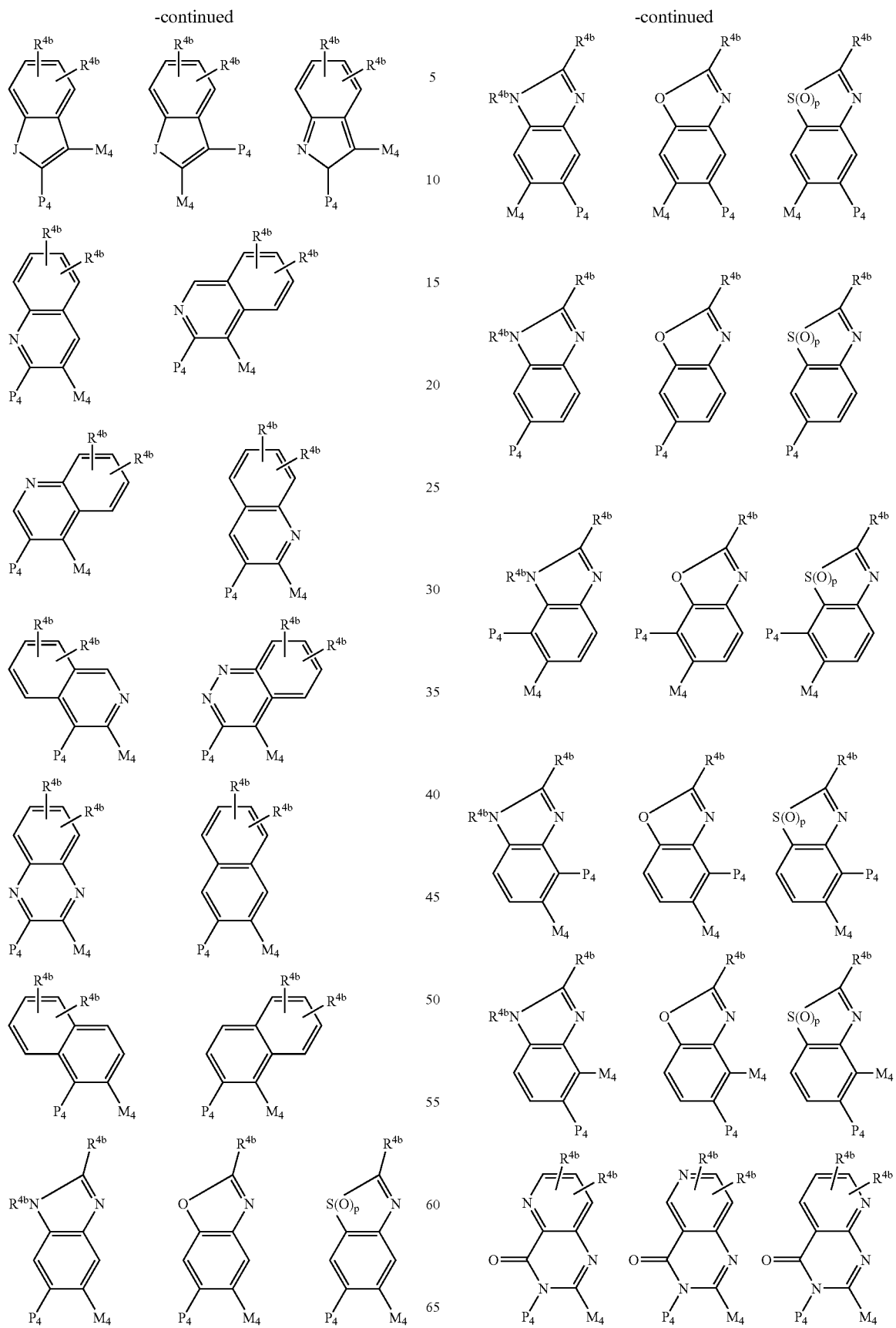

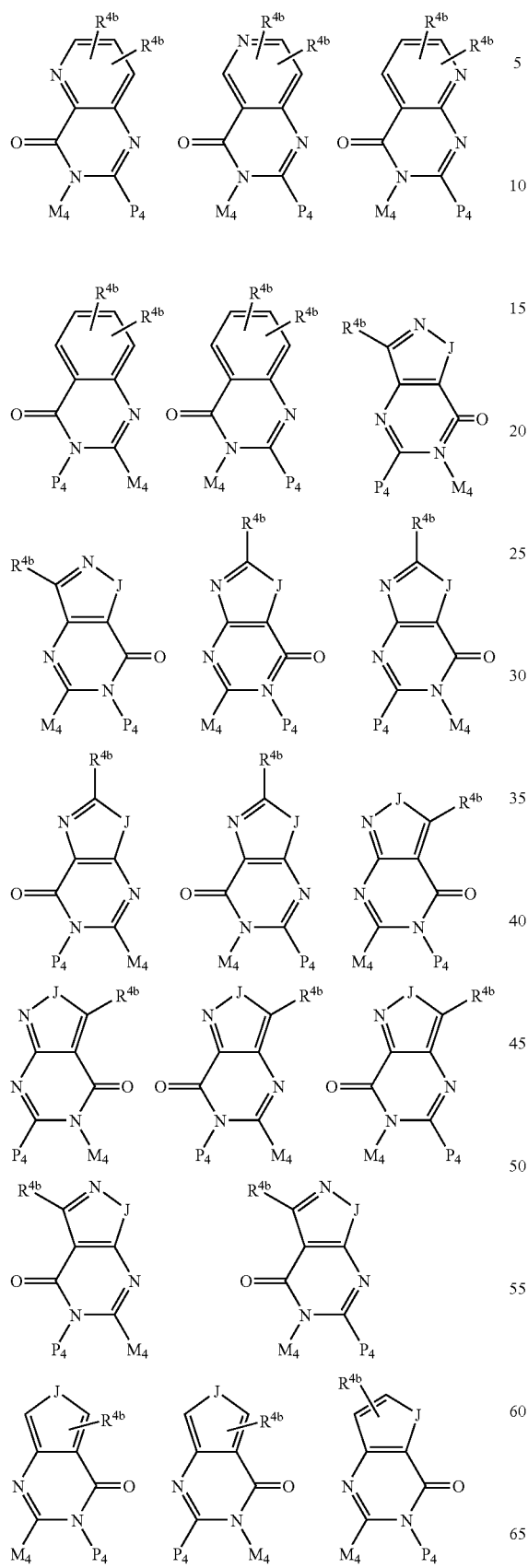
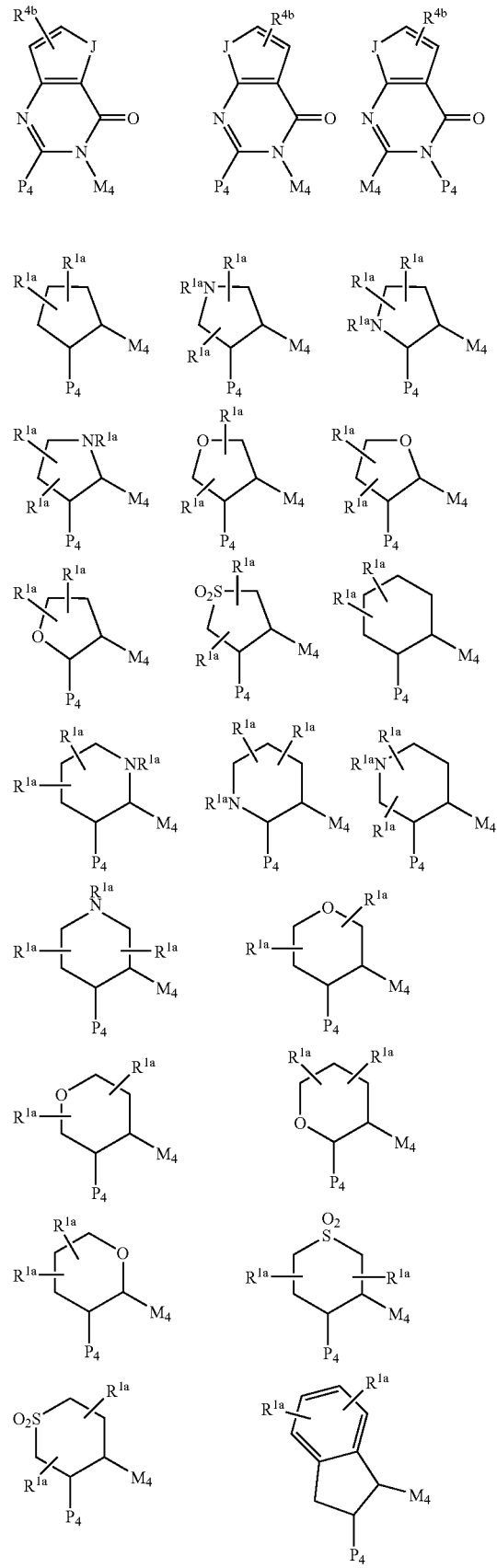

-continued
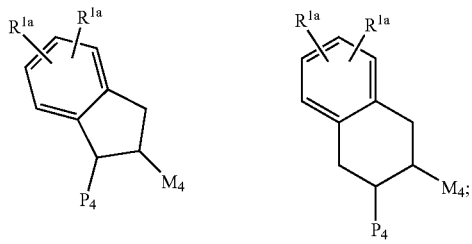
J is selected from O, S, NH, and NR$^{1a}$;
G is selected from the group:
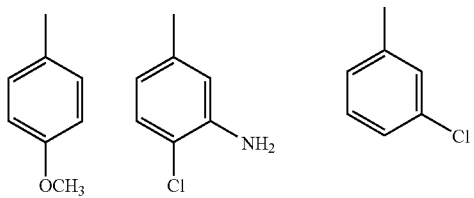
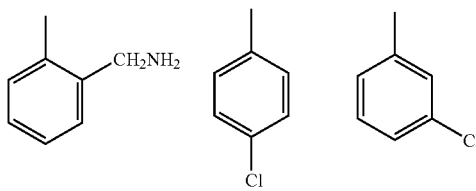
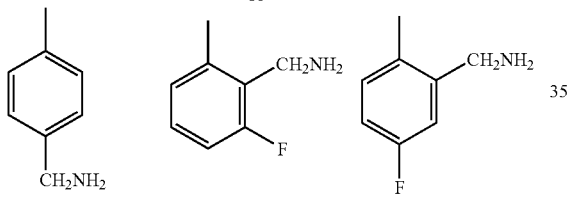
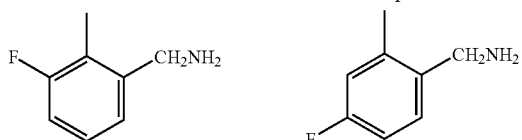
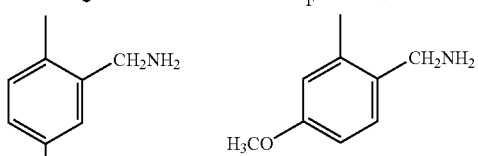
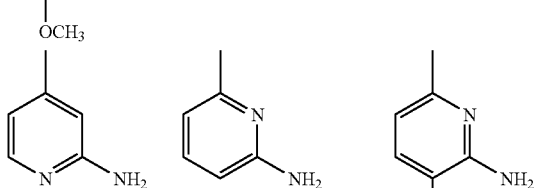
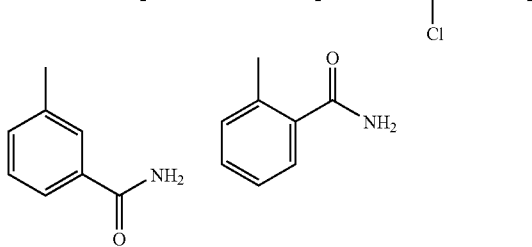
-continued
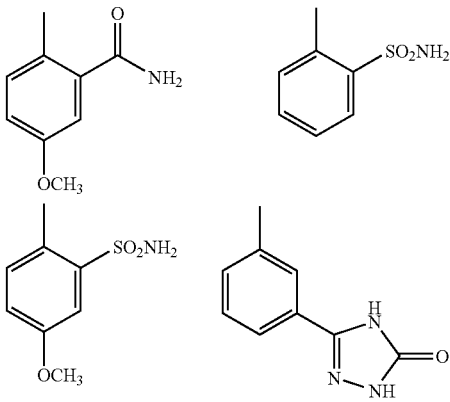
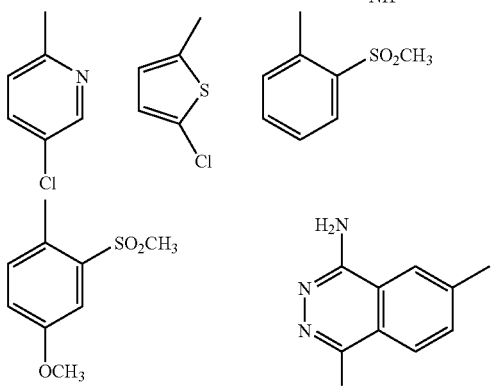
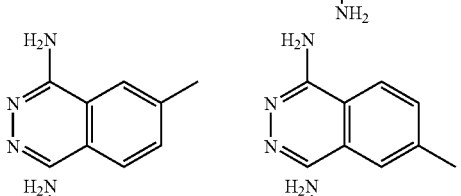
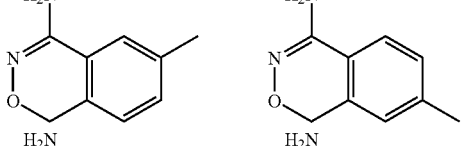
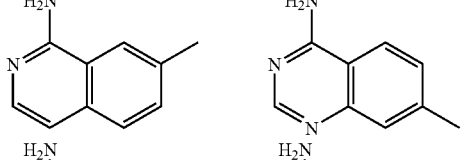
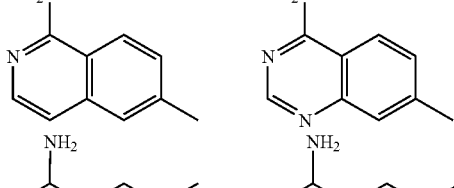
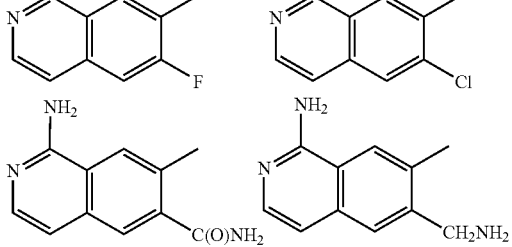

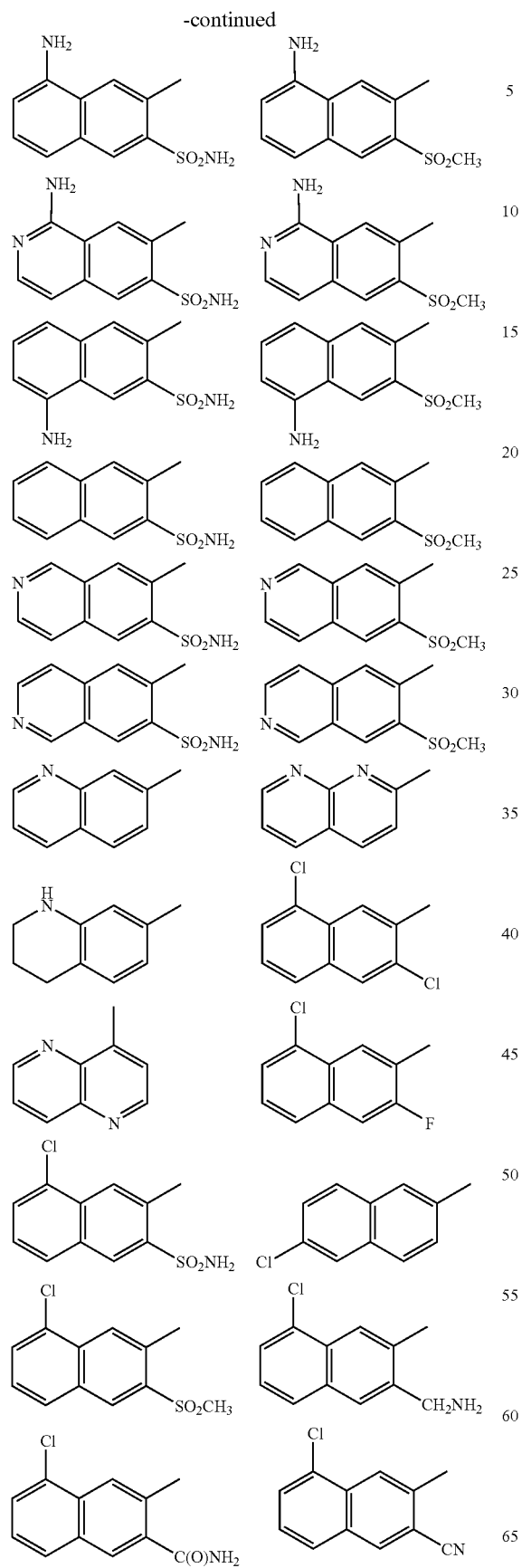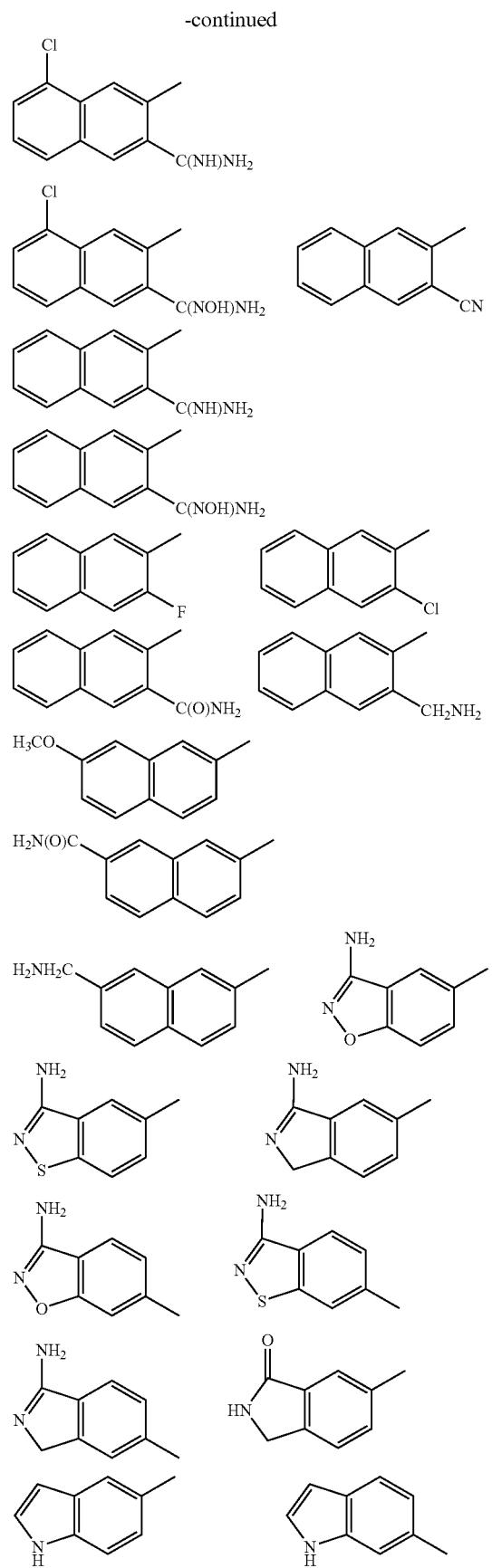

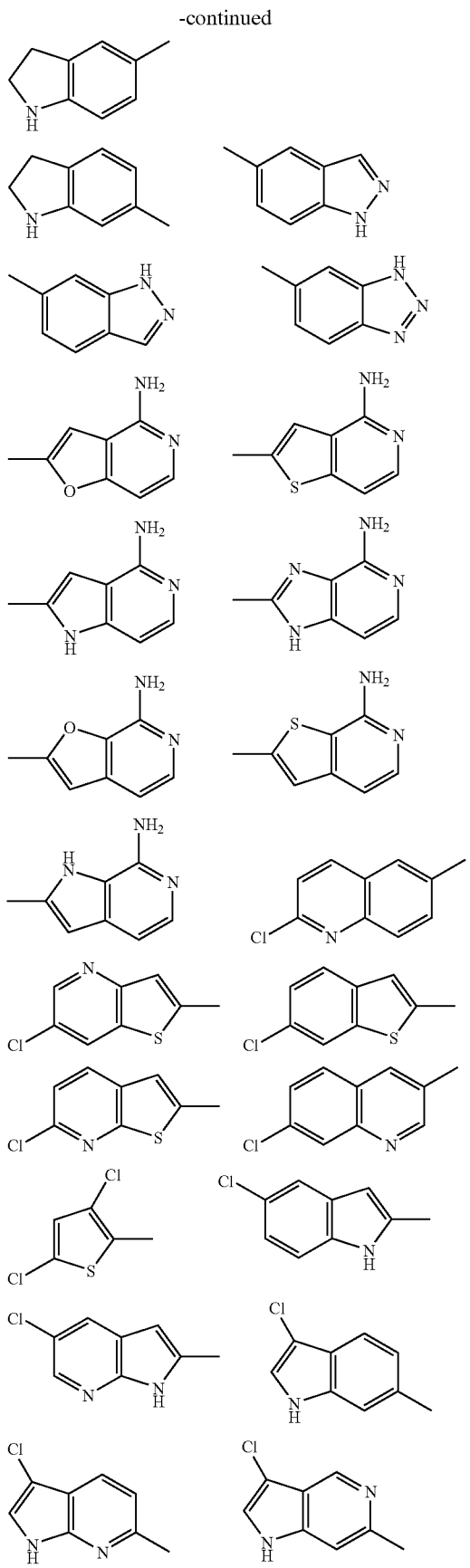

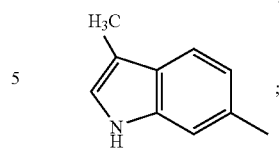

$G_1$ is absent or is selected from $CH_2$, $CH_2CH_2$, $CH_2O$, $OCH_2$, NH, $CH_2NH$, $NHCH_2$, $CH_2C(O)$, $C(O)CH_2$, $C(O)NH$, $NHC(O)$, $NHC(O)NH$, $C(O)NHS(O)_2$, $CH_2S(O)_2$, $S(O)_2(CH_2)$, $SO_2NH$, and $NHSO_2$, provided that $G_1$ does not form a N—S, $NCH_2N$, $NCH_2O$, or $NCH_2S$ bond with either group to which it is attached;

A is selected from indolinyl, phenyl, pyridyl, and pyrimidyl, and is substituted with 0–2 $R^4$;

B is $N(B^1)C(O)C(R^3R^{3a})NB^2B^3$, provided that Z and B are attached to different atoms on A;

$B^1$ is selected from H, $CH_3$, $CH_2CH_3$, $CH_2CH_2CH_3$, and $CH(CH_3)_2$;

$B^2$ is selected from H, $CH_3$, $CH_2CH_3$, $CH_2CH_2CH_3$, and $CH(CH_3)_2$;

$B^3$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{2-5}$ alkyl substituted with 1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

alternatively, $NB^2B^3$ is a 5–6 membered heterocycle consisting of: the shown N, carbon atoms, and 0–2 additional heteroatoms selected from the group consisting of N, O, and $S(O)_p$ and substituted with 0–1 $R^5$;

$R^{1a}$ is selected from H, $R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle containing from 1–4 heteroatoms selected from the group consisting of N, O, and $S(O)_p$ and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and —$(CH_2)$—5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N-C-halo, $S(O)_p$-halo, O-halo, N-S, S-N, $S(O)_p$–$S(O)_p$, S-O, O-N, O-S, or O-O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CH_2)$—$C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and —$(CH_2)$—5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)-$S(O)_p$ moiety;

$R^4$, at each occurrence, is selected from OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $R^{4c}$, at each occurrence, is selected from =O, $OR^2$, $CH_2OR^2$, F, Br, Cl, $CF_3$, $C_{1-4}$ alkyl, —CN, $NO_2$, $NR^2R^{2a}$, $CH_2NR^2R^{2a}$, $N(\to O)R^2R^{2a}$, $CH_2N(\to O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, $CF_2CF_3$, $C_{3-6}$ carbocycle substituted with 0–2 $R^{4b}$, $(CH_2)C_{3-6}$ carbocycle substituted with 0–2 $R^{4b}$, 5–6 membered heterocycle consisting of carbon atoms and from 1–4 heteroatoms selected from the group consisting of N, O, and $S(O)_p$ and substituted with 0–2 $R^{4b}$, and $(CH_2)$-5–6 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[12] In another preferred embodiment, the present invention provides a novel compound, wherein the compound is selected from:

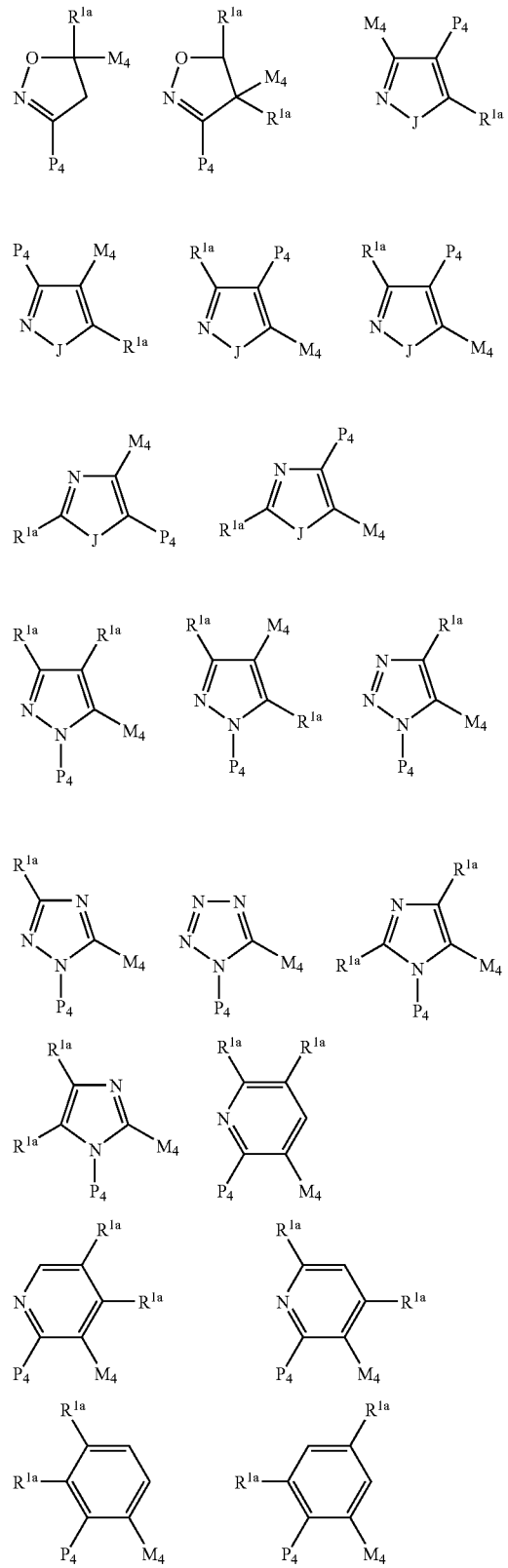

-continued
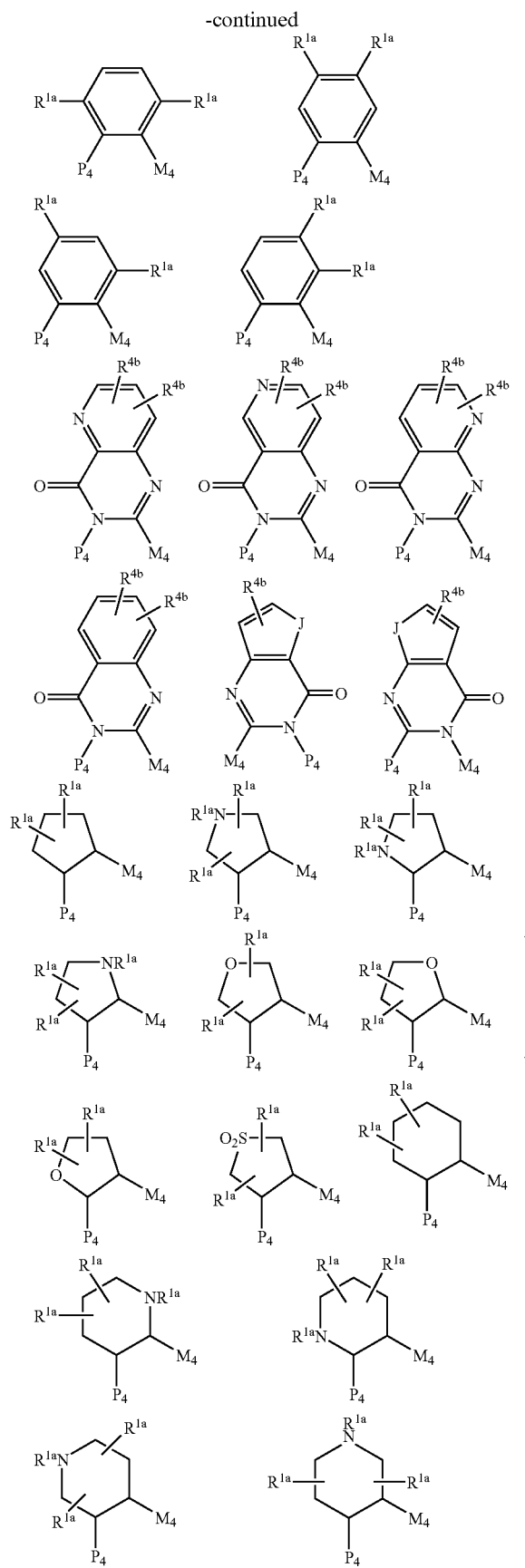
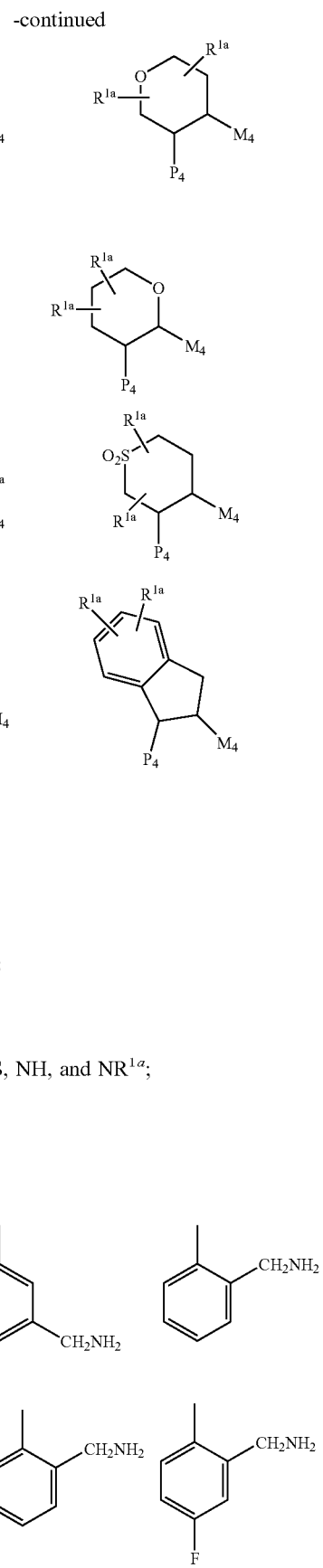
J is selected from O, S, NH, and $NR^{1a}$;
$P_4$ is $-G_1-G$;
$M_4$ is -Z-A-B;
G is selected from:
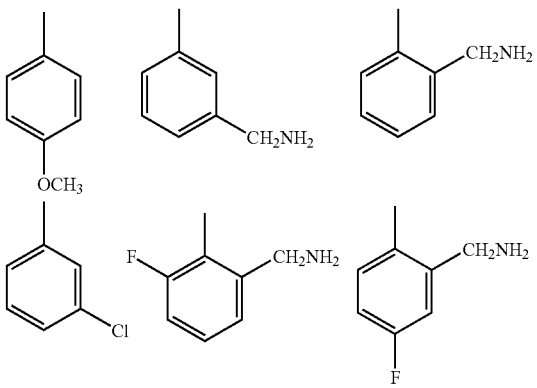

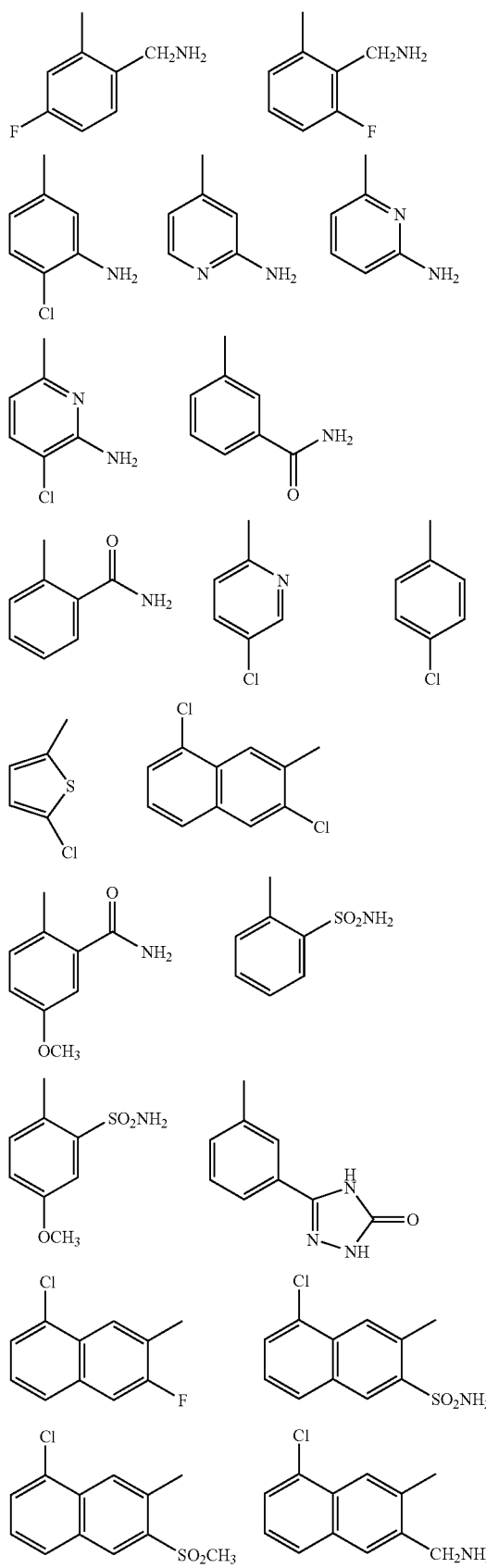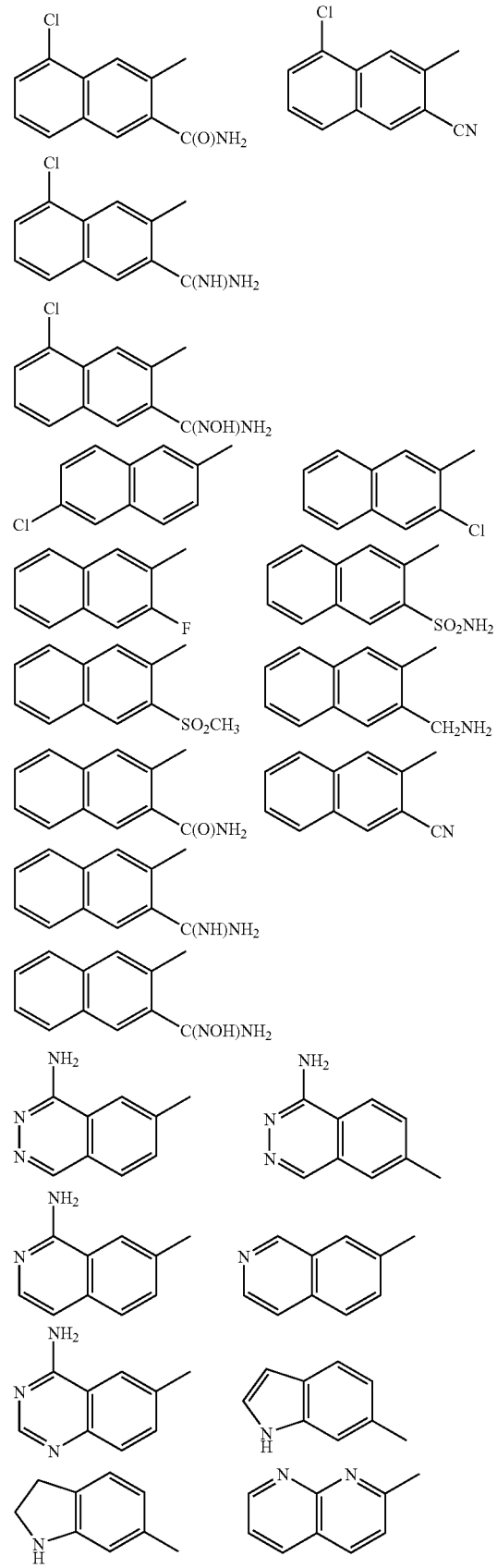

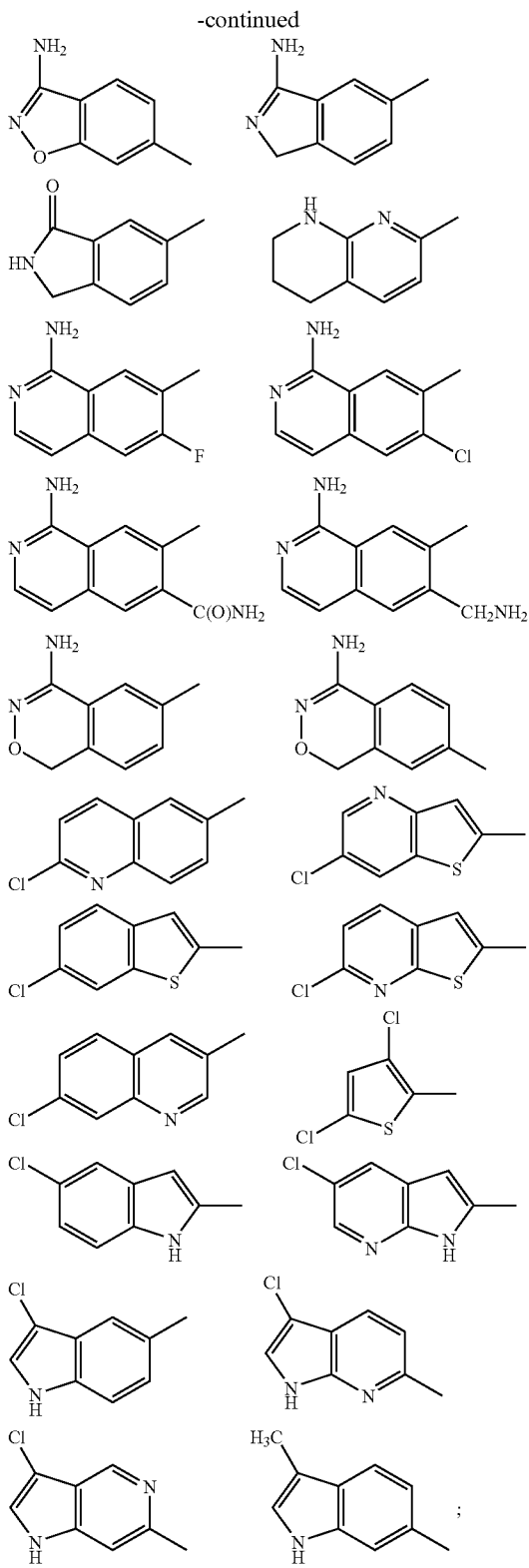

$G_1$ is absent or is selected from $CH_2NH$, $NHCH_2$, $CH_2C(O)$, $C(O)CH_2$, $C(O)NH$, $NHC(O)$, $NHC(O)NH$, $CH_2S(O)_2$, $S(O)_2(CH_2)$, $SO_2NH$, and $NHSO_2$, provided that $G_1$ does not form a N—S, $NCH_2N$, $NCH_2O$, or $NCH_2S$ bond with either group to which it is attached;

A is selected from the group: indolinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

$B^1$ is selected from H, $CH_3$, $CH_2CH_3$, and $CH_2CH_2CH_3$;

$B^2$ is selected from H, $CH_3$, and $CH_2CH_3$;

$B^3$ is selected from $CH_3$, $CH_2CH_3$, $CH_2CH_2CH_3$, $CH(CH_3)_2$, $CH_2CH_2CH_2CH_3$, $C(CH_3)_3$, $CH(CH_3)CH_2CH(CH_3)_2$, $CH_2CH_2OH$, $CH(CH_3)CH_2OH$, $CH(phenyl)CH_2CH_3$, cyclopropyl, cyclobutyl, cyclopentyl, and $CH_2$-cyclopropyl;

alternatively, $NB^2B^3$ is a ring selected from pyrrolidinyl, piperidinyl, and morpholinyl;

$R^{1a}$ is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from OH, $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, C(O)R³, C(O)OR³ᶜ, NR³C(O)R³ᵃ, C(O)NR³R³ᵃ, SO₂NR³R³ᵃ, NR³SO₂-phenyl, S(O)₂CH₃, S(O)₂-phenyl, and CF₃;

R⁴ᶜ, at each occurrence, is selected from =O, OH, OCH₃, OCH₂CH₃, OCH₂CH₂CH₃, OCH(CH₃)₂, CH₃, CH₂CH₃, CH₂CH₂CH₃, CH(CH₃)₂, CH₂OH, CH₂OCH₃, CH₂OCH₂CH₃, CH₂OCH₂CH₂CH₃, CH₂OCH(CH₃)₂, F, Br, Cl, CF₃, NR²R²ᵃ, CH₂NR²R²ᵃ, N(→O)R²R²ᵃ, CH₂N(→O)R²R²ᵃ, C(O)R²ᶜ, CH₂C(O)R²ᶜ, NR²C(O)R²ᵇ, CH₂NR²C(O)R²ᵇ, C(O)NR²R²ᵃ, CH₂C(O)NR²R²ᵃ, SO₂NR²R²ᵃ, CH₂SO₂NR²R²ᵃ, NR²SO₂R⁵ᵃ, CH₂NR²SO₂R⁵ᵃ, S(O)ₚR⁵ᵃ, CH₂S(O)ₚR⁵ᵃ, CF₃, cyclopropyl substituted with 0–1 R⁴ᵇ, cyclobutyl substituted with 0–1 R⁴ᵇ, cyclopentyl substituted with 0–1 R⁴ᵇ, phenyl substituted with 0–1 R⁴ᵇ, —CH₂-cyclopropyl substituted with 0–1 R⁴ᵇ, —CH₂-cyclobutyl substituted with 0–1 R⁴ᵇ, —CH₂-cyclopentyl substituted with 0–1 R⁴ᵇ, benzyl substituted with 0–2 R⁴ᵇ, 5–6 membered aromatic heterocycle consisting of carbon atoms and from 1–4 heteroatoms selected from the group consisting of N, O, and S(O)ₚ and substituted with 0–2 R⁴ᵇ, and (CH₂)-5–6 membered aromatic heterocycle consisting of carbon atoms and from 1–4 heteroatoms selected from the group consisting of N, O, and S(O)ₚ and substituted with 0–2 R⁴ᵇ;

R⁵, at each occurrence, is selected from H, =O, CH₃, CH₂CH₃, OR³, CH₂OR³, F, Cl, NR³R³ᵃ, CH₂NR³R³ᵃ, C(O)R³, C(O)OR³ᶜ, NR³C(O)R³ᵃ, C(O)NR³R³ᵃ, SO₂NR³R³ᵃ, NR³SO₂—C₁₋₄ alkyl, NR³SO₂-phenyl, S(O)₂—CH₃, S(O)₂-phenyl, CF₃, phenyl substituted with 0–2 R⁶, naphthyl substituted with 0–2 R⁶, and benzyl substituted with 0–2 R⁶; and, R⁶, at each occurrence, is selected from H, OH, OR², F, Cl, CH₃, CH₂CH₃, NR²R²ᵃ, CH₂NR²R²ᵃ, C(O)R²ᵇ, CH₂C(O)R²ᵇ, NR²C(O)R²ᵇ, and SO₂NR²R²ᵃ.

[13] In another preferred embodiment, the present invention provides a novel compound, wherein the compound is selected from:

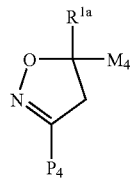
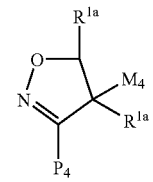

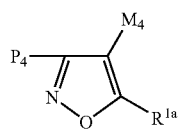
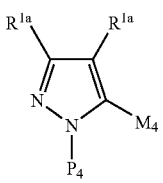

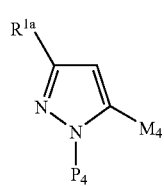
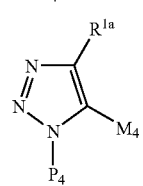

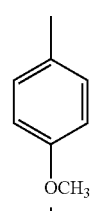
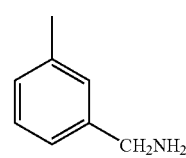

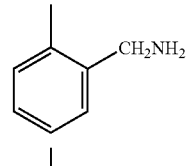
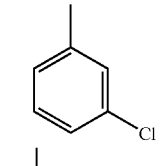

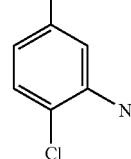
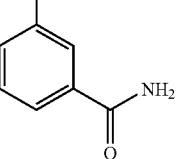

G is selected from:

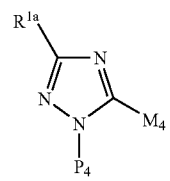
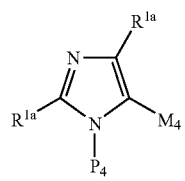

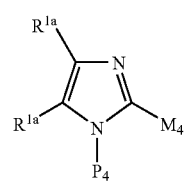
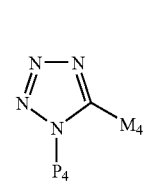

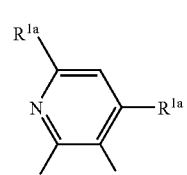
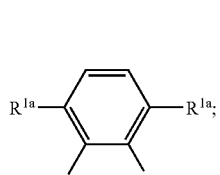

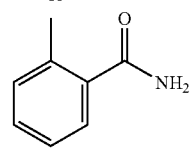
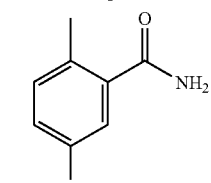

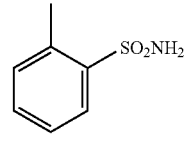
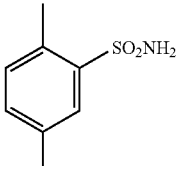

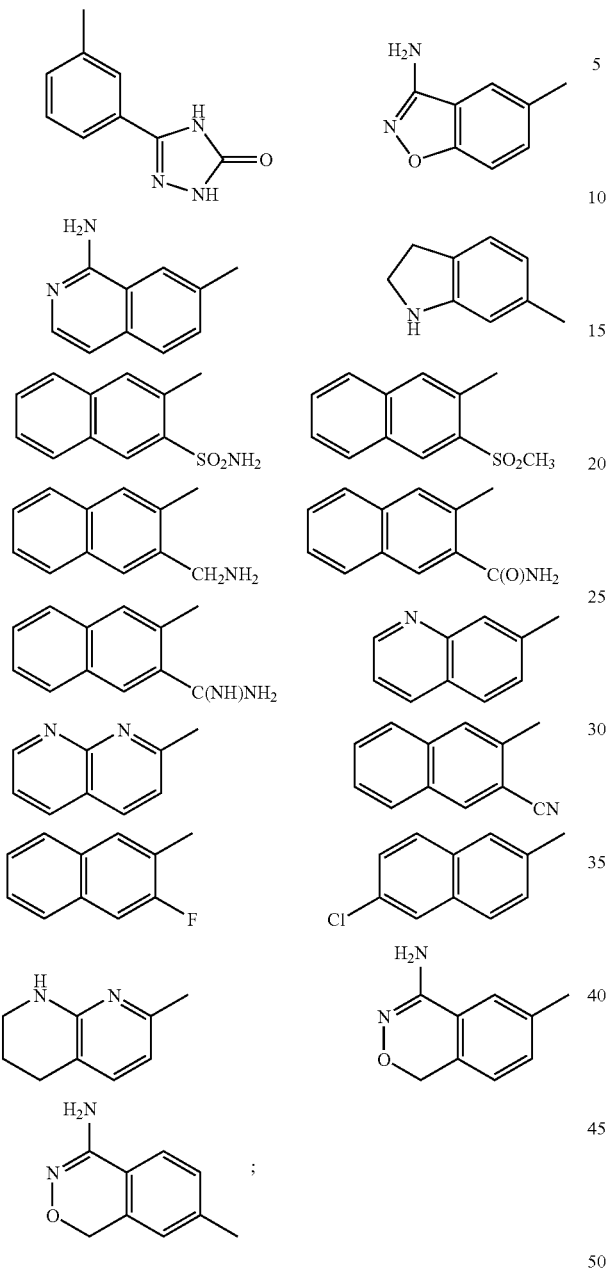
A-B is selected from:
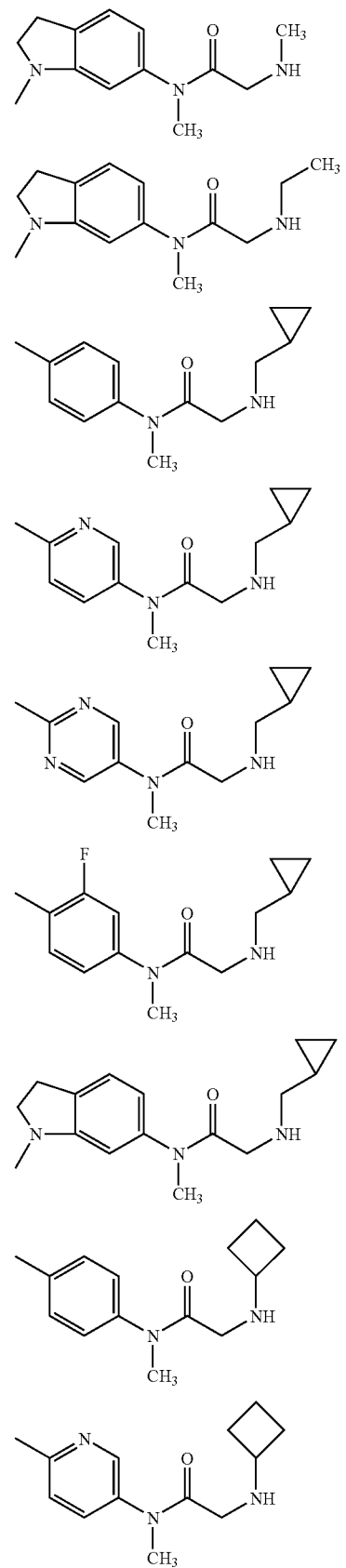

-continued
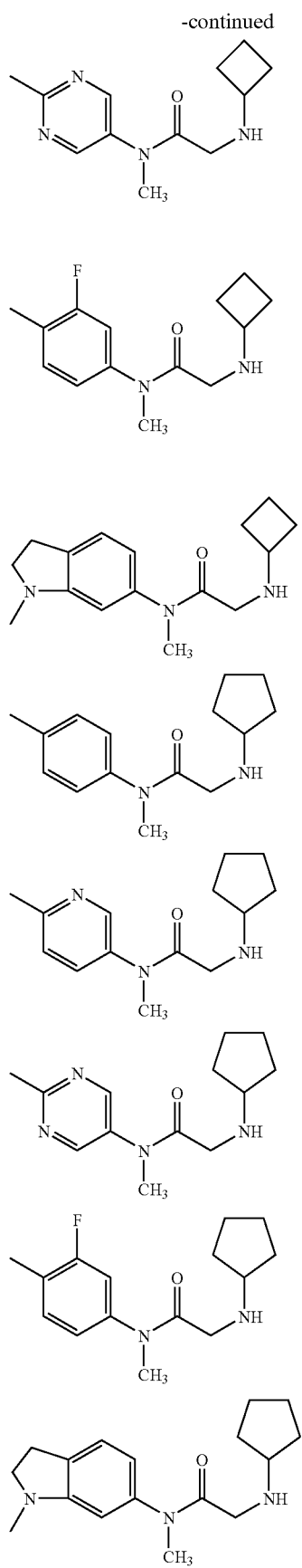
-continued
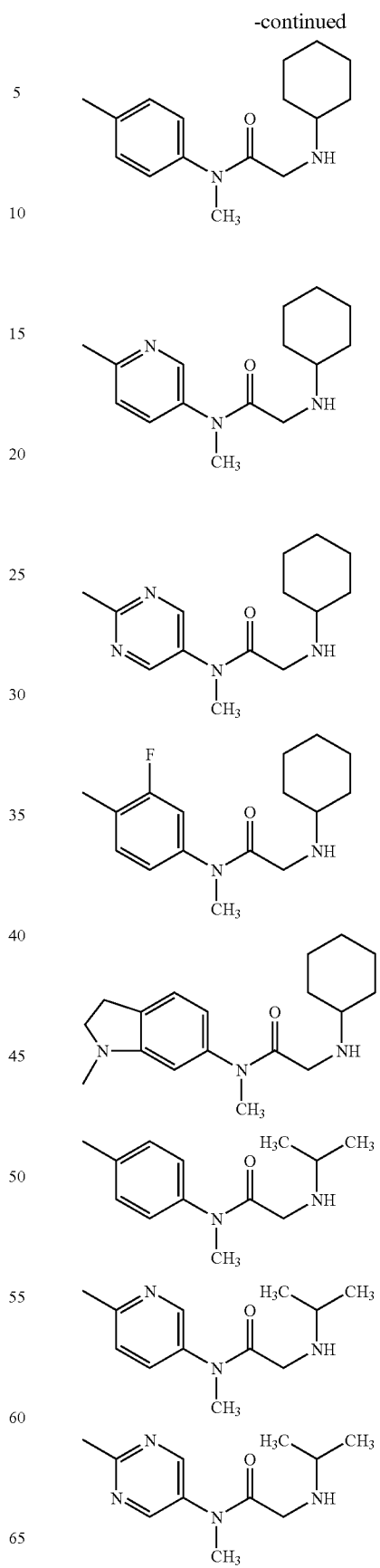

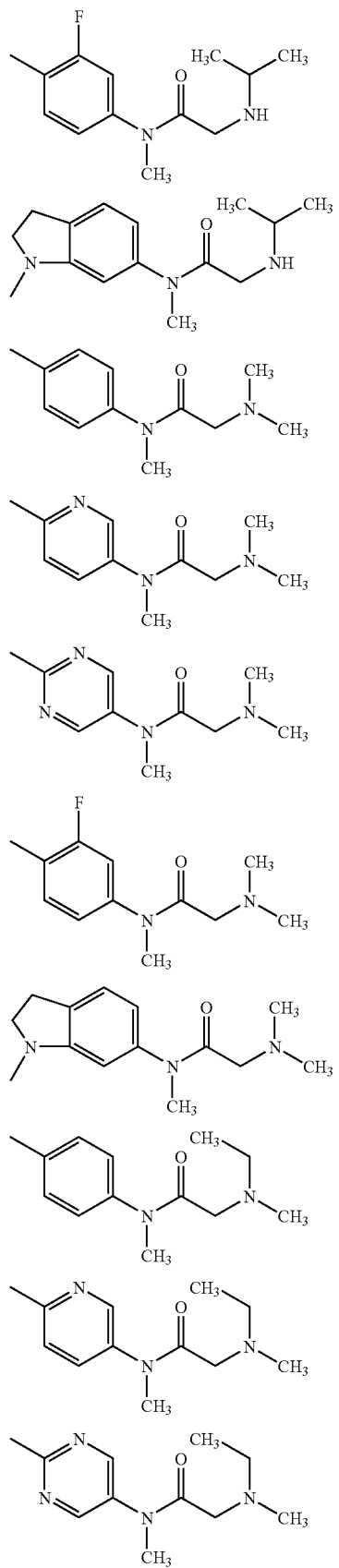
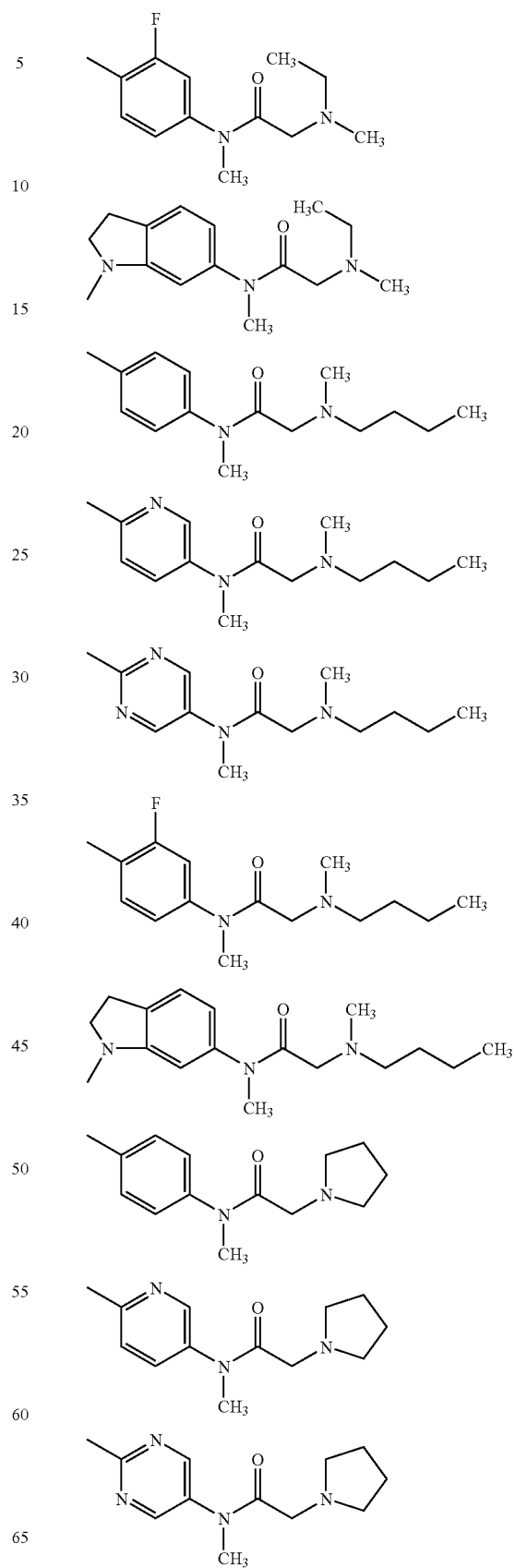

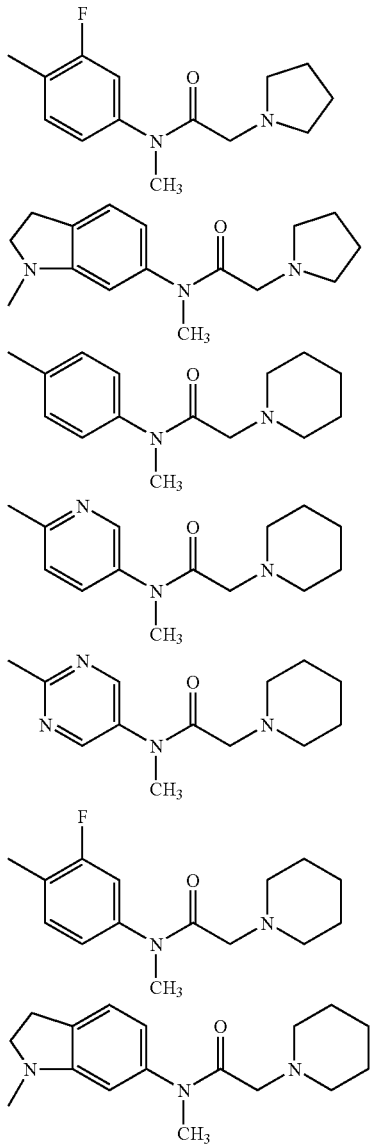

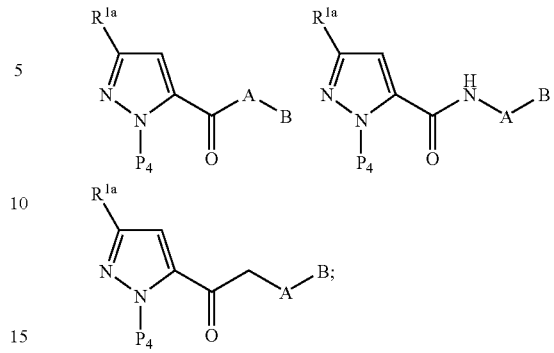

P$_4$ is -G.

[15] In another preferred embodiment, the present invention provides a novel compound, wherein the compound is selected from the group:
1-(3-amino-1,2-benzisoxazol-5-yl)-5-({5-[N,N-dimethylglycyl(methyl)amino]-2,3-dihydro-1H-indol-1-yl}carbonyl)-1H-pyrazole-3-carboxamide;
1-(3-amino-1,2-benzisoxazol-5-yl)-5-({6-[N,N-dimethylglycyl(methyl)amino]-2,3-dihydro-1H-indol-1-yl}carbonyl)-1H-pyrazole-3-carboxamide;
3-Chloro-1H-indole-6-carboxylic acid (2-{4-[methyl-(2-pyrrolidin-1-yl-acetyl)-amino]-benzoylamino}-cyclohexyl)-amide;
5-Chloro-1H-indole-2-carboxylic acid (2-{4-[methyl-(2-pyrrolidin-1-yl-acetyl)-amino]-benzoylamino}-cyclohexyl)-amide;
5-Chloro-thiophene-2-carboxylic acid (2-{4-[methyl-(2-pyrrolidin-1-yl-acetyl)-amino]-benzoylamino}-cyclohexyl)-amide;
4-Methoxy-phenylcarboxylic acid (2-{4-[methyl-(2-pyrrolidin-1-yl-acetyl)-amino]-benzoylamino}-cyclohexyl)-amide;
5-chloro-N-(5-chloropyridin-2-yl)-2-({4-[methyl(pyrrolidin-1-ylacetyl)amino]benzyl}amino)benzamide;
5-chloro-N-(5-chloropyridin-2-yl)-2-({4-[(N,N-dimethylglycyl)(methyl)amino]benzyl}amino)benzamide;
2-({4-[acetyl(methyl)amino]benzyl}amino)-5-chloro-N-(5-chloropyridin-2-yl)benzamide;
N-(5-chloropyridin-2-yl)-2-({4-[(N,N-dimethylglycyl)(methyl)amino]benzyl}amino)-5-methylbenzamide;
N-(5-chloropyridin-2-yl)-2-({4-[(N,N-dimethylglycyl)(methyl)amino]benzyl}amino)-5-methoxybenzamide;
N-(5-chloropyridin-2-yl)-2-({4-[(N,N-dimethylglycyl)(methyl)amino]-benzyl}amino)benzamide;
5-chloro-N-(5-chloropyridin-2-yl)-2-({4-[methyl(pyrrolidin-1-ylacetyl)amino]benzoyl}amino)benzamide;
5-chloro-N-(5-chloropyridin-2-yl)-2-({4-[(N,N-dimethylglycyl)(methyl)amino]benzoyl}amino)benzamide;
5-chloro-N-(5-chloropyridin-2-yl)-2-(methyl{4-[(morpholin-4-ylacetyl)amino]benzoyl}amino)benzamide;
2-[{4-[(N-butyl-N-methylglycyl)amino]benzoyl}(methyl)amino]-5-chloro-N-(5-chloropyridin-2-yl)benzamide;
2-({4-[acetyl(methyl)amino]benzoyl}amino)-N-(5-chloropyridin-2-yl)-5-methylbenzamide;
N-(5-chloropyridin-2-yl)-5-methyl-2-({4-[methyl(morpholin-4-ylacetyl)amino]benzoyl}amino)benzamide;
N-(5-chloropyridin-2-yl)-5-methoxy-2-({4-[methyl(pyrrolidin-1-ylacetyl)amino]benzoyl}amino)benzamide;

R$^{2d}$, at each occurrence, is selected from H, R$^{4c}$, C$_{1-4}$ alkyl substituted with 0–1 R$^{4c}$, cyclopropyl, cyclobutyl, cyclopentyl, cyclohexyl, phenyl, and a 5–6 membered aromatic heterocycle consisting of: carbon atoms and 1–4 heteroatoms selected from the group consisting of N, O, and S(O)$_p$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_{1-4}$ alkyl substituted with 0–1 R$^{4c}$, cyclopropyl, cyclobutyl, cyclopentyl, cyclohexyl, phenyl, and 5–6 membered aromatic heterocycle consisting of: carbon atoms and 1–4 heteroatoms selected from the group consisting of N, O, and S(O)$_p$, provided that R$_{2e}$ forms other than a C(O)-halo or C(O)—S(O)$_p$ moiety.

[14] In another preferred embodiment, the present invention provides a novel compound, wherein the compound is selected from:

2-({4-[acetyl(methyl)amino]benzoyl}amino)-N-(5-chloropyridin-2-yl)benzamide;

N-(5-chloropyridin-2-yl)-2-({4-[(N,N-dimethylglycyl)(methyl)amino]benzoyl}amino)-5-methoxybenzamide;

N-(5-chloropyridin-2-yl)-2-({4-[(N,N-dimethylglycyl)(methyl)amino]benzoyl}amino)benzamide;

2-({4-[acetyl(methyl)amino]benzoyl}amino)-5-chloro-N-(5-chloropyridin-2-yl)benzamide;

N-{4-[6-Chloro-3-(5-chloro-pyridin-2-yl)-4-oxo-3,4-dihydro-quinazolin-2-yl]-phenyl}-2-dimethylamino-N-methyl-acetamide;

N-{4-[6-Chloro-3-(5-chloro-pyridin-2-yl)-4-oxo-3,4-dihydro-quinazolin-2-yl]-phenyl}-N-methyl-2-morpholin-4-yl-acetamide;

2-(Butyl-methyl-amino)-N-{4-[6-chloro-3-(5-chloro-pyridin-2-yl)-4-oxo-3,4-dihydro-quinazolin-2-yl]-phenyl}-N-methyl-acetamide;

$N^1$-{4-[6-chloro-3-(5-chloropyridin-2-yl)-4-oxo-3,4-dihydroquinazolin-2-yl]phenyl}-$N^1$,$N^2$-dimethylglycinamide;

$N^1$-{4-[6-chloro-3-(5-chloropyridin-2-yl)-4-oxo-3,4-dihydroquinazolin-2-yl]phenyl}-$N^2$-cyclobutyl-$N^1$-methylglycinamide;

N-(5-chloropyridin-2-yl)-2-({4-[methyl(pyrrolidin-1-ylacetyl)amino]benzoyl}amino)benzamide;

N-(5-chloropyridin-2-yl)-5-fluoro-2-({4-[methyl(pyrrolidin-1-ylacetyl)amino]benzoyl}amino)benzamide;

N-(5-chloropyridin-2-yl)-2-({4-[(N,N-dimethylglycyl)(methyl)amino]benzoyl}amino)-5-fluorobenzamide;

N-(5-chloropyridin-2-yl)-2-({4-[(N,N-dimethylglycyl)(methyl)amino]benzoyl}amino)-3-methoxybenzamide;

N-(5-chloropyridin-2-yl)-5-methyl-2-({4-[methyl(pyrrolidin-1-ylacetyl)amino]benzoyl}amino)benzamide;

N-(5-chloropyridin-2-yl)-2-({4-[(N,N-dimethylglycyl)(methyl)amino]benzoyl}amino)-5-methylbenzamide;

2-({4-[acetyl(methyl)amino]benzoyl}amino)-N-(5-chloropyridin-2-yl)-5-methoxybenzamide;

N-(5-chloropyridin-2-yl)-2-({4-[(N,N-dimethylglycyl)(methyl)amino]benzoyl}amino)-4,5-difluorobenzamide;

N-(5-chloropyridin-2-yl)-5-methoxy-2-({4-[methyl(piperidin-1-ylacetyl)amino]benzoyl}amino)benzamide;

N-(5-chloropyridin-2-yl)-5-methyl-2-({4-[methyl(piperidin-1-ylacetyl)amino]benzoyl}amino)benzamide;

5-chloro-N-(5-chloropyridin-2-yl)-2-({4-[methyl(N-methylglycyl)amino]benzoyl}amino)benzamide;

5-chloro-N-(5-chloropyridin-2-yl)-2-({4-[(N-cyclobutylglycyl)(methyl)amino]benzoyl}amino)benzamide;

N-(5-chloropyridin-2-yl)-2-({4-[methyl(piperidin-1-ylacetyl)amino]benzoyl}amino)benzamide;

N-(5-chloropyridin-2-yl)-5-fluoro-2-({4-[methyl(piperidin-1-ylacetyl)amino]benzoyl}amino)benzamide;

2-({4-[(N-butyl-N-methylglycyl)(methyl)amino]benzoyl}amino)-N-(5-chloropyridin-2-yl)-5-methoxybenzamide;

2-({4-[(N-butyl-N-methylglycyl)(methyl)amino]benzoyl}amino)-N-(5-chloropyridin-2-yl)-5-fluorobenzamide;

2-({4-[(N-butyl-N-methylglycyl)(methyl)amino]benzoyl}amino)-N-(5-chloropyridin-2-yl)benzamide;

N-(5-chloropyridin-2-yl)-5-methoxy-2-({4-[methyl(N-methylglycyl)amino]benzoyl}amino)benzamide;

N-(5-chloropyridin-2-yl)-2-({4-[(N-cyclobutylglycyl)(methyl)amino]benzoyl}amino)-5-methoxybenzamide;

N-(5-chloropyridin-2-yl)-2-({4-[methyl(N-methylglycyl)amino]benzoyl}amino)benzamide;

2-({4-[(N-butyl-N-methylglycyl)(methyl)amino]benzoyl}amino)-N-(5-chloropyridin-2-yl)-5-methylbenzamide;

N-(5-chloropyridin-2-yl)-2-({4-[(N-ethyl-N-methylglycyl)(methyl)amino]benzoyl}amino)-5-methoxybenzamide;

N-(5-chloropyridin-2-yl)-2-({4-[(N-ethyl-N-methylglycyl)(methyl)amino]benzoyl}amino)-5-methylbenzamide;

N-(5-chloropyridin-2-yl)-2-({4-[(N-ethyl-N-methylglycyl)(methyl)amino]benzoyl}amino)benzamide;

N-(5-chloropyridin-2-yl)-2-({4-[(N-ethyl-N-methylglycyl)(methyl)amino]benzoyl}amino)-5-fluorobenzamide;

N-(5-chloropyridin-2-yl)-5-methyl-2-({4-[(pyrrolidin-1-ylacetyl)amino]benzoyl}amino)benzamide;

N-(5-chloropyridin-2-yl)-5-fluoro-2-({4-[(pyrrolidin-1-ylacetyl)amino]benzoyl}amino)benzamide;

N-(5-chloropyridin-2-yl)-2-({4-[(N,N-dimethylglycyl)amino]benzoyl}amino)-5-methylbenzamide;

N-(5-chloropyridin-2-yl)-5-methoxy-2-({4-[(pyrrolidin-1-ylacetyl)amino]benzoyl}amino)benzamide;

N-(5-chloropyridin-2-yl)-2-({4-[(N-cyclobutylglycyl)(methyl)amino]benzoyl}amino)benzamide;

or a pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used for the treatment of a thromboembolic disorder.

In another preferred embodiment, the present invention provides a novel article of manufacture, further comprising:
(d) a second container;
wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic disorder.

In another preferred embodiment, the present invention provides a novel article of manufacture, further comprising:
(d) a second container;
wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with an oxidizing agent (e.g., MCPBA and/or hydrogen peroxides) to afford other compounds of this invention. Thus, all shown and claimed amines are considered to cover both the shown amine and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactionsare performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

The synthesis of compounds of the present invention that involves the usage of intermediate A-B is accomplished via methods known to those skilled in the art. The general route that involves this type of methodology is outlined in Scheme Scheme 1

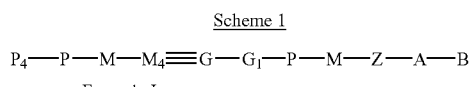
Formula I

↑ NH$_2$—A—B, HO—A—B,
HS—A—B, ClCH$_2$—A—B
Standard Couplings

G—G$_1$—P—M—(acid chloride, acid, sulfonylchloride, amino, alkylhahide, etc)
Formula Ia A-B intermediates can be obtained via Ullman or Buchwald methodologies that are outlined in the schemes below.

Scheme 2

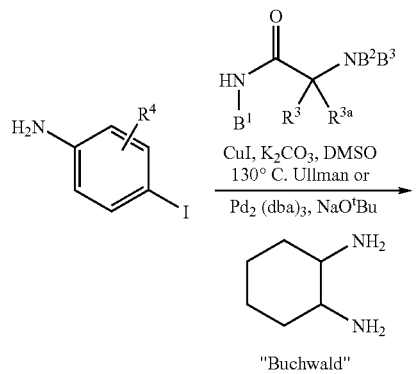
"Buchwald"

-continued

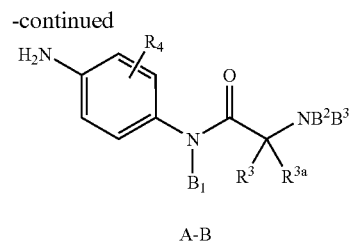
A-B

The methodologies described in Scheme 2 can also be applied to amide homologues such as NH(B$^1$)C(O)C(R$^3$R$^{3a}$)$_{2-4}$NB$^2$B$^3$ to afford other compounds of this invention. The intermediates A-B can also be prepared from readily available nitro anilines as shown in Scheme 3.

Scheme 3

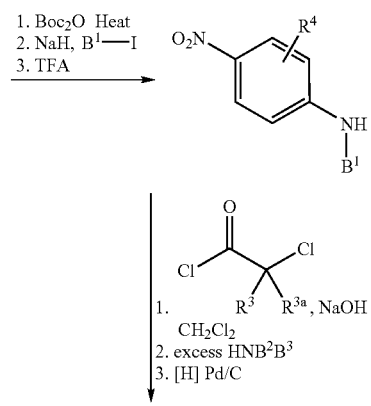

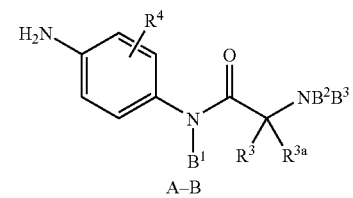
A–B

The methodologies described in Scheme 3 can also be applied to amide homologues such as NH(B$^1$)C(O)C(R$^3$R$^{3a}$)$_{2-4}$NB$^2$B$^3$ to afford other compounds of this invention. The methodologies shown in scheme 2 and 3 can also afford the pyridyl and pyrimidyl analogs shown below.

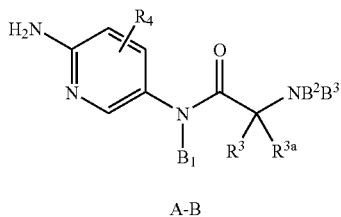
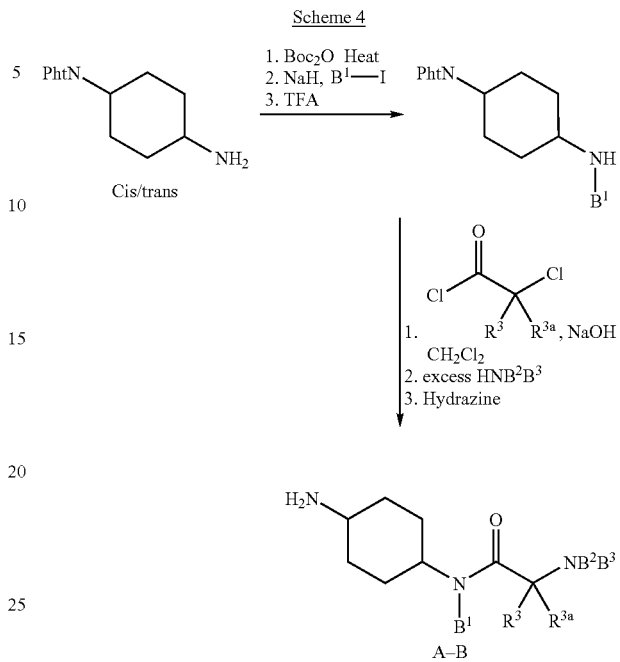
Finally, non-aromatic intermediates A-B (Scheme 4) of this invention can also be synthesized via the procedures shown in Scheme 3.
Other non-aromatic intermediates can be synthesized via procedures known to those skilled in the art, e.g., see Scheme 5. Further modifications of the ester functionality can be done via procedures described above.
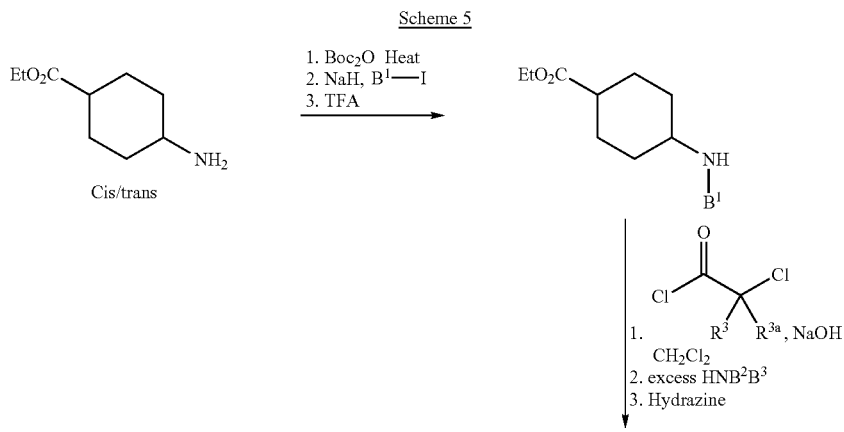

-continued

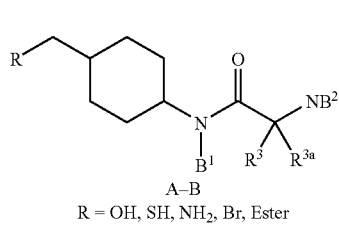 ⇌ 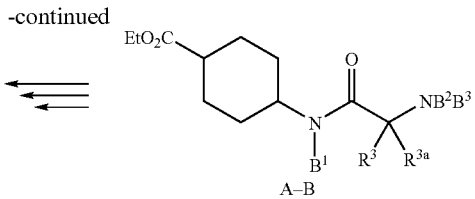

In a similar manner, other benzo A-B intermediates of this invention can be synthesized from readily available amino benzoates or iodo benzoates (Scheme 6).

The remaining portions of the compounds of the present invention, G-G$_1$-P-M-Z, G-G$_1$-M-P-Z, G-G$_1$-P-M, G-G$_1$-M-P, G-G$_1$-M-Z, and G-G$_1$-M, can be prepared using meth- Scheme 6

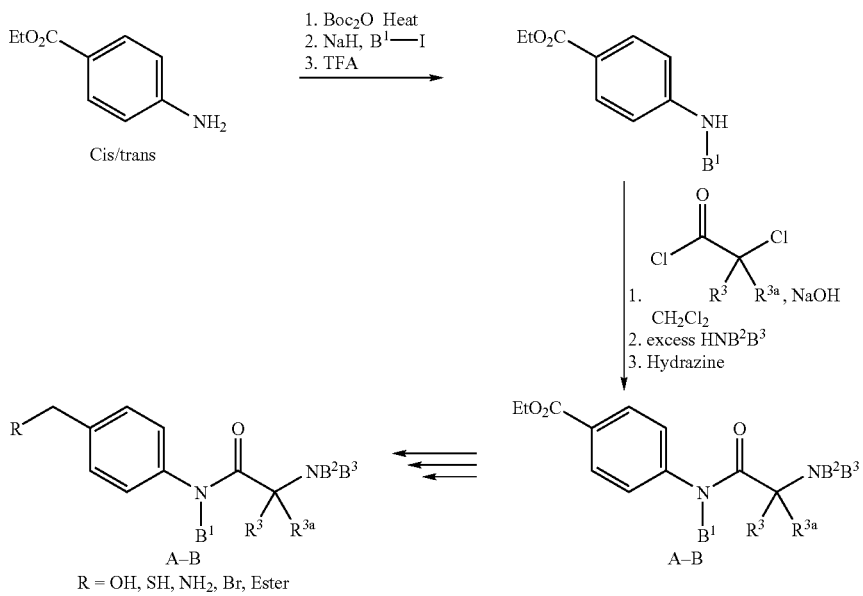

The intermediates prepared above can be suitably coupled to other intermediates P$_4$-P-M-V wherein V is either a carboxylic acid, acid chloride, amino, sulfonylchloride, alkyl halide to obtain other compounds of this invention.

Alternatively compounds of this invention can be synthesized via the procedures described in Schemes 2 and 3 using the more fully elaborated intermediates shown below.

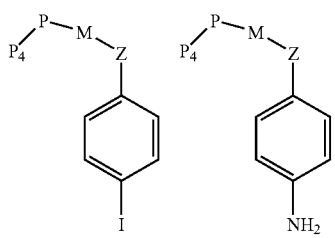

For the iodo intermediate shown above, either the Ullman or the Buchwald procedures described in Scheme 2 should afford compounds of this invention. For the anilino intermediate, utilization of the step-wise methodology shown in Scheme 3 should afford other compounds of this invention.

ods known to those of ordinary skill in the art. All of the following patents and publications are incorporated herein by reference. For compounds wherein ring P is absent and ring M is a 5-, 6-, or 7-membered ring, one of ordinary skill in the art can look to U.S. Pat. No. 5,939,418, U.S. Pat. No. 5,925,635, U.S. Pat. No. 6,057,342, U.S. Pat. No. 6,187,797, U.S. Pat. No. 6,020,357, U.S. Pat. No. 6,060,491, U.S. Pat. No. 5,998,424, U.S. Pat. No. 6,191,159, WO98/57951, WO99/32454, WO00/039,108, WO00/059,902, WO01/32628, WO01/005785, U.S. Ser. No. 09/892,319, U.S. Ser. No. 60/313,552, U.S. Ser. No. 60/246,108, and U.S. Ser. No. 09/887,936 for starting materials and intermediates to which the present B and/or A-B groups can be coupled. For compounds wherein ring P is fused to ring M (i.e., a bicyclic moiety is present), one of ordinary skill in the art can look to WO00/39131, U.S. Ser. No. 60/246,125, U.S. Ser. No. 60/292,665, U.S. Ser. No. 60/278,173, U.S. Ser. No. 60/278,165, and U.S. Ser. No. 09/887,850 for starting materials and intermediates to which the present B and/or A-B groups can be coupled.

For compounds wherein G is a ring substituted with a basic moiety, one of ordinary skill in the art can look to U.S. Pat. No. 5,939,418, U.S. Pat. No. 5,925,635, U.S. Pat. No. 6,057,342, U.S. Pat. No. 6,187,797, U.S. Pat. No. 6,020,357, U.S. Pat. No. 6,060,491, U.S. Pat. No. 6,191,159, WO98/57951, WO99/32454 WO00/059902, WO01/32628, WO00/39131, U.S. Ser. No. 09/892,319, U.S. Ser. No. 60/313,552, U.S. Ser. No. 60/246,108, U.S. Ser. No. 60/246,125, U.S. Ser. No. 60/292,665, U.S. Ser. No. 60/278,173, and U.S. Ser. No. 60/278,165 for starting materials and intermediates to form the present G-$G_1$-P-M-Z, G-$G_1$-M-P-Z, G-$G_1$-P-M-Z-A, and/or G-$G_1$-M-P-Z-A groups to which the present B and/or A-B groups can be coupled. For compounds wherein G is a ring substituted with a non-basic group, one of ordinary skill in the art can look to U.S. Pat. No. 5,998,424, WO00/39131, WO00/059,902, WO01/32628, U.S. Ser. No. 09/892,319, U.S. Ser. No. 60/313,552, U.S. Ser. No. 60/246,108, U.S. Ser. No. 60/246,125, U.S. Ser. No. 60/292,665, U.S. Ser. No. 60/278,173, and U.S. Ser. No. 60/278,165 for starting materials and intermediates to form the present G-$G_1$-P-M-Z, G-$G_1$-M-P-Z, G-$G_1$-P-M-Z-A, and/or G-$G_1$-M-P-Z-A groups to which the present B and/or A-B groups can be coupled. For compounds wherein G is a bicyclic moiety, one of ordinary skill in the art can look to WO98/57951 WO00/039,108, WO00/39131, U.S. Ser. No. 09/892,319, U.S. Ser. No. 60/313,552, U.S. Ser. No. 60/246,108, U.S. Ser. No. 60/246,125, U.S. Ser. No. 60/292,665, U.S. Ser. No. 60/278,173, and U.S. Ser. No. 60/278,165 for starting materials and intermediates to form the present G-$G_1$-P-M-Z, G-$G_1$-M-P-Z, G-$G_1$-P-M-Z-A, and/or G-$G_1$-M-P-Z-A groups to which the present B and/or A-B groups can be coupled. For compounds wherein A is an indoline or similar bicycle, one of ordinary skill in the art can look to WO01/005785 for starting materials and intermediates to which the present B group can be coupled or from which the present A-B groups can be formed. Scheme 7 illustrates some of the numerous pyrrole intermediates that can be used to prepare compounds of the present invention ($R^z$ is the point of attachment for Z-A-B and can be H, a protecting group, a group modifiable to Z or Z-A, Z, Z-A, or A). These intermediates are described in the above-noted patents and publications.

Scheme 8 illustrates some of the numerous imidazole, triazole, and tetrazole intermediates that can be used to prepare compounds of the present invention. These intermediates are described in the above-noted patents and publications. In Scheme 8, V is nitro, amino, thio, hydroxy, sulfonic acid, sulfonic ester, sulfonyl chloride, ester, acid, or halide. In Scheme 8, U is aldehyde, ester, acid, amide, amino, thio, hydroxy, sulfonic acid, sulfonic ester, sulfonyl chloride, or methylene halide.

Scheme 7

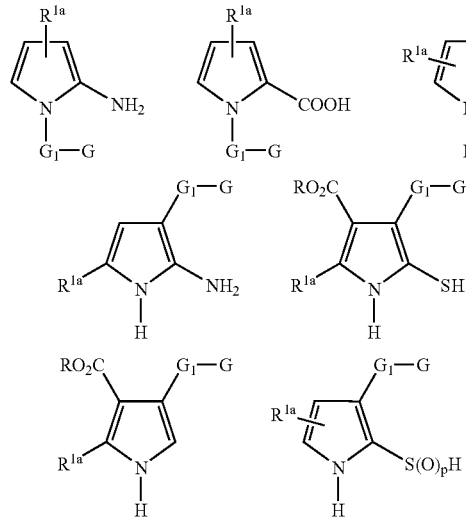

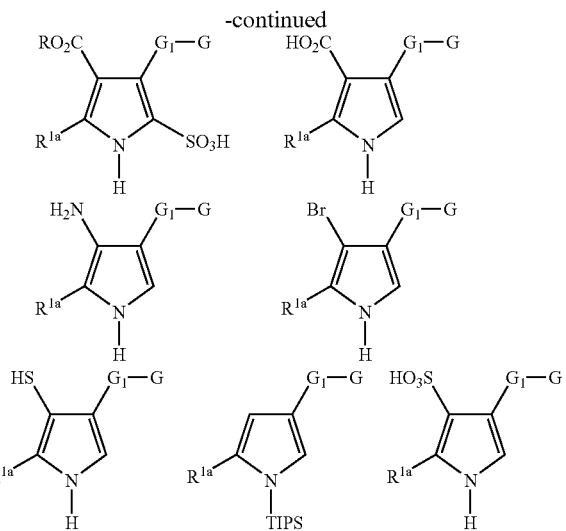

Scheme 8

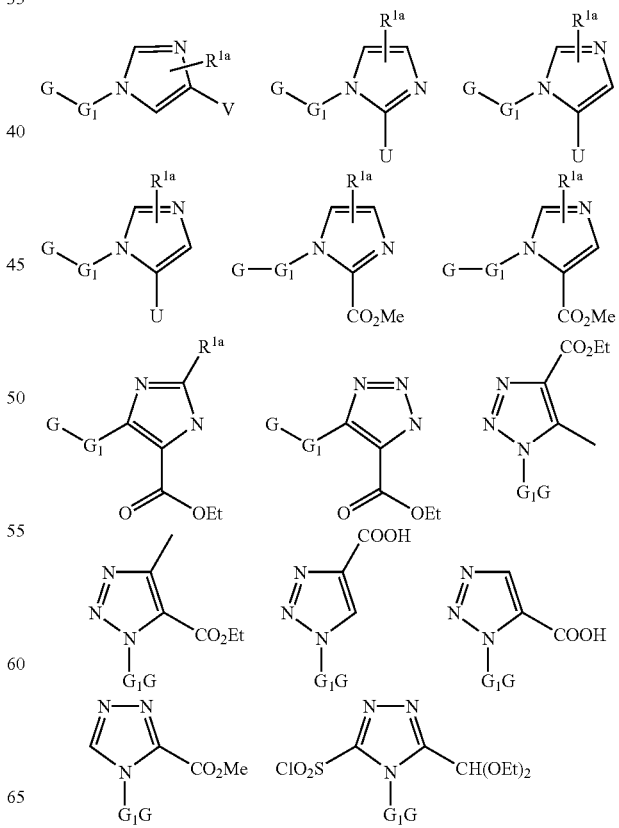

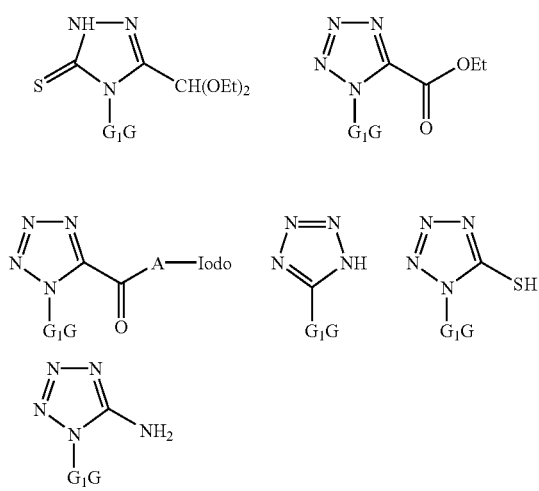

Scheme 9 shows some of the numerous pyrazole intermediates that can be used to prepare compounds of the present invention. These intermediates are described in the above-noted patents and publications.

Scheme 9

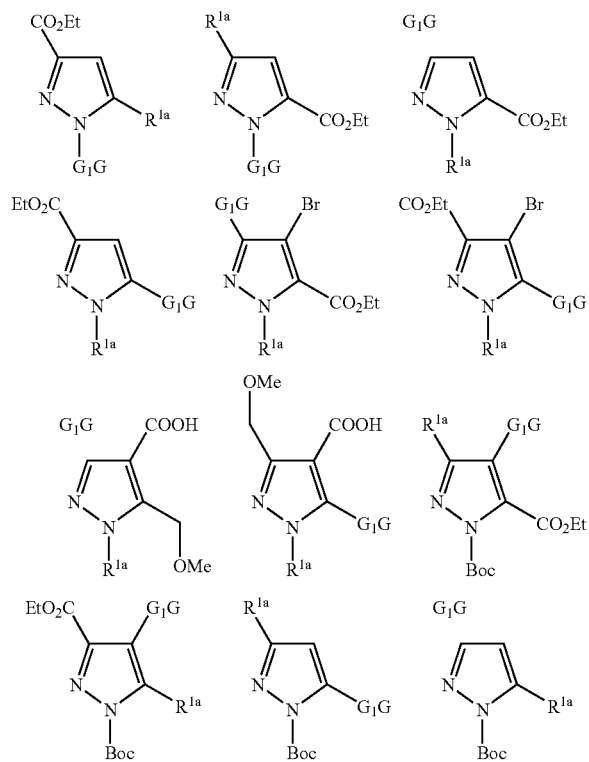

Scheme 10 depicts some of the numerous oxazole, thiazole, isoxazole, oxadiazole, and thiadiazole intermediates that can be used to prepare compounds of the present invention. These intermediates are described in the above-noted patents and publications. In Scheme 10, V is nitro, amino, ester, or acid.

Scheme 10

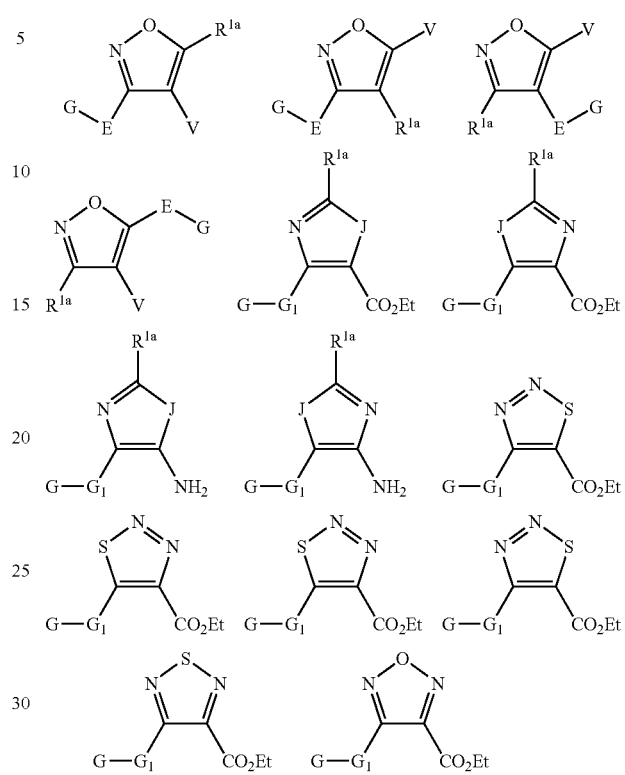

Scheme 11 illustrates two intermediates useful for making a compound of the present invention wherein ring P is fused to ring M. Scheme 11 also illustrates a number of bicyclic compounds that can be made from these intermediates or derivatives thereof. These intermediates and their modification are described in the above-noted patents and publications.

Scheme 11

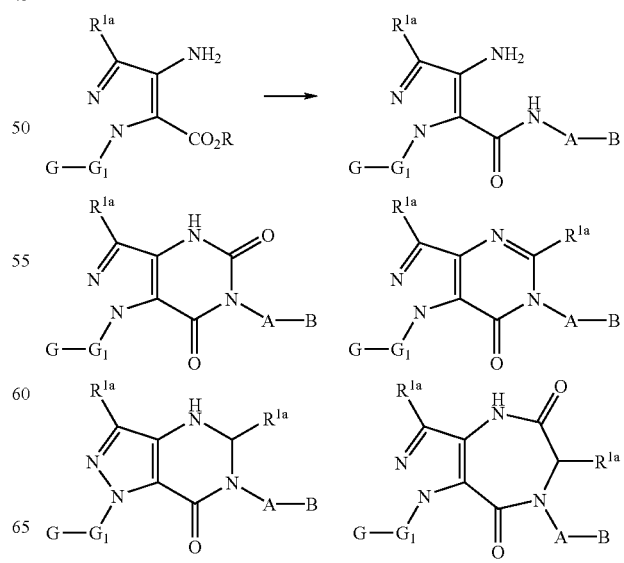

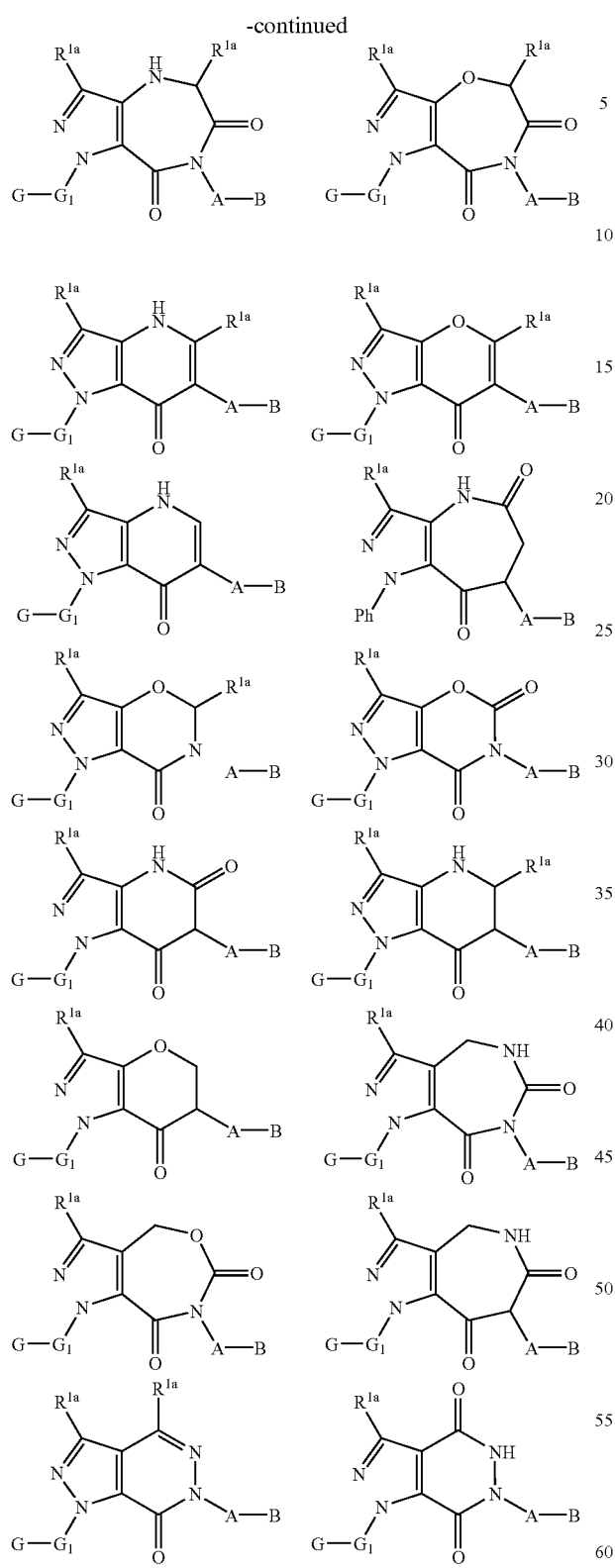

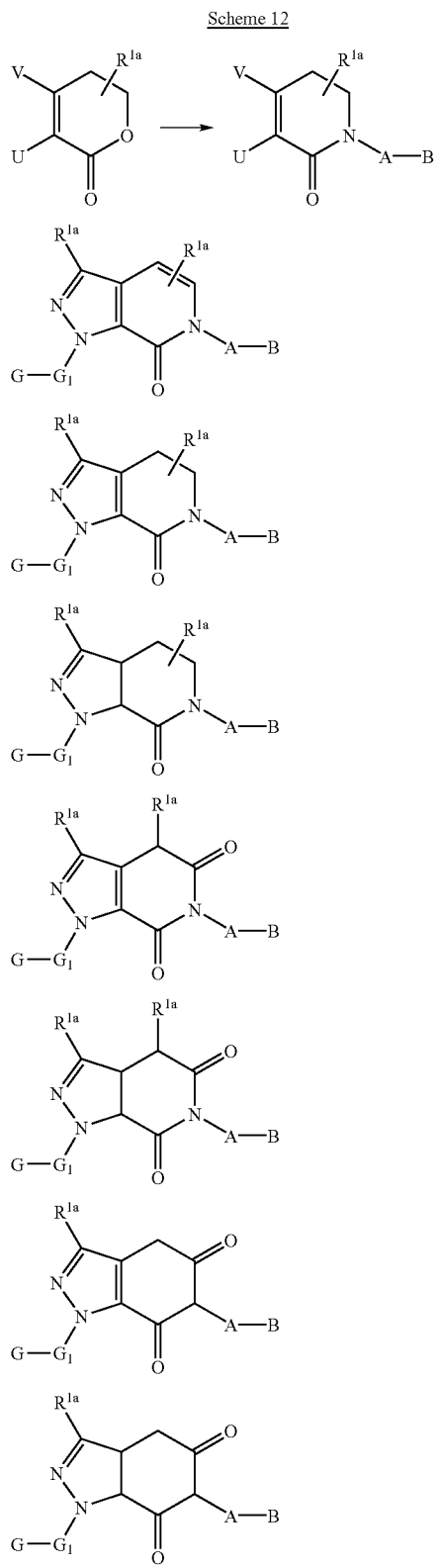

In Scheme 12, U is OH or morpholine and V is H or $C(O)R^{1a}$. This intermediate, derivatives thereof, and their modification are described in the above-noted patents and publications.

Scheme 12 depicts another intermediate useful for making a compound of the present invention wherein ring P is fused to ring M. Scheme 12 also illustrates a number of bicyclic compounds that can be made from this intermediate or derivatives thereof (e.g., the corresponding cyclohexenone).

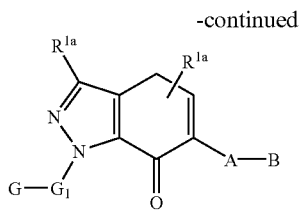
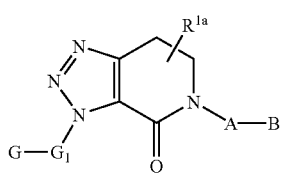
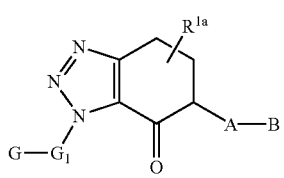
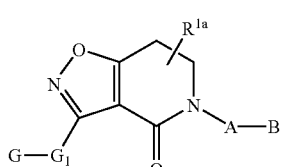
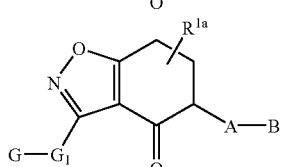
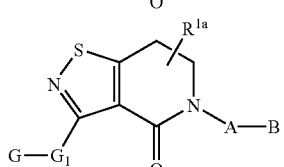
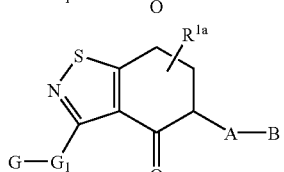
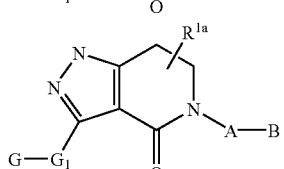
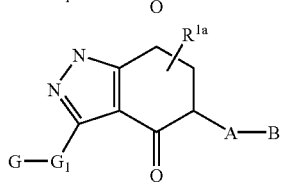

Scheme 13 shows another intermediate useful for making a compound of the present invention wherein ring P is fused to ring M. Scheme 13 also illustrates a number of bicyclic compounds that can be made from this intermediate or derivatives thereof. This intermediate, derivatives thereof, and their modification are described in the above-noted patents and publications.

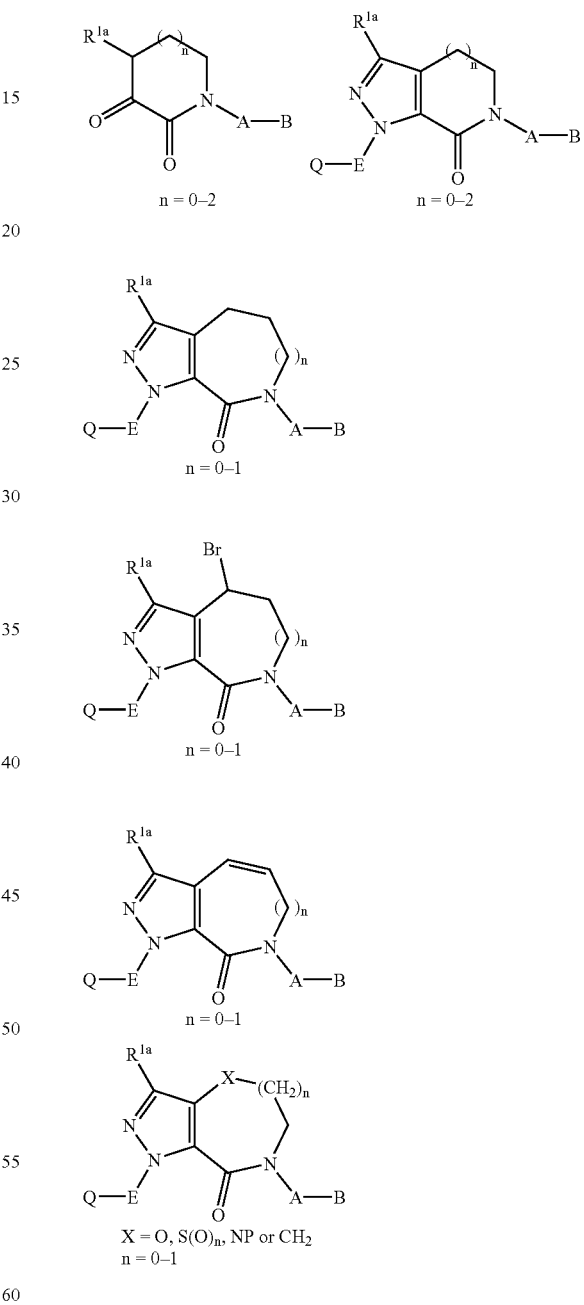

Scheme 14 illustrates a number of other bicyclic rings that are considered to be part of the present bicyclic group, rings P-M. Scheme 14 also describes a method of converting the shown rings to compounds of the present invention. As one of ordinary skill in the art would recognize, this method would be applicable to other heterobicyclics not shown.

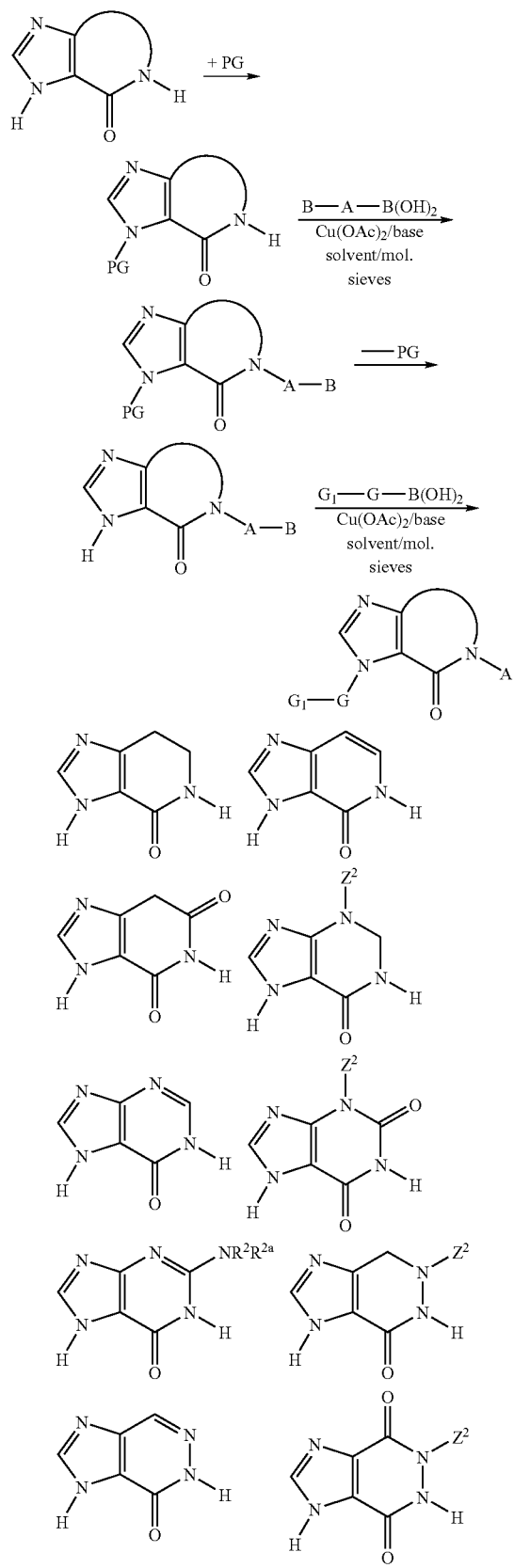

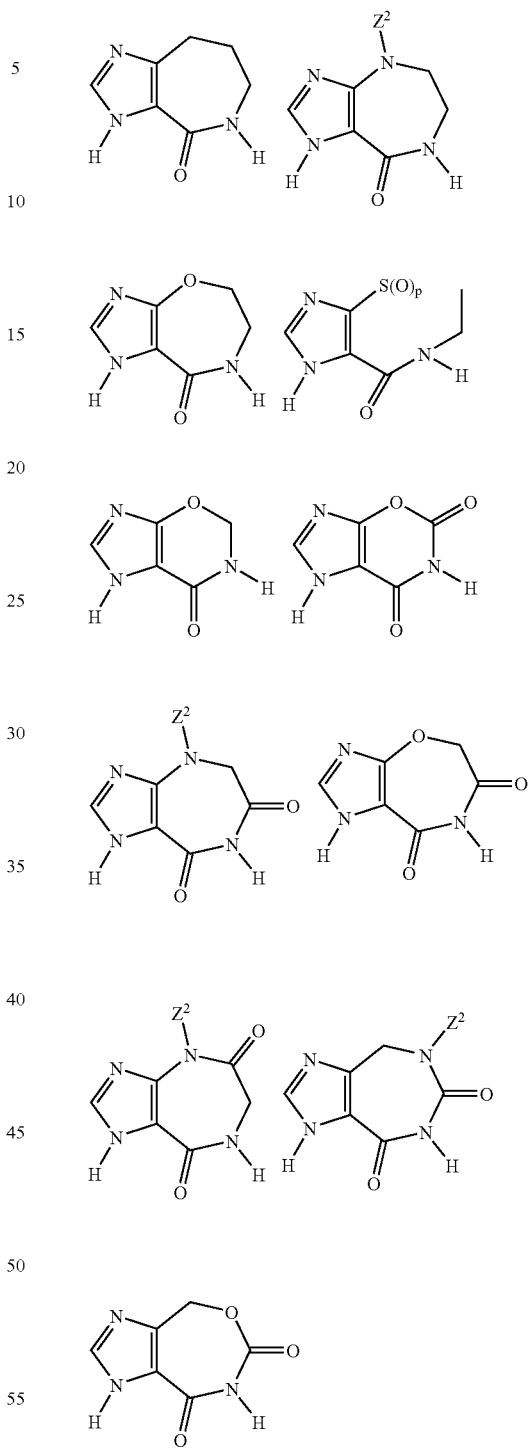

Other useful pyrazole intermediates wherein $G_1$ is an amide are exemplified in Scheme 15. Compounds of the present invention wherein the $G_1$ group is other than an amide can be easily manipulated to other linker functionality's according to the methodologies known in the art, including the methodologies outlined in WO98/28269 and WO98/28282, the contents of both are incorporated herein by reference.

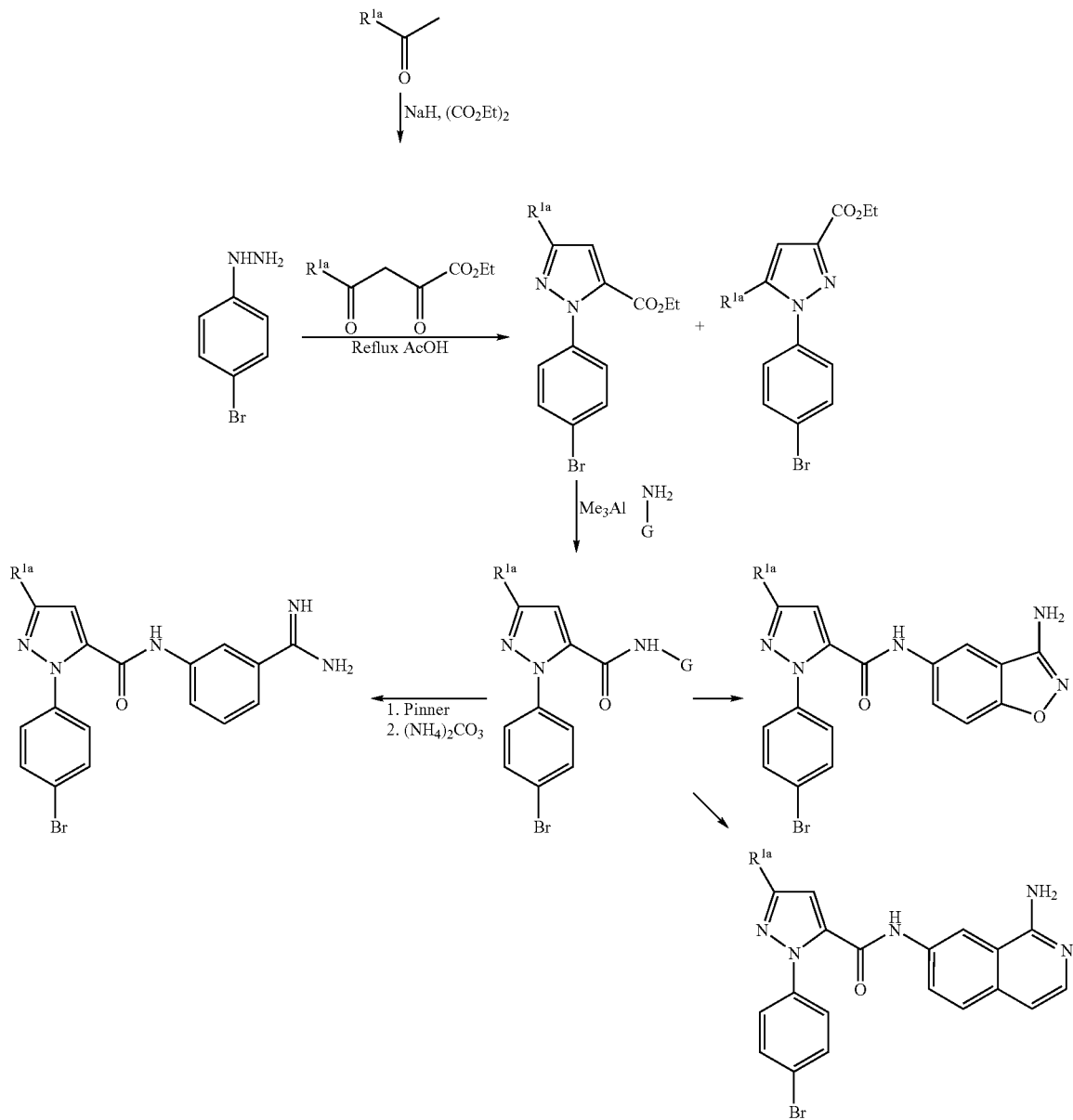
Scheme 15
Scheme 16 depicts some of the numerous 6-membered aromatic ring intermediates that can be used to prepare compounds of the present invention. These intermediates are described in the above-noted patents and publications. In Scheme 16, V is nitro, protected sulfonamide, or ester group and is a precursor of group Z of the present invention.
Scheme 16
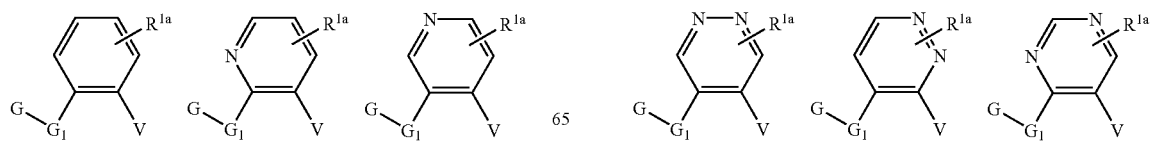
-continued
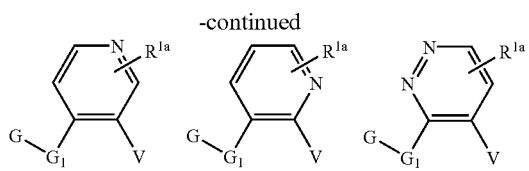

-continued
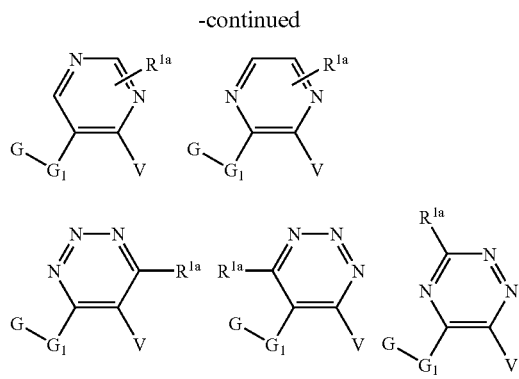
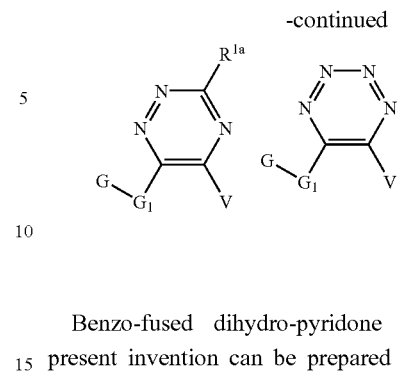
Benzo-fused dihydro-pyridone intermediates of the present invention can be prepared from readily available starting materials as shown in Scheme 17.
Scheme 17
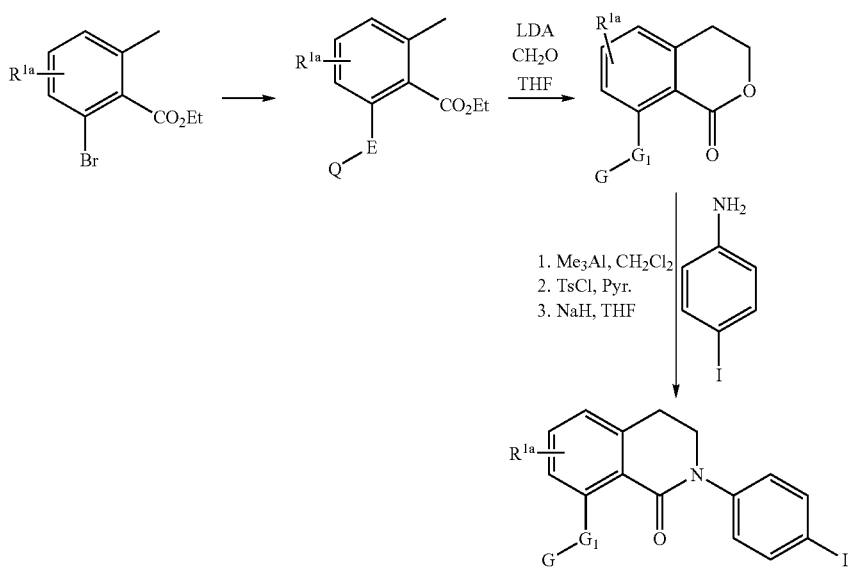
Other benzo-bicyclic compounds can be obtained as shown in schemes 18 and 19.
Scheme 18
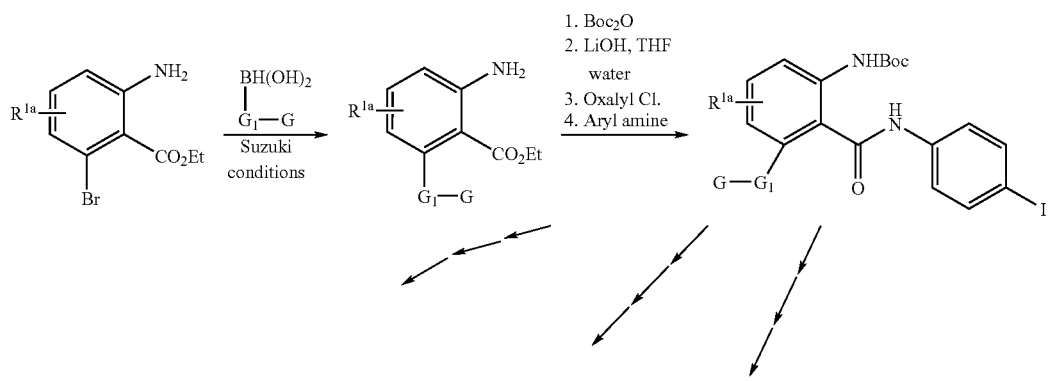

-continued
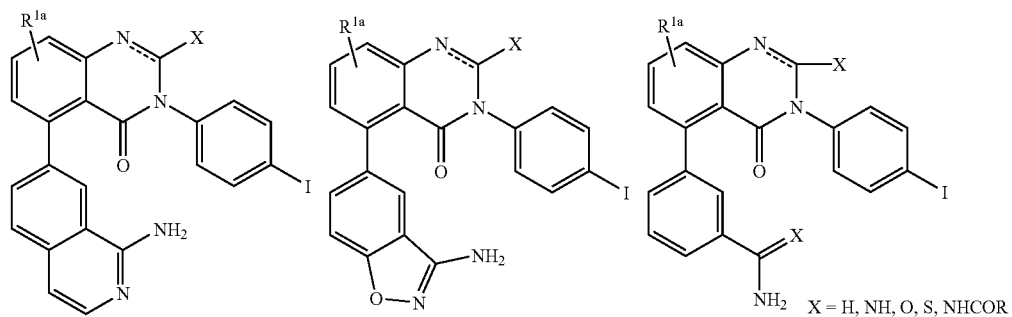
Scheme 19
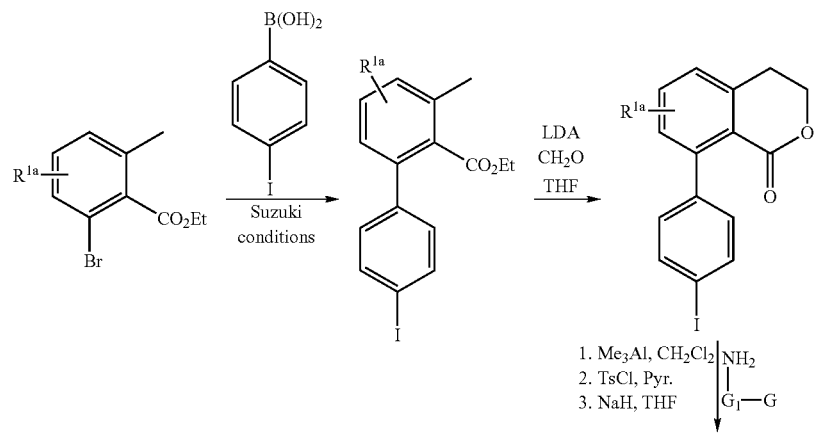
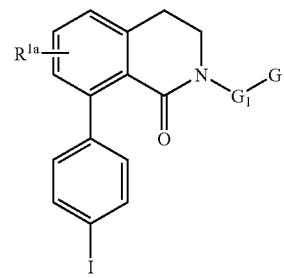
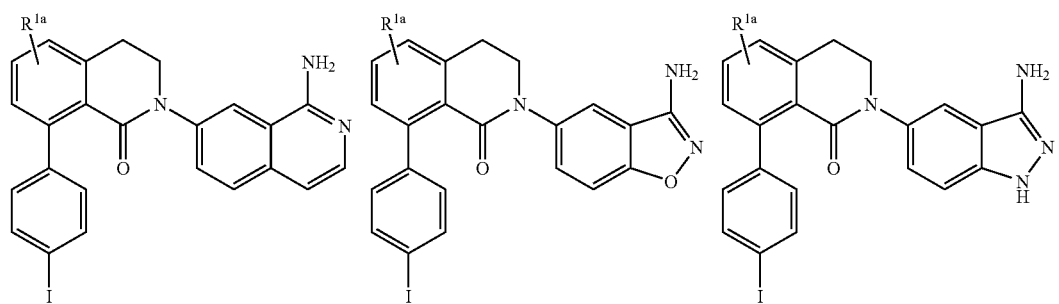

Intermediates A-B of the present invention wherein A is indoline can be prepared as shown in Scheme 20. This type of intermediate can then be attached to the remainder of the desired compound as described previously.

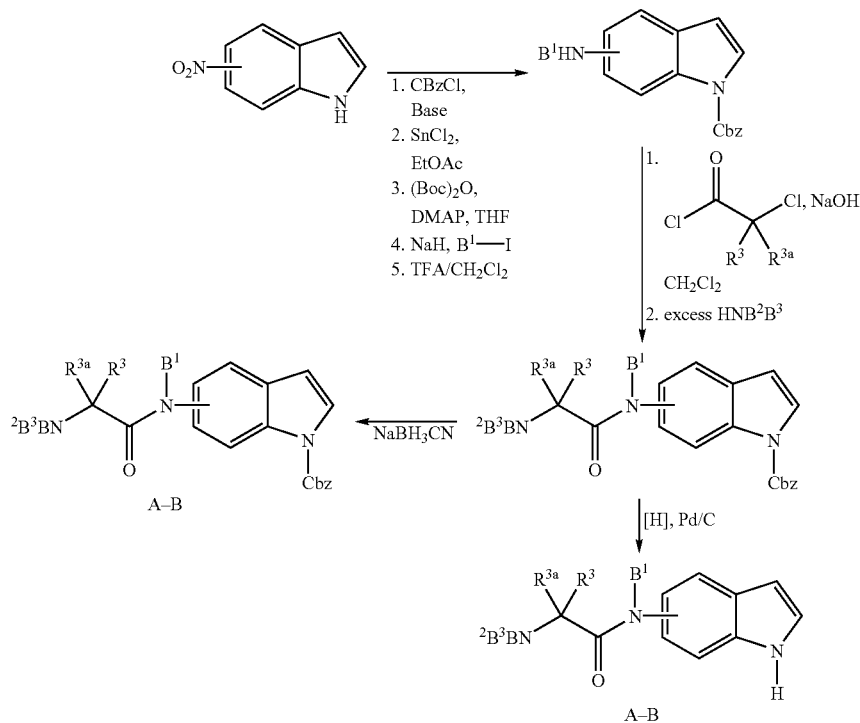

Compounds of the present invention wherein ring P is absent and ring M is a six-membered ring can be obtained as shown in Scheme 21. These types of compounds can be obtained from commercially available anthranilic acids or their anthranilates. Anthranilic acids or their nitro precursors can be coupled with a suitable B-A-V (wherein V is a amino functionality) in presence of a base such as triethylamine, pyridine, or DMAP. Subsequent coupling with an appropriate acid chloride or aniline or aminopyridyl should afford compounds of the present invention.

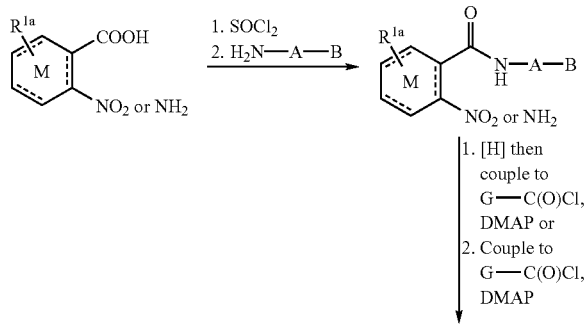

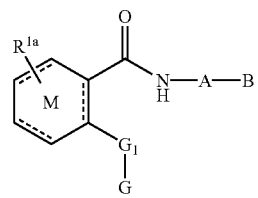

In an analogous fashion the anthranilates can be coupled with a suitable amine, aniline, or aminopyrimidyl to afford the corresponding benzamide. The benzamides can then be coupled with an appropriate B-A-V (wherein V is a acid chloride derivative, an alkyl halide, or a sulfonylchloride) to afford additional compounds of the present invention (see Scheme 22).

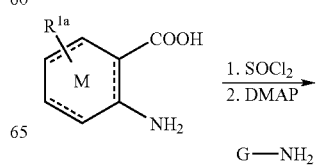

-continued

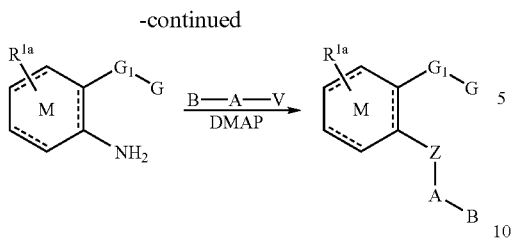

Commercially available ring M derivatives bearing a nitro and amino functionality can also be derivatized as shown above to afford bisamide analogs. In this case, coupling of the aniline with B-A-V (wherein V is an acid chloride, a sulfonylchloride, or an alkylhalide) affords an intermediate that can be subjected to treatment with an appropriate G-U (wherein U is either a acid chloride or an alkyl halide) in presence of a suitable base such as DMAP. It should be noted that the order of addition of B-A-V and G-U can be reversed to obtain other compounds of the present invention (see scheme 23).

Scheme 23

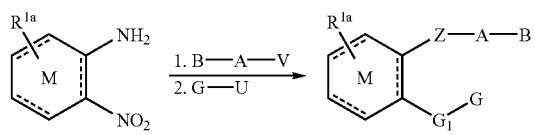

It should be noted that the syntheses shown above could be modified to use coupling intermediates such as Iodo-A-V, wherein V is an acid chloride, amino, alkylhalide, or sulfonylchloride. These in turn could be coupled to a G-U group. The iodo intermediate could then be subjected to Ullman or Buchwald coupling as described previously to afford compounds of the present invention. The iodo intermediate could also be converted to an amine via standard Buchwald conditions to afford the corresponding anilino intermediate. This in turn could be coupled as previously described to afford compounds of the present invention.

When M is a non-aromatic ring, the compounds of this invention with general structure of Formula I can be synthesized by using similar methods as described previously and by those skilled in the art. One diastereomer of a compound of Formula I may display better activity compared with the others. Thus, the following stereochemistries are considered to be a part of the present invention.

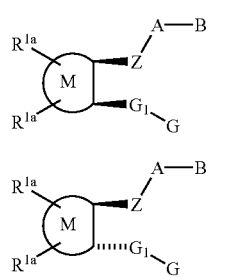

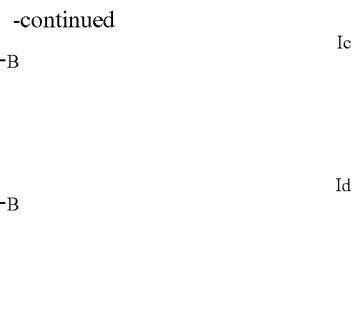

When required, separation of the racemic material can be achieved by HPLC using a chiral column or by a resolution using a resolving agent such as camphonic chloride as in Wilen, S. H. *Tables of Resolving Agents and Optical Resolutions* 1972, 308 pp or using enantiomerically pure acids and bases. A chiral compound of Formula I may also be directly synthesized using a chiral catalyst or a chiral ligand, e.g., Jacobsen, E. *Acc. Chem. Res.* 2000, 33, 421–431 or using other enantio- and diastereo-selective reactions and reagents known to one skilled in the art of asymmetric synthesis.

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, atrial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/ Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1 + S/K_m))$$

where:
- $v_o$ is the velocity of the control in the absence of inhibitor;
- $v_s$ is the velocity in the presence of inhibitor;
- I is the concentration of inhibitor;
- $K_i$ is the dissociation constant of the enzyme:inhibitor complex;
- S is the concentration of substrate;
- $K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM. Using the methodology described above, a number of compounds of the present invention were found to exhibit $K_i$'s of $\leq 10$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein, and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method ddscribed by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, IN) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat a thromboembolic condition or disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K⁺ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, and spironolactone.

Examples of suitable mineralocorticoid receptor antagonists for use in combination with the compounds of the present invention include spironolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguamides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguamide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Compounds of the present invention may further be useful as diagnostic agents and adjuncts. For example, the present compounds may be useful in maintaining whole and fractionated blood in the fluid phase such as required for analytical and biological testing.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences,* 18th ed., Mack Publishing Company, Easton, Pa., 1990, a standard reference text in this field.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but ratheR is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Example 1

3-[6-{4-[(N,N-dimethylglycyl)(methyl)amino]phenyl}-7-oxo-3-(trifluoromethyl)-4,5,6,7-tetrahydro-1H-pyrazolo[3,4-c]pyridin-1-yl]benzamide trifluoroacetic acid salt

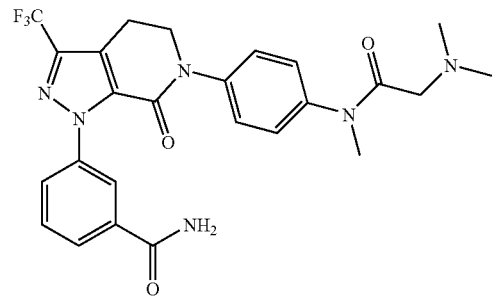

Part A. 3-Aminobenzamide (5.0 g, 36.8 mmol) and 100 mL of conc. HCl were stirred together at 0° C. and sodium nitrite (3.04 g, 44.1 mmol) in 25 mL of water was added slowly. The mixture was stirred for 30 min at 0° C. and then a solution of tin (II) chloride dihydrate (24.9 g, 110.3 mmol) in 40 mL water/40 mL conc. HCl was added and the reaction was stirred for 2 hours at 0° C. The precipitate was filtered and dried under high vacuum overnight to afford the HCl salt of the corresponding hydrazine (9.6 g, quantitative). LRMS (ES$^+$) 152.0 (M+H)$^+$.

Part B. The hydrazine made above (5.26 g, 28.12 mmol) was added to 3-hydroxy-1-(4-iodophenyl)-4-(trifluoroacetyl)-5,6-dihydro-2(1H)-pyridinone (4.64 g, 14.06 mmol) along with 125 mL of conc. HOAc and the resulting mixture was refluxed overnight. The reaction was then cooled and the HOAc was removed in vacuo. The residue was dissolved in EtOAc and washed 2 times with water then once with brine. It was dried over sodium sulfate and evaporated to afford the cyclic pyrazole amide (6.79 g, 54% yield). LRMS (ES$^-$) 445.2 (M−).

Part C. The cyclic pyrazole amide from above (6.79 g, 15.2 mmol) was stirred together with tin (II) chloride dihydrate (10.33 g, 15.2 mmol) and 100 mL of MeOHovernight at rt. The solvent was stripped off and the solid dissolved in CHCl$_3$ and washed with water and brine, dried over sodium sulfate and evaporated to afford the corresponding amine (3.09 g, 49% yield). LRMS (ES$^+$) 416.3 (M+H)$^+$.

Part D. The crude amine (0.50 g, 1.20 mmol) was stirred together with Et$_3$N (0.15 g, 1.44 mmol) and 20 mL of dry THF. To this solution at rt was added dimethylsulfate (0.18 g, 1.44 mmol) and the reaction was refluxed overnight. The reaction was then cooled and evaporated under reduced pressure, dissolved in EtOAc, washed with water and brine and dried over sodium sulfate and evaporated to dryness. The residue was purified via silica gel column chromatography and eluted with 1:1 Hexane/EtOAc to afford the methylated product (0.11 g, 21% yield). LRMS (ES$^+$) 430.2 (M+H)$^+$.

Part E. The methylated pyrazole made above (0.080 g, 0.19 mmol) was dissolved in 3 mL of dry $CH_2Cl_2$ and DMAP was added (0.034 g, 0.28 mmol). The reaction was stirred 5 minutes at rt then chloroacetyl chloride (0.032 g, 0.28 mmol) was added and the reaction was stirred for 4 hours. After the addition of 20 mL of $CH_2Cl_2$, the mixture was transferred to a separatory funnel and washed 3× with 1N HCl. The organic layer was dried over sodium sulfate and evaporated to afford the acylated product (0.060 g, 64% yield). LRMS (ES+Na)$^+$ 528.3.

Part F. The acylated product (0.060 g, 0.12 mmol) was placed in a 20 mL vial with a screw cap along with 1 mL of dry THF, and dimethylamine (2.0 M in THF) (0.60 ml, 10 eq.). The vial was sealed and the reaction stirred at rt overnight. The solvent was removed and the residue dissolved in 2 mL of 1:1 $CH_3CN$/Water. The mixture was then purified by HPLC (C18 reverse phase, eluted with 0.5% TFA in $CH_3CN$/Water) to afford 44 mg of the title compound as a TFA salt (58%). HRMS (ES$^+$) 515.2038 (M+H)$^+$ (99% purity)

Example 2

3-[6-{4-[(N-ethyl-N-methylglycyl)(methyl)amino]phenyl}-7-oxo-3-(trifluoromethyl)-4,5,6,7-tetrahydro-1H-pyrazolo[3,4-c]pyridin-1-yl]benzamide trifluoroacetic acid salt

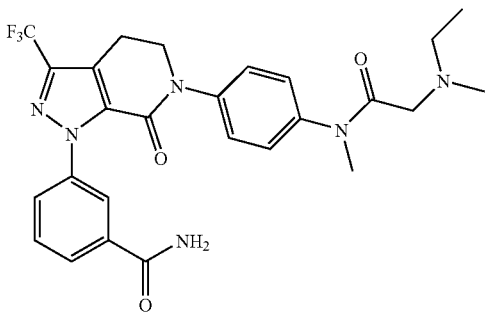

The title compound was prepared according to the procedures described for Example 1 (46% yield). HRMS (ES$^+$) 529.2165 (M+H)$^+$ (98.3% purity).

Example 3

3-[6-{4-[[(3-hydroxy-1-pyrrolidinyl)acetyl](methyl)amino]phenyl}-7-oxo-3-(trifluoromethyl)-4,5,6,7-tetrahydro-1H-pyrazolo[3,4-c]pyridin-1-yl]benzamide trifluoroacetic acid salt

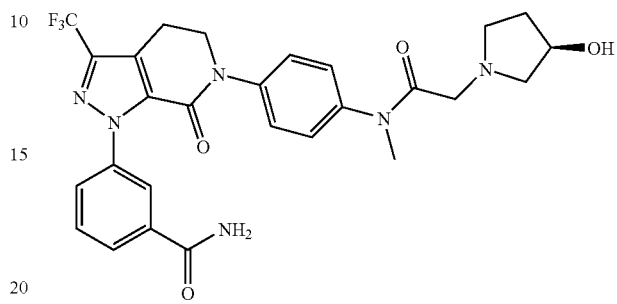

The title compound was prepared according to the procedures described for Example 1 (54% yield). HRMS (ES$^+$) 557.2123 (M+H)$^+$ (99.7% purity).

Example 4

3-[6-{4-[methyl(1-pyrrolidinylacetyl)amino]phenyl}-7-oxo-3-(trifluoromethyl)-4,5,6,7-tetrahydro-1H-pyrazolo[3,4-c]pyridin-1-yl]benzamide trifluoroacetic acid salt

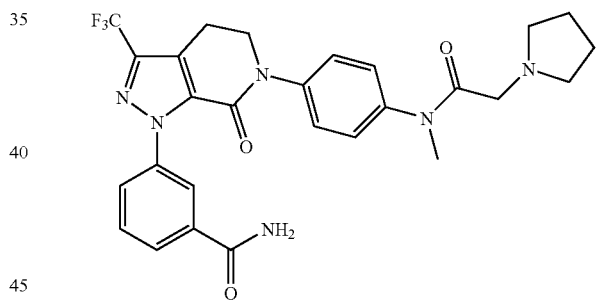

The title compound was prepared according to the procedures described for Example 1 (51% yield). HRMS (ES$^+$) 541.2202 (M+H)$^+$ (97.8% purity).

Example 5

3-[6-{4-[methyl(N-methylglycyl)amino]phenyl}-7-oxo-3-(trifluoromethyl)-4,5,6,7-tetrahydro-1H-pyrazolo[3,4-c]pyridin-1-yl]benzamide trifluoroacetic acid salt

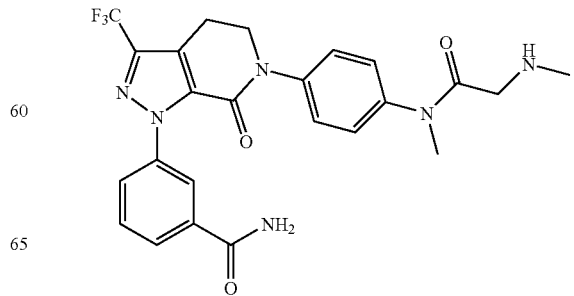

The title compound was prepared according to the procedures described for Example 1 (23% yield). HRMS (ES+) 501.1857 (M+H)+ (89% purity)

Example 6

3-[6-{4-[(N-ethyl-N-propylglycyl)(methyl)amino]phenyl}-7-oxo-3-(trifluoromethyl)-4,5,6,7-tetrahydro-1H-pyrazolo[3,4-c]pyridin-1-yl]benzamide trifluoroacetic acid salt

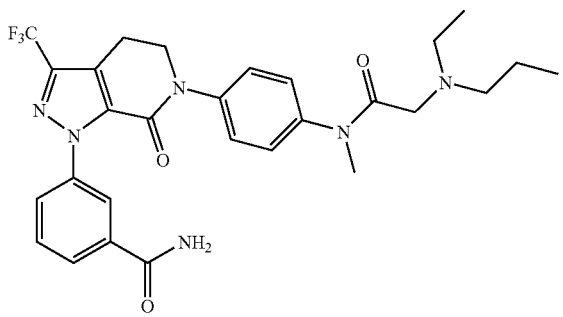

The title compound was prepared according to the procedures described for Example 1 (30% yield). HRMS (ES+) 557.2487 (M+H)+ (99% purity).

Example 7

3-[6-{4-[(N-isopropylglycyl)(methyl)amino]phenyl}-7-oxo-3-(trifluoromethyl)-4,5,6,7-tetrahydro-1H-pyrazolo[3,4-c]pyridin-1-yl]benzamide trifluoroacetic acid salt

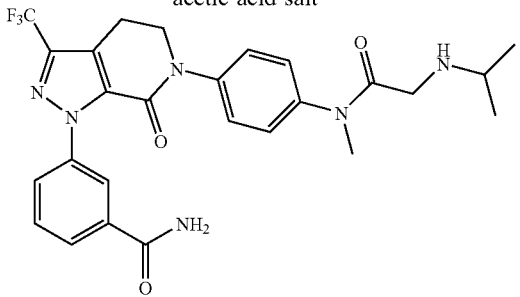

The title compound was prepared according to the procedures described for Example 1 (31% yield). HRMS (ES+) 529.2181 (M+H)+ (97% purity).

Example 8

3-[6-{4-[[(4-hydroxy-1-piperidinyl)acetyl](methyl)amino]phenyl}-7-oxo-3-(trifluoromethyl)-4,5,6,7-tetrahydro-1H-pyrazolo[3,4-c]pyridin-1-yl]benzamide trifluoroacetic acid salt

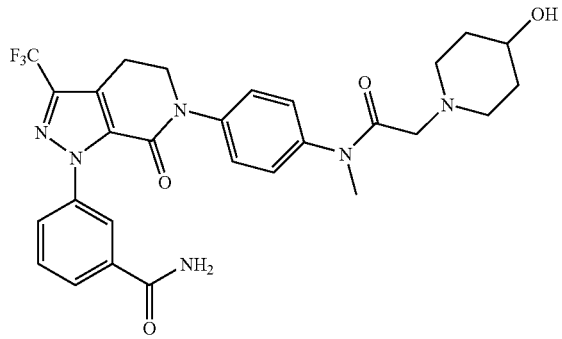

The title compound was prepared according to the procedures described for Example 1 (56% yield). HRMS (ES+) 571.2272 (M+H)+ (97% purity).

Example 9

3-[6-{4-[(N-butyl-N-methylglycyl)(methyl)amino]phenyl}-7-oxo-3-(trifluoromethyl)-4,5,6,7-tetrahydro-1H-pyrazolo[3,4-c]pyridin-1-yl]benzamide trifluoroacetic acid salt

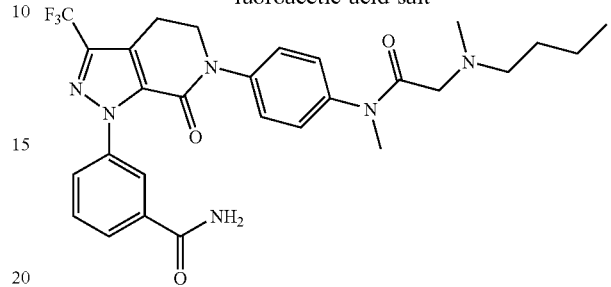

The title compound was prepared according to the procedures described for Example 1 (21% yield). HRMS (ES+) 557.2494 (M+H)+ (94% purity).

Example 10

3-[6-{4-[[N-(2-hydroxyethyl)glycyl](methyl)amino]phenyl}-7-oxo-3-(trifluoromethyl)-4,5,6,7-tetrahydro-1H-pyrazolo[3,4-c]pyridin-1-yl]benzamide trifluoroacetic acid salt

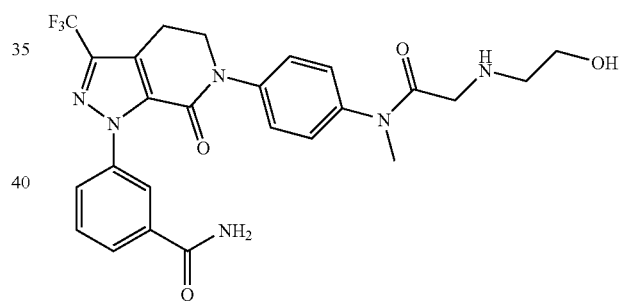

The title compound was prepared according to the procedures described for Example 1 (48% yield). HRMS (ES+) 531.1975 (M+H)+ (97% purity).

Example 11

3-[7-oxo-6-{4-[propyl(1-pyrrolidinylacetyl)amino]phenyl}-3-(trifluoromethyl)-4,5,6,7-tetrahydro-1H-pyrazolo[3,4-c]pyridin-1-yl]benzamide trifluoroacetic acid salt

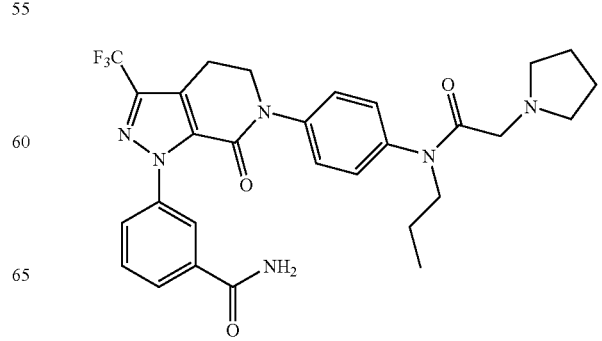

Part A. 3-Aminobenzonitrile (7.03 g, 59.5 mmol) and 75 mL of conc. HCl were stirred together at 0° C. and sodium nitrite (4.92 g, 71.4 mmol) in 40 mL of water was added slowly. The mixture was stirred for 30 min. at 0° C. and then a solution of tin (II) chloride dihydrate (40.3 g, 178.5 mmol) in 40 mL of water/40 mL conc. HCl mixture was added and the reaction stirred for 2 hours at 0° C. The precipitate was filtered and dried under high vacuum overnight to afford the HCl salt of the corresponding hydrazine (11.2 g, quantitative).

Part B. The hydrazine HCl salt made above (6.23 g, 36.8 mmol) was added to 3-hydroxy-1-(4-iodophenyl)-4-(trifluoroacetyl)-5,6-dihydro-2(1H)-pyridinone (6.08 g, 18.4 mmol) along with 200 mL of conc. HOAc and refluxed for 3 hours. The reaction was then cooled and the HOAc was removed under pressure. The residue was dissolved in EtOAc and washed 2× with water then once with brine and evaporated. The residue was placed on a silica gel column and eluted with 1:1 Hexane/EtOAc to afford the cyclic pyrazole nitrile (5.57 g, 71% yield). LRMS (ES+Cl)⁻ 462.3.

Part C. The cyclic pyrazole nitrile from above (5.57 g, 13.0 mmol) was stirred together with 100 mL of MeOH at rt and the reaction vessel was purged and evacuated 3× with $N_2$. After the addition of 10% palladium on carbon (0.56 g), the reaction was placed under a $H_2$ atmosphere at 40 psi for 2.5 hours. The mixture was filtered through Celite®, dried over sodium sulfate and evaporated to afford the corresponding amine (5.2 g, quantitative). LRMS (ES⁺) 398.4 (M+H)⁺.

Part D. The crude amine (0.70 g, 1.76 mmol) was added to 40 mL of THF and Di-tert-butyldicarbonate (0.77 g, 3.53 mmol). The mixture was refluxed overnight. The reaction was then cooled and evaporated to dryness. The residue dissolved in EtOAc, washed with water, and evaporated. The residue was applied to a silica gel column and eluted with 2:1 Hexane/EtOAc to afford the Boc-protected product (0.66 g, 75% yield). LRMS (ES⁺) 498.5 (M+H)⁺.

Part E. The Boc-protected compound from above (0.30 g, 0.60 mmol) was added to an already cooled mixture (0° C.) of 5 mL of dry DMF and NaH (0.072 g, 1.80 mmol) and stirred for 15 minutes. To the mixture was added propyl bromide (0.22 g, 1.80 mmol) and the reaction was allowed to warm to rt overnight. Water was added slowly until no bubbling was present then the mixture transferred to a separatory funnel and extracted 3× with EtOAc. The organic layer was washed 5× with water to remove DMF then evaporated. The residue was placed on a silica gel column and eluted with 2:1 Hexane/EtOAc to yield the alkylated product (0.13 g, 41% yield). LRMS (ES+Na)⁺ 562.5 (M+H)⁺.

Part F. The alkylated product from above (0.13 g, 0.24 mmol) was stirred at rt with 10 mL MeOH, 5 mL 20% NaOH, and 2.5 mL of $H_2O_2$ for 15 minutes. The reaction was quenched with 20 mL of EtOAc and 20 mL of water and the mixture poured into a sep. funnel. The organic layer was washed with water and brine then dried over sodium sulfate and evaporated to yield the m-benzamide product (0.12 g, 92% yield).

Part G. The amide from above (0.12 g, 0.21 mmol) was stirred at rt with 5 mL of TFA for 2 hours then evaporated. The residue was dissolved in $CH_2Cl_2$ and washed with 1N NaOH then brine, dried over sodium sulfate and evaporated to afford the deprotected product (0.080 g, 82% yield). LRMS (ES+Na)⁺ 480.4 (M+H)⁺.

Part H. The crude amine product from above (0.080 g, 0.17 mmol) was stirred together with 3 mL of $CH_2Cl_2$ and DMAP (0.032 g, 0.26 mmol) for 10 minutes then chloroacetyl chloride (0.030 g, 0.26 mmol) was added and the reaction stirred overnight at rt. The mixture was then poured into a separatory funnel and washed with 1N HCl 3× then brine, dried over sodium sulfate and evaporated to afford the acylated product (0.080 g, 86% yield).

Part F. The acylated product from above (0.080 g, 0.15 mmol) was placed in a 20 mL vial with a screw cap along with 3 mL of dry THF, and pyrrolidine (0.053 g, 0.75 mmol). The vial was sealed and the reaction stirred at rt overnight. The solvent was removed and the residue dissolved in 2 mL of 1:1 $CH_3CN$/Water. The mixture was then purified by HPLC (C18 reverse phase, eluted with 0.5% TFA in $CH_3CN$/Water) to afford 47.2 mg of the title compound as a TFA salt (46%). HRMS (ES⁺) 569.2483(M+H)⁺ (98% purity)

Example 12

3-[6-{4-[ethyl(1-pyrrolidinylacetyl)amino]phenyl}-7-oxo-3-(trifluoromethyl)-4,5,6,7-tetrahydro-1H-pyrazolo[3,4-c]pyridin-1-yl]benzamide trifluoroacetic acid salt

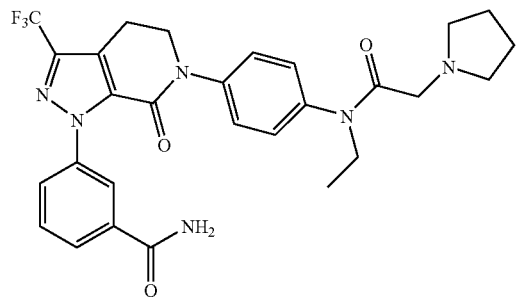

The title compound was prepared according to the procedures described for Example 11. HRMS (ES⁺) 555.2344 (M+H)⁺ (96% purity)

Intermediate A

3-Hydroxy-1-(4-methoxyphenyl)-6-(4-nitrophenyl)-1,4,5,6-tetrahydro-7H-pyrazolo[3,4-c]pyridin-7-one

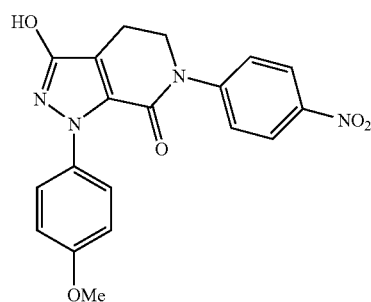

Part A. To solution of 2.42 g of DMAP in 10 mL of methylene chloride was added 1.84 mL of trichloroacetyl chloride at 0° C. After being stirred at rt for 30 min, to the mixture was added 1.0 g of 1-(4-nitrophenyl)-3-(4-morpholinyl)-5,6-dihydro-2(1H)-pyridinone. The reaction mixture was refluxed overnight, quenched with water, and extracted with ether. The organic layers were dried over Na₂SO₄ and concentrated to dryness to provide the crude product that was used in next step without further purification.

Part B. The material made in part A was dissolved in 20 mL of ether, 1 mL of water and 1 mL of conc. HCl. The solution was heated to reflux (Oil bath 65° C.) for 3 h. allowed to cool to rt and filtered to collect the product as a solid (1.09 g, 87% in 2 steps). $^1$H NMR (DMSO-$d_6$, 300 MHz) δ 8.27 (2H, d, J=9.1 Hz), 7.69(2H, d, J=9.1 Hz), 3.98 (2H, t, J=6.6 Hz), 2.91 (2H, t, J=6.6 Hz) ppm.

Part C. A mixture of the 3-hydroxy-1-(4-nitrophenyl)-4-(trifluoroacetyl)-5,6-dihydro-2(1H)-pyridinone made above (4.91 g, 12.94 mmol), p-methoxyphenylhyrazine HCl salt (2.37 g, 13.59 mmol) in 100 mL of THF was treated with 3.62 mL of triethylamine at rt overnight. To the reaction mixture was added 100 mL of 1N HCl. The resulting mixture was refluxed for 2 h. After cool to rt the title compound was collect by filtration (4.5 g, 92%). $^1$H NMR (DMSO-$d_6$, 300 MHz) δ 8.24 (2H, d, J=9.2 Hz), 7.64 (2H, d, J=9.0 Hz), 7.39 (2H, d, J=9.0 Hz), 6.94(2H, t, J=9.2 Hz), 4.13 (2H, t, J=6.6 Hz), 3.77 (3H, s), 2.85 (2H, t, J=6.6 Hz) ppm.

Example 13

N$^1$-{4-[3-methoxy-1-(4-methoxyphenyl)-7-oxo-1,4,5,7-tetrahydro-6H-pyrazolo[3,4-c]pyridin-6-yl]phenyl}-N$^1$,N$^2$,N$^2$-trimethylglycinamide trifluoroacetic acid salt

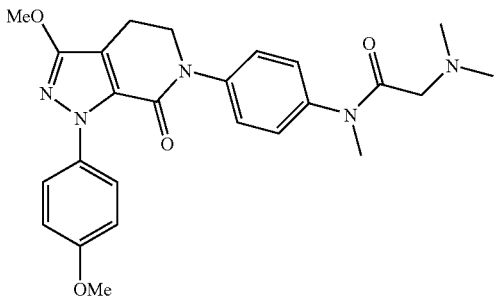

Part. A. To the 3-Hydroxy-1-(4-methoxyphenyl)-6-(4-nitrophenyl)-1,4,5,6-tetrahydro-7H-pyrazolo[3,4-c]pyridin-7-one compound prepared above (3.6 g, 9.47 mmol) was added to a cooled (0° C.) mixture of NaH (60%) (0.57 g, 14.2 mmol) in 50 mL of dry DMF. The mixture was stirred for 10 minutes and then MeI (2.69 g, 18.95 mmol) was added. The reaction was allowed to warm to rt over 2 hours. Water was slowly added until bubbling had completely stopped then the mixture was transferred to a separatory funnel and extracted 3× with EtOAc. The organic layer was washed 5× with water to remove DMF then dried over sodium sulfate and evaporated to afford the dimethoxy intermediate (3.35 g, 90% yield). LRMS (ES$^+$) 395.4 (M+H)$^+$.

Part B. The dimethoxy compound from above (1.42 g, 3.60 mmol) was dissolved in 40 mL of MeOH and the reaction vessel was purged and evacuated 3× with N$_2$. After the addition of 0.142 g of 10% Pd/C, the vessel was then placed under a H$_2$ atmosphere at 40 psi and stirred at rt for 3 hours. The mixture was filtered through Celite®, evaporated, and placed on a silica gel column eluting with 1:1 Hexane/EtOAc to 2:1 EtOAc/Hexane to afford the amine (0.78 g, 59% yield). LRMS (ES$^+$) 365.4 (M+H)$^+$.

Part C. The product from part B (0.78 g, 2.14 mmol) was refluxed overnight with 20 mL of THF and di-tert-butyl dicarbonate (1.40 g, 6.43 mmol). The reaction was then cooled, evaporated, stirred with toluene and evaporated 3× to remove butanol. The residue was placed on a silica gel column and eluted with 2:1 Hexane/EtOAc to afford the BOC protected intermediate (1.22 g, quantitative). LRMS (ES$^+$) 465.4 (M+H)$^+$.

Part D. The BOC-protected compound from part C (0.55 g, 1.18 mmol) was added to a cooled mixture (0° C.) of 5 mL dry DMF and NaH (0.14 g, 3.55 mmol). The reaction was stirred for 10 minutes then MeI (0.50 g, 3.55 mmol) was added and the reaction was allowed to warm to rt overnight. Water was slowly added until no bubbling was evident then the mixture was poured into a separatory funnel and extracted with EtOAc 3×. The organic layer was washed 5× with water to remove the DMF. The organic layer was dried over sodium sulfate and evaporated to afford the alkylated product (0.46 g, 80% yield). LRMS (AP$^+$) 479.2 (M+H)$^+$.

Part E. The alkylated product from part D (0.46 g, 0.96 mmol) was stirred at rt in TFA for 2 hours concentrated, dissolved in CH$_2$Cl$_2$, washed with 1N NaOH 3×, dried over sodium sulfate and evaporated to afford the deprotected dimethoxy amino compound (0.37 g, quantitative). LRMS (ES$^+$) 379.4 (M+H)$^+$.

Part F. The free amino compound from part E (0.37 g, 0.98 mmol) was stirred together with 5 mL of dry CH$_2$Cl$_2$ and DMAP (0.18 g, 1.47 mmol) at rt for 10 minutes. A solution of chloroacetyl chloride (0.16 g, 1.47 mmol) in 2 mL of CH$_2$Cl$_2$ was added and the reaction was stirred at rt for 2.5 hours. Then the reaction was transferred to a separatory funnel and washed with 1N HCl 3× then brine, dried over sodium sulfate and evaporated to afford the dimethoxy amide compound (0.33 g, 75% yield). LRMS (ES$^+$) 455.3 (M+H)$^+$.

Part G. The dimethoxy amide compound from part F (0.066 g, 0.14 mmol) was placed in a 20 mL vial with a screw cap along with 2 mL of dry THF and dimethylamine solution (2.0M, 0.70 ml, 10 eq.). The mixture was stirred overnight at rt then 1 mL of CH$_3$CN and 2–3 drops of TFA were added and the resulting mixture was purified by HPLC (C18 reverse phase, eluted with 0.5% TFA in CH$_3$CN/Water) to afford the TFA salt of the title product (21 mg, 31% yield). HRMS (ES$^+$) 464.2305 (M+H)$^+$ (78% purity).

Example 14

N-{4-[3-methoxy-1-(4-methoxyphenyl)-7-oxo-1,4,5,7-tetrahydro-6H-pyrazolo[3,4-c]pyridin-6-yl]phenyl}-N-methyl-2-(1-pyrrolidinyl)acetamide trifluoroacetic acid salt

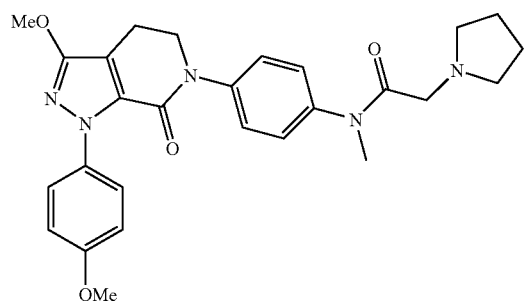

The title compound was prepared according to the procedure described for Example 13 (32% yield). HRMS(ES+) 490.2459 (M+H)+ (74% purity).

Example 15

N²-ethyl-N1-{4-[3-methoxy-1-(4-methoxyphenyl)-7-oxo-1,4,5,7-tetrahydro-6H-pyrazolo[3,4-c]pyridin-6-yl]phenyl}-N¹,N²-dimethylglycinamide trifluoroacetic acid salt

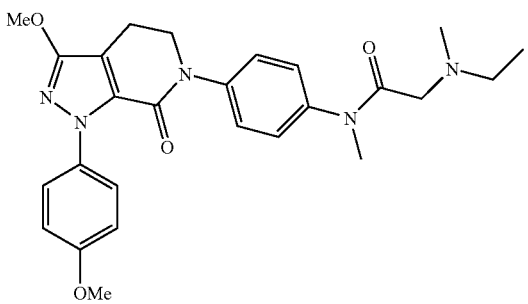

The title compound was prepared according to the procedure described for Example 13 (25% yield). HRMS(ES+) 478.2464 (M+H)+ (98% purity).

Example 16

2-(3-hydroxy-1-pyrrolidinyl)-N-{4-[3-methoxy-1-(4-methoxyphenyl)-7-oxo-1,4,5,7-tetrahydro-6H-pyrazolo[3,4-c]pyridin-6-yl]phenyl}-N-methylacetamide trifluoroacetic acid salt

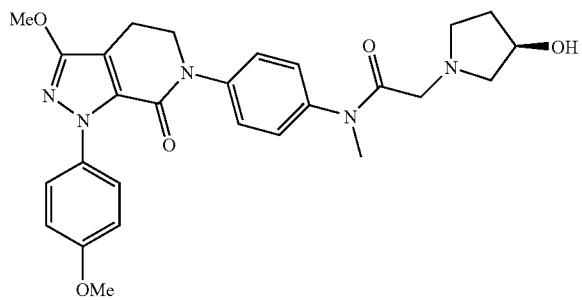

The title compound was prepared according to the procedure described for Example 13 (20% yield). HRMS(ES+) 506.2433 (M+H)+ (83% purity).

Example 17

N²-isopropyl-N¹-{4-[3-methoxy-1-(4-methoxyphenyl)-7-oxo-1,4,5,7-tetrahydro-6H-pyrazolo[3,4-c]pyridin-6-yl]phenyl}-N¹-methylglycinamide trifluoroacetic acid salt

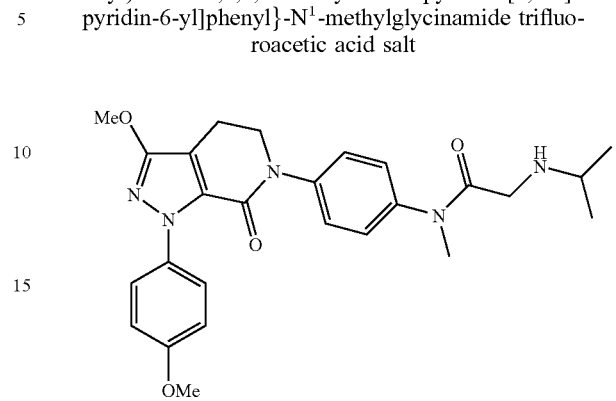

The title compound was prepared according to the procedure described for Example 13 (19% yield). HRMS(ES+) 478.2444 (M+H)+ (82% purity).

Example 18

N²-butyl-N¹-{4-[3-methoxy-1-(4-methoxyphenyl)-7-oxo-1,4,5,7-tetrahydro-6H-pyrazolo[3,4-c]pyridin-6-yl]phenyl}-N¹,N²-dimethylglycinamide trifluoroacetic acid salt

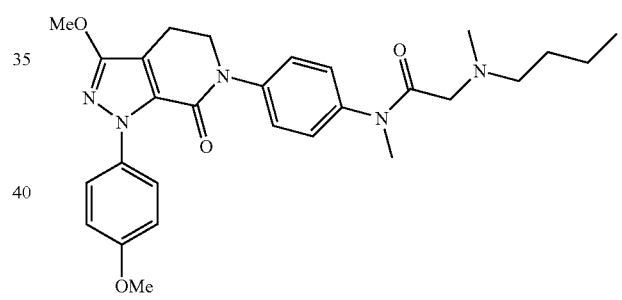

The title compound was prepared according to the procedure described for Example 13 (17% yield). HRMS(ES+) 506.2788 (M+H)+ (75% purity).

Example 19

N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹,N²,N²-trimethylglycinamide trifluoroacetic acid salt

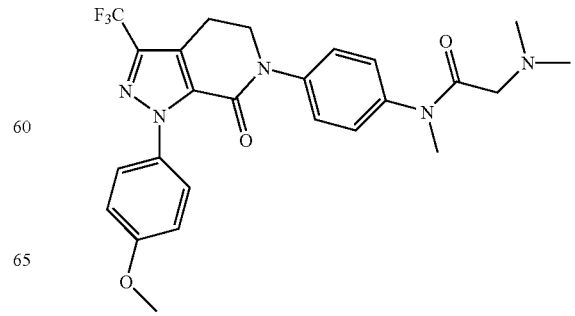

Part A. 4-iodoaniline (45.82 g, 209.2 mmol) and triethylamine (65.61 ml, 470.7 mmol) were dissolved into THF (800 mL) and cooled to 0° C. 5-Bromovaleryl chloride (50.0 g, 251.1 mmol) dissolved in THF (200 mL) was added dropwise to the reaction. The reaction was warmed to room temperature and stirred overnight. Reaction was cooled to 0° C. and potassium tert-butoxide (70.43 g, 627.6 mmol) was slowly added. The reaction was warmed to room temperature and stirred overnight. The reaction was concentrated and then re-dissolved in ethyl acetate (500 mL) and 3N HCl (500 mL), extracted with ethyl acetate (2×250 mL), washed with 1N HCl (3×250 mL), washed with brine (1×250 mL), and dried ($Na_2SO_4$). Purification by silica gel chromatography using 0%–100% ethyl acetate/hexane gradient as eluent to afford 51.03 g (81%): $^1$H NMR ($CDCl_3$) δ 7.70 (d, j=8.4 Hz, 2H), 7.03 (d, j=8.8 Hz, 2H), 3.62 (t, j=5.9 Hz, 2H), 2.56 (t, j=5.7 Hz, 2H), 2.50–1.88 (m, 4H) ppm.

Part B. The product from part A (85.17 g, 282.8 mmol) and phosphorus pentachloride (205.91 g, 990.0 mmol) was dissolved into $CHCl_3$ (750 mL) and refluxed for 3½ hours. Reaction was poured over ice and then quenched further with water, extracted with $CHCl_3$ (3×400 mL), washed with brine (1×400 mL), dried ($MgSO_4$), and concentrated. This residue was dissolved in morpholine (400 mL) and refluxed overnight. Reaction was concentrated and purified by silica gel chromatography using 0%–100% ethyl acetate/hexane gradient as eluent to afford 68 g (63%): $^1$H NMR ($CDCl_3$) δ 7.68 (d, j=8.8 Hz, 2H), 7.11 (d, j=8.8 Hz, 2H), 5.66 (t, j=4.8 Hz, 1H), 3.82 (t, j=4.8 Hz, 4H), 3.77 (t, j=6.8 Hz, 2H), 2.89 (t, j=4.8 Hz, 4H), 2.53–2.47 (m, 2H) ppm.

Part C. 4-Dimethylaminopyridine (3.92 g, 32.01 mmol) was dissolved into $CH_2Cl_2$ (130 mL) and cooled to 0° C. Trifluoroacetic anhydride (4.54 g, 32.01 mmol) was added and the mixture was stirred at 0° C. for 30 min. The above morpholine-enamine from part B (10.25 g, 26.68 mmol) dissolved in $CH_2Cl_2$ (370 mL) was added slowly and the reaction was warmed to room temperature and stirred overnight. Reaction was concentrated and purified by silica gel chromatography using 0%–50% ethyl acetate/hexane gradient to isolate the intermediate. The intermediate was dissolved in 20% HCl (50 mL) and diethyl ether (200 mL) and stirred at room temperature overnight. Reaction was quenched with water, extracted with ether (3×100 mL), washed with brine (1×100 mL), and dried ($Na_2SO_4$). The residue was re-dissolved in petroleum ether and the solids filtered. The filtrate was concentrated to afford 9.99 g (78%): $^1$H NMR ($CDCl_3$) δ 7.77 (d, j=8.8 Hz, 2H), 7.11 (d, j=8.8 Hz, 2H), 3.93 (t, j=6.8 Hz, 2H), 2.92 (t, j=6.8 Hz, 2H) ppm.

Part D. The product from part C (10.0 g, 24.3 mmol) and 4-methoxyhydrazine hydrochloride (4.28 g, 24.3 mmol) were dissolved in 1N HCl (200 mL) and methanol (400 mL) and refluxed overnight. The reaction was cooled to room temperature and quenched with water, extracted with ethyl acetate (3×250 mL), washed with brine (1×250 mL), and dried ($Na_2SO_4$). Purification by silica gel chromatography using 0%–100% ethyl acetate/hexane gradient as eluent afforded 9.28 g (74%); $^1$H NMR ($CDCl_3$) δ 7.69 (d, j=9.4 Hz, 2H), 7.45 (d, j=8.8 Hz, 2H), 7.06 (d, j=8.8 Hz, 2H), 6.92 (d, j=9.2 Hz, 2H), 4.11 (t, j=6.8 Hz, 2H), 3.81 (s, 3H), 3.15 (t, j=6.5 Hz, 2H) ppm; Mass Spec (M+H)$^+$ 514.3.

Part E. To a toluene solution consisting of the product from part D (3.52 g, 6.86 mmol), benzophenone imine (1.49 g, 8.22 mmol), BINAP (0.314 g, 0.343 mmol) and sodium tert-butoxide (1.99 g, 20.70 mmol) was added $Pd_2(dba)_3$. The reaction mixture was heated at gentle reflux overnight, cooled and quenched with water (100 mL). The organics were extracted with ethyl acetate (2×100 mL) and dried (magnesium sulfate). The solution was concentrated to a brown oil which was dissolved in methanol (200 mL), and to this was added hydroxylamine hydrochloride (1.47 g, 21.15 mmol) and sodium acetate (3.47 g, 42.3 mmol). The reaction mixture was stirred at room temperature for 3 h concentrated and quenched with water (100 mL). The organics were extracted with dichloromethane (2×100 mL) and dried (magnesium sulfate). The organics were concentrated and purified via silica gel column chromatography (7:3, hexane:ethylacetate) to afford 2.67 g of pure aniline intermediate.

Part F. Approximately 1 g of the product from part E was fused at 80° C. with 1 equivalent of Boc-anhydride for 4 h. The product was dissolved in THF (20 mL) and to this was added 0.13 g of NaH. The reaction mixture was stirred at room temperature for 0.5 h followed by the addition of iodomethane (1 equivalent). Reaction mixture was stirred at room temperature over night and quenched with water (100 mL). The organics were extracted with ethylacetate (2×100 mL) dried and concentrated to a oil. Purification via silica gel column chromatography (hexane:ethyl acetate 6:4) afforded pure methylated Boc anilino intermediate. ESI mass spec. 539(M+Na). $^1$H NMR ($CDCl_3$) δ 7.48(d, J=8.8 Hz, 2H), 7.27 (m, 4H), 6.94(d, J=8.8 Hz, 2H), 4.15(t, 2H), 3.81 (s, 3H), 3.23 (s, 3H), 3.18 (t, 2H), 1.45 (s, 9H) ppm Part G. To a solution of the product from part F (0.995 g) in dichloromethane (50 mL) was added 1 mL of TFA. The reaction mixture was stirred at room temperature for 2 h and concentrated, quenched with saturated sodium bicarbonate solution. The organics were extracted with dichloromethane and concentrated to a tan solid (0.734 g). The tan solid was dissolved in dichloromethane and to this was added sodium hydroxide (1N, 2 mL) followed by the addition of chloroacetyl chloride 1 equiv.). The reaction mixture was stirred at room temperature for 1 h and the organic layer separated, dried and concentrated. To this concentrated mixture was added 10 mL of dimethylamine (2M in dichloromethane). The reaction mixture was sealed and the reaction mixture was stirred at room temperature overnight. The reaction mixture was concentrated and the crude product was purified via reverse phase HPLC. ESI mass spectrum analysis 502 (M+H). $^1$H NMR (DMSO $d_6$) δ 7.4 (d, J=8.8 Hz, 2H), 7.28 (d, J=8 Hz, 2H), 6.95 (d, J=9.2 Hz, 2H), 4.20 (t, 2H), 3.81 (s, 3H), 3.59 (bs, 1H), 3,26((bs, 3H), 2.89 bs, 6H) ppm.

Example 20

N-{4-[1-(4-methoxyphenyl)-7-oxo-3-(trifluoromethyl)-1,4,5,7-tetrahydro-6H-pyrazolo[3,4-c]pyridin-6-yl]phenyl}-N-methyl-2-(1-pyrrolidinyl)acetamide trifluoroacetic acid salt

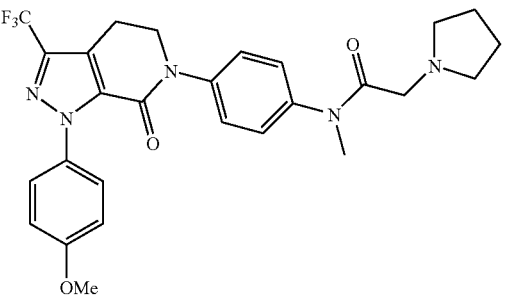

The title compound was prepared according to the procedure described for Example 19. $^1$H NMR ($CDCl_3$, 300 MHz) δ 7.51~7.38 (6H, m), 6.97(2H, d, J=9.2 Hz), 4.12 (2H, t, J=6.6 Hz), 3.92 (2H, s), 3.81 (3H, s), 3.66 (2H, m), 3.29 (3H, s), 3.17 (2H, t, J=6.6 Hz), 2.97 (2H, m), 2.01 (4H, m) ppm. HRMS(ES$^+$) 528.2224 (M+H)$^+$.

Example 21

N²-(tert-butyl)-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide trifluoroacetic acid salt

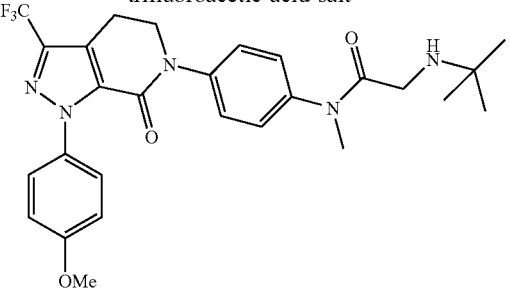

The title compound was prepared according to the procedure described in Example 19. ¹H NMR (CDCl₃, 300 MHz) δ 7.53~7.40 (6H, m), 7.00(2H, d, J=8.3 Hz), 4.17 (2H, t, J=5.3 Hz), 3.82 (3H, s), 3.56 (2H, s), 3.18 (2H, t, J=5.3 Hz), 1.24 (9H, s) ppm. HRMS(ES⁺) 530.2364 (M+H)⁺.

Example 22

N²-cyclobutyl-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide trifluoroacetic acid salt

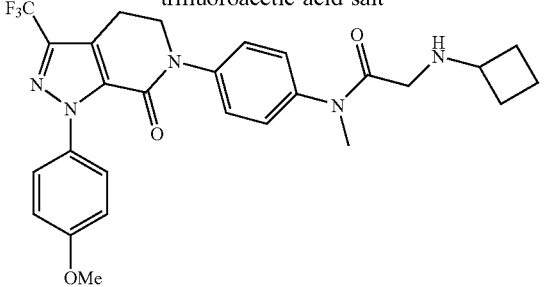

The title compound was prepared according to the procedure described for Example 19. ¹H NMR (CDCl₃, 300 MHz) δ 7.51~7.37 (6H, m), 6.97(2H, d, J=9.1 Hz), 4.16 (2H, t, J=6.6 Hz), 3.82 (3H, s), 3.62 (1H, m), 3.52 (2H, s), 3.29 (3H, s), 3.17 (2H, t, J=6.6 Hz), 2.20~2.01 (4H, m), 1.80 (2H, m) ppm. HRMS(ES⁺) 528.2228 (M+H)⁺.

Example 23

N²-(cyclopropylmethyl)-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide trifluoroacetic acid salt

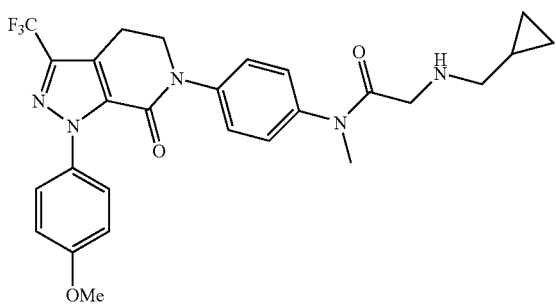

The title compound was prepared according to the procedure described in Example 19. ¹H NMR (CDCl₃, 300 MHz) δ 7.51~7.38 (6H, m), 6.98(2H, d, J=9.1 Hz), 4.16 (2H, t, J=6.6 Hz), 3.82 (3H, s), 3.67 (2H, s), 3.30 (3H, s), 3.17 (2H, t, J=6.6 Hz), 2.80 (2H, d, J=7.3 Hz), 1.0 (1H, m), 0.63 (2H, m), 0.30 (2H, m) ppm. HRMS(ES⁺) 528.2239 (M+H)⁺.

Example 24

N²-cyclopentyl-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide trifluoroacetic acid salt

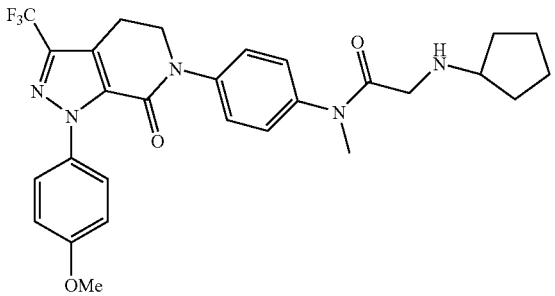

The title compound was prepared according to the procedure described for Example 19. ¹H NMR (CDCl₃, 300 MHz) δ 7.52~7.38 (6H, m), 6.98(2H, d, J=9.1 Hz), 4.17 (2H, t, J=6.0 Hz), 3.82 (3H, s), 3.63 (2H, s), 3.41 (1H, m), 3.29 (3H, s), 3.18 (2H, t, J=9.1 Hz), 1.97 (2H, m), 1.74~1.53 (6H, m) ppm. HRMS(ES⁺) 542.2376 (M+H)⁺.

Example 25

N²-((R)-2-hydroxyl-1-methylethyl)-N¹-{4-[1-(4-methoxyphenyl)-7-oxo-3-(trifluoromethyl)-1,4,5,7-tetrahydro-6H-pyrazolo[3,4-c]pyridin-6-yl]phenyl}-N¹-methylglycinamide trifluoroacetic acid salt

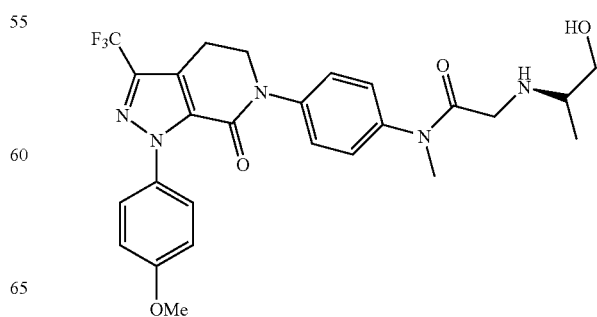

The title compound was prepared according to the procedure described for Example 19. $^{1}$H NMR (CDCl$_{3}$, 300 MHz) δ 7.52~7.38 (6H, m), 6.98(2H, d, J=9.1 Hz), 4.17 (2H, t, J=6.0 Hz), 3.82 (3H, s), 3.69 (3H, m), 3.30 (5H, m, including a 3-proton-singlet), 3.18 (2H, t, J=6.0 Hz), 1.98 (3H, d, J=6.9 Hz) ppm. HRMS(ES$^{+}$) 532.2190 (M+H)$^{+}$.

Example 26

6-{4-[(N,N-dimethylglycyl)(methyl)amino]phenyl}-1-(4-methoxyphenyl)-7-oxo-4,5,6,7-tetrahydro-1H-pyrazolo[3,4-c]pyridine-3-carboxamide trifluoroacetic acid salt

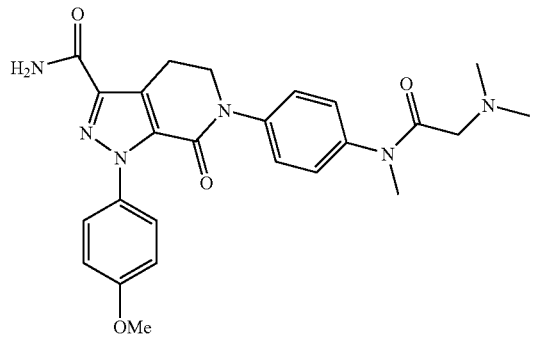

Part A. 4-nitroaniline (45.82 g, 209.2 mmol) and triethylamine (65.61 ml, 470.7 mmol) were dissolved into THF (800 mL) and cooled to 0° C. 5-Bromovaleryl chloride (50.0 g, 251.1 mmol) dissolved in THF (200 mL) was added dropwise to the reaction. The reaction was warmed to room temperature and stirred overnight. Reaction was cooled to 0° C. and potassium tert-butoxide (70.43 g, 627.6 mmol) was slowly added. The reaction was warmed to room temperature and stirred overnight. The reaction was concentrated and then re-dissolved in ethyl acetate (500 mL) and 3N HCl (500 mL), extracted with ethyl acetate (2×250 mL), washed with 1N HCl (3×250 mL), washed with brine (1×250 mL), and dried (Na$_2$SO$_4$). Purification by silica gel chromatography using 0%–100% ethyl acetate/hexane gradient as eluent to afford 42.56 g: $^{1}$H NMR (CDCl$_3$) δ 8.26 (d, j=8.4 Hz, 2H), 7.51 (d, j=8.8 Hz, 2H), 3.73 (t, j=5.9 Hz, 2H), 2.12 (m, 4H).

Part B. The above lactam intermediate from Part A (85.17 g) and phosphorus pentachloride (205.91 g, 990.0 mmol) were dissolved into CHCl$_3$ (750 mL) and refluxed for 3½ hours. Reaction was poured over ice and then quenched further with water, extracted with CHCl$_3$ (3×400 mL), washed with brine (1×400 mL), dried (MgSO$_4$), and concentrated. This residue was dissolved in morpholine (400 mL) and refluxed overnight. Reaction was concentrated and purified by silica gel chromatography using 0%–100% ethyl acetate/hexane gradient as eluent to afford 56 g of pure compound. $^{1}$H NMR (CDCl$_3$) δ 8.27(d, J=8 Hz, 2H), 7.57(d, J=8 Hz, 2H), 5.77(t, 1H), 3.92(m, 6H), 2.90(m, 4H), 2.58(m, 2H) ppm.

Part C. To p-anisidine (16 g, 0.129 mol) in conc. HCl (40 mL) and water (100 mL) at 0° C. was slowly added sodium nitrite (9.4 g, 0.136 mol) in water (60 mL). The reaction was stirred cold for 0.5 h. To the above reaction was poured a mixture of ethylchloroacetoacetate (22 g, 0.133 mol), ethanol (100 mL), sodium acetate (32 g, 0.389 mmol), and water (400 mL). The reaction was stirred 2 h at rt. The precipitate was filtered-off and dried to afford the hydrazone as a red gum (30.3 g, 91%): $^{1}$H NMR (CDCl$_3$) δ 8.28 (s, 1H), 7.18 (d, j=9.1 Hz, 2H), 6.90 (d, j=9.2 Hz, 2H), 4.41(q, j=8 Hz, 2H), 3.80 (s, 3H), 1.42 (t, j=6.9 Hz, 3H) ppm.

Part D. To the hydrazone from Part C (23.15 g, 90.08 mmol) and the morpholine compound from Part B (27.29 g, 90.08 mol) in toluene (700 mL) was added triethylamine (38 ml, 0.27 mol) and the reaction was heated to reflux for 6 h. The reaction was cooled to rt and water was added. The mixture was extracted with ethyl acetate, washed with water, 1N HCl, sat'd NaHCO$_3$ and dried (Na$_2$SO$_4$). Purification on silica gel using 3:2 hexanes/ethyl acetate afforded a morpholine intermediate that was dissolved in CH$_2$Cl$_2$ (50 mL) and TFA (2 mL). After 24 h the reaction was diluted with CH$_2$Cl$_2$, washed with water and sat'd NaHCO$_3$ and dried (Na$_2$SO$_4$) to afford 21.31 g: $^{1}$H NMR (CDCl$_3$) δ 8.23 (d, j=8.5 Hz, 2H), 7.51 (d, j=9.1 Hz, 2H), 7.45 (d, j=9.2 Hz, 2H), 6.93 (d, j=9.2 Hz, 2H), 4.48(q, 2H), 4.18 (t, 2H), 3.80 (s, 3H), 3.38 (t, j=6.6 Hz, 2H), 1.44 (t, 3H) ppm; Mass Spec ESI(M+H) 437.

Part E. The product from part D (4.70 g) was dissolved in a mixture of ethylacetate and methanol (1:1, 50 mL). To this solution was added palladium on carbon (10%) and the combined solution was hydrogenated in a Parr shaker apparatus at 40 psi for 1 h. The solution was filtered through a Celite® pad and concentrated to a tan solid. The solid obtained from above was then dissolved in minimal amount of dichloromethane (5 mL) and to this was added 2.7 g of boc-anhydride. The combined solution was heated gently for 4 h at 80° C., cooled and re-dissolved in dichloromethane. The crude mixture was purified via silica gel column chromatography (hexane:ethylacetate, 6:4) to afford 5.72 g of desired product. ESI mass spectra (M+Na) 529.

Part F. The product from part E was dissolved in DMF (25 mL). To this solution was added NaH (60% in oil, 0.54 g, 13.56 mmol) and the reaction mixture was stirred at room temperature for 0.5 h. To this solution was added iodomethane (0.63 ml, 1.31 mmol) and the reaction mixture was stirred at room temperature overnight. The mixture was quenched with saturated ammonium chloride and the organics were extracted with ethyl acetate (2×100 mL), dried (magnesium sulfate) and evaporated to a oil. Purification via silica gel column chromatography (8:2 to 6:4 hexane/ethylacetate) afforded the desired compound (5.90 g). ESI mass spectrum (M+H) 521. The product thus obtained was dissolved in dichloromethane (100 mL) and to this was added TFA (1 mL). The reaction mixture was stirred at room temperature for 4 h and concentrated and quenched with saturated sodium bicarbonate (100 mL). The organics were extracted with ethylacetate (2×100 mL), dried (magnesium sulfate) and evaporated to a tan solid mass. ESI mass spectrum (M+H) 421.

Part G. The product from part F (1.00 g) was dissolved in dichloromethane (25 mL). To this solution was added chloroacetyl chloride (1 equiv.) and sodium hydroxide (2 ml, 1N). The reaction mixture was stirred at room temperature for 1 h and the organic layer separated, dried (magnesium sulfate) and filtered. The filtrate was treated 5 mL of a dichloromethane solution of NN-dimethylamine (2M). The reaction mixture was stirred at room temperature for 18 h and concentrated. The crude product was purified via silica gel column chromatography (hexane:ethylacetate, 7:3) to afford 0.35 g of pure product. To this product was added 5% NH$_3$ in ethylene glycol (40 mL) and the mixture was heated to 80° C. for 4 h in sealed vessel. Water was added and the resulting solid was collected. Purification by reverse phase HPLC afforded the title compound 0.69 g. $^{1}$H NMR (CDCl$_3$) δ 7.49 (dd, j=8.8 Hz, 4H), 7.27 (d, j=9.1 Hz, 2H), 6.98 (d, j=8.8 Hz, 2H), 6.88 (s, 1H), 5.64 (s, 1H), 4.16 (t, j=6.6 Hz, 2H), 3.81 (s, 3H), 3.61 (s, 2H), 3.40 (t, j=6.6 Hz, 2H), 3.26 (t, j=6.2 Hz, 2H), 3.26 (s, 3H), 2.97 (s, 6H) ppm. ESI mass spectrum (M+H) 477.

Example 27

1-(4-methoxyphenyl)-6-{4-[methyl(1-pyrrolidiny-lacetyl)amino]phenyl}-7-oxo-4,5,6,7-tetrahydro-1H-pyrazolo[3,4-c]pyridine-3-carboxamide trifluoroacetic acid salt

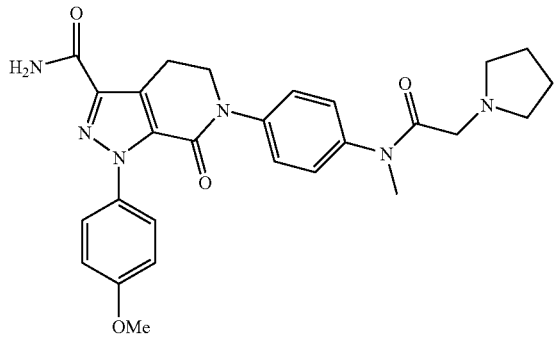

The title compound was prepared following procedures adopted for compound 26. $^1$H NMR (CDCl$_3$) δ 7.46 (dd, J=2.2 and 9.4 Hz, 4H), 7.22(d, J=9 Hz, 2H), 6.98(bs, 1H), 6.95(d, J=9 Hz, 2H), 6.22(bs, 1H), 4.15(t, 2H), 3.89(bs, 2H), 3.80 (s, 3H), 3.79 (s, 2H), 3.38(t, 2H), 3.23 (s, 2H), 2.93(bs, 2H), 2.08(bs, 4H) ppm; ESI mass spectrum (M+H) 503.

Example 28

N$^1$-{4-[1-(4-methoxyphenyl)-3-(methylsulfonyl)-7-oxo-1,4,5,7-tetrahydro-6H-pyrazolo[3,4-c]pyridin-6-yl]phenyl}-N$^1$,N$^2$,N$^2$-trimethylgycinamide, trifluoroacetic acid salt

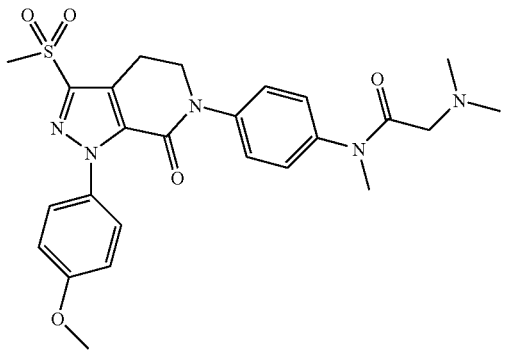

Part A. para-Methoxyphenyl-chlorosulfonyl hydrazone (16.0 g, 61.08 mmol), 3-(4-morpholinyl)-1-(4-nitrophenyl)-5,6-dihydro-2(1H)-pyridinone (15.43 g, 50.9 mmol), and triethylamine (17.73 ml, 127.25 mmol) were heated to reflux in toluene (250 mL) overnight. The reaction was cooled and treated with excess TFA and stirred at room temperature overnight, then concentrated, quenched with water (500 mL) and ethyl acetate (300 mL), extracted with ethyl acetate (3×250 mL), washed with water, washed with brine, and dried (MgSO$_4$). Purification by silica gel chromatography using 0–100% gradient of ethyl acetate/hexane, followed by 0–100% gradient of methanol/ethyl acetate as eluent to afford 16.48 g (73%) of the methylsulfone/nitro: $^1$H NMR (CDCl$_3$) δ 8.24(d, j=9.1 Hz, 2H), 7.53–7.43(m, 4H), 6.96(d, j=9.1 Hz, 2H), 4.22(t, j=6.6 Hz, 2H), 3.84 (s, 3H), 3.39(t, j=6.6 Hz, 2H), 3.33 (s, 3H) ppm.

Part B. The nitro compound from Part A (16.48 g, 37.20 mmol) was dissolved into ethanol (75 mL) in a Parr Shaker bottle. 10% Pd/C (0.328 g) was added. Hydrogenation was performed on a Parr Shaker at 50 psi for 3.5 hours. The reaction was filtered over Celite® and the Celite® pad washed with ethanol. Concentration of the washings afforded 15.21 g (99%): $^1$H NMR (DMSO-d$_6$) δ 7.45(d, j=8.8 Hz, 2H), 7.17(d, j=8.4 Hz, 2H), 6.98–6.89(m, 4H), 3.98(t, j=6.4 Hz, 2H), 3.75 (s, 3H), 3.15–3.10(m, 2H), 3.11 (s, 3H) ppm. Mass Spec (M+H)$^+$ 413.4.

Part C. The above aniline (8.00 g, 19.37 mmol) and Di-tert-buytl dicarbonate (4.44 g, 20.34 mmol) was dissolved into CH$_2$Cl$_2$ (20 mL) and heated at 80° C. for 3 hours. Quenched reaction with water (200 mL) and ethyl acetate (200 mL), extracted with ethyl acetate (3×150 mL), washed with brine (1×200 mL), dried (MgSO$_4$) and concentrated. Purification by flash chromatography and 0–100% gradient of ethyl acetate/hexane, followed by 0–100% methanol/ethyl acetate gradient to afford 4.21 g (42%): $^1$H NMR (CDCl$_3$) δ 7.47(d, j=8.8 Hz, 2H), 7.36(d, j=9.1 Hz, 2H), 7.21(d, j=8.8 Hz, 2H), 6.93(d, j=9.2 Hz, 2H), 6.54 (s, 1H), 4.09(t, j=6.6 Hz, 2H), 3.82 (s, 3H), 3.35–3.28(m, 2H), 3.30 (s, 3H), 1.51 (s, 9H) ppm; Mass Spec (M+H)$^+$ 513.4.

Part D. The above protected aniline (4.21 g, 8.21 mmol) was dissolved in DMF (40 mL) was cooled with an ice water bath. 60% Sodium Hydride (0.256 g, 10.67 mmol) was added and the reaction was stirred for 30 minutes. Iodomethane (0.613 ml, 9.85 mmol) was added and the reaction was stored at room temperature overnight. Quenched reaction with water and ethyl acetate, extracted with ethyl acetate, washed with water, water was brine, dried, and conc. Purification by flash chromatography with ethyl acetate/hexane gradient to afford 4.23 g (98%): $^1$H NMR (CDCl$_3$) δ 7.47(d, j=8.8 Hz, 2H) 7.28–7.22(m, 4H), 6.94(d, j=8.8 Hz, 2H), 4.12(t, j=6.6 Hz, 2H), 3.82 (s, 3H), 3.36–3.26(m, 2H), 3.31 (s, 3H), 3.23 (s, 3H), 1.45 (s, 9H) ppm.

Part E. The above protected methyl aniline (4.23 g, 8.04 mmol) with dissolved in CH$_2$Cl$_2$ (200 mL) and trifluoroacetic acid (50 mL) and stirred overnight at room temperature. Concentrated reaction and quenched with water and ethyl acetate, extracted with ethyl acetate, washed with brine, dried, and concentrated. Re-dissolved in saturated sodium bicarbonate and ethyl acetate, extracted with ethyl acetate, washed with saturated sodium bicarbonate, dried, and concentrated to afford 2.7 g (79%): $^1$H NMR (CDCl$_3$) δ 7.48(d, j=9.2 Hz, 2H) 7.09(d, j=8.8 Hz, 2H), 6.92(d, j=9.1 Hz, 2H), 6.58(d, j=8.8 Hz, 2H), 4.06(t, j=6.8 Hz, 2H), 3.81 (s, 3H), 3.30 (s, 3H), 3.30(t, j=6.8 Hz, 2H), 2.81 (s, 3H) ppm.

Part F. To the aniline from Part E (0.8 g, 1.87 mmol) in CH$_2$Cl$_2$ (50 mL) and sat'd aqueous NaHCO$_3$ (25 mL) was added chloroacetyl chloride (0.18 ml, 2.2 mmol). After 1 h, the phases were separated and the aqueous layer extracted with CH$_2$Cl$_2$ and dried (Na$_2$SO$_4$). To the crude chloride (0.3 g, 0.59 mmol) in THF(25 mL) was added 2M dimethylamine in THF (6 ml, 0.0118 mmol) and the reaction was stirred a total of 24 h. The reaction was concentrated and the crude product purified by HPLC and freeze-dried to afford 340 mg (91%): HRMS (M+H)+ for C$_{25}$H$_{30}$N$_5$O$_5$S was 512.1956; $^1$H NMR (CDCl₃) δ 7.48 (d, j=9.2 Hz, 2H), 7.45(d, j=6.9 Hz, 2H), 7.26 (d, j=6.9 Hz, 2H), 6.96 (d, j=8.8 Hz, 2H), 4.24 (t, j=6.6 Hz, 2H), 3.83 (s, 3H), 3.68 (s, 2H), 3.39 (t, j=6.6 Hz, 2H), 3.32 (s, 3H), 3.25 (s, 3H), 2.94 (s, 6H) ppm; Analysis: calc'd for $C_{25}H_{29}N_5O_5S(TFA)1.3(H_2O)$ C: 48.91, H: 4.80, N: 10.33, found C: 48.79, H: 4.55, N: 10.22.

Example 29

N¹-{4-[1-(4-methoxyphenyl)-3-(methylsulfonyl)-7-oxo-1,4,5,7-tetrahydro-6H-pyrazolo[3,4-c]pyridin-6-yl]phenyl}-N¹,N²-dimethylglycinamide, trifluoroacetic acid salt

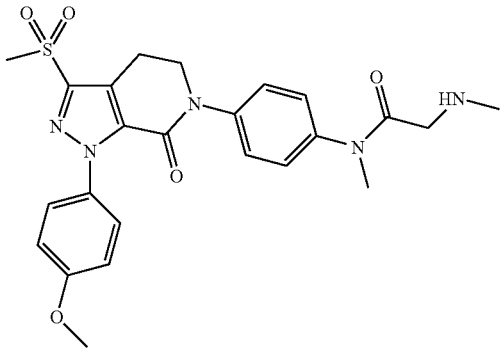

The same procedure as the previous Example 28 using n-methylamine in ethanol afforded 92% yield of the title compound: LRMS (M+H)⁺ 498.5; ¹H NMR (CDCl₃) δ 7.48 (d, j=8.8 Hz, 2H), 7.44(d, j=8.4 Hz, 2H), 7.29(d, j=8.4 Hz, 2H), 6.96(d, j=8.8 Hz, 2H), 4.24 (t, j=6.6 Hz, 2H), 3.83 (s, 3H), 3.57 (s, 2H), 3.40(t, j=6.6 Hz, 2H), 3.32 (s, 3H), 3.23 (s, 3H), 2.72 (s, 3H) ppm; Analysis: calc'd for $C_{24}H_{27}N_5O_5S$ (TFA)1.3 C: 49.47, H: 4.42, N: 10.84, found C: 48.25, H: 4.49, N: 10.82.

Example 30

N¹-{4-[1-(4-methoxyphenyl)-3-(methylsulfonyl)-7-oxo-1,4,5,7-tetrahydro-6H-pyrazolo[3,4-c]pyridin-6-yl]phenyl}-N-methyl-2-(1-pyrrolidinyl)acetamide trifluoroacetic acid salt

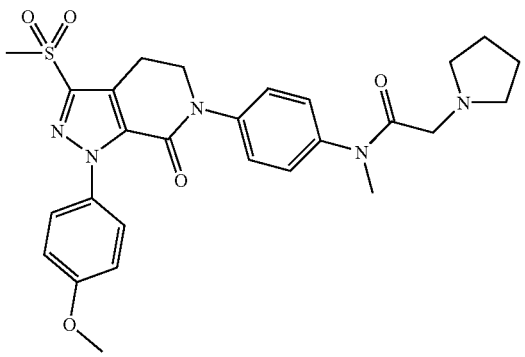

The title compound prepared following the general procedure for Example 28. ESI mass spectrum 538 (M+H).

Intermediate B 3-(aminocarbonyl)-1-(3-cyano-4-fluorophenyl)-1H-pyrazole-5-carboxylic acid

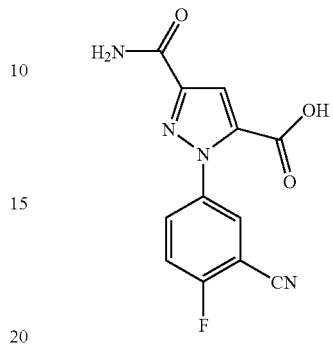

Part A. A 1-L flame-dried flask was charged with 130 mL of LiHMDS (130 mmol; 1.0 M in THF) and 410 mL of ethyl ether. The resulting solution was cooled to 78° C. and 2-acetylfuran (14 g, 12 m mmol) was added in one portion. After 5 min, di-tert-butyloxalate was added dropwise over 1 h as a solution in 100 mL of ether. The resulting mixture was warmed to 23° C. over a period of 3 h and was maintained at room temperature for 20 h. The mixture was then filtered, and the resulting beige precipitate was washed with 100 mL of ether. The filter cake was then dried in a vacuum oven for 1 h to afford lithium 1-tert-butoxy-4-(2-furyl)-1,4-dioxo-2-buten-2-olate (25 g, 83%) as a cream colored solid. ¹H NMR (DMSO-d₆) δ 7.75(t, 1H), 6.96 (m, 1H), 6.56 (m, 1H), 3.34 (s, 2H), 1.46 (s, 9H).

Part B. To the product (13 g, 54 mmol) from Part A was added 2-fluoro-5-hydrazinobenzonitrile hydrochloride (10 g, 54 mmol) and 250 mL of acetic acid. The resulting orange mixture was maintained at room temperature for 20 h and then concentrated to dryness. The resulting residue was taken up in 30% CHCl₃ in hexanes and filtered to afford tert-butyl 1-(3-cyano-4-fluorophenyl)-5-(2-furyl)-1H-pyrazole-3-carboxylate (18 g, 95%) as a light brown solid. LC/MS (ESI⁺): 354.2 (M+H)⁺. ¹H NMR (CDCl₃) δ 7.64–7.78(m, 3H), 7.42 (s, 1H), 7.05 (s, 1H), 6.45 (s, 1H), 6.30 (s, 1H), 1.61 (s, 9H).

Part C. To the product from Part B (10 g, 28 mmol) was added 125 mL of CH₂Cl₂ and 125 mL of trifluoroacetic acid. The resulting black solution was maintained at room temperature under N₂ for 2 h and was then concentrated to dryness. The resulting solid was dried in a vacuum oven for 4 h to afford 1-(3-cyano-4-fluorophenyl)-5-(2-furyl)-1H-pyrazole-3-carboxylate (8.4 g, 99%) as a brown solid. LC/MS (ESI⁺): 298.1 (M+H)⁺. ¹H NMR (CD₃OD) δ 7.90 (m, 1H), 7.75 (m, 1H), 7.51 (s, 1H), 7.46 (t, 1H), 6.98 (s, 1H), 6.47 (m, 1H), 6.35 (m, 1H).

Part D. To the product (4.1 g, 14 mmol) from Part C was added 23 mL of CH₂Cl₂ and 2.0 M oxalyl chloride (10 ml, 21 mmol) in CH₂Cl₂. Upon dropwise addition of DMF (10 drops) to the brown mixture, all solids dissolved over a period of 30 min. When no more gas evolved, the brown solution was concentrated. The resulting residue was re-dissolved in 100 mL of CH₂Cl₂ and 0.5 M ammonia in dioxane (110 ml, 55 mmol) was added via cannula. After 30 min, the resulting suspension was concentrated and poured into H₂O. The aqueous layer was washed with ethyl acetate (3×70 mL), and the combined organic)layers were washed with brine, dried over Na₂SO₄, filtered and concentrated.

The resulting residue was dissolved in 10 mL of CH$_2$Cl$_2$ and 50 mL of hexanes were added. The resulting suspension was filtered, and the filter cake was washed with 50 mL of hexanes. The filter cake was dried in a vacuum oven to afford 1-(3-cyano-4-fluorophenyl)-5-(2-furyl)-1H-pyrazole-3-carboxamide (2.5 g, 62%) as a brown solid. LC/MS (ESI$^+$): 297.1 (M+H)$^+$. $^1$H NMR (CDCl$_3$) δ 7.75(m, 1H), 7.64 (m, 1H), 7.42 (s, 1H), 7.33 (t, 1H), 7.16 (s, 1H), 6.79 (br s, 1H), 6.46(m, 1H), 6.36 (m, 1H), 5.50 (br s, 1H).

Part E. To the product (2.5 g, 8.3 mmol) from Part D was added H$_2$O (51 mL), 5% aqueous NaH$_2$PO$_4$ (35 mL), and tert-butanol (51 mL). The resulting mixture was warmed to 60° C., and KMnO$_4$ (8.0 g, 51 mmol) was added over a period of 10 min. After an additional 10 min, the resulting purple slurry was cooled to 0° C., and the reaction was quenched by the addition of 200 mL of saturated aqueous sodium bisulfite. The resulting mixture was filtered, washed with 300 mL of H$_2$O, and the filtrate was acidified with conc. HCl. The aqueous layer was extracted with EtOAc (6×100 mL) and the combined organic layers were washed with brine, dried over Na$_2$SO$_4$, and filtered. Concentration afforded 3-(aminocarbonyl)-1-(3-cyano-4-fluorophenyl)-1H-pyrazole-5-carboxylic acid (1.6 g, 71%) as a yellow solid. LC/MS (ESI$^+$): 275.1 (M+H)$^+$. $^1$H NMR (CD$_3$OD) δ 8.03 (m, 1H), 7.90 (m, 1H), 7.5 (t, 1H), 7.44 (s, 1H).

Example 31

1-(3-amino-1,2-benzisoxazol-5-yl)-5-({5-[N,N-dimethylglycyl(methyl)amino]-2,3-dihydro-1H-indol-1-yl}carbonyl)-1H-pyrazole-3-carboxamide trifluoroacetic acid salt

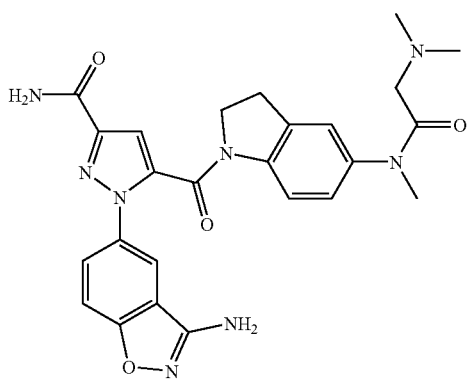

Part A. To the product (1.0 g, 4.2 mmol) from Example 2, Part B, was added N,N-dimethylglycine (490 mg, 4.7 mmol), triethylamine (1.80 ml, 13 mmol), and DMF (30 mL). To this mixture was added benzotriazol-1-yloxytripyrrolidino-phosphonium hexafluorophosphate (2.2 g, 4.3 mmol). After 10 min, the clear yellow solution was poured into EtOAc (80 mL) and washed with H$_2$O (2×50 mL). The organic layer was washed with brine, dried over Na$_2$SO$_4$, and filtered. The resulting residue was purified by radial chromatography (5% MeOH in CH$_2$Cl$_2$) to afford tert-butyl 5-[(N,N-dimethylglycyl)amino]-1-indolinecarboxylate (1.50 g, 110%) containing a small amount of DMF. LC/MS (ESI$^+$): 320.1 (M+H)$^+$.

Part B. Product (700 mg, 2.2 mmol) from Part A was dissolved in 10 mL of Et$_2$O and 10 mL of DMF. Sodium hydride (97 mg, 2.4 mmol; 60% dispersion in mineral oil) was added in one portion. After 5 min of stirring, iodomethane (0.14 ml, 2.2 mmol) in Et$_2$O (10 mL) was added dropwise until the reaction became a cloudy white suspension (~¾ CH$_3$I added). The reaction was immediately poured into EtOAc (70 mL) and washed with H$_2$O (2×20 mL). The organic layer was washed with brine, dried over Na$_2$SO$_4$, and filtered. Purification of the resulting residue via radial chromatography (10% MeOH in CH$_2$Cl$_2$) afforded tert-butyl 5-[(N,N-dimethylglycyl)-(methyl)amino]-1-indolinecarboxylate (400 mg, 55%) as a yellow oil. LC/MS (ESI$^+$): 334.2 (M+H)$^+$. $^1$H NMR (CDCl$_3$) δ 7.4–8.0 (br m, 1H), 6.93–6.96 (m, 2H), 4.06 (br t, 2H), 3.22 (s, 3H), 3.11 (t, 2H), 2.96 (s, 2H), 2.34 (s, 6H), 1.57 (s, 9H).

Part C. To the product from Part B (400 mg, 1.2 mmol) was added 5 mL of trifluoroacetic acid and 5 mL of CH$_2$Cl$_2$. The solution was stirred for 3 h and was then concentrated. The brown residue was dissolved in a minimal amount of saturated aqueous NaHCO$_3$ (10 mL) and washed with CH$_2$Cl$_2$ (3×50 mL). The combined organic layers were washed with brine, dried over Na$_2$SO$_4$, filtered and concentrated to afford N$^1$-(2,3-dihydro-1H-indol-5-yl)-N$^1$,N$^2$,N$^3$-trimethylglycinamide (140 mg, 50%) as a pale brown oil. LC/MS (ESI$^+$): 234.2 (M+H)$^+$. $^1$H NMR (CDCl$_3$) δ 6.85 (s, 1H), 6.74 (d, 1H), 6.57 (d, 1H), 3.60 (t, 2H), 3.19 (s, 3H), 3.05 (t, 2H), 2.89 (s, 2H), 2.24 (s, 6H.

Part D. To the product from Part C (140 mg, 0.61 mmol), was added 3-(aminocarbonyl)-1-(3-cyano-4-fluorophenyl)-1H-pyrazole-5-carboxylic acid (140 mg, 0.51 mmol), 4.8 mL of pyridine and 1.2 mL of DMF. 1,3-Diisopropylcarbodiimide (0.087 ml, 0.57 mmol) was added, and the resulting mixture was stirred for 14 h. The red mixture was purified without workup by preparative LC/MS (C18 reverse phase, eluted with 0.05% TFA in CH$_3$CN/H$_2$O) to give 1-(3-cyano-4-fluorophenyl)-5-({5-[N,N-dimethylglycyl)(methyl)amino]-2,3-dihydro-1H-indol-1-yl}carbonyl)-1H-pyrazole-3-carboxamide trifuloroacetate (100, 35% mg) as a pink solid. LC/MS (ESI$^+$): 490.2 (M+H−TFA)$^+$.

Part E. To the product from Part D (100 mg, 0.20 mmol) was added potassium carbonate (140 mg, 0.01 mmol), acetohydroxamic acid (38 mg, 0.51 mmol), DMF (10 mL), and H$_2$O (3.7 mL). The resulting mixture was warmed to 50□C under an N$_2$ atmosphere. After 2 h, the reaction was cooled to room temperature and poured into EtOAc (50 mL). The organic layer was washed with H$_2$O (2×15 mL), brine, and dried over Na$_2$SO$_4$. Filtration and concentration afforded a brown oily residue that was purified by preparative LC/MS (C18 reverse phase, eluted with 0.05% TFA in CH$_3$CN/H$_2$O) to give 1-(3-amino-1,2-benzisoxazol-5-yl)-5-({5-[N,N-dimethylglycyl)(methyl)amino]-2,3-dihydro-1H-indol-1-yl}carbonyl)-1H-pyrazole-3-carboxamide bis(trifluoroacetate) (7.8 mg, 6.2%) as a white solid after lyophilization from ACN/H$_2$O. LC/MS (ESI$^+$): 503.2 (M+H−2(TFA))$^+$.

Example 32
1-(3-amino-1,2-benzisoxazol-5-yl)-5-({6-[N,N-dimethylglycyl(methyl)amino]-2,3-dihydro-1H-indol-1-yl}carbonyl)-1H-pyrazole-3-carboxamide trifluoroacetic acid salt

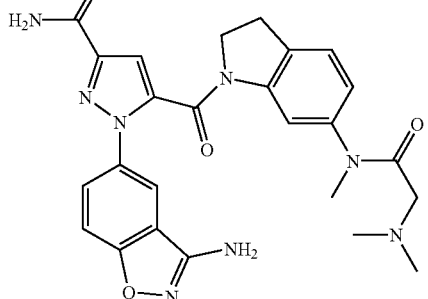

The title compound was prepared in the same manner as Example 31 using tert-butyl-6-amino-1-indolinecarboxylate as starting material in Part A. LC/MS (ESI$^+$): 503.2 (M+H−2(TFA))$^+$.

Example 33
3-[6-[4-(ethyl{[3-(methylsulfonyl)-1-pyrrolidinyl]acetyl}amino)phenyl]-7-oxo-3-(trifluoromethyl)-4,5,6,7-tetrahydro-1H-pyrazolo[3,4-c]pyridin-1-yl]benzamide trifluoroacetic acid salt

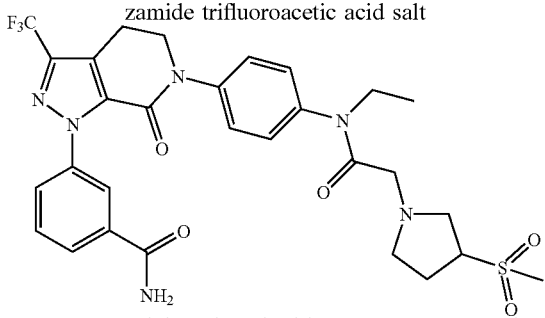

In a 20 mL vial equipped with a screw cap was placed 3-[6-{4-[(chloroacetyl)(ethyl)amino]phenyl}-7-oxo-3-(trifluoromethyl)-4,5,6,7-tetrahydro-1H-pyrazolo[3,4-c]pyridin-1-yl]benzamide (0.057 g, 0.11 mmol), 3-(methylsulfonyl)pyrrolidine (0.080 g, 0.55 mmol), and 5 mL of dry THF. The vial was sealed and the reaction heated to 60° C. overnight. The solvent was removed and the residue dissolved in 2 mL of 1:1 CH$_3$CN/Water. The mixture was then purified by HPLC (C18 reverse phase, eluted with 0.05% TFA in CH$_3$CN/water to give 29 mg of the title compound as the TFA salt (35%). HRMS (ES+) 633.2100 (M+H)$^+$ (99% purity).

Example 34
3-[6-[4-[{[3-(cyclohexylmethyl)-1-piperidinyl]acetyl}(ethyl)amino]phenyl]-7-oxo-3-(trifluoromethyl)-4,5,6,7-tetrahydro-1H-pyrazolo[3,4-c]pyridin-1-yl]benzamide

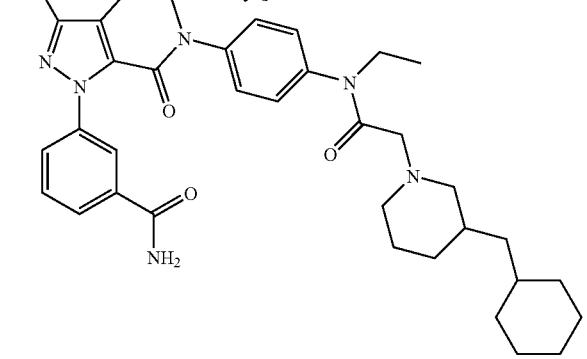

The title compound was prepared according to the procedure described in Example 31 using 3-(cyclohexylmethyl)piperidine as the amine (22% yield). HRMS (ES+) 665.3454 (M+H)+ (99% purity).

Example 35
3-[6-[4-(ethyl{N-[(1S)-1-phenylpropyl]glycyl}amino)phenyl]-7-oxo-3-(trifluoromethyl)-4,5,6,7-tetrahydro-1H-pyrazolo[3,4-c]pyridin-1-yl]benzamide trifluoroacetic acid salt

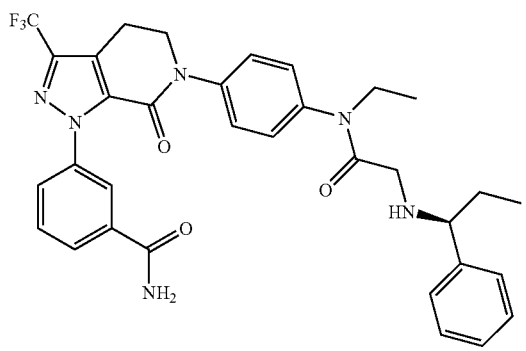

The title compound was prepared using the procedure described in Example 31 using (s)(−)-1-phenylpropylamine as the amine (35% yield). HRMS (ES+) 619.2645 (M+H)+ (99% purity).

Example 36
3-[6-{4-[[N-(1,3-dimethylbutyl)glycyl](ethyl)amino]phenyl}-7-oxo-3-(trifluoromethyl)-4,5,6,7-tetrahydro-1H-pyrazolo[3,4-c]pyridin-1-yl]benzamide trifluoroacetic acid salt

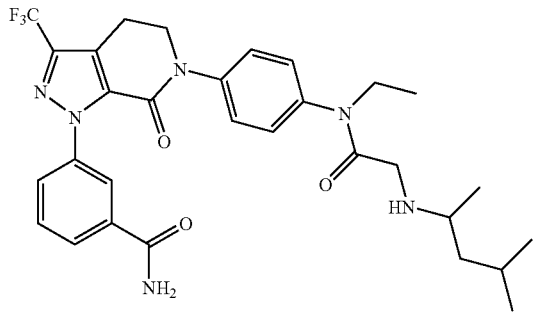

The title compound was prepared using the procedure described in Example 31 using 1,3-dimethylbutylamine as the amine (33% yield). HRMS (ES+) 585.2802 (M+H)+ (86% purity)

Example 37

N-{4-[1-(3-amino-1,2-benzisoxazol-5-yl)-3-methoxy-7-oxo-1,4,5,7-tetrahydro-6H-pyrazolo[3,4-c]pyridin-6-yl]phenyl}-N-methyl-2-(1-pyrrolidinyl)acetamide

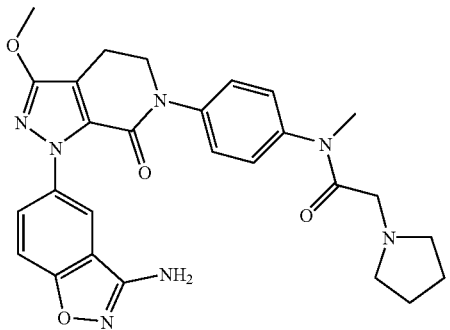

Part A: 4-Nitroaniline (30.0 g, 217.2 mmol) and 400 mL of dry THF were stirred together at 0° C. and N,N-diisopropylethylamine (28.3 g, 219.0 mmol) dissolved in 100 mL of THF was slowly added. Then 5-bromovaleryl chloride (43.3 g, 217.2 mmol) in 180 mL of THF was slowly added while maintaining the temperature at 0–5° C. After addition was complete, the reaction was allowed to warm to rt over 2.5 hours.

The reaction was again cooled to 0° C. and potassium t-butoxide (1.0 M in THF, 434 ml, 434 mmol) was added and the reaction allowed to warm to rt overnight. The reaction was evaporated, dissolved in EtOAc and washed with NaHCO$_3$, water, then brine. Next it was dried over sodium sulfate and evaporated to give the corresponding lactam (44.68 g, 96% yield). LRMS (AP+) 221.1 (M+H)$^+$.

Part B: The lactam (44.68 g, 203.1 mmol) was dissolved in 550 mL of CHCl$_3$ and stirred at rt for 5 minutes then PCl$_5$ (143.6 g, 690.5 mmol) was added portionwise followed by an additional 100 mL of CHCl$_3$. The nitrogen outlet was replaced with a scrubber system consisting of 1N NaOH and the reaction was refluxed for 2 hours. The reaction was then cooled and slowly poured into a 4-liter beaker containing 860 mL of water and 250 mL of CHCl$_3$ already cooled to 0° C. The mixture was stirred about ½ hour then transferred to a separatory funnel and separated. The organic layer was dried over sodium sulfate and evaporated to give the chlorinated intermediate (51.9 g, 90% yield). The intermediate was added to morpholine (172.6 g, 1.98 mol) neat and heated to reflux for 2 hours then cooled. Next 500 mL of CHCl$_3$ and a mixture of 500 mL saturated NaH$_2$PO$_4$ monohydrate and 50 mL of conc. HCl was added. The reaction was transferred to a separatory funnel and washed with saturated NaH$_2$PO$_4$ monohydrate then water and dried over sodium sulfate and evaporated. The residue was recrystallized in EtOAc to yield the enamine (28.46 g, 53% yield) LRMS (ES+) 304.8 (M+H)$^+$.

Part C: The enamine (19.1 g, 63.0 mmol) was added together with 200 mL of CH$_2$Cl$_2$ and DMAP (46.2 g, 278.2 mmol). The solution was cooled to 0° C. and trichloroacetyl chloride (57.3 g, 315.2 mmol) was added and the reaction refluxed overnight. The reaction was cooled and 100 mL of water was added. The mixture was extracted 3× with diethyl ether, dried over sodium sulfate, and evaporated to yield chloroacetyl derivative (23.85 g, 86% yield).

Part D: The compound from above (23.85 g, 53.3 mmol) was stirred together with 400 mL of diethyl ether, 20 mL of water, and 20 mL of conc. HCl. The reaction was heated to 65° C. for 3 hours then cooled. The resulting precipitate was filtered to yield hydroxy derivative (13.68 g, 70% yield) LRMS (ES–) 377.2.

Part E: The hydroxy derivative from above (5.0 g, 13.23 mmol) along with IJ705 (2.60 g, 13.89 mmol), 100 mL of THF and Et$_3$N (2.67 g, 26.45 mmol) were stirred together at rt overnight. Next 100 mL of 1N HCl was added and the reaction refluxed for 2 hours then cooled. The resulting precipitate was filtered and vacuum dried to yield the bicyclic pyrazole core (2.17 g, 42% yield) LRMS (ES+) 394.3 (M+H)$^+$.

Part F: NaH (60%) (0.33 g, 8.28 mmol) and 10 mL of DMF were cooled to 0° C. and the pyrazole from above (2.17 g, 5.52 mmol) was added. The reaction was stirred 10 minutes then MeI (1.57 g, 11.04 mmol) was added neat and the reaction warmed to rt over 2.5 hours. Next, 25 mL of sat'd NH$_4$Cl was added and the reaction extracted 3× with EtOAc. The EtOAc was washed 5× with water then evaporated. The residue was applied to a silica gel column and eluted with 1:1 hexane/EtOAc then dried over sodium sulfate to yield the methylated product (1.99 g, 88% yield) LRMS (ES–) 406.4.

Part G: The product from above (1.99 g, 4.89 mmol) was stirred together with 100 mL of MeOH at rt. The vessel was purged and evacuated 3× with nitrogen then 10% Pd/C catalyst was added (0.489 g). The vessel was again purged and evacuated, with nitrogen then placed under a hydrogen atmosphere for 5 hours. The reaction was filtered thru Celite® then dried and evaporated to give the amine product (1.64 g, 89% yield) LRMS (ES+) 378.4 (M+H)$^+$.

Part H: The amine from above (1.41 g, 3.74 mmol) was refluxed overnight with 25 mL of THF and (Boc)$_2$O (1.63 g, 7.48 mmol). The reaction was then cooled, evaporated and placed on a silica gel column eluting with 3:1 hexane/EtOAc. The mixture was dried over sodium sulfate and evaporated to give the Boc-protected material (1.36 g, 76% yield) LRMS (ES+Na)$^+$ 500.4.

Part I: NaH (60%) (0.23 g, 5.70 mmol) and 10 mL of DMF were cooled to 0° C. and the Boc-protected material from above was added. The reaction was stirred for 10 minutes then MeI (0.81 g, 5.70 mmol) was added and the reaction allowed to warm to rt over 3 hours. Next the mixture was cooled to 0° C. and 10 mL of 1N HCl followed by 10 mL of water was added. The mixture was transferred to a separatory funnel and extracted 3× with EtOAc. The EtOAc layer was washed 5× with water then brine, dried over sodium sulfate and evaporated to give the di-methylated product (1.26 g, 90% yield) LRMS (M+Na)$^+$ 514.4.

Part J: Acetohydroxamic acid (0.096 g, 1.28 mmol), potassium carbonate (0.35 g, 2.57 mmol), 3 mL of DMF and 1 mL of water were stirred together for 10 minutes at rt then the product from above (0.21 g, 0.43 mmol) in 2 mL of DMF was added and the reaction stirred overnight. Next EtOAc was added and the mixture transferred to a separatory funnel where it was washed 5× with water then brine and dried over sodium sulfate to give the amino benzisoxazole compound (0.16 g, 76% yield) LRMS (ES+) 505.5 (M+H)+.

Part K: The compound from above (0.16 g, 0.32 mmol) was stirred together with 5 mL of TFA at rt for ½ hour then evaporated. The residue was dissolved in EtOAc and washed with 1N NaOH 3× then brine, dried over sodium sulfate and evaporated to give the de-protected compound (0.16 g, quant.). LRMS (ES+) 405.4 (M+H)+.

Part L: The de-protected compound from above (0.16 g, 0.40 mmol) was mixed together with 5 mL of CH$_2$Cl$_2$ and DMAP (0.072 g, 0.59 mmol). The solution was stirred at rt and chloroacetyl chloride (0.067 g, 0.59 mmol) in 2 mL of CH$_2$Cl$_2$ was added. The reaction was stirred at rt overnight. Next it was poured into a separatory funnel and washed with 1N HCl 3×, brine, dried over sodium sulfate and evaporated to give the amide compound (0.15 g, 79% yield).

Part M: The amide compound from above (0.15 g, 0.27 mmol) was placed in a 20 mL vial along with 5 mL of THF and pyrrolidine (0.096 g, 1.35 mmol). The reaction was heated to 40° C. overnight then cooled. Next the solvent was removed and the residue dissolved in 2 mL of 1:1 CH$_3$CN/Water. The mixture was then purified by HPLC (C18 reverse phase, eluted with 0.05% TFA in CH$_3$CN/Water to give 7 mg of the title compound as the TFA salt (4%) HRMS (M+H)+ (95% purity).

Example 38

N-{4-[1-(4-methoxyphenyl)-3-(methylsulfonyl)-7-oxo-1,4,5,7-tetrahydro-6H-pyrazolo[3,4-c]pyridin-6-yl]phenyl}-N-methyl-2-(2-methyl-1H-imidazol-1-yl) acetamide

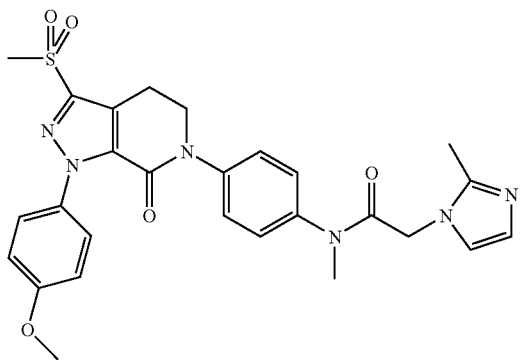

To 1-(4-methoxyphenyl)-6-[4-(methylamino)phenyl]-3-(methylsulfonyl)-1,4,5,7-tetrahydro-7H-pyrazolo[3,4-c]pyridin-7-one (0.224 g, 0.53 mmol) in CH$_2$Cl$_2$ (25 mL) and water (20 mL) was added chloroacetylchloride (0.051 ml, 0.63 mmol) and NaHCO$_3$ (0.2 g, 2 mmol) and the reaction was stirred for 24 h. The reaction was extracted with CH$_2$Cl$_2$ and dried (Na$_2$SO$_4$). To the above intermediate was added CH$_3$CN (25 mL) and 2-methylimidazole (83 mg, 1 mmol). The reaction was stirred 24 h but was incomplete. The reaction was driven to completion after an additional 100 mg of 2-methylimidazole was added and it was heated for 4 h at reflux. The reaction was stripped and purified by HPLC and freeze-dried to afford 260 mg (78%) product: $^1$H NMR (CDCl$_3$) δ 7.52 (d, j=8.7 Hz, 2H), 7.48 (d, j=8.8 Hz, 2H), 7.36 (d, j=8.4 Hz, 2H), 7.20 (d, j=1.8 Hz, 1H), 6.99 (d, j=2 Hz, 1H), 6.97 (d, j=9.2 Hz, 2H), 4.57 (s, 2H), 4.23(t, j=6.6 Hz, 2H), 3.84 (s, 3H), 3.41 (t, j—6.6 Hz, 2H), 3.33 (s, 3H), 3.30 (s, 3H), 2.55 (s, 3H) ppm; HRMS (M+H)+ for C$_{27}$H$_{29}$N$_6$O$_5$S 549.1919.

Example 39

N-{4-[1-(4-methoxyphenyl)-3-(trifluoromethyl)-7-oxo-1,4,5,7-tetrahydro-6H-pyrazolo[3,4-c]pyridin-6-yl]phenyl}-N-methyl-2-(2-methyl-1H-imidazol-1-yl) acetamide

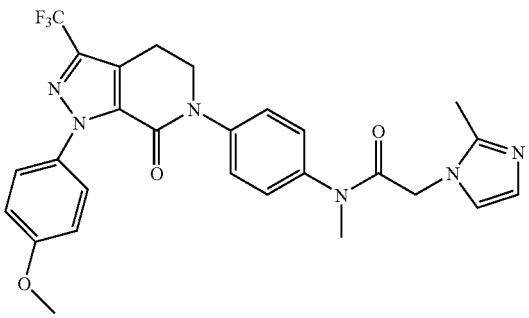

ESI mass spectrum analysis 539 (M+H). $^1$H NMR (CDCl$_3$) δ: 7.57 (m, 4H), 7.31 (d, J=8.4 Hz, 2H), 7.19 (s, 1H), 6.93 (d, J=8.8 Hz, 3H), 4.52 (s, 2H), 4.20 (t, 2H), 3.80 (s, 3H), 3.27 (s, 2H), 3.20 (t, 2H), 2.62 (s, 3H) ppm.

Example 40

3-Chloro-1H-indole-6-carboxylic acid (2-{4-[methyl-(2-pyrrolidin-1-yl-acetyl)-amino]-benzoylamino}-cyclohexyl)-amide

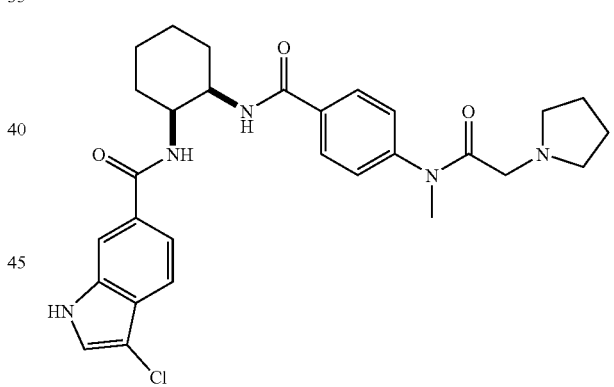

Part A. 4-[(2-Chloro-acetyl)-methyl-amino]-benzoic acid (0.23 g, 1.0 mmol.) was stirred in DMF (2 mL) at RT under N$_2$. (2-Amino-cyclohexyl)-carbamic acid tert-butyl ester (0.21 g, 1.0 mmol), HATU (0.57 g, 1.5 eq) and DIEA (0.5 mL, 2.9 eq) were added. The mixture was stirred at RT for 30 min. It was partitioned between EtOAc and water. The organic layer was washed with brine, dried over MgSO$_4$, filtered, and concentrated to dryness to give (2-{4-[(2-chloro-acetyl)-methyl-amino]-benzoylamino}-cyclohexyl)-carbamic acid tert-butyl ester (0.40 g, yield: 95%).

Part B. To a solution of the product from step A (0.40 g, 0.95 mmol) in DMSO (0.4 mL) was added pyrrolidine (0.05 mL) followed by the addition of K$_2$CO$_3$ (50 mg). The mixture was stirred at 60–70° C. for 1.5 h. The residue was partitioned between EtOAc and H$_2$O. The organics were washed with brine, dried over MgSO$_4$, filtered, and concentrated to dryness. The residue was dissolved in CH$_2$Cl$_2$ (15 mL) and TFA (5 mL). The mixture was stirred at RT for 30 min. It was evaporated to dryness to give N-(2-aminocyclohexyl)-4-[methyl-(2-pyrrolidin-1-yl-acetyl)-amino]-benzamide (0.21 g, yield: 62%).

Part C. A mixture of the product from Part B (40 mg, 0.11 mmol), (33 mg, 0.17 mmol), HATU (65 mg, 0.17 mmol), and DIEA (0.06 mL) was stirred in DMF (0.5 mL) at RT under N$_2$ overnight. The mixture was purified by reverse phase HPLC (0–100% CH$_3$CN in H$_2$O) to give pure titled compound (16 mg, yield: 27%). LC/MS (ESI$^+$) 536.4 (M+H)

Example 41

5-Chloro-1H-indole-2-carboxylic acid (2-{4-[methyl-(2-pyrrolidin-1-yl-acetyl)-amino]-benzoylamino}-cyclohexyl)-amide

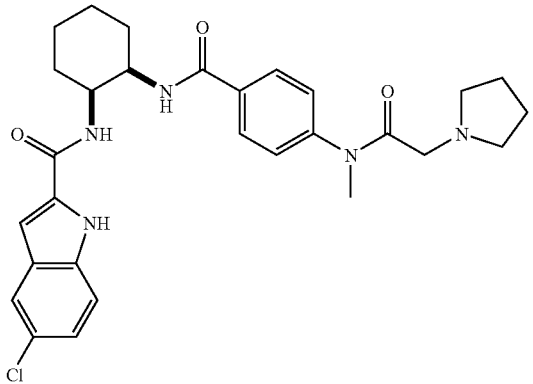

Following a procedure analogous to that described in previous example, the title compounds was obtained. LC/MS ESI(M+H)$^+$ 535.6.

Example 42

5-Chloro-thiophene-2-carboxylic acid (2-{4-[methyl-(2-pyrrolidin-1-yl-acetyl)-amino]-benzoylamino}-cyclohexyl)-amide

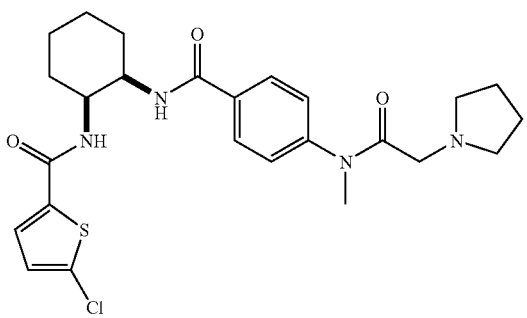

Following a procedure analogous to that described the previous example, the title compounds was obtained. LC/MS ESI (M+H)$^+$ 503.4.

Example 43

4-Methoxy-phenylcarboxylic acid (2-{4-[methyl-(2-pyrrolidin-1-yl-acetyl)-amino]-benzoylamino}-cyclohexyl)-amide

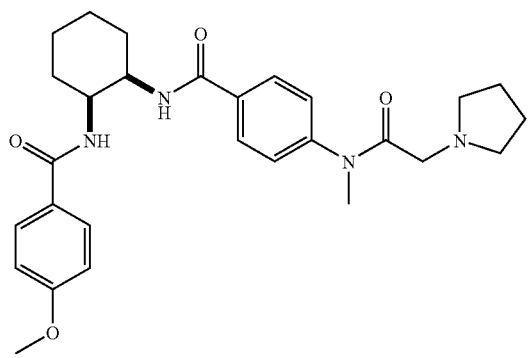

Following a procedure analogous to that described in the previous example, the title compounds was obtained. LC/MS ESI (M+H)$^+$ 494.4.

Example 44

5-chloro-N-(5-chloropyridin-2-yl)-2-({4-[methyl(pyrrolidin-1-ylacetyl)amino]benzyl}amino)benzamide

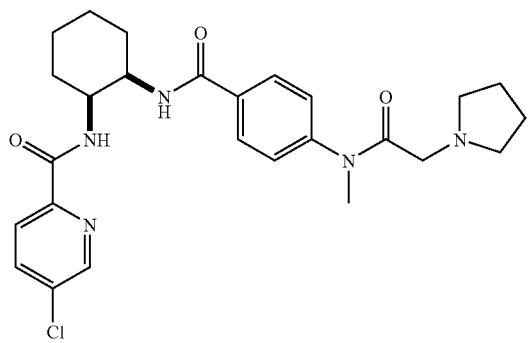

Part A: To a solution of 2-amino-4-chloropyridine (129 mg, 1.0 mmol) in anhydrous THF at −78° C. was added KHMDS (4.0 mL, 0.5 M solution in toluene). The mixture was stirred at this temperature under N$_2$ for 30 min and a solution of 5-chloro-isatoic anhydride (198.0 mg, 1.0 mmol) in THF was added. The resulting mixture was warmed to room temperature gradually and stirred for 10 hr. The reaction mixture was quenched with sat. NH$_4$Cl solution, most of the solvent was evaporated, and the residue was diluted with ethyl acetate, washed with brine, and dried over MgSO$_4$. Removal of the solvent and chromatography on silica gel (20% ethyl acetate in hexane) yielded the desired product as a light brown solid. LC/MS ESI found: (M+1)$^+$ =282.2.

Part B: To a solution of methyl 4-aminobenzoate (151.0 mg, 1.0 mmol) and (Boc)$_2$O (284.0 mg, 1.3 mmol) in THF was added Et$_3$N (0.3 mL) and DMAP (5.0 mg). The reaction mixture was stirred at room temperature for 6 hr. Most of the solvent was evaporated and the residue was diluted with ethyl acetate; washed with water, 1N HCl solution, and brine; and dried over $Na_2SO_4$. Removal of the solvent and chromatography on silica gel (15% ethyl acetate in hexane) provided the desired product as a white solid. LC/MS ESI found: $(M+1)^+=252.1$.

Part C: NaH (2.0 mmol, 60% in mineral oil) was added to a solution of the product from Step b (1.0 mmol) and MeI (2.0 mmol) in DMF. After stirring at room temperature for 1 hr and at 60° C. for 1.5 hr, the reaction mixture was cooled, quenched with sat. $NH_4Cl$, and most of the solvent was evaporated. The residue was diluted with ethyl acetate; washed with water, 1N HCl, and brine; and dried over $Na_2SO_4$. Concentration under vacuum provided the crude product as a light brown solid.

The above solid was dissolve in $CH_2Cl_2$ and TFA (2.0 mL) was added. The resulted mixture was stirred at room temperature for 1.5 hr. Removal of solvent and chromatography on silica gel (1% methanol in methylene chloride) provided the desired product as a white solid.

Part D: To the mixture of the product from Step C (412.0 mg, 2.5 mmol) and $Et_3N$ (0.5 mL) in $CH_2Cl_2$ at 0° C. was added chloroacetyl chloride (0.24 mL, 3.0 mmol) and DMAP (15 mg). After stirring at this temperature for 1.5 hr, the reaction mixture was washed with water and brine and dried over $MgSO_4$. The residue was purified by chromatography on silica gel (20% ethyl acetate in hexane) to give the desired product as a white solid. LC/MS ESI found: $(M+1)^+=242.3$.

Part E: To a solution of the product from Step D (603 mg, 2.5 mmol) in $CH_2Cl_2$ at 0° C. was added pyrrolidine (0.6 mL, 7.3 mmol). After stirring at this temperature for 1 hr, the mixture was washed with water and brine and dried over $MgSO_4$. Removal of the solvent and chromatography on silica gel (50% ethyl acetate in hexane) provided the desired product as a light brown solid. LC/MS ESI found: $(M+1)^+=277.3$.

Part F: To a solution of the product from Step D (276 mg, 1.0 mmol) in THF was added $LiBH_4$. The mixture was stirred at reflux for 3 hr, and then the reaction mixture was cooled to room temperature and quenched with water. The residue was purified by reverse phase HPLC (20% $CH_3CN/H_2O$, 40 mL/min). MS found: LC/MS ESI $(M+1)^+=249.2$.

Part G: To a solution of the product from Step F (248 mg, 1.0 mmol) in $CH_2Cl_2$ was added Dess-Martin reagent (508.0 mg, 1.2 mmol). The mixture was stirred for 3 hr under $N_2$. The solid was filtered and the solution was concentrated and dried under vacuum to give the aldehyde. To a solution of the above aldehyde in ethanol was added product from part A (180 mg, 0.64 mmol), and the reaction mixture was heated to reflux for 6 hr and then cooled to room temperature. To this mixture was added $NaBH_4$ (102 mg) at room temperature and the resulted mixture was stirred for 3 hr. The reaction mixture was quenched with water and purified by reverse phase HPLC (20% $CH_3CN/H_2O$, 40 mL/min) to give the desired product as a light yellow solid. LC/MS ESI: $(M+1)^+=512.0$.

Example 45

5-chloro-N-(5-chloropyridin-2-yl)-2-({4-[(N,N-dimethylglycyl)(methyl)amino]benzyl}amino)benzamide

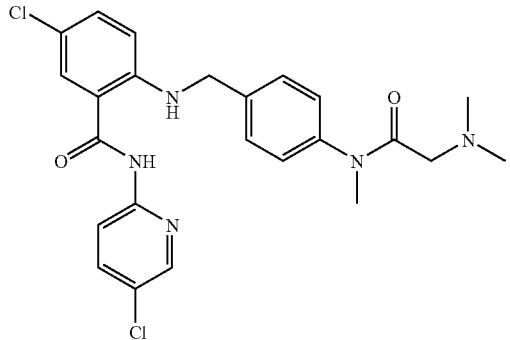

Following a procedure analogous to that described previously, the title compound the title compound was obtained as a yellow solid. LC/MS ESI: $(M+1)^+=486.2$.

Example 46

2-({4-[acetyl(methyl)amino]benzyl}amino)-5-chloro-N-(5-chloropyridin-2-yl)benzamide

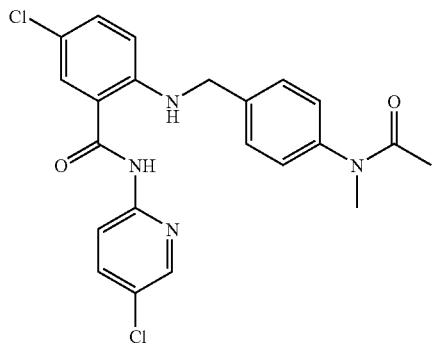

Following a procedure analogous to that previously described, the title compound was obtained as a yellow solid. LC/MS ESI: $(M+1)^+=442.9$.

Example 47

N-(5-chloropyridin-2-yl)-2-({4-[(N,N-dimethylglycyl)(methyl)amino]benzyl}amino)-5-methylbenzamide

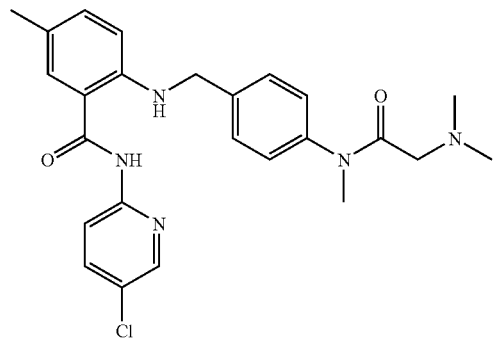

Following a procedure analogous to that described previously, the title compound the title compound was obtained as a yellow solid. LC/MS ESI: (M+1)+=466.6.

Example 48

N-(5-chloropyridin-2-yl)-2-({4-[(N,N-dimethylglycyl)(methyl)amino]benzyl}amino)-5-methoxybenzamide

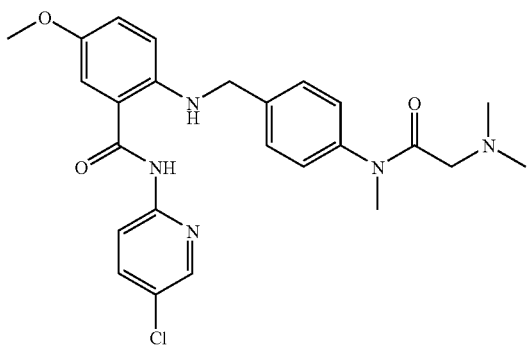

Following a procedure analogous to that described previously, the title compound the title compound was obtained as a brown solid. LC/MS ESI: (M+1)+=482.1.

Example 49

N-(5-chloropyridin-2-yl)-2-({4-[(N,N-dimethylglycyl)(methyl)amino]-benzyl}amino)benzamide

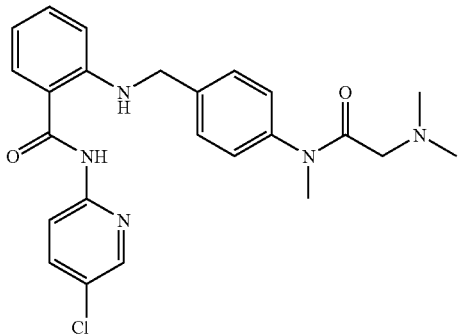

Following a procedure analogous to that described previously, the title compound the title compound was obtained as a light brown solid. LC/MS ESI: (M+1)+=452.1.

Example 50

5-chloro-N-(5-chloropyridin-2-yl)-2-({4-[methyl(pyrrolidin-1-ylacetyl)amino]benzoyl}amino)benzamide

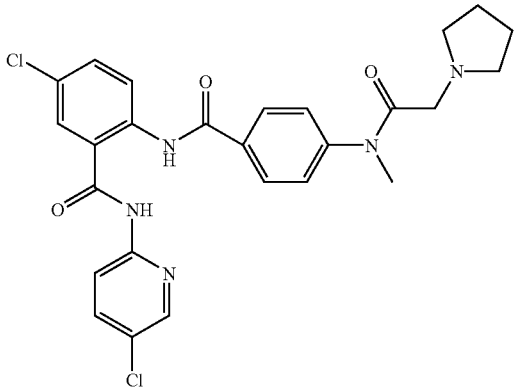

Part A: To a solution of 4-[methyl-(2-pyrrolidin-1-yl-acetyl)-amino]-benzoic acid methyl ester (276 mg, 1.0 mmol) in THF/H$_2$O (1:1) at 0° C. was added 1N LiOH solution (2.0 mL). After stirring for 4 hr, the mixture was acidified to pH=3 using 1N HCl. The mixture was then purified using reverse phase HPLC (20% CH$_3$CN/H$_2$O, 40 mL/min) to provide the desired acid as a white solid. LC/MS ESI: (M+1)+=277.2.

Part B: To the suspension of the product from above (262.0 mg, 1.0 mmol) in CH$_2$Cl$_2$ and DMF (0.5 mL) was added oxalyl chloride (2.0 mmol). The mixture was stirred for 2 hr under N$_2$. The solvent was removed, and the residue was dried under vacuum to give the acyl chloride. To a mixture of the product from part A (124 mg, 0.44 mmol), TEA (0.25 mL), and DAMP (11.0 mg) in CH$_2$Cl$_2$ was added a solution of the acyl chloride in CH$_2$Cl$_2$ at 0° C. The mixture was warmed to room temperature and stirred over night under N$_2$. The mixture was washed with water and purified with reverse phase HPLC (20% CH$_3$CN/H$_2$O, 40 mL/min) to provide the desired product as a white solid. LC/MS ESI: (M+1)+=526.0.

Example 51

5-chloro-N-(5-chloropyridin-2-yl)-2-({4-[(N,N-dimethylglycyl)(methyl)amino]benzoyl}amino)benzamide

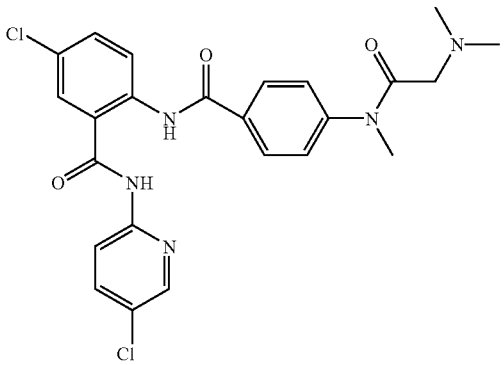

Following a procedure analogous to that described previously, the title compound the title compound was obtained as a white solid. LC/MS ESI: (M+1)+=500.0.

Example 52

5-chloro-N-(5-chloropyridin-2-yl)-2-(methyl{4-[(morpholin-4-ylacetyl)amino]benzoyl}amino)benzamide

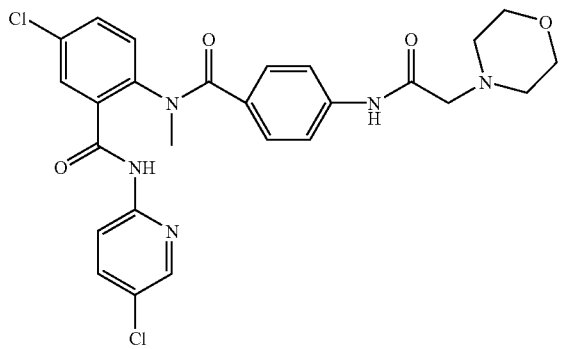

Following a procedure analogous to that described previously, the title compound the title compound was obtained as a white solid. LC/MS ESI: (M+1)+=542.0.

Example 53

2-[{4-[(N-butyl-N-methylglycyl)amino]benzoyl}(methyl)amino]-5-chloro-N-(5-chloropyridin-2-yl)benzamide

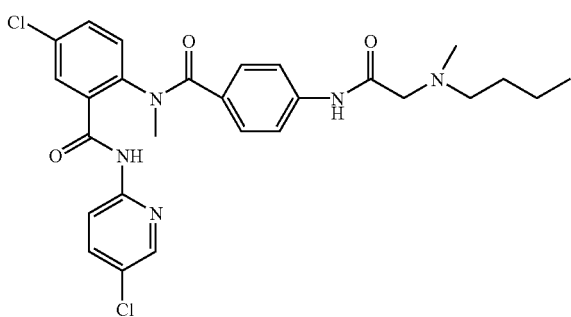

Following a procedure analogous to that described previously, the title compound the title compound was obtained as a white solid. LC/MS (ESI): (M+1)$^+$=542.0.

Example 54

2-({4-[acetyl(methyl)amino]benzoyl}amino)-N-(5-chloropyridin-2-yl)-5-methylbenzamide

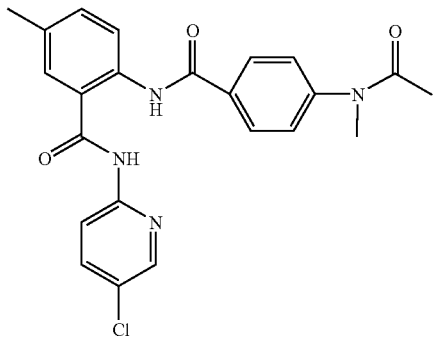

Following a procedure analogous to that described previously, the title compound the title compound was obtained as a white solid. LC/MS (ESI): (M+1)$^+$=437.4.

Example 55

N-(5-chloropyridin-2-yl)-5-methyl-2-({4-[methyl(morpholin-4-ylacetyl)amino]benzoyl}amino)benzamide

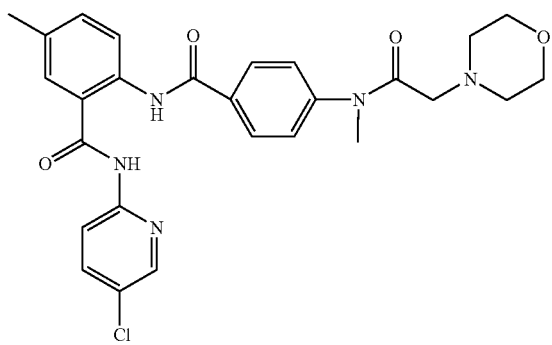

Following a procedure analogous to that described previously, the title compound the title compound was obtained as a white solid. LC/MS (ESI): (M+1)$^+$=522.6.

Example 56

N-(5-chloropyridin-2-yl)-5-methoxy-2-({4-[methyl(pyrrolidin-1-ylacetyl)amino]benzoyl}amino)benzamide

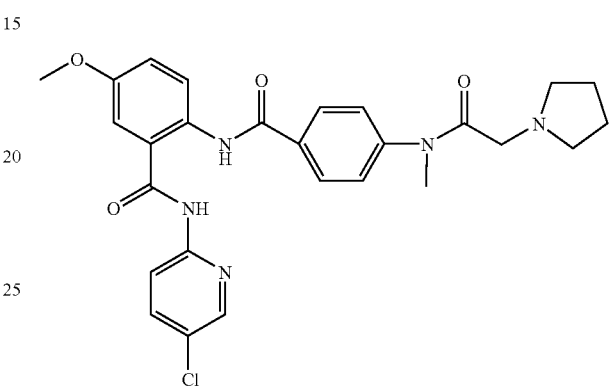

Following a procedure analogous to that described previously, the title compound the title compound was obtained as a white solid. LC/MS (ESI): (M+1)$^+$=522.5.

Example 57

2-({4-[acetyl(methyl)amino]benzoyl}amino)-N-(5-chloropyridin-2-yl)benzamide

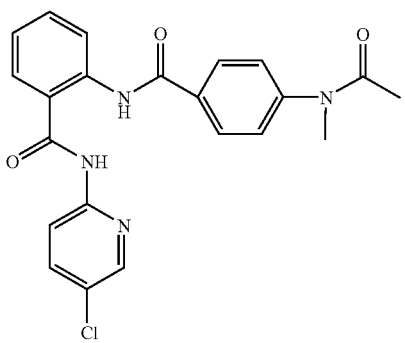

Following a procedure analogous to that described previously, the title compound 2-({4-[acetyl(methyl)amino]benzoyl}amino)-N-(5-chloropyridin-2-yl)benzamide was obtained as a white solid. LC/MS (ESI): (M+1)$^+$=423.0.

Example 58

N-(5-chloropyridin-2-yl)-2-({4-[(N,N-dimethylglycyl)(methyl)amino]benzoyl}amino)-5-methoxybenzamide

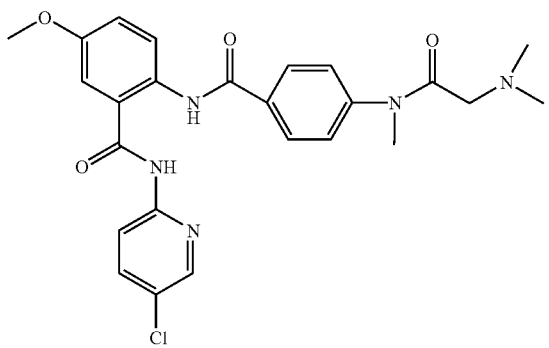

Following a procedure analogous to that described previously, the title compound the title compound was obtained as a white solid. LC/MS (ESI): (M+1)$^+$=496.1.

Example 59

N-(5-chloropyridin-2-yl)-2-({4-[(N,N-dimethylglycyl)(methyl)amino]benzoyl}amino)benzamide

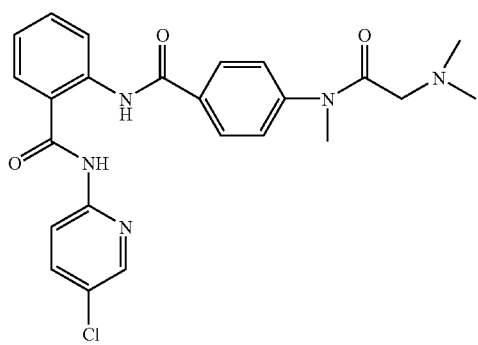

Following a procedure analogous to that described previously, the title compound the title compound was obtained as a white solid. LC/MS (ESI): (M+1)$^+$=466.0.

Example 60

2-({4-[acetyl(methyl)amino]benzoyl}amino)-5-chloro-N-(5-chloropyridin-2-yl)benzamide

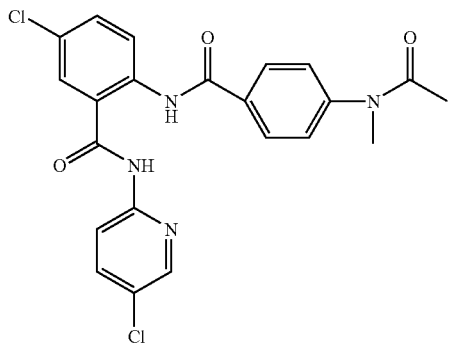

Following a procedure analogous to that described previously, the title compound the title compound was obtained as a white solid. LC/MS (ESI): (M+1)$^+$=456.9.

Example 61

N-{4-[6-Chloro-3-(5-chloro-pyridin-2-yl)-4-oxo-3,4-dihydro-quinazolin-2-yl]-phenyl}-2-dimethylamino-N-methyl-acetamide

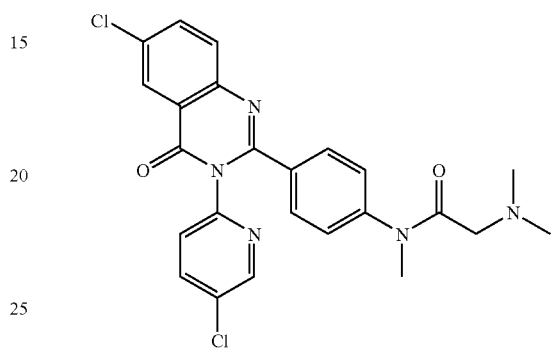

A solution of 5-chloro-N-(5-chloropyridin-2-yl)-2-({4-[(N,N-dimethylglycyl)(methyl)amino]-benzoyl}amino)benzamide (25.0 mg, 0.05 mmol, product from Example 8) in 5 mL of 4N HCl in dioxane and 1.0 mL of THF was refluxed for 6 hr. The mixture was cooled to room temperature and purified with reverse phase HPLC (10% CH$_3$CN in H$_2$O, 20 mL/min) to give the desired product as a white solid. LC/MS (ESI): (M+1)$^+$=482.0.

Example 61

N-{4-[6-Chloro-3-(5-chloro-pyridin-2-yl)-4-oxo-3,4-dihydro-quinazolin-2-yl]-phenyl}-N-methyl-2-morpholin-4-yl-acetamide

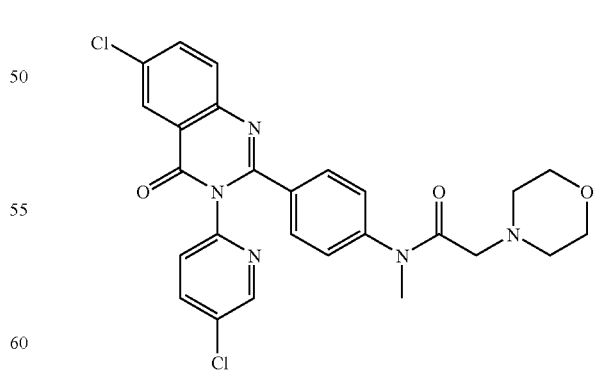

Following a procedure analogous to that described previously, the title compound was obtained as a white solid. LC/MS (ESI): (M+1)$^+$=523.9.

Example 62

2-(Butyl-methyl-amino)-N-{4-[6-chloro-3-(5-chloro-pyridin-2-yl)-4-oxo-3,4-dihydro-quinazolin-2-yl]-phenyl}-N-methyl-acetamide

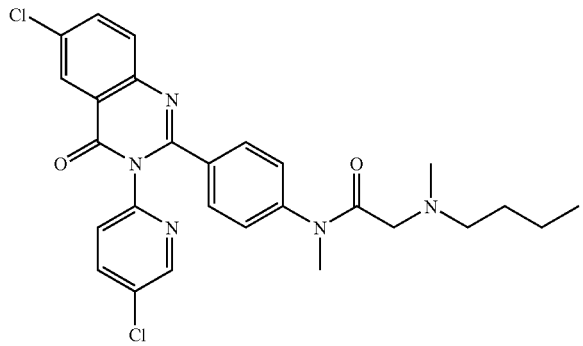

Following a procedure analogous to that described previously, the title compound the title compound was obtained as a white solid. LC/MS (ESI): (M+1)$^+$=524.0.

Example 63

1-(3-Chloro-phenyl)-6-{4-[methyl-(2-pyrrolidin-1-yl-acetyl)-amino]-phenyl}-7-oxo-4,5,6,7-tetrahydro-1H-pyrazolo[3,4-c]pyridine-3-carboxylic acid amide

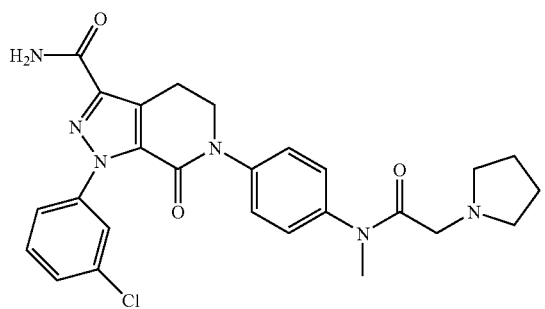

Part A: A 500 mL flask was charged with N-(3-chlorophenyl)-1-(ethoxycarbonyl)-methanehydrazonoyl chloride (3.67 g, 14.1 mmol), 3-morpholin-4-yl-1-(4-nitro-phenyl)-5,6-dihydro-1H-pyridin-2-one (2.14 g, 7.05 mmol), 50 mL of toluene, and triethylamine (3.57 g, 35.3 mmol). The mixture was heated at 80° C. overnight. After cooling to room temperature, the reaction mixture was treated with trifuloroacetic acid (10.1 g) at rt for 5 h. The mixture was concentrated to dryness under reduced pressure. The residue was dissolved in methylene chloride, washed water and brine, and dried with sodium sulfate. The crude product, after evaporation of the solvent, was purified by silica gel chromatography, eluting with 1:2 ethyl acetate/hexane to yield 1-(3-chloro-phenyl)-6-(4-nitro-phenyl)-7-oxo-4,5,6,7-tetrahydro-1H-pyrazolo[3,4-c]pyridine-3-carboxylic acid ethyl ester (1.48 g). $^1$H NMR (300 MHz, CDCl$_3$) δ 8.24 (2H, d, J=9.1 Hz), 7.60 (1H, t, J=1.8 Hz), 7.52 (2H, d, J=9.1 Hz), 7.47~7.36(2H, m), 4.48 (2H, q, J=7.0 Hz), 4.22 (2H, t, J=6.6 Hz), 3.39 (2H, t, J=6.6 Hz), 1.45 (3H, t, J=7.0 Hz) ppm.

Part B: A 200 mL flask was charged with 1-(3-chloro-phenyl)-6-(4-nitro-phenyl)-7-oxo-4,5,6,7-tetrahydro-1H-pyrazolo[3,4-c]pyridine-3-carboxylic acid ethyl ester (1.48 g, 3.36 mmol) and ethyl acetate (50 mL). After being purged with nitrogen, 0.15 g of 10% Pd/C was added. The reaction mixture was then stirred under an atmosphere of pressure of hydrogen overnight. The mixture was filtered through a pad of Celite®. The filtration was concentrated to dryness to provide 1.0 g of corresponding aniline compound. ESI MS m/z 411 (M$^+$+1).

Part C: A solution of 6-(4-amino-phenyl)-1-(3-chloro-phenyl)-7-oxo-4,5,6,7-tetrahydro-1H-pyrazolo[3,4-c]pyridine-3-carboxylic acid ethyl ester (1.0 g, 2.44 mmol) and Boc anhydride (1.06 g, 4.88 mmol) in THF (40 mL) was heated to reflux overnight. The mixture was concentrated to dryness and then purified by silica gel chromatography, eluting with 1:1 ethyl acetate/hexane, to give the protected product (1.45 g). ESI MS m/z 511 (M$^+$+1)

Part D. In a 200 mL of flask was placed 60% sodium hydride (0.23 g, 5.69 mmol) and DMF (10 mL). After being cooled to 0° C., a solution of 6-(4-tert-butoxycarbonylamino-phenyl)-1-(3-chloro-phenyl)-7-oxo-4,5,6,7-tetrahydro-1H-pyrazolo[3,4-c]pyridine-3-carboxylic acid ethyl ester (1.45 g, 2.84 mmol) in DMF (5 mL) was then added. The reaction was stirred for 30 min and then treated with methyl iodide (0.86 g, 5.69 mmol). The reaction was allowed to stir at rt overnight. After quenching with water, the mixture was extracted with ethyl acetate. The combined organic layers were washed with water and brine, dried with sodium sulfate, and concentrated to give 6-[4-(tert-butoxycarbonyl-methyl-amino)-phenyl]-1-(3-chloro-phenyl)-7-oxo-4,5,6,7-tetrahydro-1H-pyrazolo[3,4-c]pyridine-3-carboxylic acid ethyl ester (1.12 g). APCI MS m/z 525 (M$^+$+1).

Part E. The crude product from part D was treated with TFA (25 mL) at rt for 4 h. After evaporation of the TFA under reduced pressure, the residue was dissolved in ethyl acetate, washed with 1N NaOH and brine, dried (Na$_2$SO$_4$), and concentrated to dryness. The residue was applied to silica gel column, eluting with 1:1 ethyl acetate/hexane, to give the deprotected methylaniline (0.39 g). ESI MS m/z 425 (M$^+$+1).

Part F. To a solution of 1-(3-chloro-phenyl)-6-(4-methylamino-phenyl)-7-oxo-4,5,6,7-tetrahydro-1H-pyrazolo[3,4-c]pyridine-3-carboxylic acid ethyl ester (0.39 g, 0.92 mmol) in methylene chloride (5 mL) was added DMAP (0.17 g, 1.38 mmol), followed by chloroacetyl chloride (0.16 g, 1.38 mmol). The mixture was stirred at rt overnight, washed with 1N HCl and brine, dried (Na$_2$SO$_4$), and concentrated to dryness to give the crude chloride product. ESI MS m/z 501 (M$^+$+1).

The crude chloride (0.15 g, 0.30 mmol) was treated with pyrrolidine (0.10 g, 1.5 mmol) in THF (3 mL) at rt overnight. The mixture was concentrated to dryness to afford crude 1-(3-chloro-phenyl)-6-{4-[methyl-(2-pyrrolidin-1-yl-acetyl)-amino]-phenyl}-7-oxo-4,5,6,7-tetrahydro-1H-pyrazolo[3,4-c]pyridine-3-carboxylic acid ethyl ester (0.19 g). ESI MS m/z 536 (M$^+$+1).

Part G. A solution of 0.19 g (0.35 mmol) of the crude product from part F in 5 mL of 5% ammonia in ethylene glycol was heated at 80° C. in a sealed flask for 4 h. After cooling to rt, the mixture was concentrated to dryness under reduced pressure and applied to RP-HPLC to give the title compound (49.9 mg). $^1$H NMR (300 MHz, CDCl$_3$) δ 7.60 (1H, t, J=1.8 Hz), 7.49~7.40 (5H, m), 7.27 (2H, d, J=8.8 Hz), 6.86 (1H, br s), 5.62 (1H, br s), 4.17 (2H, t, J=6.6 Hz), 3.84

(2H, m), 3.77 (2H, s), 3.42 (2H, t, J=6.6 Hz), 3.02 (2H, m), 2.18 (4H, m) ppm. HR ESIMS: calc for $C_{26}H_{28}N_6O_3Cl$, 507.1911; found, 507.1918.

Example 64

$N^1$-{4-[6-chloro-3-(5-chloropyridin-2-yl)-4-oxo-3,4-dihydroquinazolin-2-yl]phenyl}-$N^1$,$N^2$-dimethylglycinamide

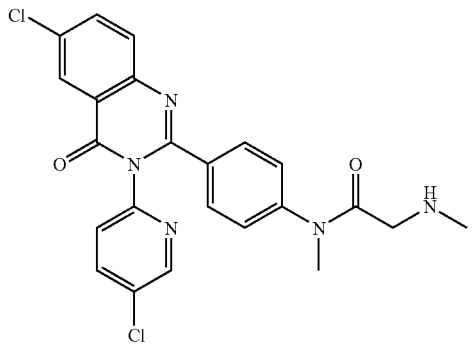

Following a procedure analogous to that described previously, the title compound the title compound was obtained as a white solid. LC/MS (ESI): (M+1)$^+$=468.13.

Example 65

$N^1$-{4-[6-chloro-3-(5-chloropyridin-2-yl)-4-oxo-3,4-dihydroquinazolin-2-yl]phenyl}-$N^2$-cyclobutyl-$N^1$-methylglycinamide

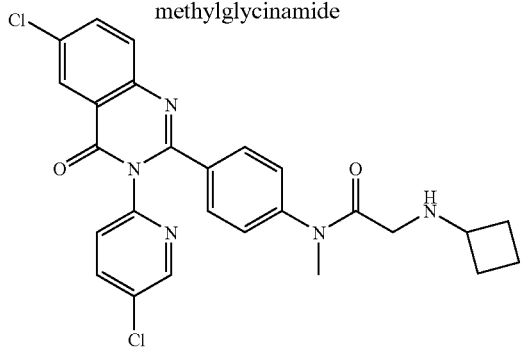

Following a procedure analogous to that described previously, the title compound the title compound was obtained as a white solid. LC/MS (ESI): (M+1)$^+$=508.13.

Example 66

N-(5-chloropyridin-2-yl)-2-({4-[methyl(pyrrolidin-1-ylacetyl)amino]benzoyl}amino)benzamide

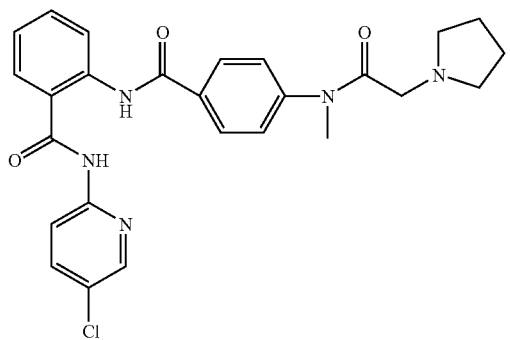

Following a procedure analogous to that described previously, the title compound the title compound was obtained as a white solid. LC/MS (ESI): (M+1)$^+$=492.2.

Example 67

N-(5-chloropyridin-2-yl)-5-fluoro-2-({4-[methyl(pyrrolidin-1-ylacetyl)amino]benzoyl}amino)benzamide

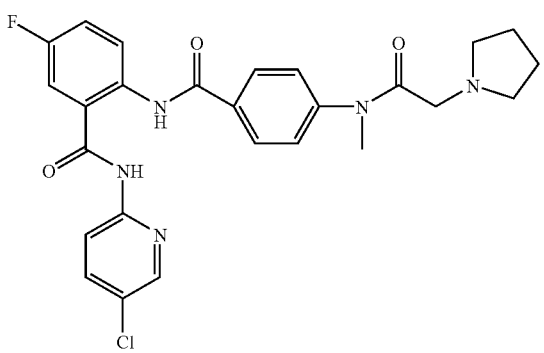

Following a procedure analogous to that described previously, the title compound the title compound was obtained as a white solid. LC/MS (ESI): (M+1)$^+$=510.1.

Example 68

N-(5-chloropyridin-2-yl)-2-({4-[(N,N-dimethylglycyl)(methyl)amino]benzoyl}amino)-5-fluorobenzamide

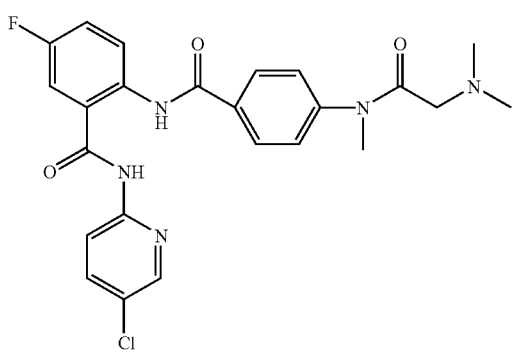

Following a procedure analogous to that described previously, the title compound the title compound was obtained as a white solid. LC/MS (ESI): (M+1)$^+$=484.1.

Example 69

N-(5-chloropyridin-2-yl)-2-({4-[(N,N-dimethylglycyl)(methyl)amino]benzoyl}amino)-3-methoxybenzamide

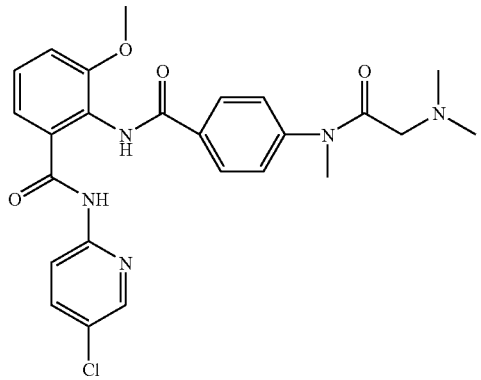

Following a procedure analogous to that described previously, the title compound the title compound was obtained as a white solid. LC/MS (ESI): (M+1)$^+$=496.2.

Example 70

N-(5-chloropyridin-2-yl)-5-methyl-2-({4-[methyl(pyrrolidin-1-ylacetyl)amino]benzoyl}amino)benzamide

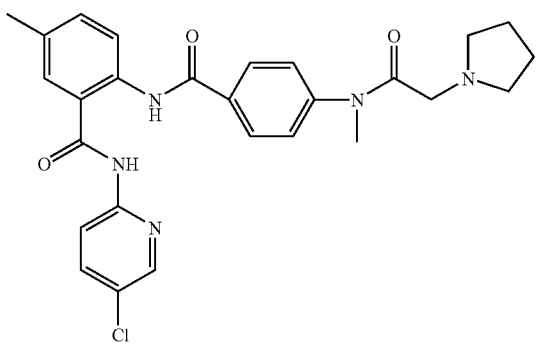

Following a procedure analogous to that described previously, the title compound the title compound was obtained as a white solid. LC/MS (ESI): (M+1)$^+$=506.2.

Example 71

N-(5-chloropyridin-2-yl)-2-({4-[(N,N-dimethylglycyl)(methyl)amino]benzoyl}amino)-5-methylbenzamide

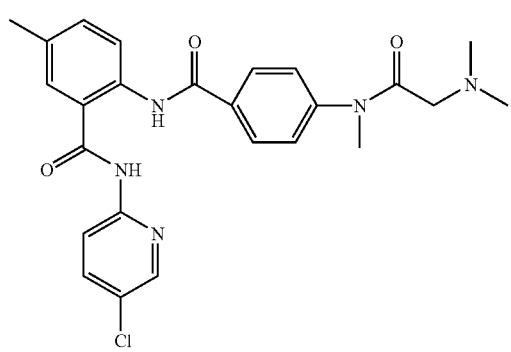

Following a procedure analogous to that described 7, previously, the title compound was obtained as a white solid. LC/MS (ESI): (M+1)$^+$=480.2.

Example 72

2-({4-[acetyl(methyl)amino]benzoyl}amino)-N-(5-chloropyridin-2-yl)-5-methoxybenzamide

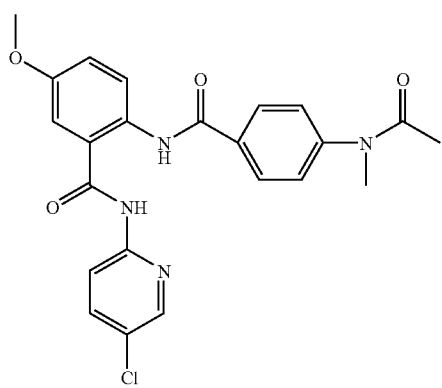

Following a procedure analogous to that described previously, the title compound the title compound was obtained as a white solid. LC/MS (ESI): (M+1)$^+$=453.1.

Example 73

N-(5-chloropyridin-2-yl)-2-({4-[(N,N-dimethylglycyl)(methyl)amino]benzoyl}amino)-4,5-difluorobenzamide

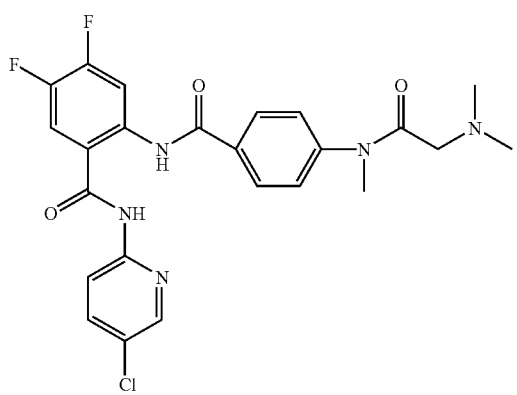

Following a procedure analogous to that described previously, the title compound was obtained as light yellow solid. LC/MS (ESI): (M+1)$^+$=502.3.

Example 74

N-(5-chloropyridin-2-yl)-5-methoxy-2-({4-[methyl(piperidin-1-ylacetyl)amino]benzoyl}amino)benzamide

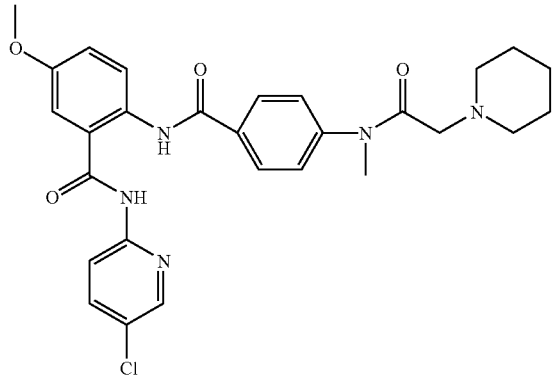

Following a procedure analogous to that described previously, the title compound was obtained as a white solid. LC/MS (ESI): (M+1)$^+$=536.2.

Example 75

N-(5-chloropyridin-2-yl)-5-methyl-2-({4-[methyl(piperidin-1-ylacetyl)amino]benzoyl}amino)benzamide

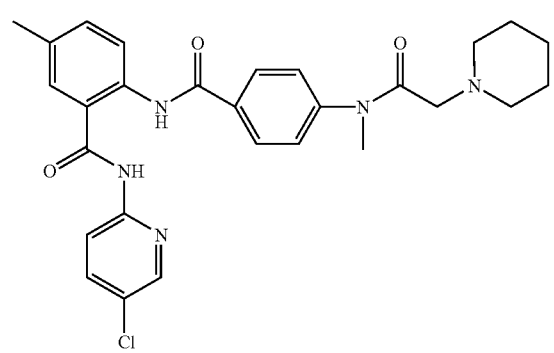

Following a procedure analogous to that described previously, the title compound was obtained as a white solid. LC/MS (ESI): (M+1)$^+$=520.0.

Example 76

5-chloro-N-(5-chloropyridin-2-yl)-2-({4-[methyl(N-methylglycyl)amino]benzoyl}amino)benzamide

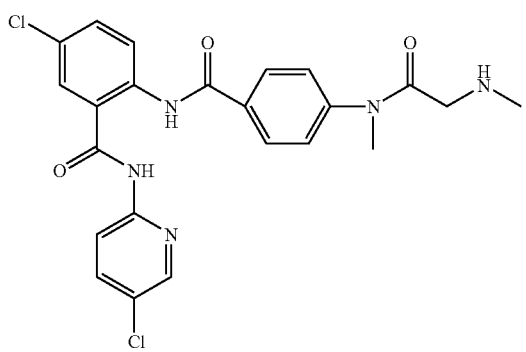

Following a procedure analogous to that described previously, the title compound was obtained as light yellow solid. LC/MS (ESI): (M+1)$^+$=486.1.

Example 77

5-chloro-N-(5-chloropyridin-2-yl)-2-({4-[(N-cyclobutylglycyl)(methyl)amino]benzoyl}amino)benzamide

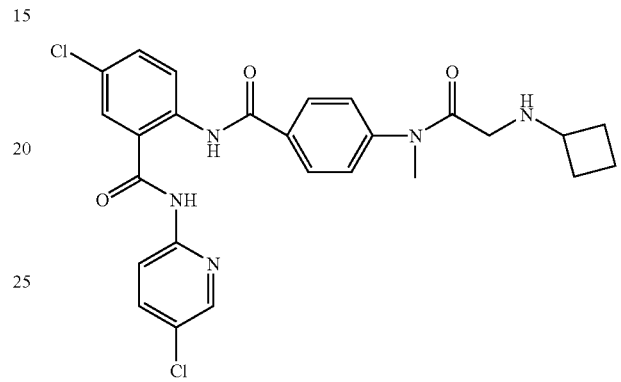

Following a procedure analogous to that described previously, the title compound was obtained as a white solid. LC/MS (ESI): (M+1)$^+$=526.1.

Example 78

N-(5-chloropyridin-2-yl)-2-({4-[methyl(piperidin-1-ylacetyl)amino]benzoyl}amino)benzamide

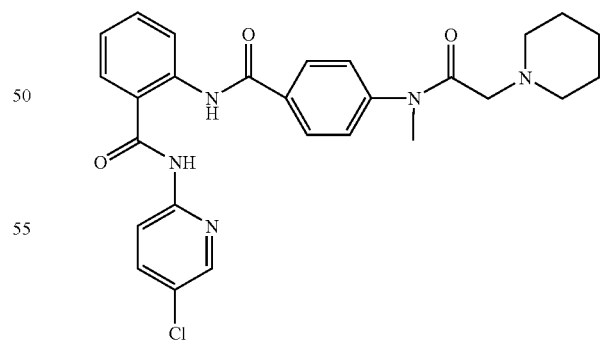

Following a procedure analogous to that described previously, the title compound was obtained as a white solid. LC/MS (ESI): (M+1)$^+$=506.2.

Example 79

N-(5-chloropyridin-2-yl)-5-fluoro-2-({4-[methyl(piperidin-1-ylacetyl)amino]benzoyl}amino)benzamide

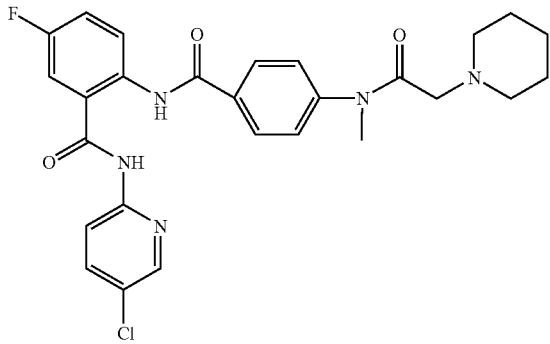

Following a procedure analogous to that described previously, the title compound was obtained as a white solid. LC/MS (ESI): (M+1)⁺=524.1.

Example 80

2-({4-[(N-butyl-N-methylglycyl)(methyl)amino]benzoyl}amino)-N-(5-chloropyridin-2-yl)-5-methoxybenzamide

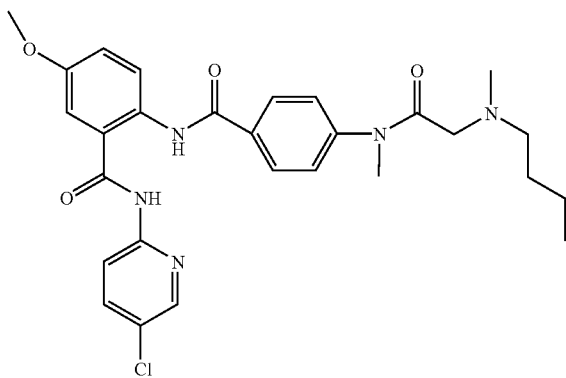

Following a procedure analogous to that described previously, the title compound was obtained as a white solid. LC/MS (ESI): (M+1)⁺=538.0.

Example 81

2-({4-[(N-butyl-N-methylglycyl)(methyl)amino]benzoyl}amino)-N-(5-chloropyridin-2-yl)-5-fluorobenzamide

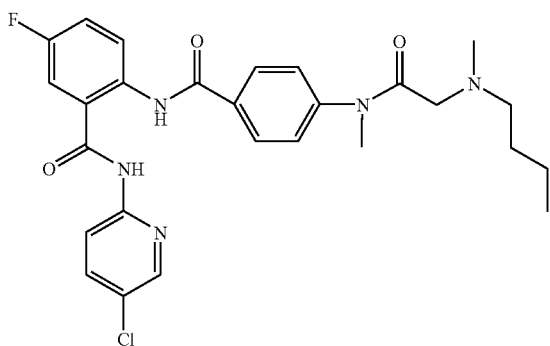

Following a procedure analogous to that described previously, the title compound was obtained as a white solid. LC/MS (ESI): (M+1)⁺=526.3.

Example 82

2-({4-[(N-butyl-N-methylglycyl)(methyl)amino]benzoyl}amino)-N-(5-chloropyridin-2-yl)benzamide

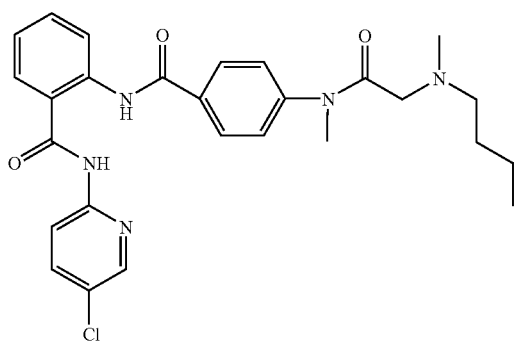

Following a procedure analogous to that described previously, the title compound was obtained as a white solid. LC/MS (ESI): (M+1)⁺=508.3.

Example 83

N-(5-chloropyridin-2-yl)-5-methoxy-2-({4-[methyl(N-methylglycyl)amino]benzoyl}amino)benzamide

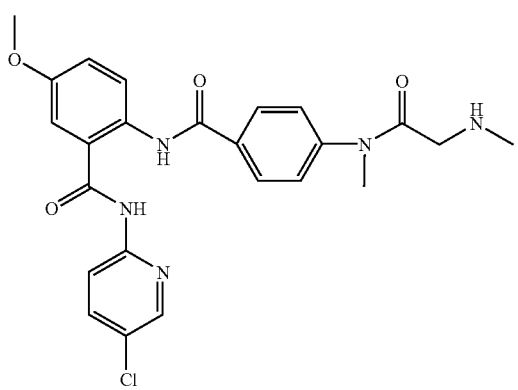

Following a procedure analogous to that described previously, the title compound was obtained as light yellow solid. LC/MS (ESI): (M+1)⁺=482.2.

Example 84

N-(5-chloropyridin-2-yl)-2-({4-[(N-cyclobutylglycyl)(methyl)amino]benzoyl}amino)-5-methoxybenzamide

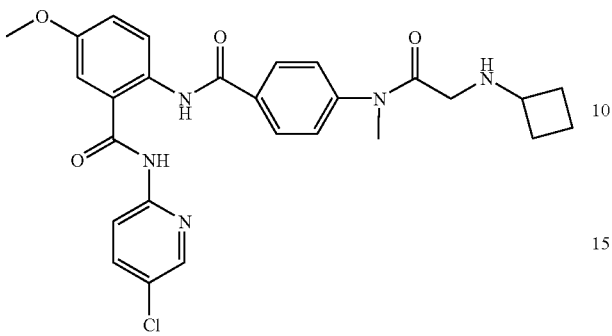

Following a procedure analogous to that described previously, the title compound was obtained as a light brown solid. LC/MS (ESI): (M+1)$^+$=522.2.

Example 85

N-(5-chloropyridin-2-yl)-2-({4-[methyl(N-methylglycyl)amino]benzoyl}amino)benzamide

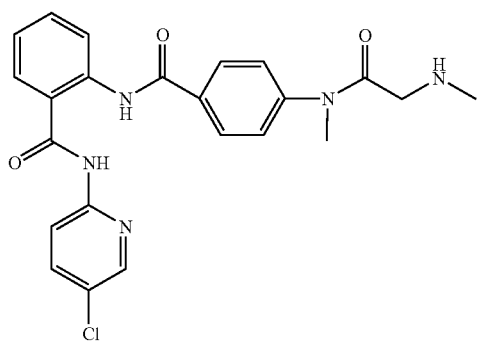

Following a procedure analogous to that described previously, the title compound was obtained as light yellow solid. LC/MS (ESI): (M+1)$^+$=452.1.

Example 86

2-({4-[(N-butyl-N-methylglycyl)(methyl)amino]benzoyl}amino)-N-(5-chloropyridin-2-yl)-5-methylbenzamide

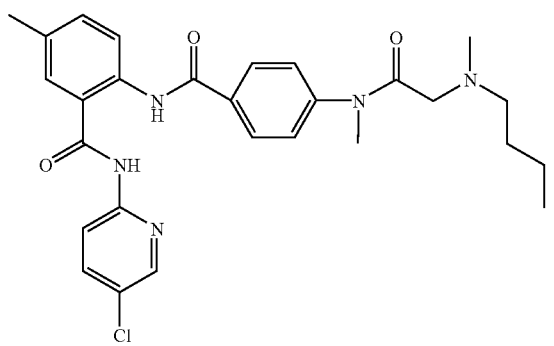

Following a procedure analogous to that described previously, the title compound was obtained as a white solid. LC/MS (ESI): (M+1)$^+$=522.1.

Example 87

N-(5-chloropyridin-2-yl)-2-({4-[(N-ethyl-N-methylglycyl)(methyl)amino]benzoyl}amino)-5-methoxybenzamide

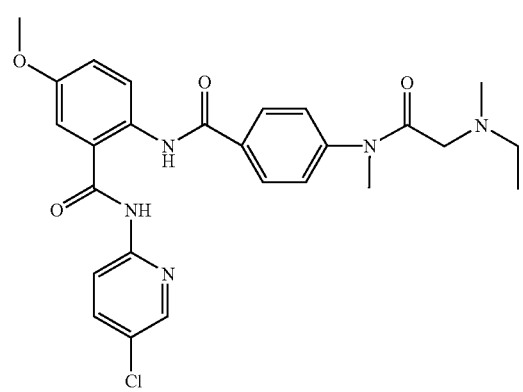

Following a procedure analogous to that described previously, the title compound was obtained as a white solid. LC/MS (ESI): (M+1)$^+$=510.2.

Example 88

N-(5-chloropyridin-2-yl)-2-({4-[(N-ethyl-N-methylglycyl)(methyl)amino]benzoyl}amino)-5-methylbenzamide

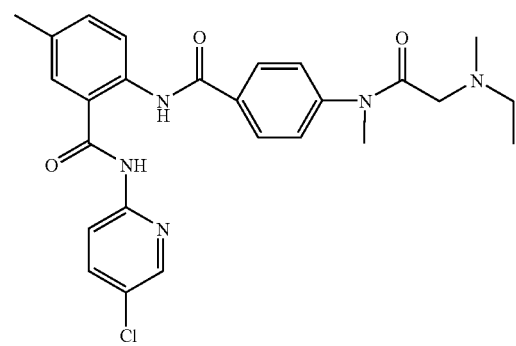

Following a procedure analogous to that described previously, the title compound was obtained as a white solid. LC/MS (ESI): (M+1)$^+$=494.3.

Example 89

N-(5-chloropyridin-2-yl)-2-({4-[(N-ethyl-N-methylglycyl)(methyl)amino]benzoyl}amino)benzamide

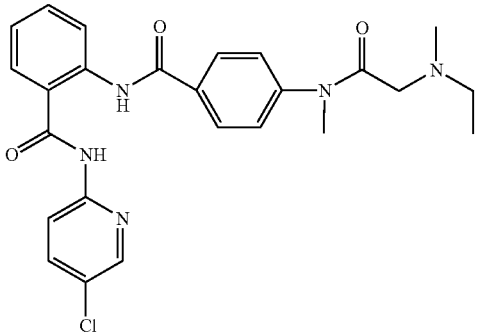

Following a procedure analogous to that described previously, the title compound was obtained as a white solid. LC/MS (ESI): $(M+1)^+=480.3$.

Example 90

N-(5-chloropyridin-2-yl)-2-({4-[(N-ethyl-N-methylglycyl)(methyl)amino]benzoyl}amino)-5-fluorobenzamide

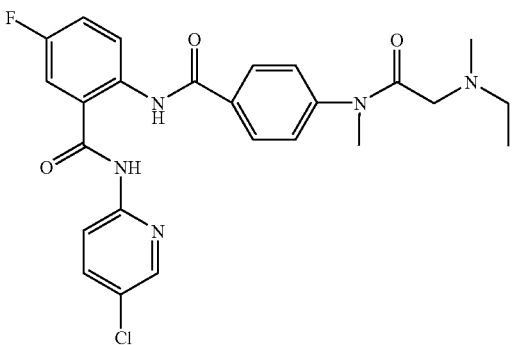

Following a procedure analogous to that described previously, the title compound was obtained as a white solid. LC/MS (ESI): $(M+1)^+=498.2$.

Example 91

N-(5-chloropyridin-2-yl)-5-methyl-2-({4-[(pyrrolidin-1-ylacetyl)amino]benzoyl}amino)benzamide

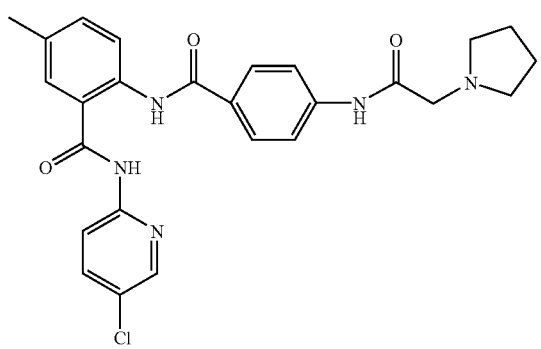

Following a procedure analogous to that described previously, the title compound was obtained as a white solid. LC/MS (ESI): $(M+1)^+=492.1$.

Example 92

N-(5-chloropyridin-2-yl)-5-fluoro-2-({4-[(pyrrolidin-1-ylacetyl)amino]benzoyl}amino)benzamide

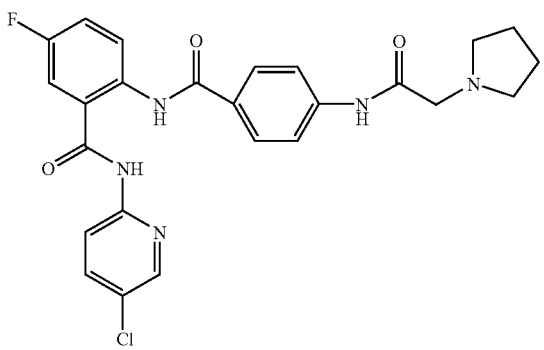

Following a procedure analogous to that described previously, the title compound was obtained as a white solid. LC/MS (ESI): $(M+1)^+=496.1$.

Example 93

N-(5-chloropyridin-2-yl)-2-({4-[(N,N-dimethylglycyl)amino]benzoyl}amino)-5-methylbenzamide

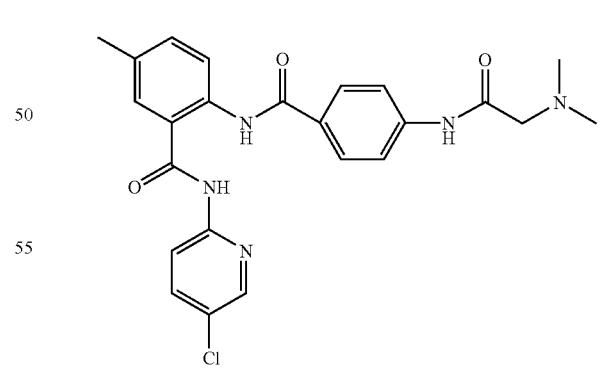

Following a procedure analogous to that described previously, the title compound was obtained as a white solid. LC/MS (ESI): $(M+1)^+=466.0$.

Example 94

N-(5-chloropyridin-2-yl)-5-methoxy-2-({4-[(pyrrolidin-1-ylacetyl)amino]benzoyl}amino)benzamide

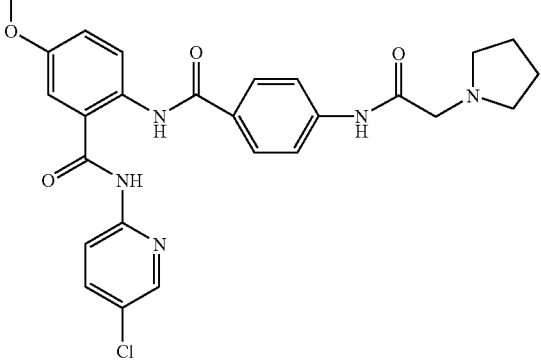

Following a procedure analogous to that described previously, the title compound was obtained as a white solid. LC/MS ESI): (M+1)$^+$=508.3.

Example 95

N-(5-chloropyridin-2-yl)-2-({4-[(N-cyclobutylglycyl)(methyl)amino]benzoyl}amino)benzamide

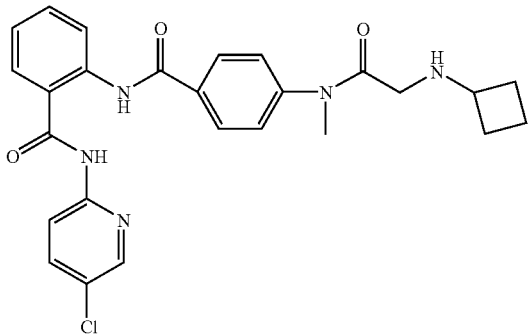

Following a procedure analogous to that described previously, the title compound was obtained as a white solid. LC/Ms (ESI): (M+1)$^+$=492.2.

Example 96

N-{4-[1-(4-Methoxy-phenyl)-3-(4-methyl-oxazol-2-yl)-7-oxo-1,4,5,7-tetrahydro-pyrazolo[3,4-c]pyridin-6-yl]-phenyl}-N-methyl-2-pyrrolidin-1-yl-acetamide

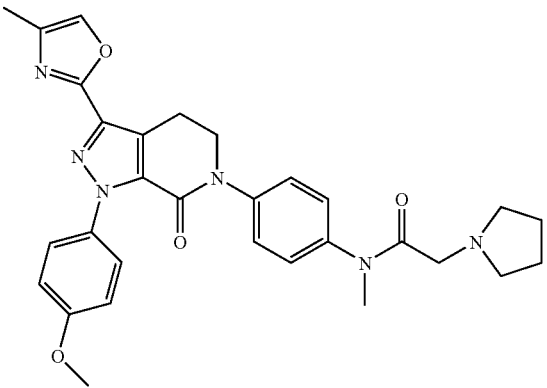

Part A. To 6-[4-(tert-butoxycarbonyl-methyl-amino)-phenyl]-1-(4-methoxy-phenyl)-7-oxo-4,5,6,7-tetrahydro-1H-pyrazolo[3,4-c]pyridine-3-carboxylic acid ethyl ester (2 g, 3.8 mmol) in a THF (20 mL), water (15 mL), and MeOH (15 mL) was added lithium hydroxide (0.65 g, 15 mmol) and the reaction was stirred for 24 h. The solvents were removed, and the remaining aqueous residue was acidified with 1N HCl, extracted with EtOAc, and dried (Na$_2$SO$_4$) to afford a solid (1.7 g, 89%); $^1$H NMR (CDCl$_3$) δ 7.50 (d, j=8.8 Hz, 2H), 7.26(m, 4H) 6.93(d, j=8.8 Hz, 2H), 4.13(t, j=6.6 Hz, 2H), 3.82(s, 3H), 3.35(t, j=6.6 Hz, 2H), 3.23(s, 3H), 1.45(s, 9H)ppm.

Part B. To the product of Part A (0.42 g, 0.85 mmol) in CH$_2$Cl$_2$ (10 mL) was added 1-[3-(dimethylamino)propyl]-3-ethyl carbodiimide hydrochloride (0.19 g, 0.10 mmol) and TEA (0.35 mL, 2.5 mmol) and the reaction was stirred for 15 min. To the reaction was added 1-hydroxybenzotriazole (0.138 g, 0.10 mmol) and stirred 15 min. DL-2-aminopropanol (0.2 mL, 2.5 mmol) was then added, and the reaction stirred for 24 h. After quenching with water, the product was extracted with CH$_2$Cl$_2$ and dried (MgSO$_4$). Purification by chromatography using 0–10% MeOH/CH$_2$Cl$_2$ afforded the product (77 mg, 16%); LC/MS (ESI): (M+H)+ 550.4, (M+Na)$^+$572.

Part C. To the product of Part B (0.24 g, 0.43 mmol) in THF (15 mL) was added (methoxycarbonylsulfamyl)triethyl ammonium hydroxide, inner salt (Burgess reagent) (0.8 g, 3.6 mmol), and the reaction was heated to reflux for 2.5 h. The solvent was removed and purification by chromatography using 1:1 hexanes/EtOAc afforded a tan foam (0.21 g 90%). LC/MS (ESI): (M+H)$^+$ 532.3.

Part D. To the product of Part C (88 mg, 0.16 mmol) in benzene (10 mL) was added 2,3-dichloro-5,6-dicyano-1,4-benzoquinone (DDQ) (94 mg, 0.4 mmol) and the reaction was heated to reflux 24 h. The solvent was stripped and purification by chromatography using 0–3% MeOH/CH$_2$Cl$_2$ afforded the product. LC/MS (ESI): (M+H)$^+$ 530.3, (M+Na)$^+$ 552.3.

Part E. To the product of Part D in CH$_2$Cl$_2$ was added excess TFA and the reaction was stirred 3 h. The solvents were removed, the residue taken up in CH$_2$Cl$_2$ and sat'd NaHCO$_3$, and several drops of chloroacetyl chloride were added. The reaction was shaken for 10 min, separated, and washed with brine. The solvent was removed and replaced with THF (20 mL) containing excess pyrrolidine. Purification by HPLC and freeze-drying afforded the desired product (17 mg, 19% from Part D). High resolution LC/MS (ESI): (M+H)$^+$ for C$_{30}$H$_{33}$N$_6$O$_4$ 541.2544.

Example 97

2-Dimethylamino-N-{4-[1-(4-methoxy-phenyl)-3-(4-methyl-oxazol-2-yl)-7-oxo-1,4,5,7-tetrahydro-pyrazolo[3,4-c]pyridin-6-yl]-phenyl}-N-methyl-acetamide

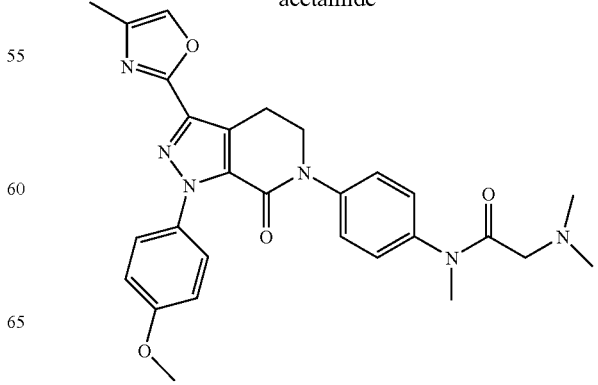

Example 98

N-{4-[1-(4-Methoxy-phenyl)-3-(4-methyl-oxazol-2-yl)-7-oxo-1,4,5,7-tetrahydro-pyrazolo[3,4-c]pyridin-6-yl]-phenyl}-N-methyl-3-pyrrolidin-1-yl-propionamide

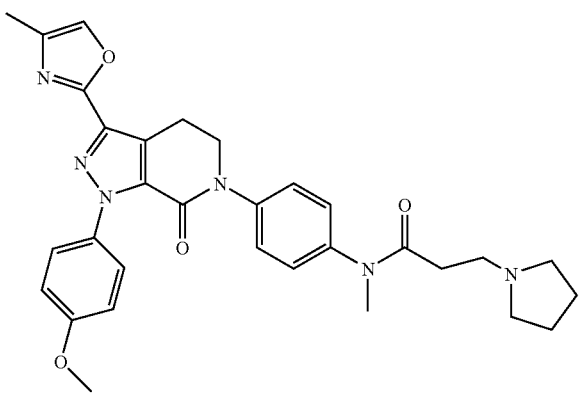

The title compound was synthesized as described in Example 96. High resolution LC/MS (ESI): (M+H)$^+$ for $C_{31}H_{35}N_6O_4$ 555.2724.

Example 99

6-[4-(2-hydroxy-2-methyl-propionylamino)-phenyl]-1-(4-methoxy-phenyl)-7-oxo-4,5,6,7-tetrahydro-1H-pyrazolo[3,4-c]pyridine-3-carboxylic acid amide

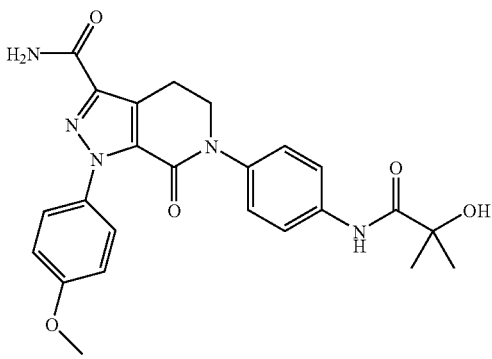

Part A. To 4-iodoaniline (3 g, 13.6 mmol) in CH$_2$Cl$_2$ (50 mL) at 0° C. was added 2M trimethylaluminum in heptanes (11 mL, 20 mmol), the reaction was stirred 20 min, and methyl-α-hydroxyisobutrate (2.4 g, 20 mmol) was added. After stirring 24 h, the reaction was quenched with dilute HCl, extracted with CH$_2$Cl$_2$, and dried (Na$_2$SO$_4$). Purification by chromatography using 0–25% Ethyl acetate/hexanes afforded the desired product (0.6 g, 14%). $^1$H NMR (CDCl$_3$) δ 8.67(s, 1H), 7.64(d, J=9.2 Hz, 2H), 7.39 (d, J=9.2 Hz, 2H), 1.55(s, 6H) ppm.

Part B. The product of Part A (0.2 g, 0.65 mmol), 1-(4-methoxy-phenyl)-7-oxo-4,5,6,7-tetrahydro-1H-pyrazolo[3,4-c]pyridine-3-carboxylic acid ethyl ester (0.19 g, 0.59 mmol), K$_2$CO$_3$ (0.25 g, 1.8 mmol), and tetrakis(acetonitrile) copper(I) hexafluorophosphate (45 mg, 0.12 mmol) were combined in degassed dimethylsulfoxide (5 mL), and the reaction was heated to 130° C. for 6 h. The reaction was quenched with sat'd NaHCO$_3$ and extracted with CH$_2$Cl$_2$ and dried (MgSO$_4$). Purification by chromatography using 0–5% MeOH/CH$_2$Cl$_2$ afforded a semipure fraction (55 mg, 18%); LC/MS (ESI): (M+H)$^+$ 493.3.

Part C. The product of Part B was heated to 80° C. in a sealed vial with 5% ammonia in ethylene glycol (1.5 mL) for 2 h. The reaction was quenched with water, extracted with CH$_2$Cl$_2$, and purified by HPLC to afford the title compound (15 mg, 29.4%); LC/MS (ESI): (M+H)$^+$ 464.3.

The following tables contain representative examples of the present invention. Each entry in each table is intended to be paired with each formulas at the start of the table. For example, in Tables 1 and 2, example 1 is intended to be paired with each of the formulas.

The following nomenclature is intended for group A in the following tables.

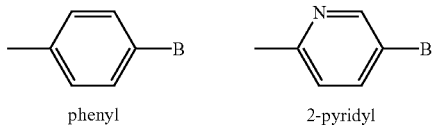

phenyl      2-pyridyl

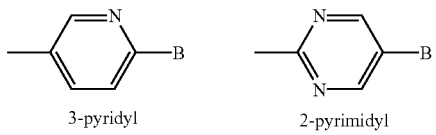

3-pyridyl      2-pyrimidyl

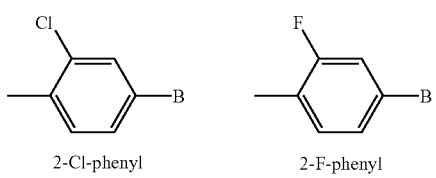

2-Cl-phenyl      2-F-phenyl

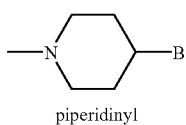

piperidinyl

TABLE 1
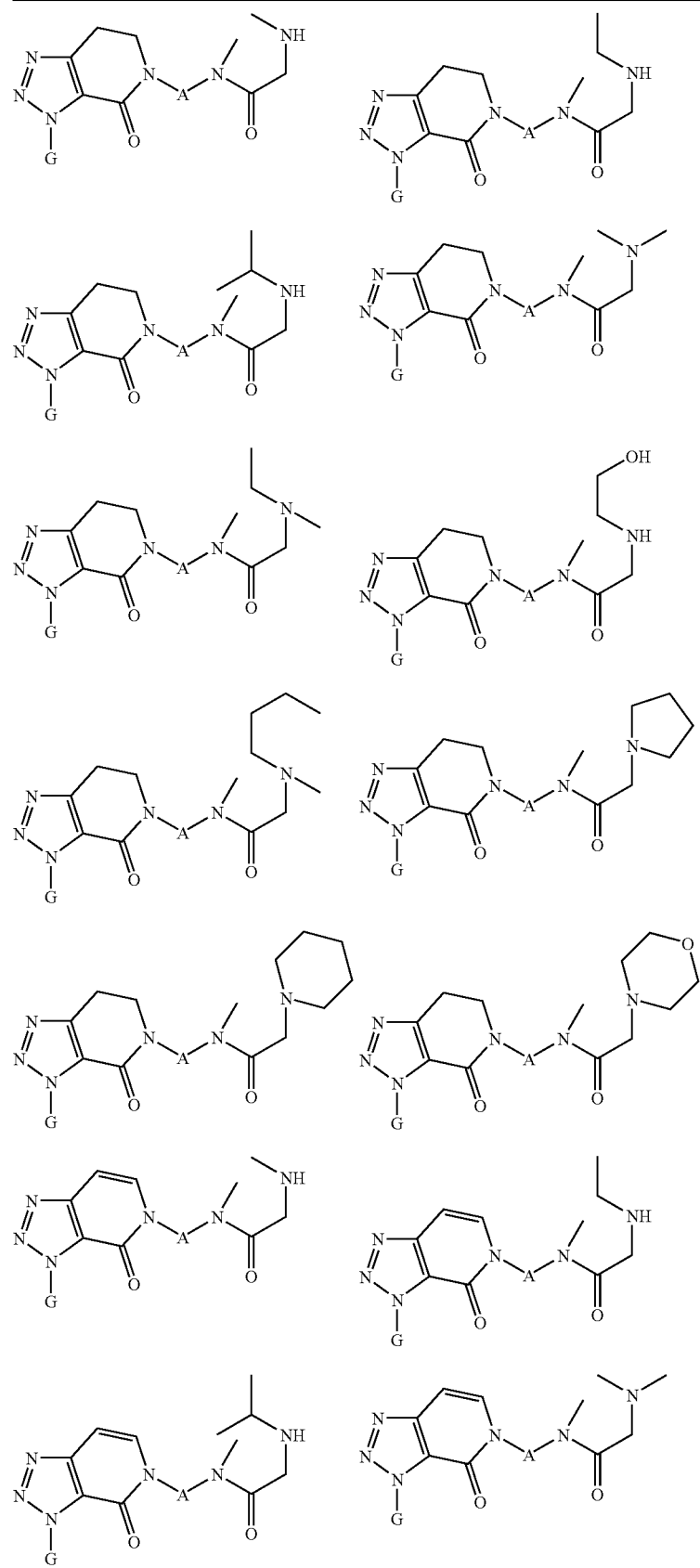

TABLE 1-continued
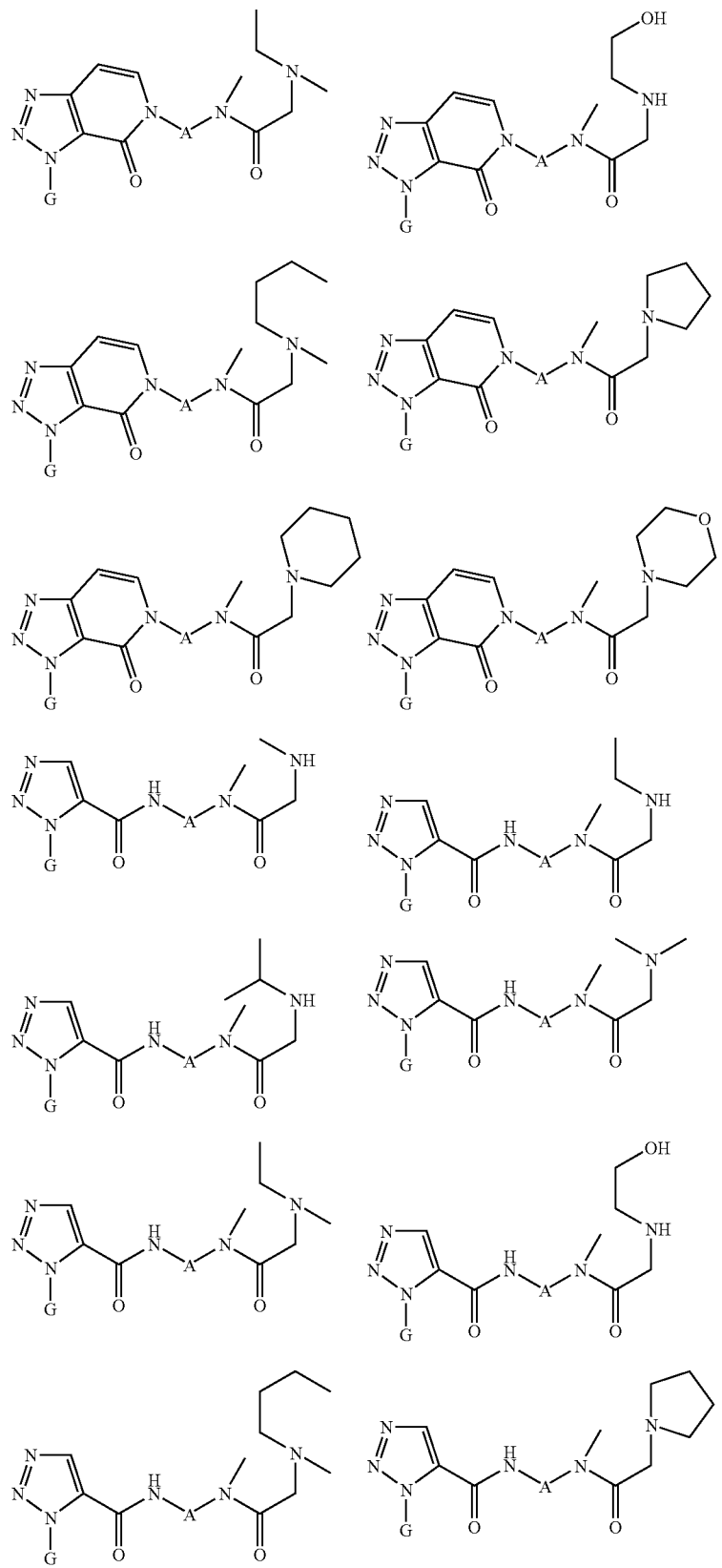

TABLE 1-continued
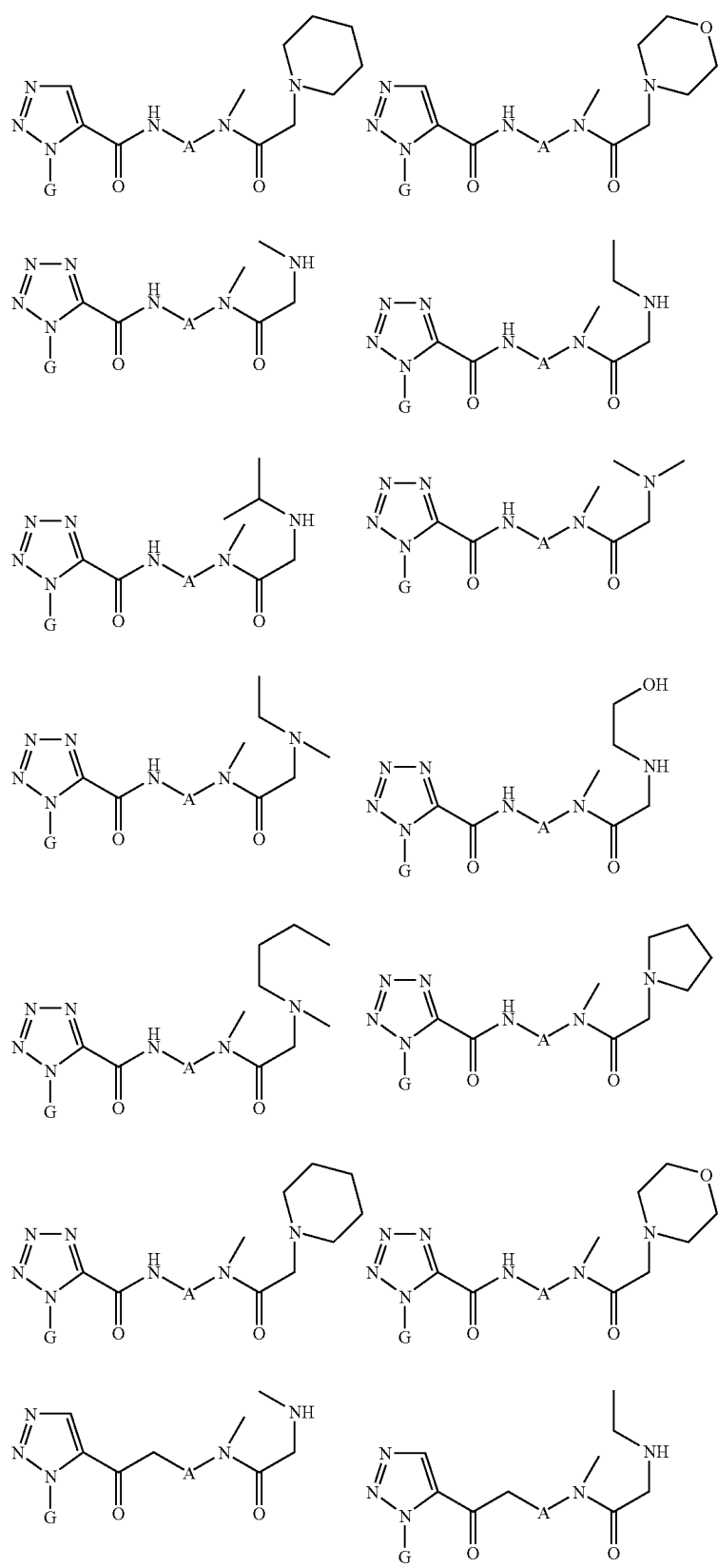

TABLE 1-continued
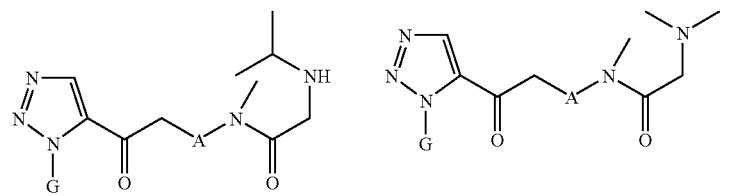
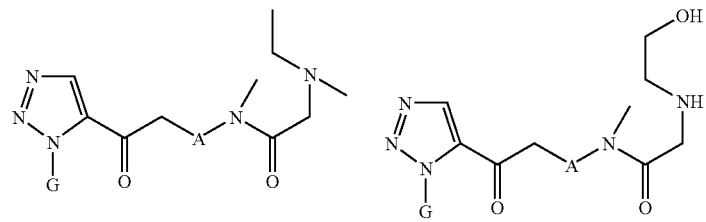
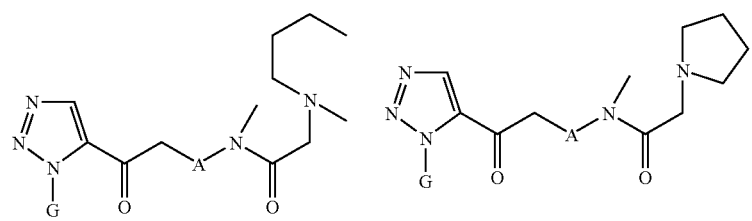
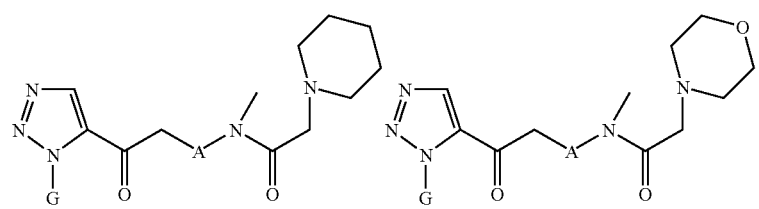
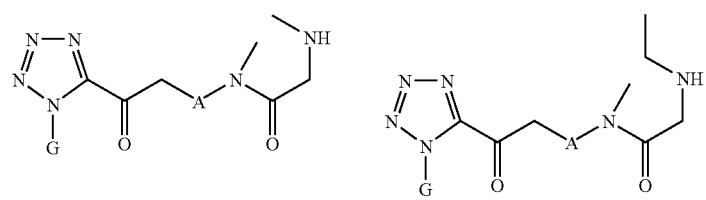
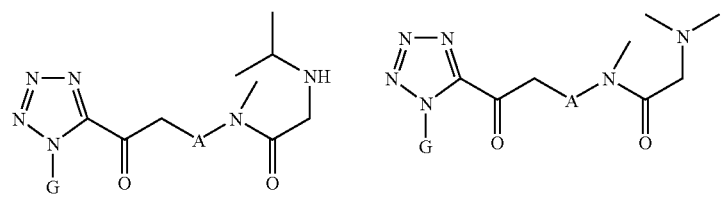
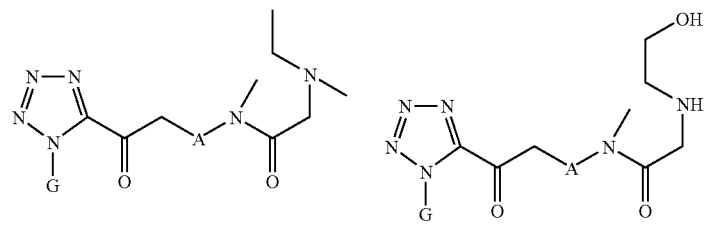

TABLE 1-continued

| Ex# | A | G |
|---|---|---|
| 1-1. | phenyl | 4-methoxyphenyl |
| 1-2. | 2-pyridyl | 4-methoxyphenyl |
| 1-3. | 3-pyridyl | 4-methoxyphenyl |
| 1-4. | 2-pyrimidyl | 4-methoxyphenyl |
| 1-5. | 2-Cl-phenyl | 4-methoxyphenyl |
| 1-6. | 2-F-phenyl | 4-methoxyphenyl |
| 1-7. | phenyl | 2-aminomethylphenyl |
| 1-8. | 2-pyridyl | 2-aminomethylphenyl |
| 1-9. | 3-pyridyl | 2-aminomethylphenyl |
| 1-10. | 2-pyrimidyl | 2-aminomethylphenyl |
| 1-11. | 2-Cl-phenyl | 2-aminomethylphenyl |
| 1-12. | 2-F-phenyl | 2-aminomethylphenyl |
| 1-13. | phenyl | 3-aminomethylphenyl |
| 1-14. | 2-pyridyl | 3-aminomethylphenyl |
| 1-15. | 3-pyridyl | 3-aminomethylphenyl |
| 1-16. | 2-pyrimidyl | 3-aminomethylphenyl |
| 1-17. | 2-Cl-phenyl | 3-aminomethylphenyl |
| 1-18. | 2-F-phenyl | 3-aminomethylphenyl |
| 1-19. | phenyl | 2-amidophenyl |
| 1-20. | 2-pyridyl | 2-amidophenyl |
| 1-21. | 3-pyridyl | 2-amidophenyl |
| 1-22. | 2-pyrimidyl | 2-amidophenyl |
| 1-23. | 2-Cl-phenyl | 2-amidophenyl |
| 1-24. | 2-F-phenyl | 2-amidophenyl |
| 1-25. | phenyl | 2-amido-4-methoxy-phenyl |
| 1-26. | 2-pyridyl | 2-amido-4-methoxy-phenyl |
| 1-27. | 3-pyridyl | 2-amido-4-methoxy-phenyl |
| 1-28. | 2-pyrimidyl | 2-amido-4-methoxy-phenyl |
| 1-29. | 2-Cl-phenyl | 2-amido-4-methoxy-phenyl |
| 1-30. | 2-F-phenyl | 2-amido-4-methoxy-phenyl |
| 1-31. | phenyl | 3-amidophenyl |
| 1-32. | 2-pyridyl | 3-amidophenyl |
| 1-33. | 3-pyridyl | 3-amidophenyl |
| 1-34. | 2-pyrimidyl | 3-amidophenyl |
| 1-35. | 2-Cl-phenyl | 3-amidophenyl |
| 1-36. | 2-F-phenyl | 3-amidophenyl |
| 1-37. | phenyl | 3-chlorophenyl |
| 1-38. | 2-pyridyl | 3-chlorophenyl |
| 1-39. | 3-pyridyl | 3-chlorophenyl |
| 1-40. | 2-pyrimidyl | 3-chlorophenyl |
| 1-41. | 2-Cl-phenyl | 3-chlorophenyl |
| 1-42. | 2-F-phenyl | 3-chlorophenyl |
| 1-43. | phenyl | 3-amino-4-chloro-phenyl |
| 1-44. | 2-pyridyl | 3-amino-4-chloro-phenyl |
| 1-45. | 3-pyridyl | 3-amino-4-chloro-phenyl |
| 1-46. | 2-pyrimidyl | 3-amino-4-chloro-phenyl |
| 1-47. | 2-Cl-phenyl | 3-amino-4-chloro-phenyl |
| 1-48. | 2-F-phenyl | 3-amino-4-chloro-phenyl |
| 1-49. | phenyl | 2-aminosulfonyl-phenyl |
| 1-50. | 2-pyridyl | 2-aminosulfonyl-phenyl |
| 1-51. | 3-pyridyl | 2-aminosulfonyl-phenyl |
| 1-52. | 2-pyrimidyl | 2-aminosulfonyl-phenyl |
| 1-53. | 2-Cl-phenyl | 2-aminosulfonyl-phenyl |
| 1-54. | 2-F-phenyl | 2-aminosulfonyl-phenyl |
| 1-55. | phenyl | 2-aminosulfonyl-4- |

TABLE 1-continued

| | | |
|---|---|---|
| 1-56. | 2-pyridyl | 2-aminosulfonyl-4-methoxyphenyl |
| 1-57. | 3-pyridyl | 2-aminosulfonyl-4-methoxyphenyl |
| 1-58. | 2-pyrimidyl | 2-aminosulfonyl-4-methoxyphenyl |
| 1-59. | 2-Cl-phenyl | 2-aminosulfonyl-4-methoxyphenyl |
| 1-60. | 2-F-phenyl | 2-aminosulfonyl-4-methoxyphenyl |
| 1-61. | phenyl | 3-(1',2',4'-triazolin-5'-on-3'-yl)phenyl |
| 1-62. | 2-pyridyl | 3-(1',2',4'-triazolin-5'-on-3'-yl)phenyl |
| 1-63. | 3-pyridyl | 3-(1',2',4'-triazolin-5'-on-3'-yl)phenyl |
| 1-64. | 2-pyrimidyl | 3-(1'2',4'-triazolin-5'-on-3'-yl)phenyl |
| 1-65. | 2-Cl-phenyl | 3-(1',2',4'-triazolin-5'-on-3'-yl)phenyl |
| 1-66. | 2-F-phenyl | 3-(1',2',4'-triazolin-5'-on-3'-yl)phenyl |
| 1-67. | phenyl | 1-aminoisoquinolin-6-yl |
| 1-68. | 2-pyridyl | 1-aminoisoquinolin-6-yl |
| 1-69. | 3-pyridyl | 1-aminoisoquinolin-6-yl |
| 1-70. | 2-pyrimidyl | 1-aminoisoquinolin-6-yl |
| 1-71. | 2-Cl-phenyl | 1-aminoisoquinolin-6-yl |
| 1-72. | 2-F-phenyl | 1-aminoisoquinolin-6-yl |
| 1-73. | phenyl | 1-aminoisoquinolin-7-yl |
| 1-74. | 2-pyridyl | 1-aminoisoquinolin-7-yl |
| 1-75. | 3-pyridyl | 1-aminoisoquinolin-7-yl |
| 1-76. | 2-pyrimidyl | 1-aminoisoquinolin-7-yl |
| 1-77. | 2-Cl-phenyl | 1-aminoisoquinolin-7-yl |
| 1-78. | 2-F-phenyl | 1-aminoisoquinolin-7-yl |
| 1-79. | phenyl | 4-aminoquinazol-6-yl |
| 1-80. | 2-pyridyl | 4-aminoquinazol-6-yl |
| 1-81. | 3-pyridyl | 4-aminoquinazol-6-yl |
| 1-82. | 2-pyrimidyl | 4-aminoquinazol-6-yl |
| 1-83. | 2-Cl-phenyl | 4-aminoquinazol-6-yl |
| 1-84. | 2-F-phenyl | 4-aminoquinazol-6-yl |
| 1-85. | phenyl | 4-aminoquinazol-6-yl |
| 1-86. | 2-pyridyl | 4-aminoquinazol-6-yl |
| 1-87. | 3-pyridyl | 4-aminoquinazol-6-yl |
| 1-88. | 2-pyrimidyl | 4-aminoquinazol-6-yl |
| 1-89. | 2-Cl-phenyl | 4-aminoquinazol-6-yl |
| 1-90. | 2-F-phenyl | 4-aminoquinazol-6-yl |
| 1-91. | phenyl | 3-aminobenzisoxazol-5-yl |
| 1-92. | 2-pyridyl | 3-aminobenzisoxazol-5-yl |
| 1-93. | 3-pyridyl | 3-aminobenzisoxazol-5-yl |
| 1-94. | 2-pyrimidyl | 3-aminobenzisoxazol-5-yl |
| 1-95. | 2-Cl-phenyl | 3-aminobenzisoxazol-5-yl |
| 1-96. | 2-F-phenyl | 3-aminobenzisoxazol-5-yl |
| 1-97. | phenyl | 3-aminobenzisoxazol-6-yl |
| 1-98. | 2-pyridyl | 3-aminobenzisoxazol-6-yl |
| 1-99. | 3-pyridyl | 3-aminobenzisoxazol-6-yl |
| 1-100. | 2-pyrimidyl | 3-aminobenzisoxazol-6-yl |
| 1-101. | 2-Cl-phenyl | 3-aminobenzisoxazol-6-yl |
| 1-102. | 2-F-phenyl | 3-aminobenzisoxazol-6-yl |
| 1-103. | phenyl | 3-aminoindazolin-5-yl |
| 1-104. | 2-pyridyl | 3-aminoindazolin-5-yl |
| 1-105. | 3-pyridyl | 3-aminoindazolin-5-yl |
| 1-106. | 2-pyrimidyl | 3-aminoindazolin-5-yl |
| 1-107. | 2-Cl-phenyl | 3-aminoindazolin-5-yl |
| 1-108. | 2-F-phenyl | 3-aminoindazolin-5-yl |
| 1-109. | phenyl | 3-aminoindazol-6-yl |
| 1-110. | 2-pyridyl | 3-aminoindazol-6-yl |
| 1-111. | 3-pyridyl | 3-aminoindazol-6-yl |
| 1-112. | 2-pyrimidyl | 3-aminoindazol-6-yl |
| 1-113. | 2-Cl-phenyl | 3-aminoindazol-6-yl |
| 1-114. | 2-F-phenyl | 3-aminoindazol-6-yl |
| 1-115. | phenyl | indolin-5-yl |
| 1-116. | 2-pyridyl | indolin-5-yl |
| 1-117. | 3-pyridyl | indolin-5-yl |
| 1-118 | 2-pyrimidyl | indolin-5-yl |
| 1-119. | 2-Cl-phenyl | indolin-5-yl |
| 1-120. | 2-F-phenyl | indolin-5-yl |
| 1-121. | phenyl | indolin-6-yl |
| 1-122. | 2-pyridyl | indolin-6-yl |

TABLE 1-continued

| | | |
|---|---|---|
| 1-123. | 3-pyridyl | indolin-6-yl |
| 1-124. | 2-pyrimidyl | indolin-6-yl |
| 1-125. | 2-Cl-phenyl | indolin-6-yl |
| 1-126. | 2-F-phenyl | indolin-6-yl |
| 1-127. | phenyl | 2-naphthyl |
| 1-128. | 2-pyridyl | 2-naphthyl |
| 1-129. | 3-pyridyl | 2-naphthyl |
| 1-130. | 2-pyrimidyl | 2-naphthyl |
| 1-131. | 2-Cl-phenyl | 2-naphthyl |
| 1-132. | 2-F-phenyl | 2-naphthyl |
| 1-133. | phenyl | 3-amido-naphth-2-yl |
| 1-134. | 2-pyridyl | 3-amido-naphth-2-yl |
| 1-135. | 3-pyridyl | 3-amido-naphth-2-yl |
| 1-136. | 2-pyrimidyl | 3-amido-naphth-2-yl |
| 1-137. | 2-Cl-phenyl | 3-amido-naphth-2-yl |
| 1-138. | 2-F-phenyl | 3-amido-naphth-2-yl |
| 1-139. | phenyl | 3-methylsulfonyl-naphth-2-yl |
| 1-140. | 2-pyridyl | 3-methylsulfonyl-naphth-2-yl |
| 1-141. | 3-pyridyl | 3-methylsulfonyl-naphth-2-yl |
| 1-142. | 2-pyrimidyl | 3-methylsulfonyl-naphth-2-yl |
| 1-143. | 2-Cl-phenyl | 3-methylsulfonyl-naphth-2-yl |
| 1-144. | 2-F-phenyl | 3-methylsulfonyl-naphth-2-yl |
| 1-145. | phenyl | 3-aminomethyl-naphth-2-yl |
| 1-146. | 2-pyridyl | 3-aminomethyl-naphth-2-yl |
| 1-147. | 3-pyridyl | 3-aminomethyl-naphth-2-yl |
| 1-148. | 2-pyrimidyl | 3-aminomethyl-naphth-2-yl |
| 1-149. | 2-Cl-phenyl | 3-aminomethyl-naphth-2-yl |
| 1-150. | 2-F-phenyl | 3-aminomethyl-naphth-2-yl |
| 1-151. | phenyl | 3-fluoro-naphth-2-yl |
| 1-152. | 2-pyridyl | 3-fluoro-naphth-2-yl |
| 1-153. | 3-pyridyl | 3-fluoro-naphth-2-yl |
| 1-154. | 2-pyrimidyl | 3-fluoro-naphth-2-yl |
| 1-155. | 2-Cl-phenyl | 3-fluoro-naphth-2-yl |
| 1-156. | 2-F-phenyl | 3-fluoro-naphth-2-yl |
| 1-157. | phenyl | 3-cyano-naphth-2-yl |
| 1-158. | 2-pyridyl | 3-cyano-naphth-2-yl |
| 1-159. | 3-pyridyl | 3-cyano-naphth-2-yl |
| 1-160. | 2-pyrimidyl | 3-cyano-naphth-2-yl |
| 1-161. | 2-Cl-phenyl | 3-cyano-naphth-2-yl |
| 1-162. | 2-F-phenyl | 3-cyano-naphth-2-yl |
| 1-163. | phenyl | 3-aminosulfonyl-naphth-2-yl |
| 1-164. | 2-pyridyl | 3-aminosulfonyl-naphth-2-yl |
| 1-165. | 3-pyridyl | 3-aminosulfonyl-naphth-2-yl |
| 1-166. | 2-pyrimidyl | 3-aminosulfonyl-naphth-2-yl |
| 1-167. | 2-Cl-phenyl | 3-aminosulfonyl-naphth-2-yl |
| 1-168. | 2-F-phenyl | 3-aminosulfonyl-naphth-2-yl |
| 1-169. | phenyl | 6-chloro-naphth-2-yl |
| 1-170. | 2-pyridyl | 6-chloro-naphth-2-yl |
| 1-171. | 3-pyridyl | 6-chloro-naphth-2-yl |
| 1-172. | 2-pyrimidyl | 6-chloro-naphth-2-yl |
| 1-173. | 2-Cl-phenyl | 6-chloro-naphth-2-yl |
| 1-174. | 2-F-phenyl | 6-chloro-naphth-2-yl |

TABLE 2

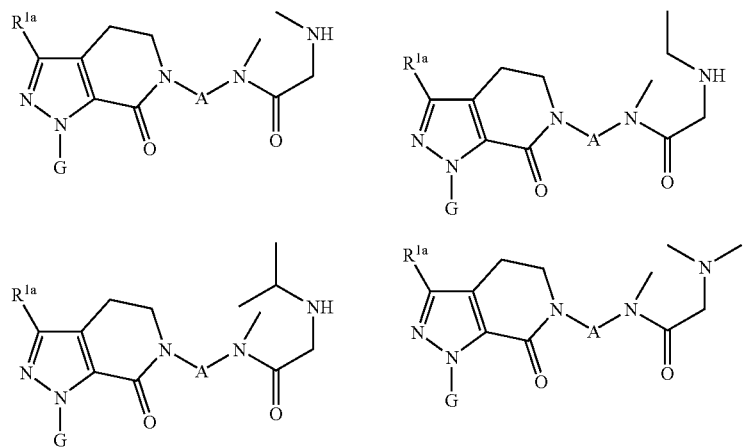

TABLE 2-continued
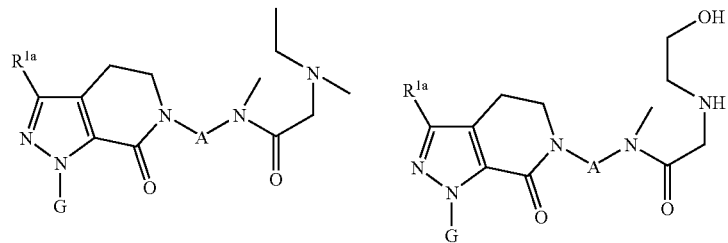
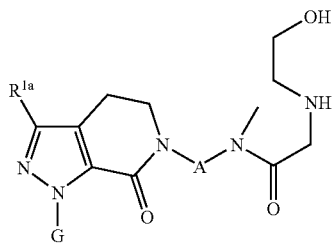
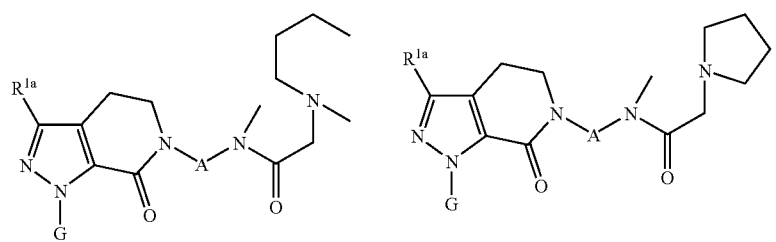
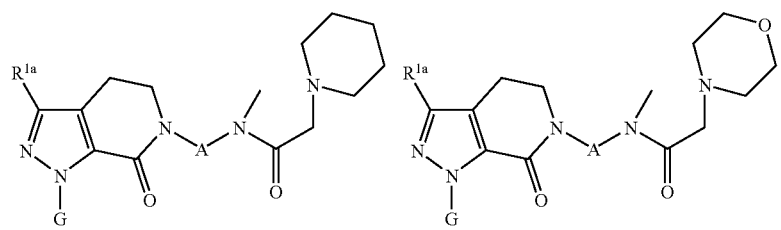
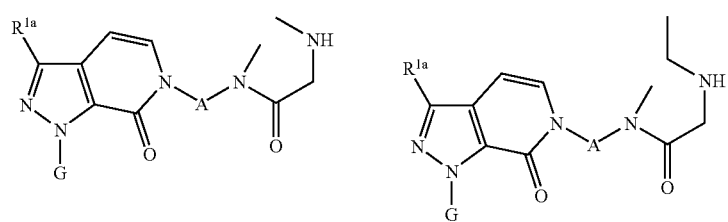
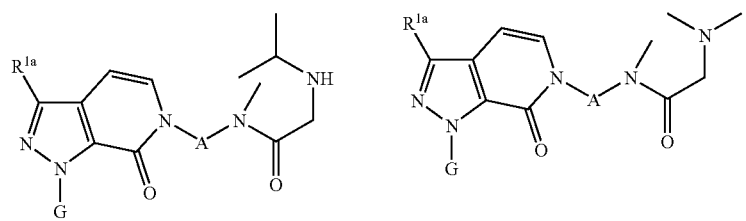
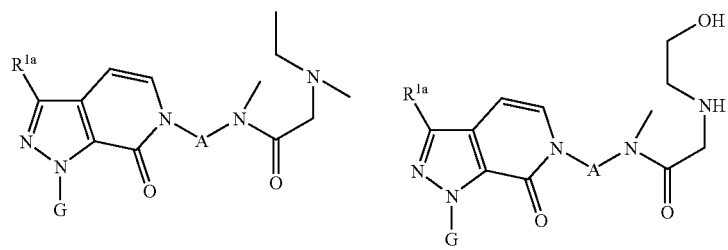

TABLE 2-continued
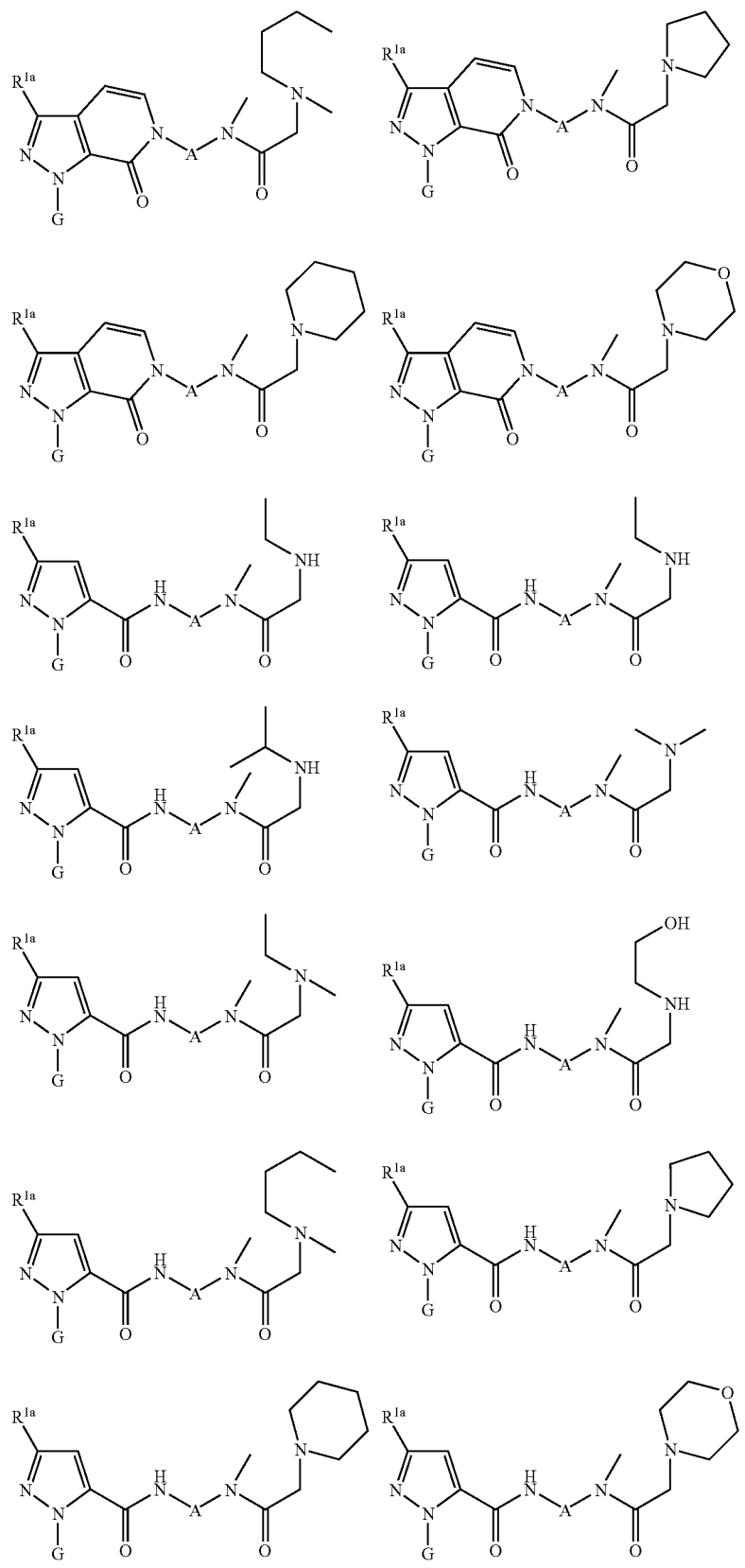

TABLE 2-continued
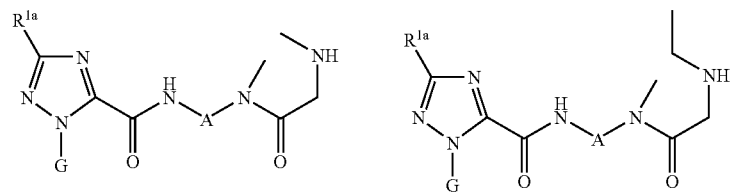
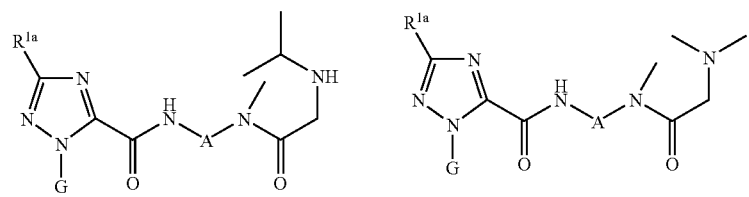
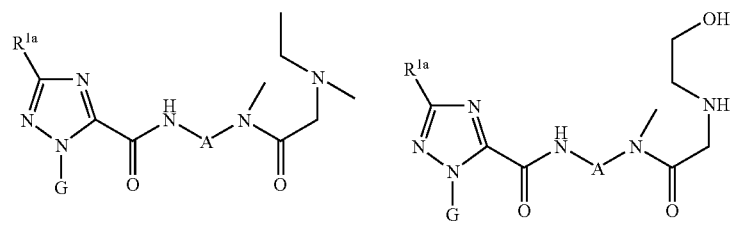
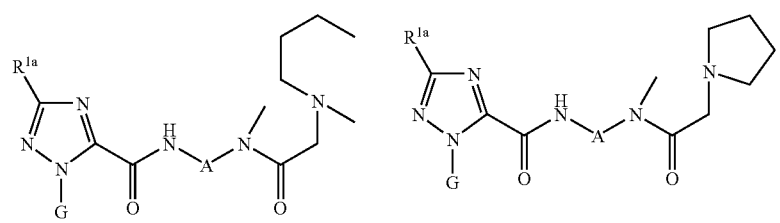
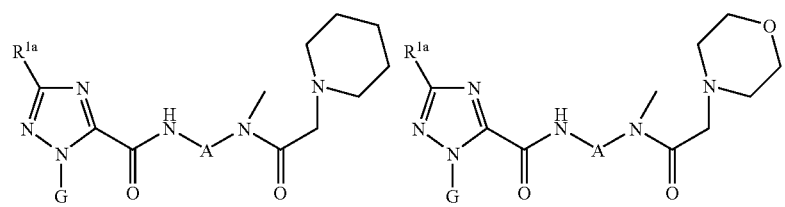
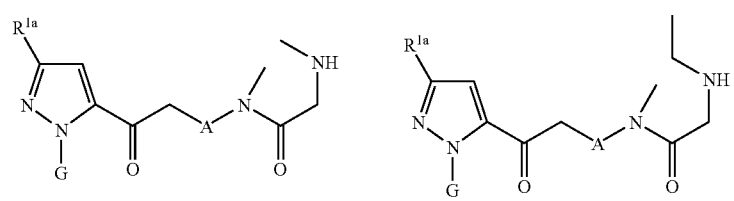
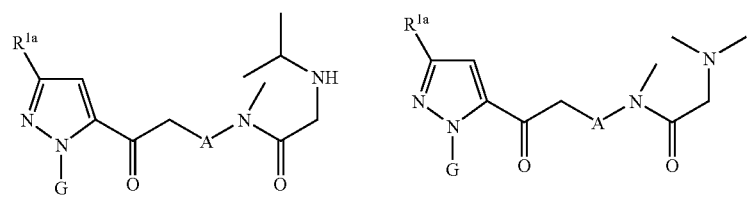

TABLE 2-continued
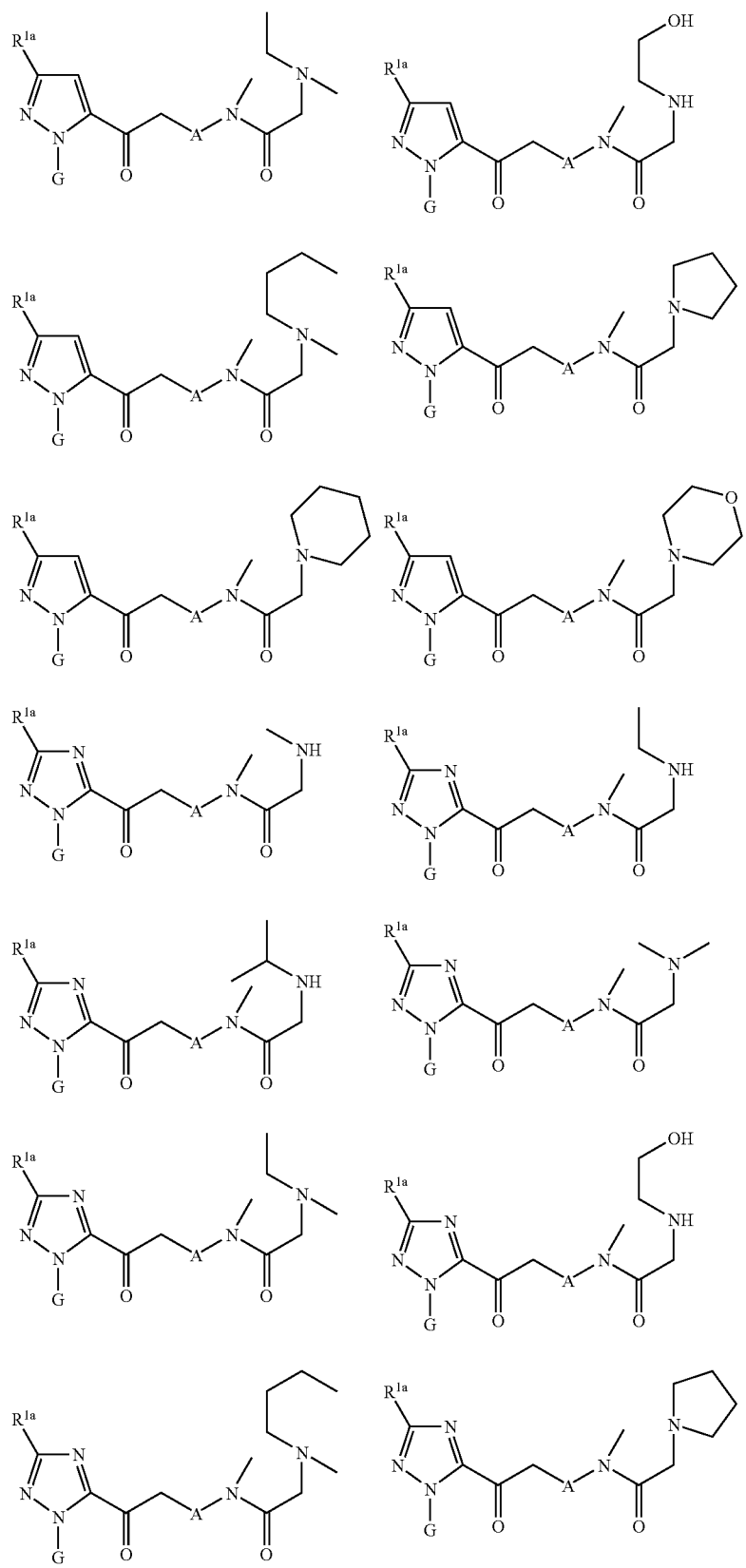

TABLE 2-continued $R^{1a}$ is $CH_3$;

| Ex# | A | G |
|---|---|---|
| 2-1. | phenyl | 4-methoxyphenyl |
| 2-2. | 2-pyridyl | 4-methoxyphenyl |
| 2-3. | 3-pyridyl | 4-methoxyphenyl |
| 2-4. | 2-pyrimidyl | 4-methoxyphenyl |
| 2-5. | 2-Cl-phenyl | 4-methoxyphenyl |
| 2-6. | 2-F-phenyl | 4-methoxyphenyl |
| 2-7. | piperidinyl | |
| 2-8. | phenyl | 2-aminomethylphenyl |
| 2-9. | 2-pyridyl | 2-aminomethylphenyl |
| 2-10. | 3-pyridyl | 2-aminomethylphenyl |
| 2-11. | 2-pyrimidyl | 2-aminomethylphenyl |
| 2-12. | 2-Cl-phenyl | 2-aminomethylphenyl |
| 2-13. | 2-F-phenyl | 2-aminomethylphenyl |
| 2-14. | piperidinyl | 2-aminomethylphenyl |
| 2-15. | phenyl | 3-aminomethylphenyl |
| 2-16. | 2-pyridyl | 3-aminomethylphenyl |
| 2-17. | 3-pyridyl | 3-aminomethylphenyl |
| 2-18. | 2-pyrimidyl | 3-aminomethylphenyl |
| 2-19. | 2-Cl-phenyl | 3-aminomethylphenyl |
| 2-20. | 2-F-phenyl | 3-aminomethylphenyl |
| 2-21. | piperidinyl | 3-aminomethylphenyl |
| 2-22. | phenyl | 2-amidophenyl |
| 2-23. | 2-pyridyl | 2-amidophenyl |
| 2-24. | 3-pyridyl | 2-amidophenyl |
| 2-25. | 2-pyrimidyl | 2-amidophenyl |
| 2-26. | 2-Cl-phenyl | 2-amidophenyl |
| 2-27. | 2-F-phenyl | 2-amidophenyl |
| 2-28. | piperidinyl | 2-amidophenyl |
| 2-29. | phenyl | 2-amido-4-methoxy-phenyl |
| 2-30. | 2-pyridyl | 2-amido-4-methoxy-phenyl |
| 2-31. | 3-pyridyl | 2-amido-4-methoxy-phenyl |
| 2-32. | 2-pyrimdyl | 2-amido-4-methoxy-phenyl |
| 2-33. | 2-Cl-phenyl | 2-amido-4-methoxy-phenyl |
| 2-34. | 2-F-phenyl | 2-amido-4-methoxy-phenyl |
| 2-35. | piperidinyl | 2-amido-4-methoxy-phenyl |
| 2-36. | phenyl | 3-amidophenyl |
| 2-37. | 2-pyridyl | 3-amidophenyl |
| 2-38. | 3-pyridyl | 3-amidophenyl |
| 2-39. | 2-pyrimidyl | 3-amidophenyl |
| 2-40. | 2-Cl-phenyl | 3-amidophenyl |
| 2-41. | 2-F-phenyl | 3-amidophenyl |
| 2-42. | piperidinyl | 3-amidophenyl |
| 2-43. | phenyl | 3-chlorophenyl |
| 2-44. | 2-pyridyl | 3-chlorophenyl |
| 2-45. | 3-pyridyl | 3-chlorophenyl |
| 2-46. | 2-pyrimidyl | 3-chlorophenyl |
| 2-47. | 2-Cl-phenyl | 3-chlorophenyl |
| 2-48. | 2-F-phenyl | 3-chlorophenyl |
| 2-49. | piperidinyl | 3-chlorophenyl |
| 2-50. | phenyl | 3-amino-4-chloro-phenyl |
| 2-51. | 2-pyridyl | 3-amino-4-chloro-phenyl |
| 2-52. | 3-pyridyl | 3-amino-4-chloro-phenyl |
| 2-53. | 2-pyrimidyl | 3-amino-4-chloro-phenyl |
| 2-54. | 2-Cl-phenyl | 3-amino-4-chloro-phenyl |
| 2-55. | 2-F-phenyl | 3-amino-4-chloro-phenyl |
| 2-56. | piperidinyl | 3-amino-4-chloro-phenyl |
| 2-57. | phenyl | 2-aminosulfonyl-phenyl |
| 2-58. | 2-pyridyl | 2-aminosulfonyl-phenyl |
| 2-59. | 3-pyridyl | 2-aminosulfonyl-phenyl |
| 2-60. | 2-pyrimidyl | 2-aminosulfonyl-phenyl |
| 2-61. | 2-Cl-phenyl | 2-aminosulfonyl-phenyl |
| 2-62. | 2-F-phenyl | 2-aminosulfonyl-phenyl |
| 2-63. | piperidinyl | 2-aminosulfonyl-phenyl |
| 2-64. | phenyl | 2-aminosulfonyl-4-methoxyphenyl |
| 2-65. | 2-pyridyl | 2-aminosulfonyl-4-methoxyphenyl |

TABLE 2-continued

| | | |
|---|---|---|
| 2-66. | 3-pyridyl | 2-aminosulfonyl-4-methoxyphenyl |
| 2-67. | 2-pyrimidyl | 2-aminosulfonyl-4-methoxyphenyl |
| 2-68. | 2-Cl-phenyl | 2-aminosulfonyl-4-methoxyphenyl |
| 2-69. | 2-F-phenyl | 2-aminosulfonyl-4-methoxyphenyl |
| 2-70. | piperidinyl | 2-aminosulfonyl-4-methoxyphenyl |
| 2-71. | phenyl | 3-(1',2',4'-triazolin-5'-on-3'-yl)phenyl |
| 2-72. | 2-pyridyl | 3-(1',2',4'-triazolin-5'-on-3'-yl)phenyl |
| 2-73. | 3-pyridyl | 3-(1',2',4'-triazolin-5'-on-3'-yl)phenyl |
| 2-74. | 2-pyrimidyl | 3-(1',2',4'-triazolin-5'-on-3'-yl)phenyl |
| 2-75. | 2-Cl-phenyl | 3-(1',2',4'-triazolin-5'-on-3'-yl)phenyl |
| 2-76. | 2-F-phenyl | 3-(1',2',4'-triazolin-5'-on-3'-yl)phenyl |
| 2-77. | piperidinyl | 3-(1',2',4'-triazolin-5'-on-3'-yl)phenyl |
| 2-78. | phenyl | 1-aminoisoquinolin-6-yl |
| 2-79. | 2-pyridyl | 1-aminoisoquinolin-6-yl |
| 2-80. | 3-pyridyl | 1-aminoisoquinolin-6-yl |
| 2-81. | 2-pyrimidyl | 1-aminoisoquinolin-6-yl |
| 2-82. | 2-Cl-phenyl | 1-aminoisoquinolin-6-yl |
| 2-83. | 2-F-phenyl | 1-aminoisoquinolin-6-yl |
| 2-84. | piperidinyl | 1-aminoisoquinolin-6-yl |
| 2-85. | phenyl | 1-aminoisoquinolin-7-yl |
| 2-86. | 2-pyridyl | 1-aminoisoquinolin-7-yl |
| 2-87. | 3-pyridyl | 1-aminoisoquinolin-7-yl |
| 2-88. | 2-pyrimidyl | 1-aminoisoquinolin-7-yl |
| 2-89. | 2-Cl-phenyl | 1-aminoisoquinolin-7-yl |
| 2-90. | 2-F-phenyl | 1-aminoisoquinolin-7-yl |
| 2-91. | piperidinyl | 1-aminoisoquinolin-7-yl |
| 2-92. | phenyl | 4-aminoquinazol-6-yl |
| 2-93. | 2-pyridyl | 4-aminoquinazol-6-yl |
| 2-94. | 3-pyridyl | 4-aminoquinazol-6-yl |
| 2-95. | 2-pyrimidyl | 4-aminoquinazol-6-yl |
| 2-96. | 2-Cl-phenyl | 4-aminoquinazol-6-yl |
| 2-97. | 2-F-phenyl | 4-aminoquinazol-6-yl |
| 2-98. | piperidinyl | 4-aminoquinazol-6-yl |
| 2-99. | phenyl | 4-aminoquinazol-7-yl |
| 2-100. | 2-pyridyl | 4-aminoquinazol-7-yl |
| 2-101. | 3-pyridyl | 4-aminoquinazol-7-yl |
| 2-102. | 2-pyrimidyl | 4-aminoquinazol-7-yl |
| 2-103. | 2-Cl-phenyl | 4-aminoquinazol-7-yl |
| 2-104. | 2-F-phenyl | 4-aminoquinazol-7-yl |
| 2-105. | piperidinyl | 4-aminoquinazol-7-yl |
| 2-106. | phenyl | 3-aminobenzisoxazol-5-yl |
| 2-107. | 2-pyridyl | 3-aminobenzisoxazol-5-yl |
| 2-108. | 3-pyridyl | 3-aminobenzisoxazol-5-yl |
| 2-109. | 2-pyrimidyl | 3-aminobenzisoxazol-5-yl |
| 2-110. | 2-Cl-phenyl | 3-aminobenzisoxazol-5-yl |
| 2-111. | 2-F-phenyl | 3-aminobenzisoxazol-5-yl |
| 2-112. | piperidinyl | 3-aminobenzisoxazol-5-yl |
| 2-113. | phenyl | 3-aminobenzisoxazol-6-yl |
| 2-114. | 2-pyridyl | 3-aminobenzisoxazol-6-yl |
| 2-115. | 3-pyridyl | 3-aminobenzisoxazol-6-yl |
| 2-116. | 2-pyrimidyl | 3-aminobenzisoxazol-6-yl |
| 2-117. | 2-Cl-phenyl | 3-aminobenzisoxazol-6-yl |
| 2-118. | 2-F-phenyl | 3-aminobenzisoxazol-6-yl |
| 2-119. | piperidinyl | 3-aminobenzisoxazol-6-yl |
| 2-120. | phenyl | 3-aminoindazol-5-yl |
| 2-121. | 2-pyridyl | 3-aminoindazol-5-yl |
| 2-122. | 3-pyridyl | 3-aminoindazol-5-yl |
| 2-123. | 2-pyrimidyl | 3-aminoindazol-5-yl |
| 2-124. | 2-Cl-phenyl | 3-aminoindazol-5-yl |
| 2-125. | 2-F-phenyl | 3-aminoindazol-5-yl |
| 2-126. | piperidinyl | 3-aminoindazol-5-yl |
| 2-127. | phenyl | 3-aminoindazol-6-yl |
| 2-128. | 2-pyridyl | 3-aminoindazol-6-yl |
| 2-129. | 3-pyridyl | 3-aminoindazol-6-yl |
| 2-130. | 2-pyrimidyl | 3-aminoindazol-6-yl |
| 2-131. | 2-Cl-phenyl | 3-aminoindazol-6-yl |
| 2-132. | 2-F-phenyl | 3-aminoindazol-6-yl |
| 2-133. | piperidinyl | 3-aminoindazol-6-yl |
| 2-134. | phenyl | indolin-5yl |
| 2-135. | 2-pyridyl | indolin-5yl |
| 2-136. | 3-pyridyl | indolin-5yl |
| 2-137. | 2-pyrimidyl | indolin-5yl |

TABLE 2-continued

| | | |
|---|---|---|
| 2-138. | 2-Cl-phenyl | indolin-5yl |
| 2-139. | 2-F-phenyl | indolin-5yl |
| 2-140. | piperidinyl | indolin-5yl |
| 2-141. | phenyl | indolin-6-yl |
| 2-142. | 2-pyridyl | indolin-6-yl |
| 2-143. | 3-pyridyl | indolin-6-yl |
| 2-144. | 2-pyrimidyl | indolin-6-yl |
| 2-145. | 2-Cl-phenyl | indolin-6-yl |
| 2-146. | 2-F-phenyl | indolin-6-yl |
| 2-147. | piperidinyl | indolin-6-yl |
| 2-148. | phenyl | 2-naphthyl |
| 2-149. | 2-pyridyl | 2-naphthyl |
| 2-150. | 3-pyridyl | 2-naphthyl |
| 2-151. | 2-pyrimidyl | 2-naphthyl |
| 2-152. | 2-Cl-phenyl | 2-naphthyl |
| 2-153. | 2-F-phenyl | 2-naphthyl |
| 2-154. | piperidinyl | 2-naphthyl |
| 2-155. | phenyl | 3-amido-naphth-2-yl |
| 2-156. | 2-pyridyl | 3-amido-naphth-2-yl |
| 2-157. | 3-pyridyl | 3-amido-naphth-2-yl |
| 2-158. | 2-pyrimidyl | 3-amido-naphth-2-yl |
| 2-159. | 2-Cl-phenyl | 3-amido-naphth-2-yl |
| 2-160. | 2-F-phenyl | 3-amido-naphth-2-yl |
| 2-161. | piperidinyl | 3-amido-naphth-2-yl |
| 2-162. | phenyl | 3-methylsulfonyl-naphth-2-yl |
| 2-163. | 2-pyridyl | 3-methylsulfonyl-naphth-2-yl |
| 2-164. | 3-pyridyl | 3-methylsulfonyl-naphth-2-yl |
| 2-165. | 2-pyrimidyl | 3-methylsulfonyl-naphth-2-yl |
| 2-166. | 2-Cl-phenyl | 3-methylsulfonyl-naphth-2-yl |
| 2-167. | 2-F-phenyl | 3-methylsulfonyl-naphth-2-yl |
| 2-168. | piperidinyl | 3-methylsulfonyl-naphth-2-yl |
| 2-169. | phenyl | 3-aminomethyl-naphth-2-yl |
| 2-170. | 2-pyridyl | 3-aminomethyl-naphth-2-yl |
| 2-171. | 3-pyridyl | 3-aminomethyl-naphth-2-yl |
| 2-172. | 2-pyrimidyl | 3-aminomethyl-naphth-2-yl |
| 2-173. | 2-Cl-phenyl | 3-aminomethyl-naphth-2-yl |
| 2-174. | 2-F-phenyl | 3-aminomethyl-naphth-2-yl |
| 2-175. | piperidinyl | 3-aminomethyl-naphth-2-yl |
| 2-176. | phenyl | 3-fluoro-naphth-2-yl |
| 2-177. | 2-pyridyl | 3-fluoro-naphth-2-yl |
| 2-178. | 3-pyridyl | 3-fluoro-naphth-2-yl |
| 2-179. | 2-pyrimidyl | 3-fluoro-naphth-2-yl |
| 2-180. | 2-Cl-phenyl | 3-fluoro-naphth-2-yl |
| 2-181. | 2-F-phenyl | 3-fluoro-naphth-2-yl |
| 2-182. | Piperidinyl | 3-fluoro-naphth-2-yl |
| 2-183. | phenyl | 3-cyano-naphh-2-yl |
| 2-184. | 2-pyridyl | 3-cyano-naphh-2-yl |
| 2-185. | 3-pyridyl | 3-cyano-naphh-2-yl |
| 2-186. | 2-pyrimidyl | 3-cyano-naphh-2-yl |
| 2-187. | 2-Cl-phenyl | 3-cyano-naphh-2-yl |
| 2-188. | 2-F-phenyl | 3-cyano-naphh-2-yl |
| 2-189. | Piperidinyl | 3-cyano-naphh-2-yl |
| 2-190. | phenyl | 3-aminosulfonyl-naphth-2-yl |
| 2-191. | 2-pyridyl | 3-aminosulfonyl-naphth-2-yl |
| 2-192. | 3-pyridyl | 3-aminosulfonyl-naphth-2-yl |
| 2-193. | 2-pyrimidyl | 3-aminosulfonyl-naphth-2-yl |
| 2-194. | 2-Cl-phenyl | 3-aminosulfonyl-naphth-2-yl |
| 2-195. | 2-F-phenyl | 3-aminosulfonyl-naphth-2-yl |
| 2-196. | piperidinyl | 3-aminosulfonyl-naphth-2-yl |
| 2-197. | phenyl | 6-chloro-naphth-2-yl |
| 2-198. | 2-pyridyl | 6-chloro-naphth-2-yl |
| 2-199. | 3-pyridyl | 6-chloro-naphth-2-yl |
| 2-200. | 2-pyrimidyl | 6-chloro-naphth-2-yl |
| 2-201. | 2-Cl-phenyl | 6-chloro-naphth-2-yl |
| 2-202. | 2-F-phenyl | 6-chloro-naphth-2-yl |
| 2-203. | Piperidinyl | 6-chloro-naphth-2-yl |

TABLE 3

Examples 3-1-through 3-6090 use the structures from Table 2 and the corresponding A and G groups from Examples 1-203 of Table 2:

Examples 3-1 to 3-203, $R^{1a}$ is $CH_2CH_3$;
Examples 3-204 to 3-406, $R^{1a}$ is $CF_3$;
Examples 3-407 to 3-609, $R^{1a}$ is $SCH_3$;
Examples 3-610 to 3-812, $R^{1a}$ is $SOCH_3$;
Examples 3-813 to 3-1015, $R^{1a}$ is $SO_2CH_3$;
Examples 3-1016 to 3-1218, $R^{1a}$ is Cl;
Examples 3-1219 to 3-1421, $R^{1a}$ is F;
Examples 3-1422 to 3-1624, $R^{1a}$ is $CO_2CH_3$;
Examples 3-1625 to 3-1827, $R^{1a}$ is $CH_2OCH_3$;
Examples 3-1828 to 3-2030, $R^{1a}$ is $CONH_2$;
Examples 3-2031 to 3-2233, $R^{1a}$ is —CN;
Examples 3-2234 to 3-2436, $R^{1a}$ is $CH_2NHCH_3$;
Examples 3-2437 to 3-2639, $R^{1a}$ is $CH_2NHSO_2CH_3$;
Examples 3-2640 to 3-2842, $R^{1a}$ is 1-imidazolyl-$CH_2$;
Examples 3-2843 to 3-3045, $R^{1a}$ is Br;
Examples 3-3046 to 3-3248, $R^{1a}$ is 5-tetrazolyl;
Examples 3-3249 to 3-3451, $R^{1a}$ is $N(CH_3)_2$;
Examples 3-3452 to 3-3654, $R^{1a}$ is $NHCH_3$;
Examples 3-3655 to 3-3857, $R^{1a}$ is $SO_2NH_2$;
Examples 3-3858 to 3-4060, $R^{1a}$ is 2-pyridine;
Examples 3-4061 to 3-4263, $R^{1a}$ is 3-pyridine;
Examples 3-4264 to 3-4466, $R^{1a}$ is 4-pyridine;
Examples 3-4467 to 3-4872, $R^{1a}$ is 2-pyridine-N-oxide;
Examples 3-4873 to 3-5075, $R^{1a}$ is 3-pyridine-N-oxide;
Examples 3-5076 to 3-5287, $R^{1a}$ is 4-pyridine-N-oxide;
Examples 3-5288 to 3-5481, $R^{1a}$ is $OCH_3$;
Examples 3-5482 to 3-5684, $R^{1a}$ is $CH_2OC(O)NHCH_3$;
Examples 3-5685 to 3-5887, $R^{1a}$ is $CH_2NHCO_2CH_3$;
Examples 3-5888 to 3-6090, $R^{1a}$ is $CH_2NHC(O)NHCH_3$; and,
Examples 3-6091 to 3-6293, $R^{1a}$ is H.

TABLE 4

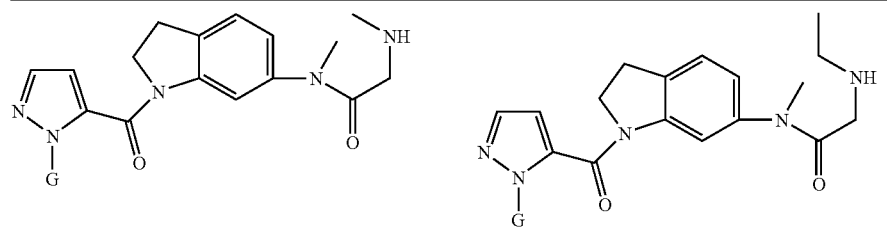

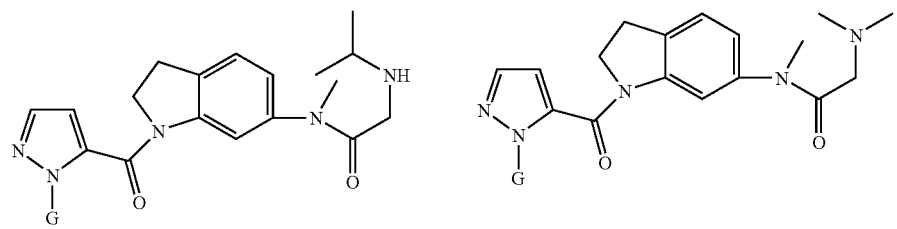

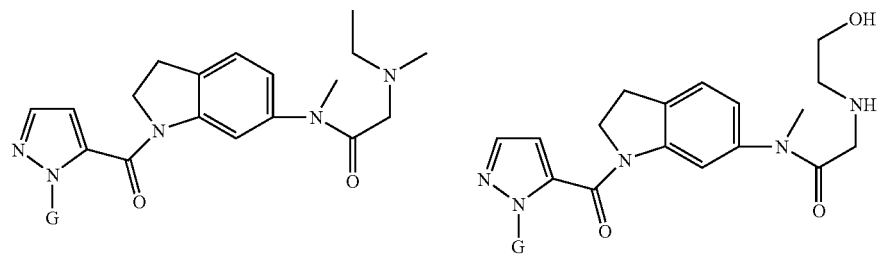

TABLE 4-continued
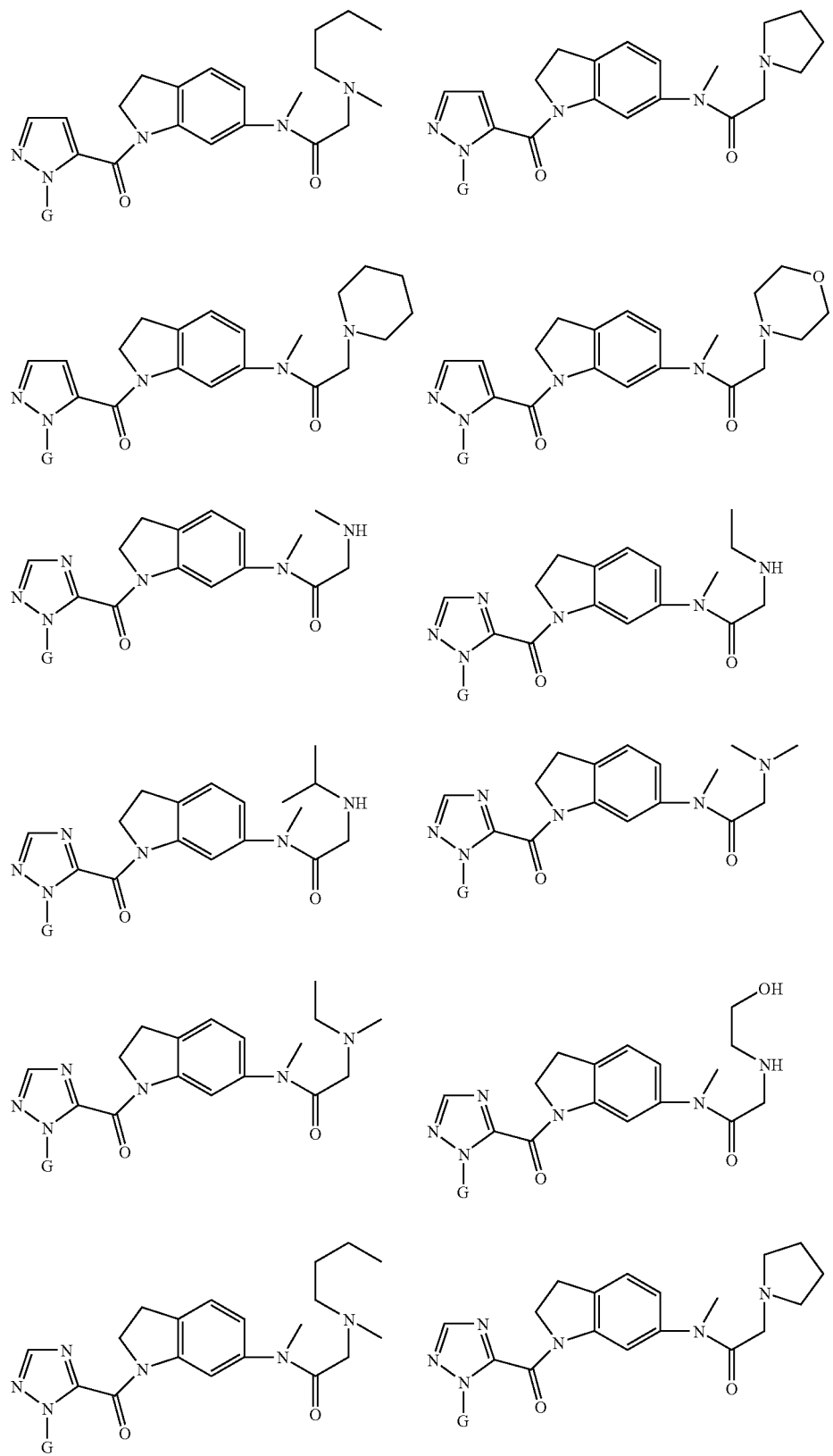

TABLE 4-continued
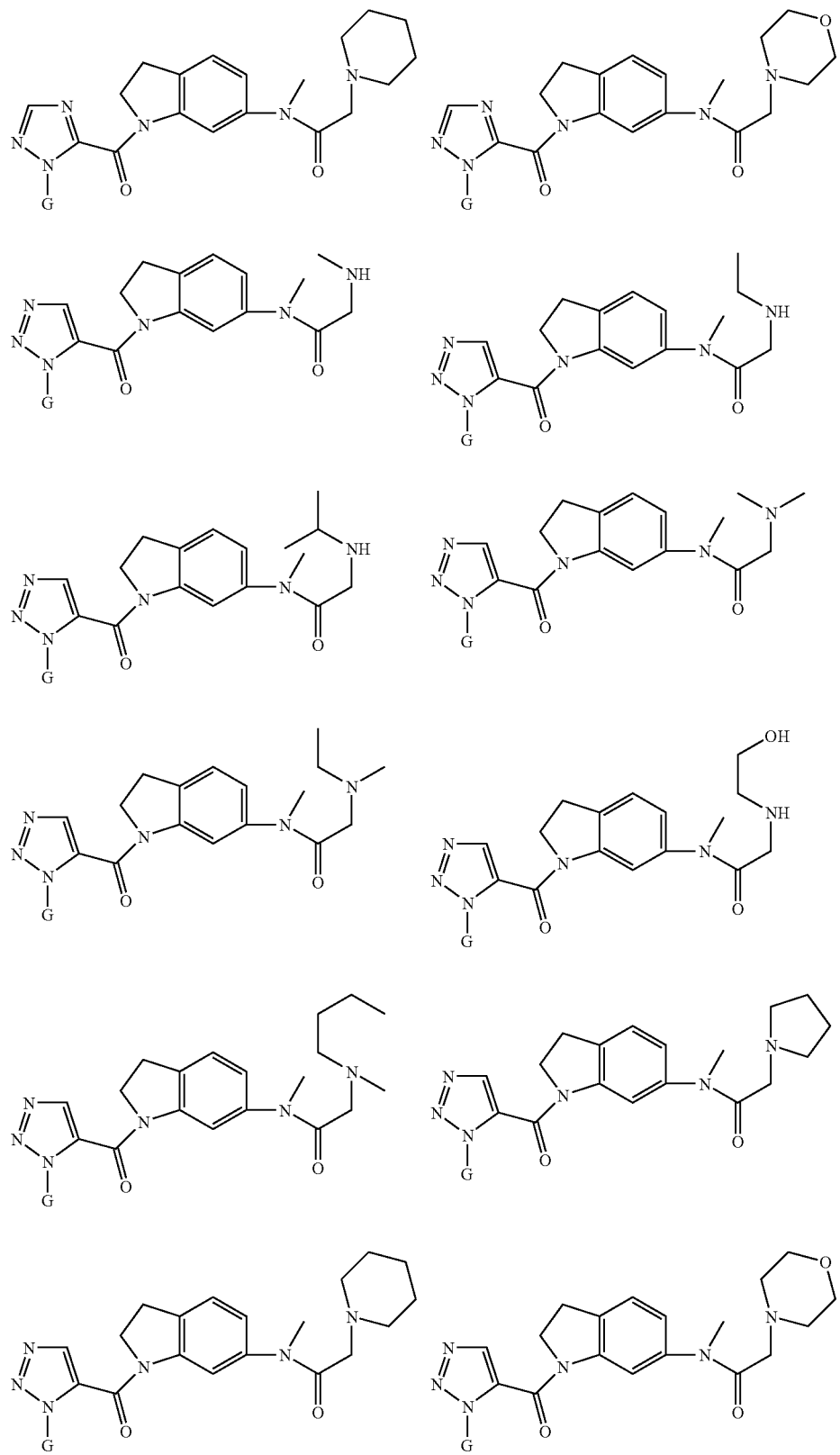

TABLE 4-continued

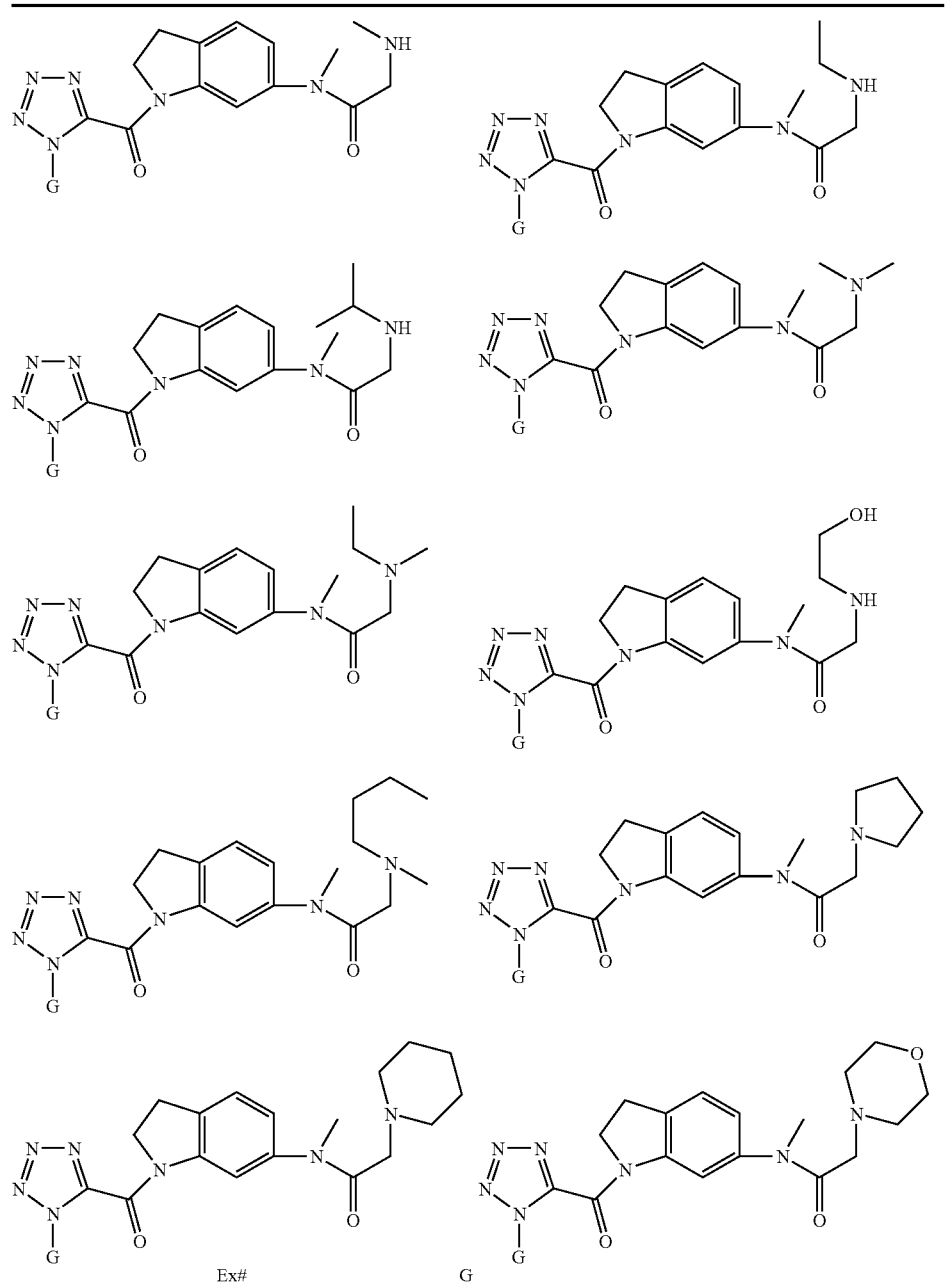

| Ex# | G |
|---|---|
| 4-1. | 4-methoxyphenyl |
| 4-2. | 2-aminomethylphenyl |
| 4-3. | 3-aminomethylphenyl |
| 4-4. | 2-amidophenyl |
| 4-5. | 2-amido-4-methoxy-phenyl |
| 4-6. | 3-amidophenyl |
| 4-7. | 3-chlorophenyl |
| 4-8. | 3-amino-4-chloro-phenyl |
| 4-9. | 2-aminosulfonyl-phenyl |
| 4-10. | 2-aminosulfonyl-4-methoxyphenyl |
| 4-11. | 3-(1',2',4'-triazolin-5'-on-3'-yl)phenyl |
| 4-12. | 1-aminoisoquinolin-6-yl |
| 4-13. | 1-aminoisoquinolin-7-yl |
| 4-14. | 4-aminoquinazol-6-yl |
| 4-15. | 4-aminoquinazol-7-yl |
| 4-16. | 3-aminobenzisoxazol-5-yl |
| 4-17. | 3-aminobenzisoxazol-6-yl |

TABLE 4-continued

| | |
|---|---|
| 4-18. | 3-aminoindazol-5-yl |
| 4-19. | 3-aminoindazol-6-yl |
| 4-20. | indolin-5-yl |
| 4-21. | indolin-6-yl |
| 4-22. | 2-naphthyl |
| 4-23. | 3-amido-naphth-2-yl |
| 4-24. | 3-methylsulfonyl-naphth-2-yl |
| 4-25. | 3-aminomethyl-naphth-2-yl |
| 4-26. | 3-fluoro-naphth-2-yl |
| 4-27. | 3-chloro-naphth-2-yl |
| 4-28. | 3-aminosulfonyl-naphth-2-yl |
| 4-29. | 6-chloro-naphth-2-yl |

TABLE 5

| Ex# | $R^{1a}$ | G |
|---|---|---|
| 5-1. | $CH_3$ | 4-methoxyphenyl |
| 5-2. | $CH_2CH_3$ | 4-methoxyphenyl |
| 5-3. | $CF_3$ | 4-methoxyphenyl |
| 5-4. | $SCH_3$ | 4-methoxyphenyl |
| 5-5. | $SOCH_3$ | 4-methoxyphenyl |
| 5-6. | $SO_2CH_3$ | 4-methoxyphenyl |
| 5-7. | Cl | 4-methoxyphenyl |
| 5-8. | F | 4-methoxyphenyl |
| 5-9. | $CO_2CH_3$ | 4-methoxyphenyl |
| 5-10. | $CH_2OCH_3$ | 4-methoxyphenyl |
| 5-11. | $CONH_2$ | 4-methoxyphenyl |
| 5-12. | CN | 4-methoxyphenyl |
| 5-13. | $CH_2NH_2$ | 4-methoxyphenyl |
| 5-14. | $CH_2NHSO_2CH_3$ | 4-methoxyphenyl |
| 5-15. | 1-imidazolyl-$CH_2$- | 4-methoxyphenyl |
| 5-16. | 1-tetrazolyl-$CH_2$- | 4-methoxyphenyl |
| 5-17. | Br | 4-methoxyphenyl |
| 5-18. | 5-tetrazolyl | 4-methoxyphenyl |
| 5-19. | $N(CH_3)_2$ | 4-methoxyphenyl |
| 5-20. | $NHCH_3$ | 4-methoxyphenyl |
| 5-21. | $SO_2NH_2$ | 4-methoxyphenyl |
| 5-22. | 2-pyridine | 4-methoxyphenyl |
| 5-23. | 3-pyridine | 4-methoxyphenyl |
| 5-24. | 4-pyridine | 4-methoxyphenyl |
| 5-25. | 2-pyridine-N-oxide | 4-methoxyphenyl |
| 5-26. | 3-pyridine-N-oxide | 4-methoxyphenyl |
| 5-27. | 4-pyridine-N-oxide | 4-methoxyphenyl |
| 5-28. | $OCH_3$ | 4-methoxyphenyl |
| 5-29. | $CH_2OC(O)NHCH_3$ | 4-methoxyphenyl |
| 5-30. | $CH_2NHCO_2CH_3$ | 4-methoxyphenyl |
| 5-31. | $CH_2NHC(O)NHCH_3$ | 4-methoxyphenyl |
| 5-32. | H | 4-methoxyphenyl |

For Examples 5-33 through 5-64, G is 2-aminomethylphenyl and $R^{1a}$ is as shown in Examples 5-1 through 5-32.

For Examples 5-65 through 5-96, G is 3-aminomethylphenyl and $R^{1a}$ is as shown in Examples 5-1 through 5-32.

For Examples 5-97 through 5-128, G is 2-amidophenyl and $R^{1a}$ is as shown in Examples 5-1 through 5-32.

For Examples 5-129 through 5-160, G is 2-amido-4-methoxyphenyl and $R^{1a}$ is as shown in Examples 5-1 through 5-32.

For Examples 5-161 through 5-192, G is 3-amidophenyl and $R^{1a}$ is as shown in Examples 5-1 through 5-32.

For Examples 5-193 through 5-224, G is 3-chlorophenyl and $R^{1a}$ is as shown in Examples 5-1 through 5-32.

For Examples 5-225 through 5-256, G is 3-amino-4-chlorophenyl and $R^{1a}$ is as shown in Examples 5-1 through 5-32.

For Examples 5-257 through 5-288, G is 2-aminosulfonylphenyl and $R^{1a}$ is as shown in Examples 5-1 through 5-32.

For Examples 5-289 through 5-320, G is 2-aminosulfonyl-4-methoxyphenyl and $R^{1a}$ is as shown in Examples 5-1 through 5-32.

For Examples 5-321 through 5-352, G is 3-(1',2',4'-triazolin-5'-on-3'-yl)phenyl and $R^{1a}$ is as shown in Examples 5-1 through 5-32.

For Examples 5-353 through 5-384, G is 1-aminoisoquinolin-6-yl and $R^{1a}$ is as shown in Examples 5-1 through 5-32.

For Examples 5-385 through 5-416, G is 1-aminoisoquinolin-7-yl and $R^{1a}$ is as shown in Examples 5-1 through 5-32.

For Examples 5-417 through 5-448, G is 4-aminoquinazol-6-yl and $R^{1a}$ is as shown in Examples 5-1 through 5-32.

For Examples 5-449 through 5-480, G is 4-aminoquinazol-7-yl and $R^{1a}$ is as shown in Examples 5-1 through 5-32.

For Examples 5-481 through 5-512, G is 3-aminobenzisoxazol-5-yl and $R^{1a}$ is as shown in Examples 5-1 through 5-32.
For Examples 5-513 through 5-544, G is 3-aminobenzisoxazol-6-yl and $R^{1a}$ is as shown in Examples 5-1 through 5-32.
For Examples 5-545 through 5-576, G is 3-aminoindazol-5-yl and $R^{1a}$ is as shown in Examples 5-1 through 5-32.
For Examples 5-577 through 5-608, G is 3-aminoindazol-6-yl and $R^{1a}$ is as shown in Examples 5-1 through 5-32.
For Examples 5-609 through 5-640, G is indolin-5-yl and $R^{1a}$ is as shown in Examples 5-1 through 5-32.
For Examples 5-641 through 5-672, G is indolin-6-yl and $R^{1a}$ is as shown in Examples 5-1 through 5-32.
For Examples 5-673 through 5-704, G is 2-naphthyl and $R^{1a}$ is as shown in Examples 5-1 through 5-32.
For Examples 5-705 through 5-736, G is 3-amido-naphth-2-yl and $R^{1a}$ is as shown in Examples 5-1 through 5-32.
For Examples 5-737 through 5-768, G is 3-methylsulfonyl-naphth-2-yl and $R^{1a}$ is as shown in Examples 5-1 through 5-32.
For Examples 5-769 through 5-800, G is 3-aminomethyl-naphth-2-yl and $R^{1a}$ is as shown in Examples 5-1 through 5-32.
For Examples 5-801 through 5-832, G is 3-flouro-naphth-2-yl and $R^{1a}$ is as shown in Examples 5-1 through 5-32.
For Examples 5-833 through 5-864, G is 3-chloro-naphth-2-yl and $R^{1a}$ is as shown in Examples 5-1 through 5-32.
For Examples 5-865 through 5-896, G is 3-aminosulfonyl-naphth-2-yl and $R^{1a}$ is as shown in Examples 5-1 through 5-32.
For Examples 5-897 through 5-928, G is 6-chloro-naphth-2-yl and $R^{1a}$ is as shown in Examples 5-1 through 5-32.

Numerous modifications and variations of the present invention are possible in light of the above teachings. It is therefore to be understood that within the scope of the appended claims, the invention may be practiced otherwise that as specifically described herein.

What is claimed is:
1. A compound of formula I:

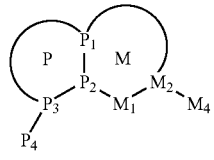

or a stereoisomer or pharmaceutically acceptable salt thereof, wherein;
ring M, including $P_1$, $P_2$, $M_1$, and $M_2$, is

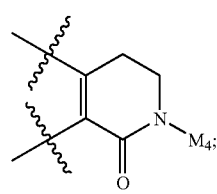

ring M is substituted with 0–3 $R^{1a}$;
ring P, including $P_1$, $P_2$, and $P_3$, is

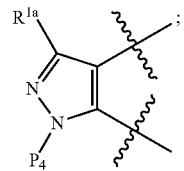

one of $P_4$ and $M_4$ is A-B and the other -G;
G is a group of formula IIa:

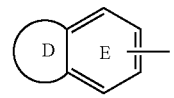

ring D, including the two atoms of Ring E to which it is attached, is a 5–6 membered ring consisting of: carbon atoms and 0–2 heteroatoms selected from the group consisting of N, O, and $S(O)_p$;
ring D is substituted with 0–2 R and there are 0–3 ring double bonds;
E is selected from phenyl, pyridyl, pyrimidyl, pyrazinyl, and pyridazinyl, and is substituted with 1–2 R;
alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–2 R;
alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–1 carbonyls and 1–2 R and has 0–3 ring double bonds;
R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $ONHC(=NR^8)NR^7R^9$, $NR^8CH(=NR^7)$, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), $CH_2CH_2N(C_{1-3}$ alkyl)$_2$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$;
alternatively, when 2 R groups are attached to adjacent atoms, they combine to form methylenedioxy or ethylenedioxy;
A is phenyl substituted with 0–2 $R^4$;
B is selected from $N(B^1)C(O)C(R^3R^{3g})OR^3$, $N(B^1)C(O)C(R^3R^{3g})NB^2B^3$, $N(B^1)C(O)C(R^3R^{3g})C(R^3R^{3g})NB^2B^3$, $N(B^1)C(O)C(R^3R^{3g})C(R^3R^{3g})C(R^3R^{3g})NB^2B^3$, and $N(B^1)C(O)C(R^3R^{3g})C(R^3R^{3g})C(R^3R^{3g})C(R^3R^{3g})NB^2B^3$;
$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-2}$—$C_{3-7}$ carbocycle substituted with 0–2 $R^{4b}$, and —$(CH_2)_{0-2}$-5–6 membered heterocycle consisting of: carbon atoms and 1–4 heteroatoms selected from the group consisting of N, O, and S(O)$_p$ and substituted with 0–2 R$^{4b}$;

B$^2$ is selected from H, C$_{1-6}$ alkyl substituted with 0–2 R$^{4c}$, C(O)R$^{2e}$, C(O)OR$^{2d}$, C(O)NR$^{2d}$R$^{2d}$, C(O)NH(CH$_2$)$_2$NR$^{2d}$R$^{2d}$, SO$_2$NR$^{2d}$R$^{2d}$, C(O)NHSO$_2$—C$_{1-4}$ alkyl, and S(O)$_p$R$^{5a}$;

B$^3$ is selected from H, C$_{1-6}$ alkyl substituted with 0–1 R$^{4c}$, —(CH$_2$)$_{0-1}$-3–8 membered carbocycle substituted with 0–2 R$^5$, and a —(CH$_2$)$_{0-1}$-3–8 membered heterocycle consisting of: carbon atoms and 1–4 heteroatoms selected from the group consisting of N, O, and S(O)$_p$ and substituted with 0–2 R$^5$;

alternatively, NB$^2$B$^3$ is a 3–8 membered heterocycle consisting of: the shown N, carbon atoms, and 0–3 additional heteroatoms selected from the group consisting of N, O, and S(O)$_p$ and substituted with 0–2 R$^5$;

R$^{1a}$, at each occurrence, is selected from H, —(CR$^3$R$^{3a}$)$_r$—R$^{1b}$, —(CR$^3$R$^{3a}$)$_r$—CR$^3$R$^{1b}$R$^{1b}$, —(CR$^3$R$^{3a}$)$_r$—O—(CR$^3$R$^{3a}$)$_r$—R$^{1b}$, —(CR$^3$R$^{3a}$)$_r$—NR$^2$—(CR$^3$R$^{3a}$)$_r$—R$^{1b}$, —(CR$^3$R$^{3a}$)$_r$—S(O)$_p$—(CR$^3$R$^{3a}$)$_r$—R$^{1b}$, —(CR$^3$R$^{3a}$)$_r$—CO$_2$—(CR$^3$R$^{3a}$)$_r$—R$^{1b}$, —(CR$^3$R$^{3a}$)$_r$—C(O)NR$^2$—(CR$^3$R$^{3a}$)$_r$—R$^{1b}$, —(CR$^3$R$^{3a}$)$_r$—C(O)—(CR$^3$R$^{3a}$)$_r$—R$^{1b}$, —C$_{2-6}$ alkenylene-R$^{1b}$, —C$_{2-6}$ alkynylene-R$^{1b}$, and —(CR$^3$R$^{3a}$)$_r$—C(=NR$^{1b}$)NR$^3$R$^{1b}$, provided that R$^{1a}$ forms other than an N-halo, N—S, O—O, or N—CN bond;

alternatively, when two R$^{1a}$ groups are attached to adjacent atoms or to the same carbon atom, together with the atoms to which they are attached, they form a 5–7 membered ring consisting of: carbon atoms and 0–2 heteroatoms selected from the group consisting of N, O, and S(O)$_p$, this ring being substituted with 0–2 R$^{4b}$ and comprising: 0–3 double bonds;

R$^{1b}$ is selected from H, C$_{1-3}$ alkyl, F, Cl, Br, I, —CN, —NO$_2$, —CHO, (CF$_2$)$_r$CF$_3$, (CR$^3$R$^{3a}$)$_r$OR$^2$, NR$^2$R$^{2a}$, C(O)R$^{2b}$, CO$_2$R$^{2b}$, OC(O)R$^2$, CH(CH$_2$OR$^2$)$_2$, (CF$_2$)$_r$CO$_2$R$^{2a}$, S(O)$_p$R$^{2b}$, NR$^2$(CH$_2$)$_r$OR$^2$, C(=NR$^{2c}$)NR$^2$R$^{2a}$, NR$^2$C(O)R$^{2b}$, NR$^2$C(O)NR$^2$R$^{2a}$, NR$^2$C(O)$_2$R$^{2a}$, OC(O)NR$^2$R$^{2a}$, C(O)NR$^2$R$^{2a}$, C(O)NR$^2$(CH$_2$)$_r$OR$^2$, SO$_2$NR$^2$R$^{2a}$, NR$^2$SO$_2$R$^2$, C(O)NR$^2$SO$_2$R$^2$, C$_{3-6}$ carbocycle substituted with 0–2 R$^{4b}$, and 5–10 membered heterocycle substituted with 0–2 R$^{4b}$ and consisting of carbon atoms and from 1–4 heteroatoms selected from the group consisting of N, O, and S(O)$_p$, provided that R$^{1b}$ forms other than an O—O, N-halo, N—S, or N—CN bond and provided that S(O)$_p$R$^2$ forms other than S(O)$_2$H or S(O)H;

R$^2$, at each occurrence, is selected from H, CF$_3$, C$_{1-6}$ alkyl, benzyl, —(CH$_2$)$_r$—C$_{3-10}$ carbocycle substituted with 0–2 R$^{4b}$, and —(CH$_2$)$_r$-5–10 membered heterocycle consisting of: carbon atoms and 1–4 heteroatoms selected from the group consisting of N, O, and S(O)$_p$ and substituted with 0–2 R$^{4b}$;

R$^{2a}$, at each occurrence, is selected from H, CF$_3$, C$_{1-6}$ alkyl, benzyl, —(CH$_2$)$_r$—C$_{3-10}$ carbocycle substituted with 0–2 R$^{4b}$, and —(CH$_2$)$_r$-5–10 membered heterocycle consisting of: carbon atoms and 1–4 heteroatoms selected from the group consisting of N, O, and S(O)$_p$ and substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and consisting of: 0–1 additional heteroatoms selected from the group consisting of N, O, and S(O)$_p$;

R$^{2b}$, at each occurrence, is selected from CF$_3$, C$_{1-4}$ alkoxy, C$_{1-6}$ alkyl substituted with 0–2 R$^{4b}$, —(CH$_2$)$_r$—C$_{3-10}$ carbocycle substituted with 0–2 R$^{4b}$, and —(CH$_2$)$_r$-5–10 membered heterocycle consisting of: carbon atoms and 1–4 heteroatoms selected from the group consisting of N, O, and S(O)$_p$ and substituted with 0–2 R$^{4b}$;

R$^{2c}$, at each occurrence, is selected from CF$_3$, OH, C$_{1-4}$ alkoxy, C$_{1-6}$ alkyl, —(CH$_2$)$_r$—C$_{3-10}$ carbocycle substituted with 0–2 R$^{4b}$, and —(CH$_2$)$_r$-5–10 membered heterocycle containing from 1–4 heteroatoms selected from the group consisting of N, O, and S(O)$_p$ and substituted with 0–2 R$^{4b}$;

R$^{2d}$, at each occurrence, is selected from H, R$^{4c}$, C$_{1-6}$ alkyl substituted with 0–2 R$^{4c}$, —(CR$^3$R$^{3a}$)$_r$—C$_{3-10}$ carbocycle substituted with 0–2 R$^{4c}$, and —(CR$^3$R$^{3a}$)$_r$-5–10 membered heterocycle consisting of: carbon atoms and 1–4 heteroatoms selected from the group consisting of N, O, and S(O)$_p$ and substituted with 0–2 R$^{4c}$, provided that R$^{2d}$ forms other than a N-halo, N—C-halo, S(O)$_p$-halo, O-halo, N—S, S—N, S(O)$_p$—S(O)$_p$, S—O, O—N, O—S, or O—O moiety;

R$^{2e}$, at each occurrence, is selected from H, R$^{4c}$, C$_{1-6}$ alkyl substituted with 0–2 R$^{4c}$, —(CR$^3$R$^{3a}$)$_r$—C$_{3-10}$ carbocycle substituted with 0–2 R$^{4c}$, and —(CR$^3$R$^{3a}$)$_r$-5–6 membered heterocycle consisting of: carbon atoms and 1–4 heteroatoms selected from the group consisting of N, O, and S(O)$_p$ and substituted with 0–2 R$^{4c}$, provided that R$^{2e}$ forms other than a C(O)-halo or C(O)—S(O)$_p$ moiety;

R$^3$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

alternatively, R$^3$ and R$^{3a}$, together with the nitrogen atom to which they are attached, combine to form a 5 or 6 membered saturated, partially unsaturated, or unsaturated ring consisting of: carbon atoms, the nitrogen atom to which R$^3$ and R$^{3a}$ are attached, and 0–1 additional heteroatoms selected from the group consisting of N, O, and S(O)$_p$;

R$^{3b}$, at each occurrence, is selected from CF$_3$, C$_{1-4}$ alkoxy substituted with 0–2 R$^{4b}$, C$_{1-6}$ alkyl substituted with 0–2 R$^{4b}$, —(CH$_2$)$_r$—C$_{3-10}$ carbocycle substituted with 0–2 R$^{4b}$, and —(CH$_2$)$_r$-5–10 membered heterocycle consisting of: carbon atoms and 1–4 heteroatoms selected from the group consisting of N, O, and S(O)$_p$ and substituted with 0–2 R$^{4b}$;

R$^{3c}$, at each occurrence, is selected from CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C$_{1-4}$ alkyl-phenyl, and C(=O)R$^{3c}$;

R$^{3g}$, at each occurrence, is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —(CH$_2$)$_r$-3–6 membered carbocycle, and —(CH$_2$)$_r$-5–6 membered heterocycle consisting of: carbon atoms and 1–4 heteroatoms selected from the group consisting of N, O, and S(O)$_p$;

alternatively, when $R^3$ and $R^{3g}$ are attached to the same carbon atom, they combine with the attached carbon atom to form a cyclopropyl group;

$R^4$, at each occurrence, is selected from H, =O, $(CR^3R^{3a})_rOR^2$, F, Cl, Br, I, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rC(=NS(O)_2R^{5a})NR^2R^{2a}$, $(CR^3R^{3a})_rNHC(=NR^2)NR^2R^{2a}$, $(CR^3R^{3a})_rC(O)NHC(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2-C_{1-4}$ alkyl, $(CR^3R^{3a})_rNR^2SO_2R^{5a}$, $(CR^3R^{3a})_rS(O)_pR^{5a}$, $(CR^3R^{3a})_r(CF_2)_rCF_3$, $NHCH_2R^{1b}$, $OCH_2R^{1b}$, $SCH_2R^{1b}$, $N(CH_2)_2(CH_2)_tR^{1b}$, $O(CH_2)_2(CH_2)_tR^{1b}$, and $S(CH_2)_2(CH_2)_tR^{1b}$;

$R^{4b}$, at each occurrence, is selected from H, =O, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_rC(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2-C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p-C_{1-4}$ alkyl, $(CH_2)_rS(O)_p$-phenyl, and $(CH_2)_r(CF_2)_rCF_3$;

$R^{4c}$, at each occurrence, is selected from =O, $(CR^3R^{3a})_rOR^2$, $(CR^3R^{3a})_rF$, $(CR^3R^{3a})_rBr$, $(CR^3R^{3a})_rCl$, $(CR^3R^{3a})_rCF_3$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rN(\rightarrow O)R^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NH(CR^3R^{3a})_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNHC(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rC(O)NHSO_2-C_{1-4}$ alkyl, $(CR^3R^{3a})_rNR^2SO_2R^{5a}$, $(CR^3R^{3a})_rS(O)_pR^{5a}$, $(CF_2)_rCF_3$, $(CR^3R^{3a})_rC_{3-10}$ carbocycle substituted with 0–2 $R^{4b}$, and $(CR^3R^{3a})_r$5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, $C_{1-6}$ alkyl, =O, $(CH_2)_rOR^3$, F, Cl, Br, I, —CN, $NO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_rCH(=NOR^{3d})$, $(CH_2)_rC(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2-C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p-C_{1-4}$ alkyl, $(CH_2)_rS(O)_p$-phenyl, $(CF_2)_rCF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_rOR^3$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CF_2)_rCF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, C(=NH)$NH_2$, NHC(=NH)$NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkyl-C(O)—, $C_{1-6}$ alkyl-O—, $(CH_2)_n$-phenyl, $C_{1-4}$ alkyl-OC(O)—, $C_{6-10}$ aryl-O—, $C_{6-10}$ aryl-OC(O)—, $C_{6-10}$ aryl-$CH_2$—C(O)—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-$NH_2$—C(O)—, phenyl-$NH_2$—C(O)—, and phenyl $C_{1-4}$ alkyl-C(O)—;

$R^8$, at each occurrence, is selected from H, $C_{1-6}$ alkyl, and $(CH_2)_n$-phenyl;

alternatively, $R^7$ and $R^8$, when attached to the same nitrogen, combine to form a 5–10 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;
p, at each occurrence, is selected from 0, 1, and 2;
r, at each occurrence, is selected from 0, 1, 2, 3, 4, 5, and 6;
t, at each occurrence, is selected from 0, 1, 2, and 3.

2. A compound according to claim 1, wherein:
ring M is substituted with 0–2 $R^{1a}$;
G is a group of formula IIa:

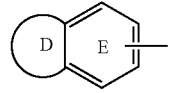

IIa ring D, including the two atoms of Ring E to which it is attached, is a 5–6 membered ring consisting of: carbon atoms and 0–2 heteroatoms selected from the group consisting of N, O, and $S(O)_p$;
ring D is substituted with 0–2 R and there are 0–3 ring double bonds;
E is selected from phenyl, pyridyl, pyrimidyl, pyrazinyl, and pyridazinyl, and is substituted with 1–2 R;
alternatively, ring D is absent, and ring E is selected from phenyl, pyridyl, pyrimidyl, and thienyl, and ring E is substituted with 1–2 R;
alternatively, ring D is absent, ring E is selected from phenyl, pyridyl; and thienyl, and ring E is substituted with 1 R and with a 5 membered heterocycle consisting of: carbon atoms and 1–4 heteroatoms selected from the group consisting of N, O, and $S(O)_p$, wherein the 5 membered heterocycle is substituted with 0–1 carbonyls and 1–2 R and there are 0–3 ring double bonds;
R is selected from H, $C_{1-4}$ alkyl, F, Cl, OH, $OCH_3$, $OCH_2CH_3$, $OCH(CH_3)_2$, CN, C(=NH)$NH_2$, C(=NH)NHOH, C(=NH)$NHOCH_3$, $NH_2$, NH($C_{1-3}$ alkyl), N($C_{1-3}$ alkyl)$_2$, C(=NH)$NH_2$, $CH_2NH_2$, $CH_2NH(C_{1-3}$ alkyl), $CH_2N(C_{1-3}$ alkyl)$_2$, $(CR^8R^9)_rNR^7R^8$, C(O)$NR^7R^8$, $CH_2C(O)NR^7R^8$, $S(O)_2R^3$, $S(O)_pNR^7R^8$, $CH_2S(O)_pNR^7R^8$, and $OCF_3$;
alternatively, when 2 R groups are attached to adjacent atoms, they combine to form methylenedioxy or ethylenedioxy;
B is selected from $N(B^1)C(O)C(R^3R^{3g})NB^2B^3$ and $N(B^1)C(O)C(R^3R^{3g})C(R^3R^{3g})NB^2B^3$;
$B^1$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —$(CH_2)_{0-1}$—$C_{3-7}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^{2d}R^{2d}$, $CH_2$—$NR^{2d}R^{2d}$, $CH_2CH_2$—$NR^{2d}R^{2d}$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–2 $R^5$, and a —$(CH_2)_{0-1}$-4–7 membered heterocycle consisting of: carbon atoms and 1–4 heteroatoms selected from the group consisting of N, O, and $S(O)_p$ and substituted with 0–2 $R^5$;

alternatively, $NB^2B^3$ is a 4–7 membered heterocycle consisting of: the shown N, carbon atoms, and 0–3 additional heteroatoms selected from the group consisting of N, O, and $S(O)_p$ and substituted with 0–2 $R^5$;

$R^{1a}$ is selected from H, —$(CH_2)_r$—$R^{1b}$, —$(CH(CH_3))_r$—$R^{1b}$, —$(C(CH_3)_2)_r$—$R^{1b}$, $NHCH_2R^{1b}$, $OCH_2R^{1b}$, $SCH_2R^{1b}$, $NH(CH_2)_2(CH_2)_tR^{1b}$, and $O(CH_2)_2(CH_2)_tR^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C_{5-6}$ carbocycle substituted with 0–2 $R^{4b}$, and 5–6 membered heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, a $C_{5-6}$ carbocyclic-$CH_2$-group substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, —$(CR^3R^{3a})_r$—$C_{3-6}$ carbocycle substituted with 0–2 $R^{4c}$, and —$(CR^3R^{3a})_r$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^{3g}$, at each occurrence, is selected from H, $CH_3$, $CH_2CH_3$, $CH_2CH_2CH_3$, $CH(CH_3)_2$, cyclopropyl, cyclopropyl-methyl, benzyl, and phenyl;

alternatively, when $R^3$ and $R^{3g}$ are attached to the same carbon atom, they combine with the attached carbon atom to form a cyclopropyl group;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, and $CF_2CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, CF$_3$, and CH$_2$—CF$_3$;

R$^{4c}$, at each occurrence, is selected from =O, (CR$^3$R$^{3a}$)$_r$ OR$^2$, (CR$^3$R$^{3a}$)$_r$F, (CR$^3$R$^{3a}$)$_r$Br, (CR$^3$R$^{3a}$)$_r$Cl, (CR$^3$R$^{3a}$)$_r$CF$_3$, C$_{1-4}$ alkyl, (CR$^3$R$^{3a}$)$_r$CN, (CR$^3$R$^{3a}$)$_r$NO$_2$, (CR$^3$R$^{3a}$)$_r$NR$^2$R$^{2a}$, (CR$^3$R$^{3a}$)$_r$N(→O)R$^2$R$^{2a}$, (CR$^3$R$^{3a}$)$_r$C(O)R$^{2c}$, (CR$^3$R$^{3a}$)$_r$NR$^2$C(O)R$^{2b}$, (CR$^3$R$^{3a}$)$_r$ C(O)NR$^2$R$^{2a}$, (CR$^3$R$^{3a}$)$_r$NR$^2$C(O)NR$^2$R$^{2a}$, (CR$^3$R$^{3a}$)$_r$ SO$_2$NR$^2$R$^{2a}$, (CR$^3$R$^{3a}$)$_r$NR$^2$SO$_2$NR$^2$R$^{2a}$, (CR$^3$R$^{3a}$)$_r$ NR$^2$SO$_2$R$^{5a}$, (CR$^3$R$^{3a}$)$_r$S(O)$_p$R$^{5a}$, (CF$_2$)$_r$ CF$_3$, (CR$^3$R$^{3a}$)$_r$C$_{3-10}$ carbocycle substituted with 0–2 R$^{4b}$, and (CR$^3$R$^{3a}$)$_r$5–10 membered heterocycle consisting of carbon atoms and from 1–4 heteroatoms selected from the group consisting of N, O, and S(O)$_p$ and substituted with 0–2 R$^{4b}$;

R$^5$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$) NR$^3$R$^{3a}$, SO$_2$NR$^3$R$^{3a}$, NR$^3$SO$_2$NR$^3$R$^{3a}$, NR$_3$SO$_2$— C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$;

R$^6$, at each occurrence, is selected from H, OH, OR$^2$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl; and, r, at each occurrence, is selected from 0, 1, and 2.

3. A compound according to claim 2, wherein:
G is selected from the group:

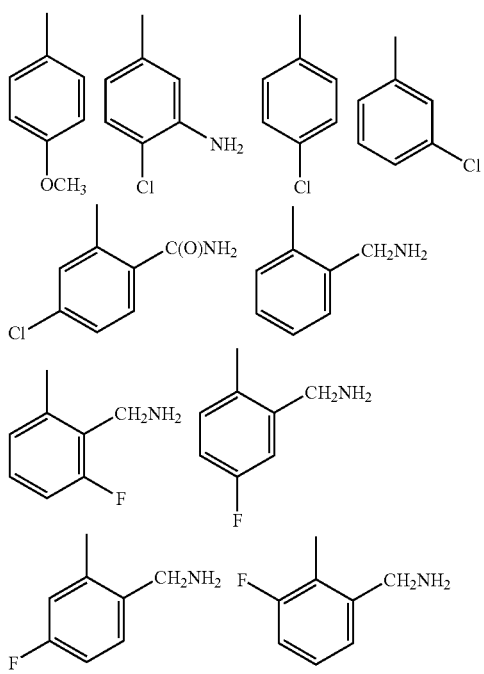

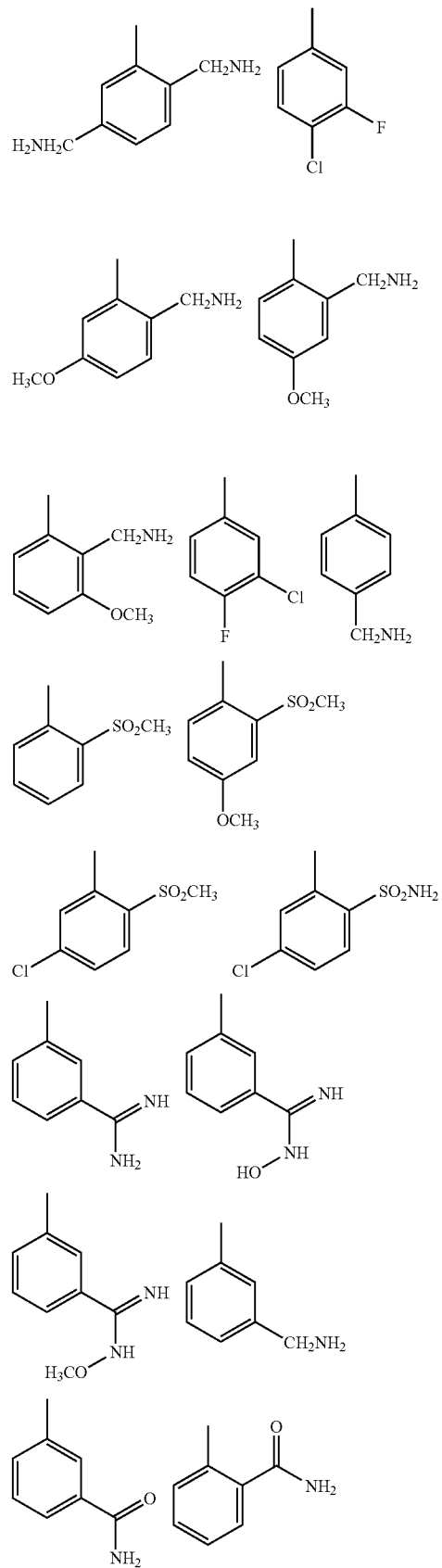

-continued
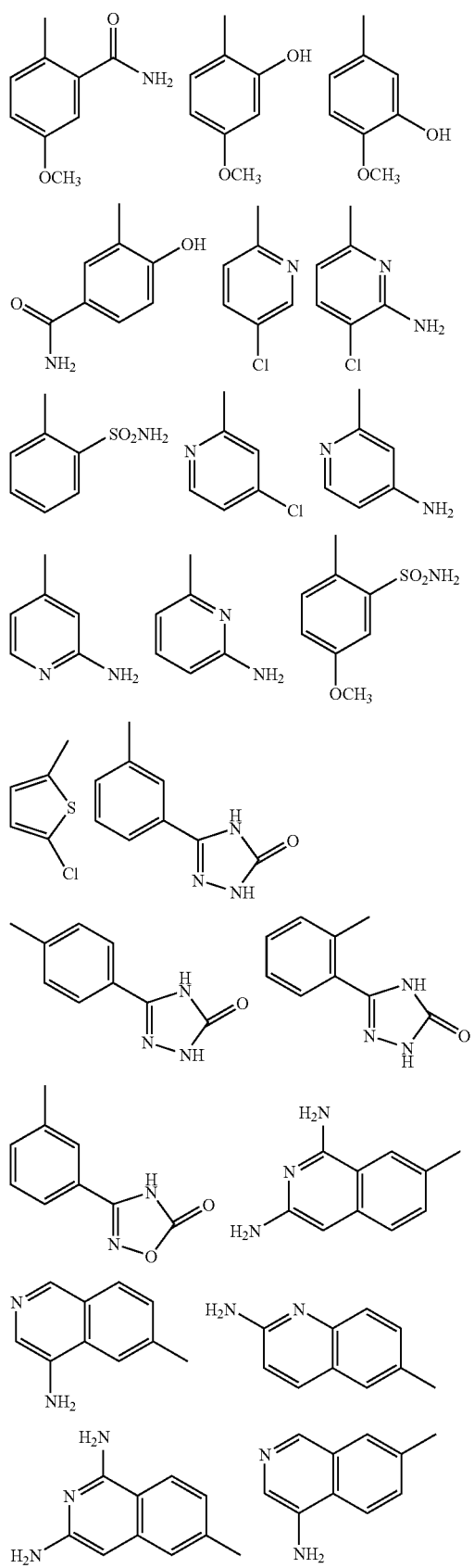
-continued
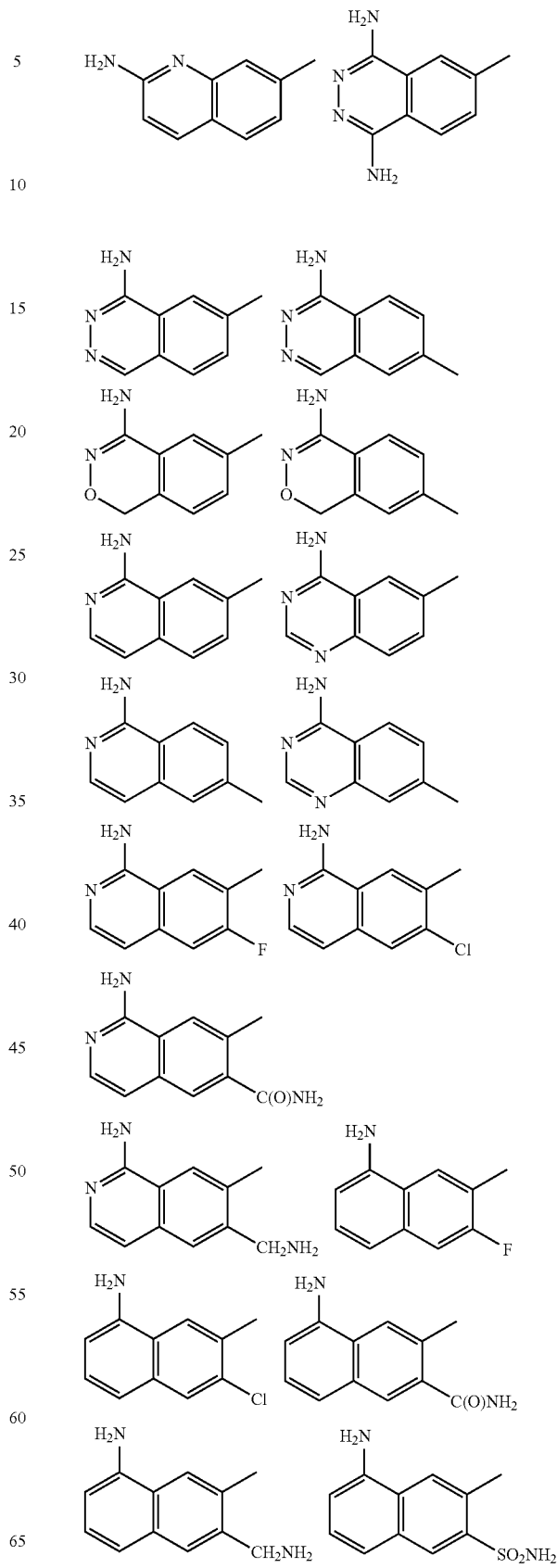

-continued
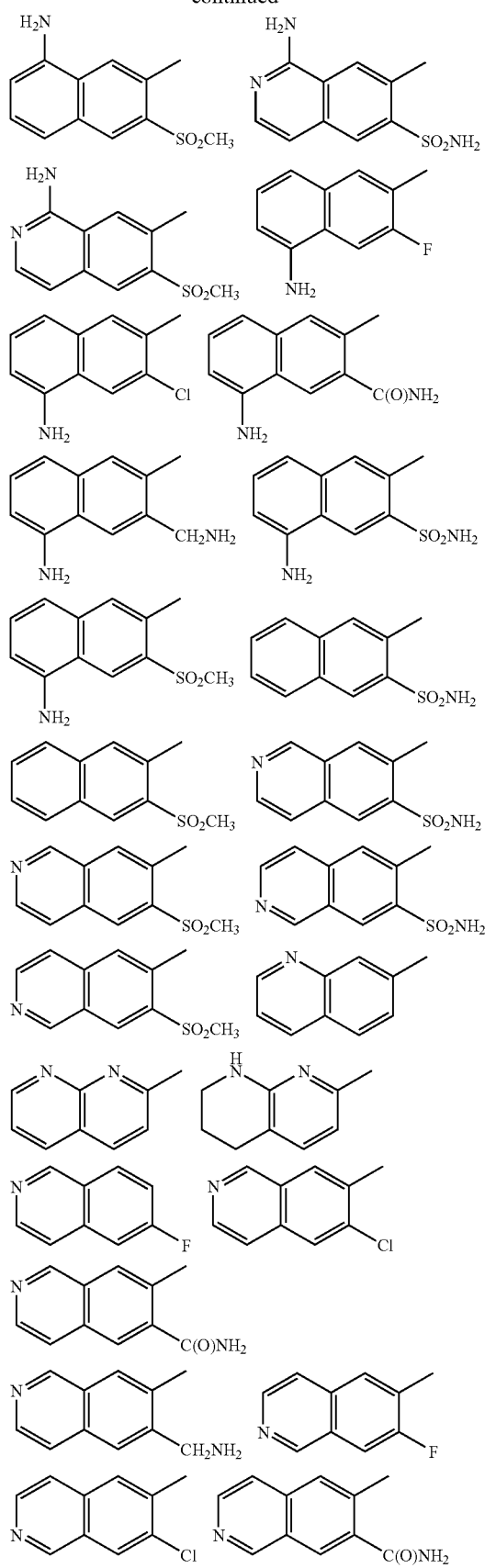
-continued
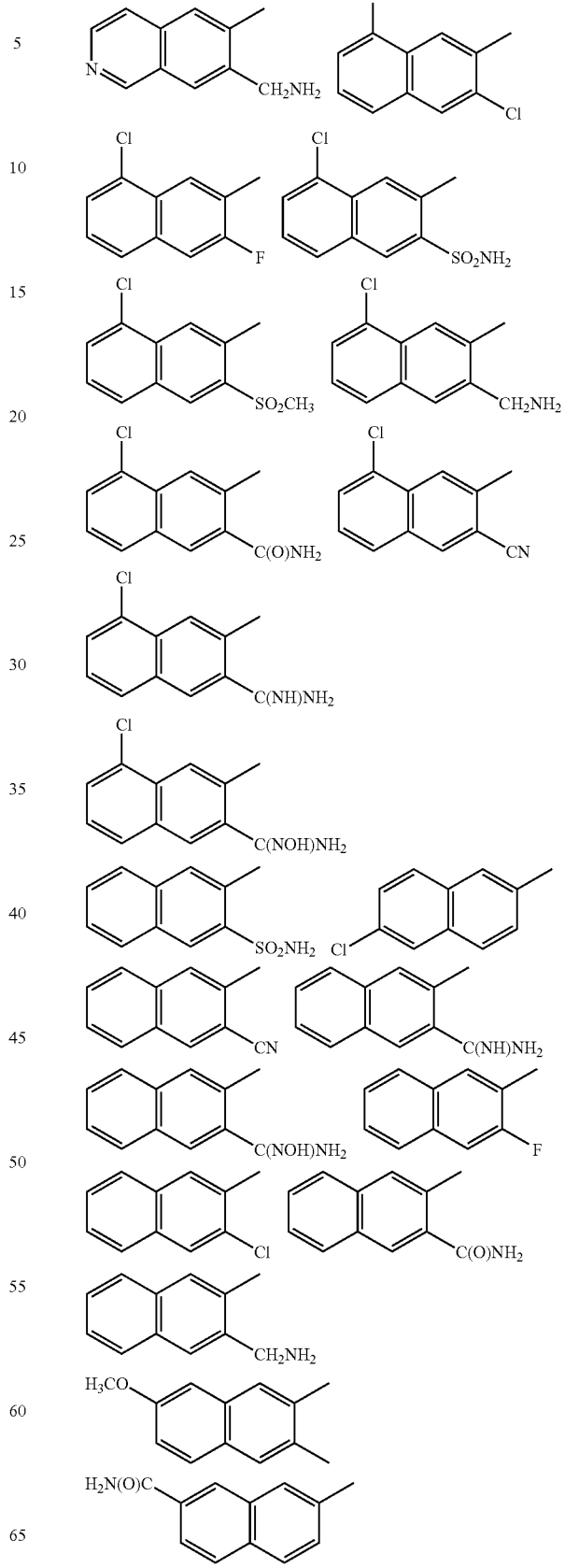

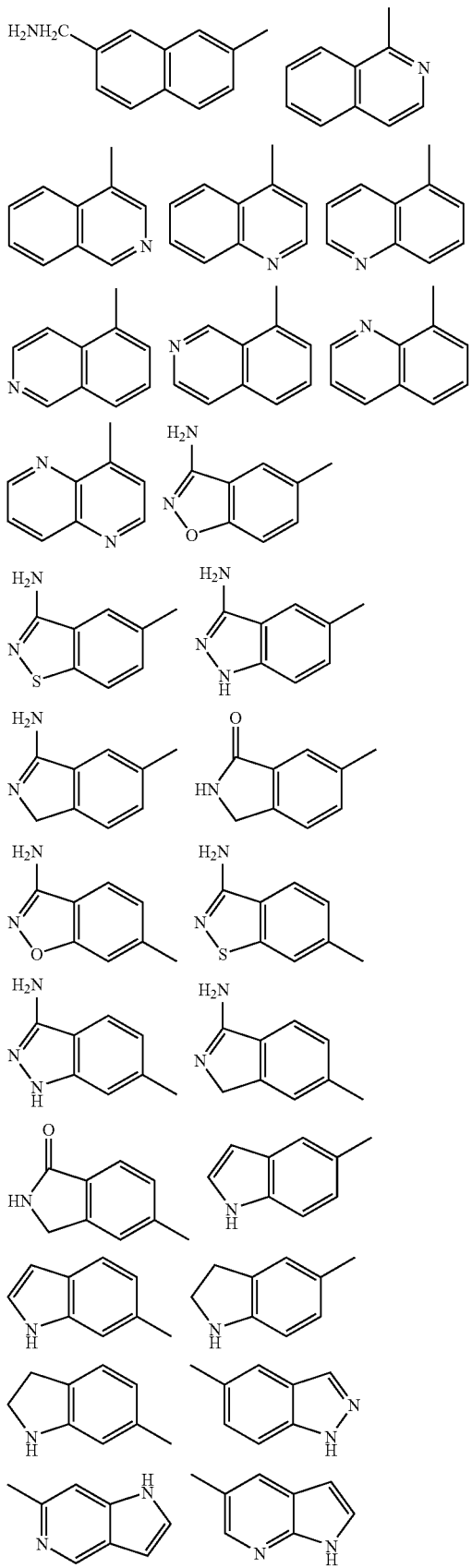
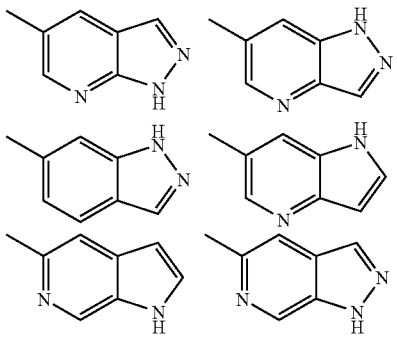

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–6 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$ and substituted with 0–2 $R^{4b}$, provided that $R^{1b}$ forms other than an O—O, N-halo, N—S, or N—CN bond;

$B^1$ is selected from H, $CH_3$, $CH_2CH_3$, $CH_2CH_2CH_3$, $CH(CH_3)_2$, —$(CH_2)_{0-1}$—$C_{5-6}$ carbocycle substituted with 0–2 $R^{4b}$, and —$(CH_2)_{0-1}$-5–6 membered heterocycle consisting of: carbon atoms and 1–4 heteroatoms selected from the group consisting of N, O, and $S(O)_p$ and substituted with 0–2 $R^{4b}$;

$B^2$ is selected from H, $CH_3$, $CH_2CH_3$, $CH_2CH_2CH_3$, $CH(CH_3)_2$, $C(O)R^{2e}$, $C(O)NR^{2d}R^{2d}$, $SO_2NR^{2d}R^{2d}$, and $S(O)_pR^{5a}$;

$B^3$ is selected from H, $C_{1-6}$ alkyl substituted with 0–1 $R^{4c}$, —$(CH_2)_{0-1}$-3–6 membered carbocycle substituted with 0–1 $R^5$, and a —$(CH_2)_{0-1}$-5–6 membered heterocycle consisting of: carbon atoms and 1–4 heteroatoms selected from the group consisting of N, O, and $S(O)_p$ and substituted with 0–1 $R^5$;

alternatively, $NB^2B^3$ is a 4–7 membered heterocycle consisting of: the shown N, carbon atoms, and 0–3 additional heteroatoms selected from the group consisting of N, O, and $S(O)_p$ and substituted with 0–1 $R^5$;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–2 $R^{4b}$, and 5–6 membered aromatic heterocycle containing from 1–4 heteroatoms selected from the group consisting of N, O, and $S(O)_p$ and substituted with 0–2 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and —$(CR^3R^{3a})$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, —$(CR^3R^{3a})$—$C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and —$(CR^3R^{3a})$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^4$, at each occurrence, is selected from H, $(CH_2)_2OR^2$, $CH_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, C(O)$R^3$, $CH_2$—C(O)$R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR_3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from =O, $OR^2$, $(CR^3R^{3a})OR^2$, F, $(CR^3R^{3a})$F, Br, $(CR^3R^{3a})$Br, Cl, $(CR^3R^{3a})$Cl, $CF_3$, $(CR^3R^{3a})CF_3$, $C_{1-4}$ alkyl, —CN, $(CR^3R^{3a})$CN, $NO_2$, $(CR^3R^{3a})NO_2$, $NR^2R^{2a}$, $(CR^3R^{3a})NR^2R^{2a}$, N(→O)$R^2R^{2a}$, $(CR^3R^{3a})$N(→O)$R^2R^{2a}$, C(O)$R^{2c}$, $(CR^3R^{3a})$C(O)$R^{2c}$, $NR^2C(O)R^{2b}$, $(CR^3R^{3a})NR^2C(O)R^{2b}$, C(O)$NR^2R^{2a}$, $(CR^3R^{3a})C(O)NR^2R^{2a}$, $NR^2C$(O)$NR^2R^{2a}$, $(CR^3R^{3a})NR^2C(O)NR^2R^{2a}$, $SO_2NR^2R^{2a}$, $(CR^3R^{3a})SO_2NR^2R^{2a}$, $NR^2SO_2NR^2R^{2a}$, $(CR^3R^{3a})$ $NR^2SO_2NR^2R^{2a}$, $NR^2SO_2R^{5a}$, $(CR^3R^{3a})NR^2SO_2R^{5a}$, $S(O)_pR^{5a}$, $(CR^3R^{3a})S(O)_pR^{5a}$, $CF_3$, $CF_2CF_3$, $C_{3-10}$ carbocycle substituted with 0–2 $R^{4b}$, $(CR^3R^{3a})C_{3-10}$ carbocycle substituted with 0–2 $R^{4b}$, 5–10 membered heterocycle consisting of carbon atoms and from 1–4 heteroatoms selected from the group consisting of N, O, and $S(O)_p$ and substituted with 0–2 $R^{4b}$, and $(CR^3R^{3a})$-5–10 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, C(O)$R^3$, $CH_2C(O)R^3$, $C(O)OR^{3c}$, $CH_2C(O)OR^{3c}$, $NR^3C(O)R^{3a}$, C(O)$NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, C(O)$R^{2b}$, $CH_2C(O)R^{2b}$, $NR^2C(O)R^{2b}$, $SO_2NR^2R^{2a}$, and $NR^2SO_2C_{1-4}$ alkyl.

4. A compound according to claim 3, wherein:

one of $P_4$ and $M_4$ is -A-B and the other -G;

G is selected from the group:

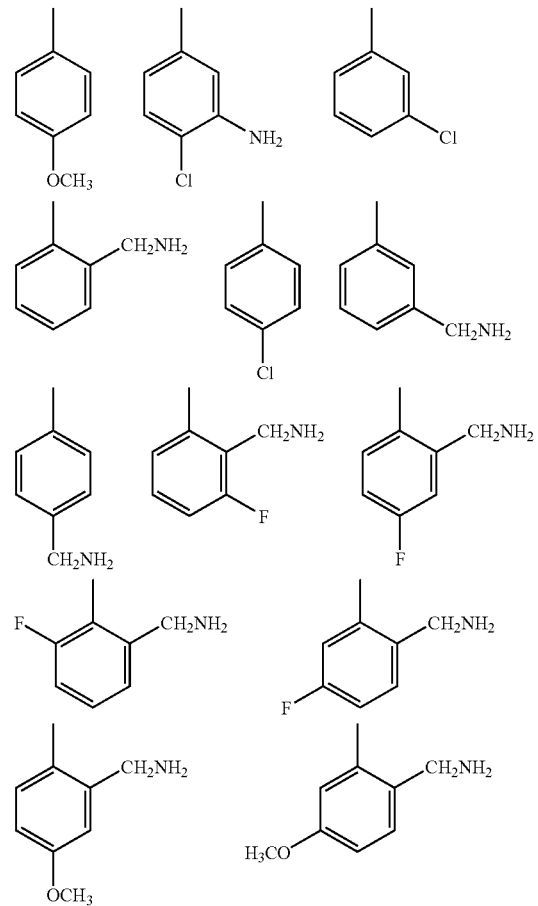

-continued
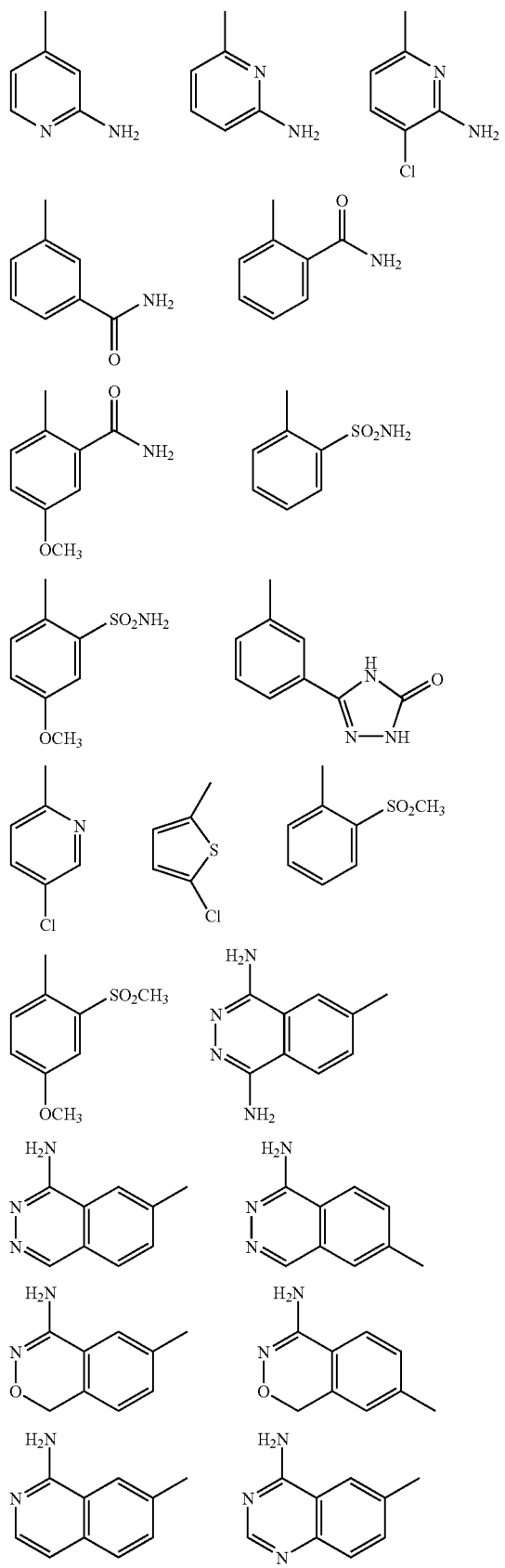
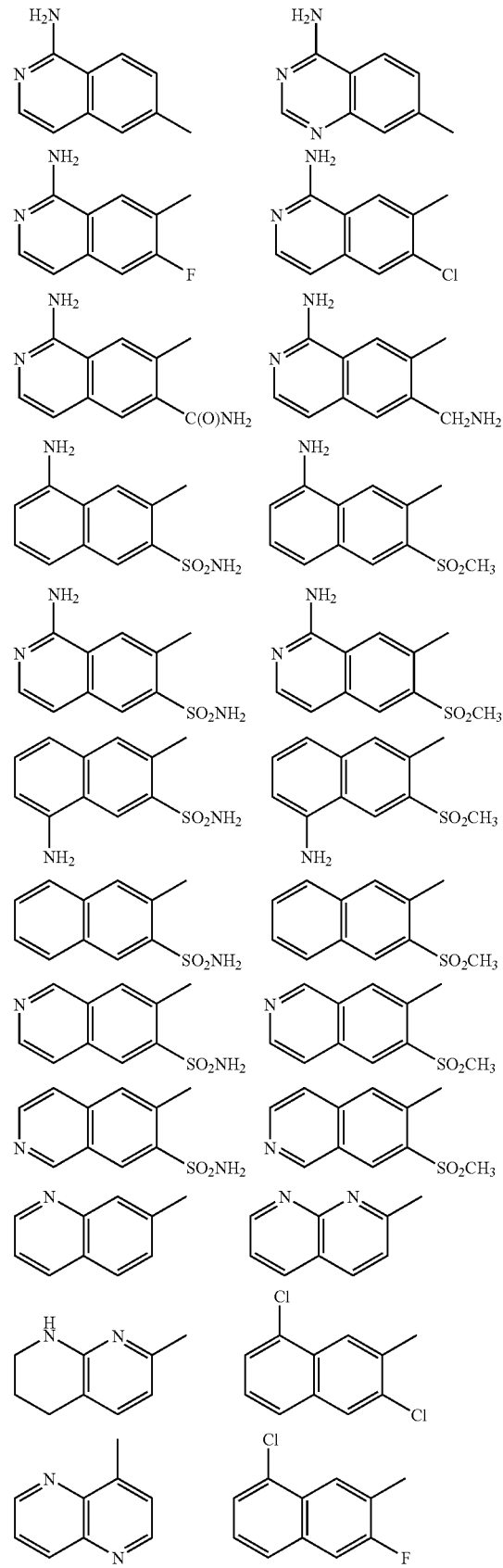

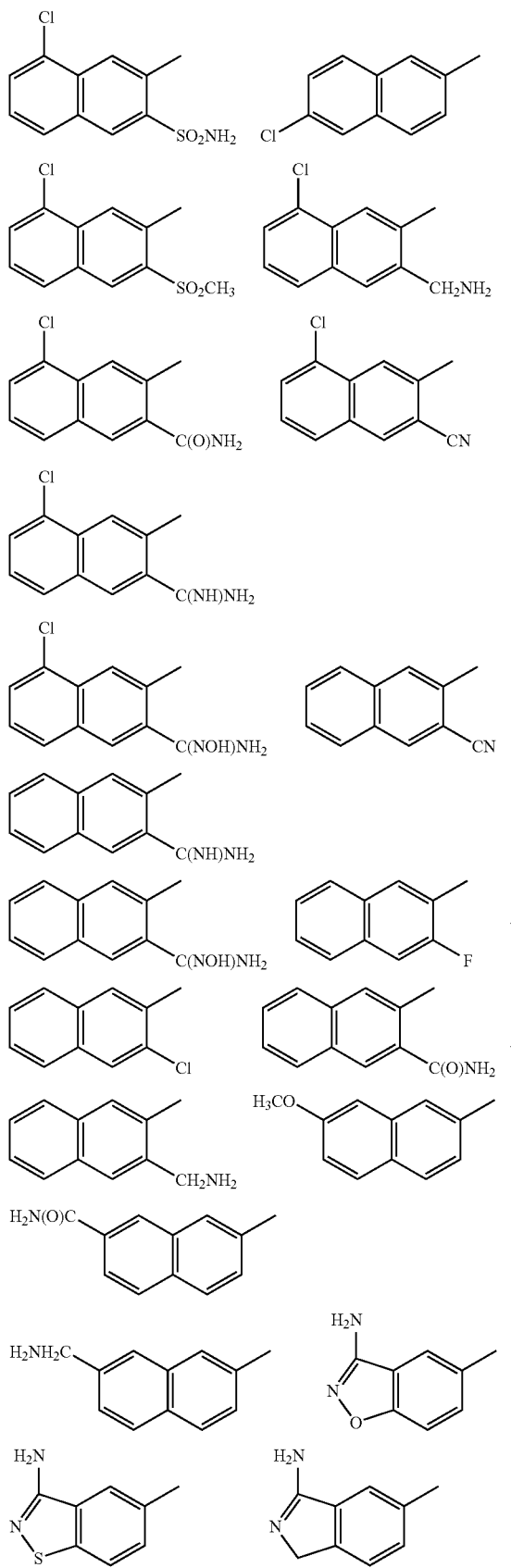
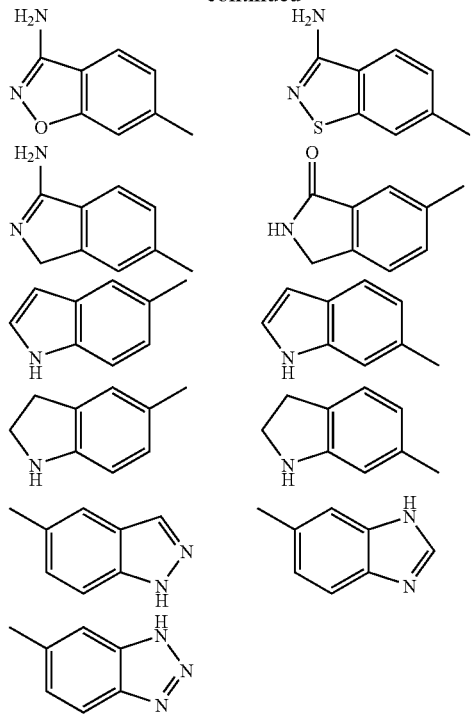

B is N(B$^1$)C(O)C(R$^3$R$^{3a}$)NB$^2$B$^3$;

B$^1$ is selected from H, CH$_3$, CH$_2$CH$_3$, CH$_2$CH$_2$CH$_3$, and CH(CH$_3$)$_2$;

B$^2$ is selected from H, CH$_3$, CH$_2$CH$_3$, CH$_2$CH$_2$CH$_3$, and CH(CH$_3$)$_2$;

B$^3$ is selected from H, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, C$_{2-5}$ alkyl substituted with 1 R$^{4c}$, —(CH$_2$)$_{0-1}$-3–6 membered carbocycle substituted with 0–1 R$^5$, and a —(CH$_2$)$_{0-1}$-5–6 membered heterocycle consisting of: carbon atoms and 1–4 heteroatoms selected from the group consisting of N, O, and S(O)$_p$ and substituted with 0–1 R$^5$;

alternatively, NB$^2$B$^3$ is a 5–6 membered heterocycle consisting of: the shown N, carbon atoms, and 0–2 additional heteroatoms selected from the group consisting of N, O, and S(O)$_p$ and substituted with 0–1 R$^5$;

R$^{1a}$ is selected from H, R$^{1b}$, C(CH$_3$)$_2$R$^{1b}$, and CH$_2$R$^{1b}$, provided that R$^{1a}$ forms other than an N-halo, N—S, or N—CN bond;

R$^{1b}$ is selected from CH$_3$, CH$_2$CH$_3$, F, Cl, Br, —CN, CF$_3$, OR$^2$, NR$^2$R$^{2a}$, C(O)R$^{2b}$, CO$_2$R$^{2b}$, CO$_2$R$^{2a}$, S(O)$_p$R$^2$, C(O)NR$^2$R$^{2a}$, SO$_2$NR$^2$R$^{2a}$, NR$^2$SO$_2$R$^2$, and 5–6 membered aromatic heterocycle consisting of carbon atoms and from 1–4 heteroatoms selected from the group consisting of N, O, and S(O)$_p$ and substituted with 0–2 R$^{4b}$, provided that R$^{1b}$ forms other than an O—O, N-halo, N—S, or N—CN bond;

R$^2$, at each occurrence, is selected from H, CH$_3$, CH$_2$CH$_3$, CH$_2$CH$_2$CH$_3$, CH(CH$_3$)$_2$, phenyl substituted with 0–1 R$^{4b}$, benzyl substituted with 0–1 R$^{4b}$, and 5–6 membered aromatic heterocycle consisting of: carbon atoms and 1–4 heteroatoms selected from the group consisting of N, O, and S(O)$_p$ and substituted with 0–1 R$^{4b}$;

R$^{2a}$, at each occurrence, is selected from H, CH$_3$, CH$_2$CH$_3$, CH$_2$CH$_2$CH$_3$, CH(CH$_3$)$_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0–1 $R^{4b}$, and 5–6 membered aromatic heterocycle containing from 1–4 heteroatoms selected from the group consisting of N, O, and $S(O)_p$ and substituted with 0–1 $R^{4b}$;

$R^{2d}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $-(CH_2)-C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and $-(CH_2)$-5–6 membered heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ carbocycle substituted with 0–2 $R^{4c}$, $-(CH_2)-C_{3-6}$ carbocycle substituted with 0–2 $R^{4c}$, 5–6 membered heterocycle consisting of: carbon atoms and 1–4 heteroatoms selected from the group consisting of N, O, and $S(O)_p$ and substituted with 0–2 $R^{4c}$, and $-(CH_2)$-5–6 membered heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^4$, at each occurrence, is selected from OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $CF_3$, and $CF_2CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2-C_{1-4}$ alkyl, $NR^3SO_2$-phenyl, $S(O)_p-C_{1-4}$ alkyl, $S(O)_p$-phenyl, and $CF_3$;

$R^{4c}$, at each occurrence, is selected from =O, $OR^2$, $CH_2OR^2$, F, Br, Cl, $CF_3$, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_p R^{5a}$, $CH_2S(O)_p R^{5a}$, $CF_3$, $CF_2CF_3$, $C_{3-6}$ carbocycle substituted with 0–2 $R^{4b}$, $(CH_2)C_{3-6}$ carbocycle substituted with 0–2 $R^{4b}$, 5–6 membered heterocycle consisting of carbon atoms and from 1–4 heteroatoms selected from the group consisting of N, O, and $S(O)_p$ and substituted with 0–2 $R^{4b}$, and $(CH_2)$-5–6 membered heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2-C_{1-4}$ alkyl, $NR^3SO_2$-phenyl, $S(O)_p-C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

5. A compound according to claim 4, wherein:

ring M is substituted with 0–1 $R^{1a}$;

G is selected from:

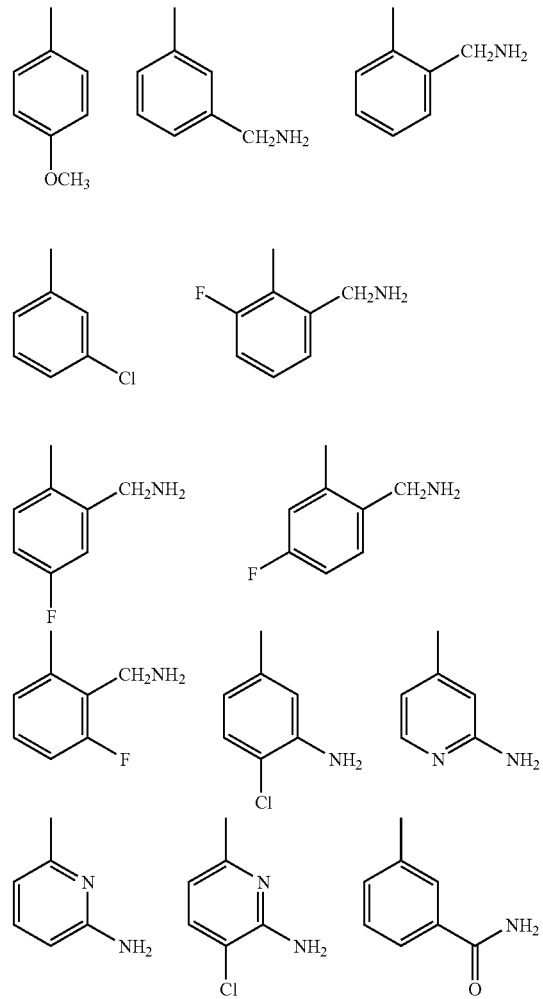

-continued
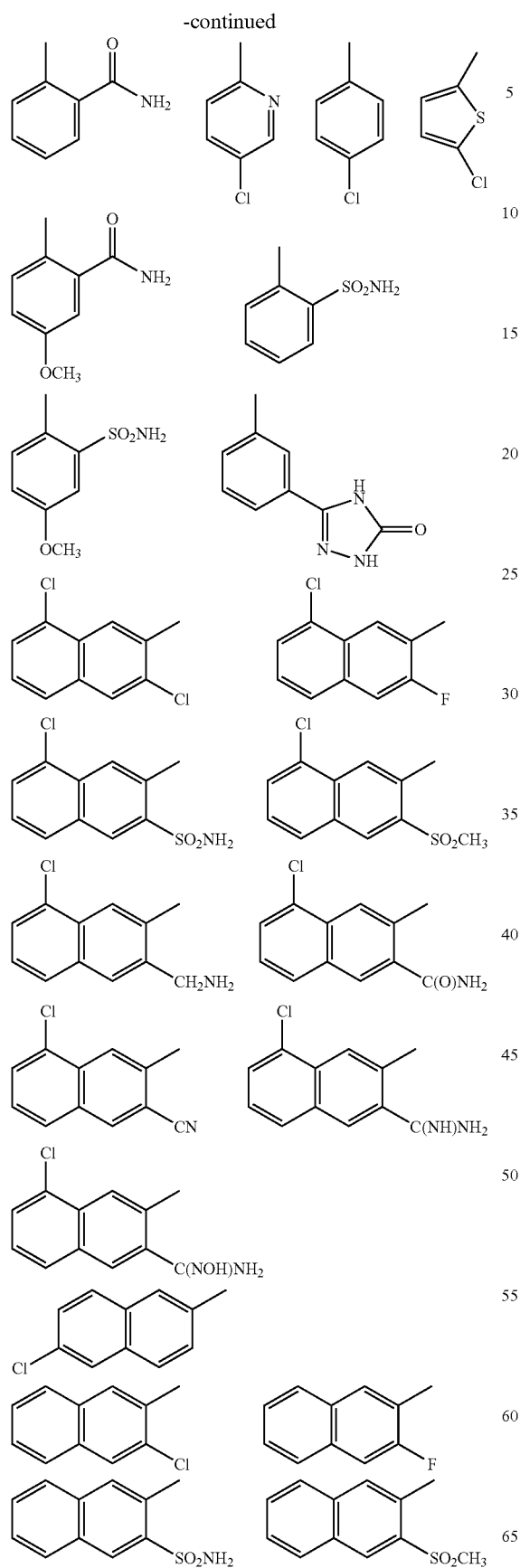
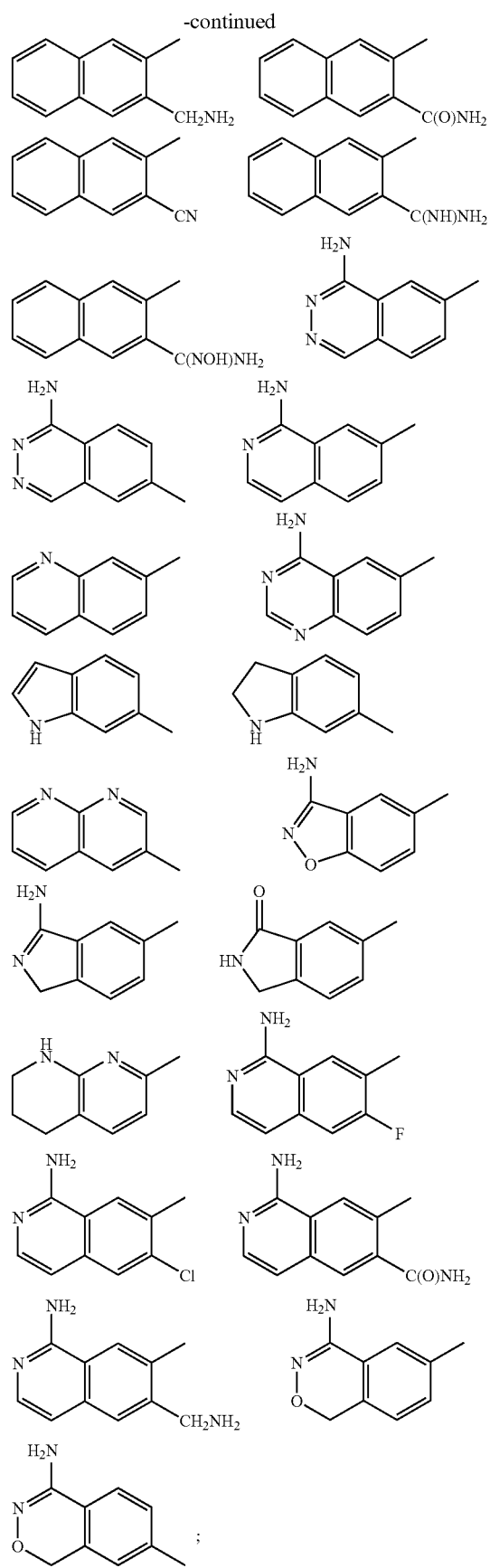

-continued

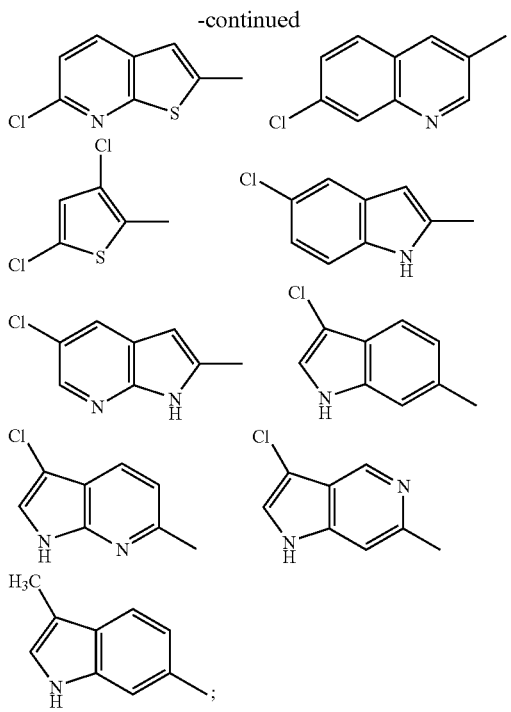

A is selected from the group: phenyl, 2-Cl-phenyl, 3-Cl-phenyl, 2-F-phenyl, 3-F-phenyl, 2-methylphenyl, 2-aminophenyl, and 2-methoxyphenyl;

$B^1$ is selected from H, $CH_3$, $CH_2CH_3$, and $CH_2CH_2CH_3$;

$B^2$ is selected from H, $CH_3$, and $CH_2CH_3$;

$B^3$ is selected from $CH_3$, $CH_2CH_3$, $CH_2CH_2CH_3$, $CH(CH_3)_2$, $CH_2CH_2CH_2CH_3$, $C(CH_3)_3$, $CH(CH_3)CH_2CH(CH_3)_2$, $CH_2CH_2OH$, $CH(CH_3)CH_2OH$, $CH(phenyl)CH_2CH_3$, cyclopropyl, cyclobutyl, cyclopentyl, and $CH_2$-cyclopropyl;

alternatively, $NB^2B^3$ is a ring selected from pyrrolidinyl, piperidinyl, and morpholinyl;

$R^{1a}$ is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$;

alternatively, $R^2$ and $R^{2a}$, together with the atom to which they are attached, combine to form a 5 or 6 membered saturated, partially saturated or unsaturated ring substituted with 0–1 $R^{4b}$ and consisting of: 0–1 additional heteroatoms selected from the group consisting of N, O, and $S(O)_p$;

$R^{2b}$, at each occurrence, is selected from OH, $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and $S(O)_p$ and substituted with 0–2 $R^{4c}$, provided that $R^{2d}$ forms other than a N-halo, N—C-halo, $S(O)_p$-halo, O-halo, N—S, S—N, $S(O)_p$—$S(O)_p$, S—O, O—N, O—S, or O—O moiety;

$R^{2e}$, at each occurrence, is selected from H, $R^{4c}$, $C_{1-4}$ alkyl substituted with 0–2 $R^{4c}$, $C_{3-6}$ cycloalkyl substituted with 0–2 $R^{4c}$, phenyl substituted with 0–2 $R^{4c}$, and 5–6 membered aromatic heterocycle consisting of: carbon atoms and 1–4 heteroatoms selected from the group consisting of N, O, and $S(O)_p$ and substituted with 0–2 $R^{4c}$, provided that $R^{2e}$ forms other than a C(O)-halo or C(O)—$S(O)_p$ moiety;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^{4c}$, at each occurrence, is selected from =O, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, $CH_2OH$, $CH_2OCH_3$, $CH_2OCH_2CH_3$, $CH_2OCH_2CH_2CH_3$, $CH_2OCH(CH_3)_2$, F, Br, Cl, $CF_3$, $NR^2R^{2a}$, $CH_2NR^2R^{2a}$, $N(\rightarrow O)R^2R^{2a}$, $CH_2N(\rightarrow O)R^2R^{2a}$, $C(O)R^{2c}$, $CH_2C(O)R^{2c}$, $NR^2C(O)R^{2b}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $NR^2SO_2R^{5a}$, $CH_2NR^2SO_2R^{5a}$, $S(O)_pR^{5a}$, $CH_2S(O)_pR^{5a}$, $CF_3$, cyclopropyl substituted with 0–1 $R^{4b}$, cyclobutyl substituted with 0–1 $R^{4b}$, cyclopentyl substituted with 0–1 $R^{4b}$, phenyl substituted with 0–1 $R^{4b}$, —$CH_2$-cyclopropyl substituted with 0–1 $R^{4b}$, —$CH_2$-cyclobutyl substituted with 0–1 $R^{4b}$, —$CH_2$-cyclopentyl substituted with 0–1 $R^{4b}$, benzyl substituted with 0–2 $R^{4b}$, 5–6 membered aromatic heterocycle consisting of carbon atoms and from 1–4 heteroatoms selected from the group consisting of N, O, and $S(O)_p$ and substituted with 0–2 $R^{4b}$, and $(CH_2)$-5–6 membered aromatic heterocycle consisting of carbon atoms and from 1–4 heteroatoms selected from the group consisting of N, O, and $S(O)_p$ and substituted with 0–2 $R^{4b}$;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_2$—$CH_3$, $S(O)_2$-phenyl, $CF_3$, phenyl substituted with 0–2 $R^6$, naphthyl substituted with 0–2 $R^6$, and benzyl substituted with 0–2 $R^6$; and, $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

6. A compound according to claim 5, wherein the compound is:

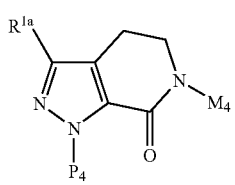
P$_4$ is -G;
M$_4$ is -A-B;
G is selected from:
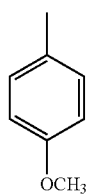 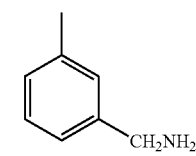 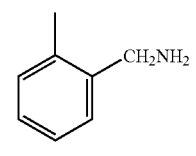
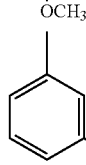 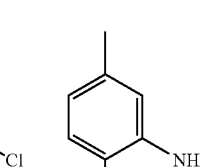 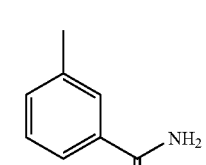
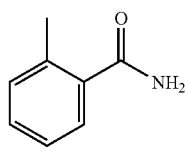 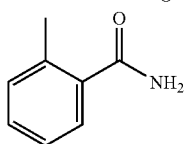
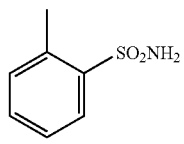 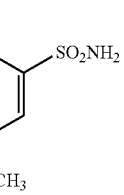
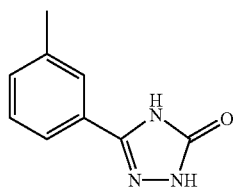
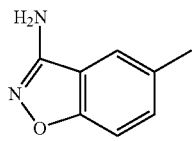
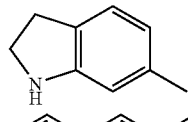
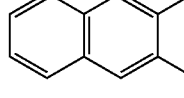
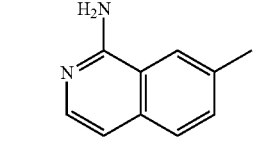
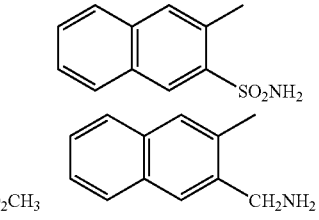
-continued
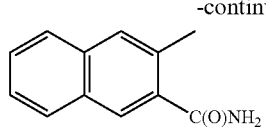
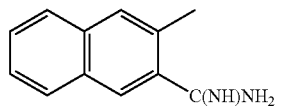 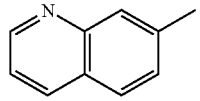
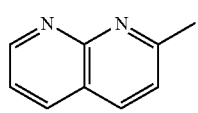 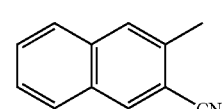
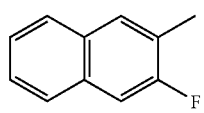 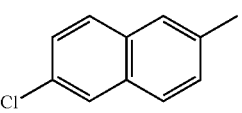
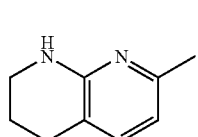 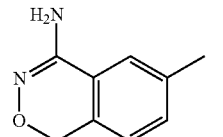
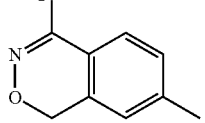
;
A-B is selected from:
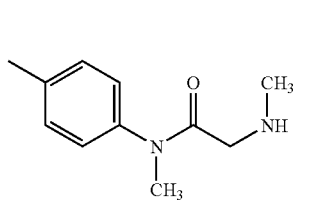
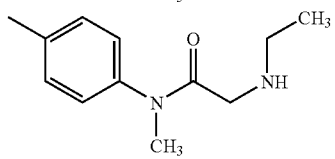
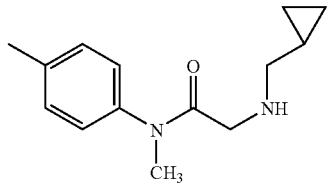
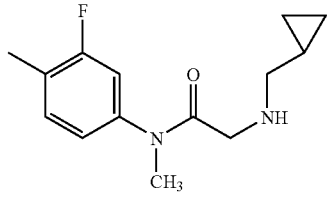

-continued
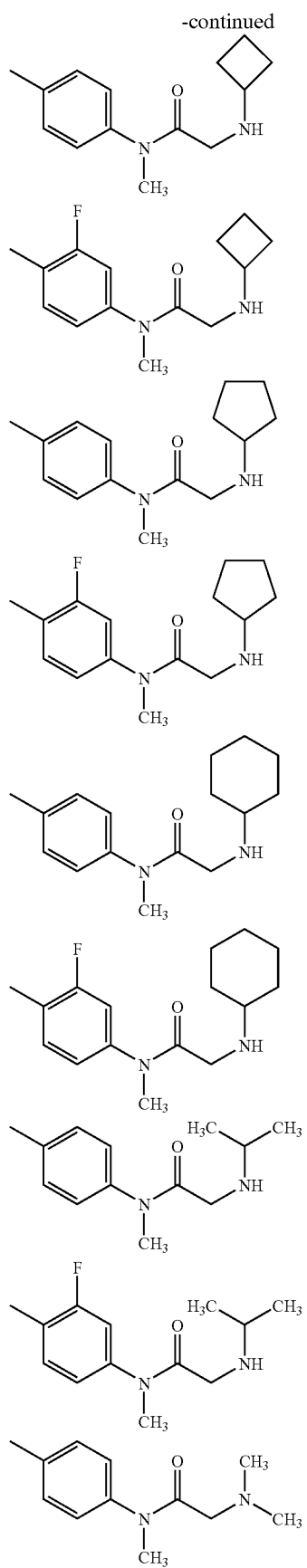
-continued
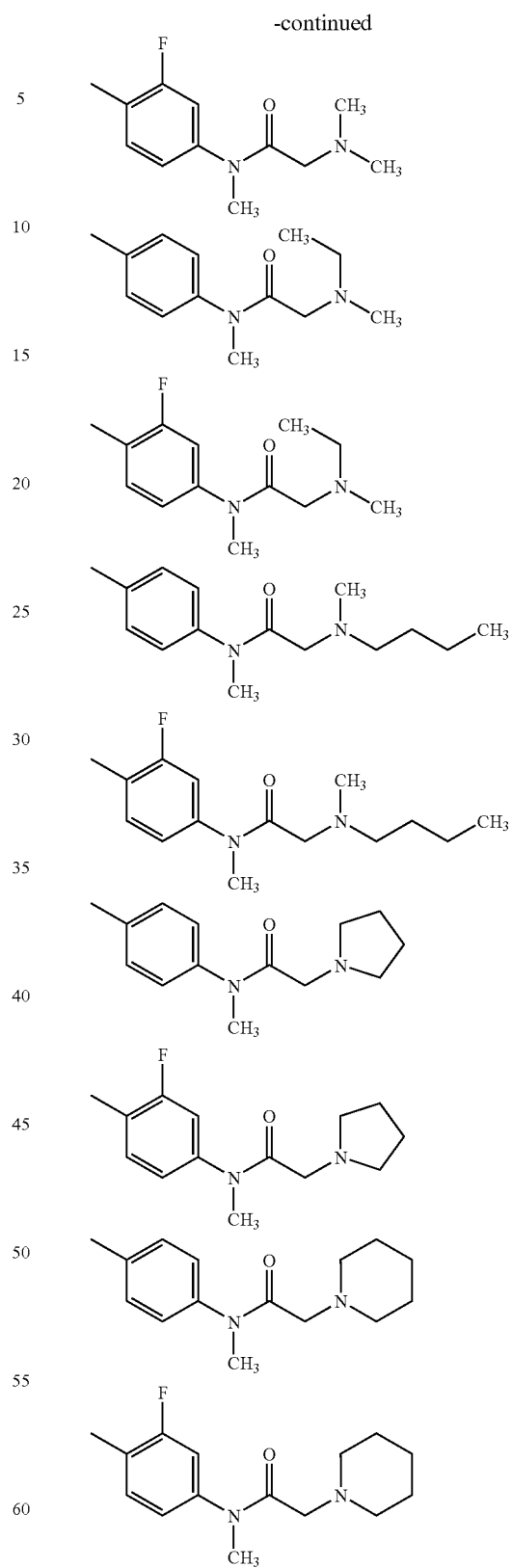
$R^{2d}$, at each occurrence, is selected from H, $R^{4c}$, $C_{1-4}$ alkyl substituted with 0–1 $R^{4c}$, cyclopropyl, cyclobutyl, cyclopentyl, cyclohexyl, phenyl, and a 5–6 membered aromatic heterocycle consisting of: carbon atoms and 1–4 heteroatoms selected from the group consisting of N, O, and $S(O)_p$, provided that $R^{2d}$ forms other than a N-halo, N—C-halo, $S(O)_p$-halo, O-halo, N—S, S—N, $S(O)_p$—$(O)_p$, S—O, O—N, O—S, or O—O moiety;

$R^{2e}$, at each occurrence, is selected from H, $R^{4c}$, $C_{1-4}$ alkyl substituted with 0–1 $R^{4c}$, cyclopropyl, cyclobutyl, cyclopentyl, cyclohexyl, phenyl, and 5–6 membered aromatic heterocycle consisting of: carbon atoms and 1–4 heteroatoms selected from the group consisting of N, O, and $S(O)_p$, provided that $R^{2e}$ forms other than a C(O)-halo or C(O)—$S(O)_p$ moiety.

7. A compound according to claim 1, wherein the compound is selected from the group:

3-[6-{4-[(N,N-dimethylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[(N-ethyl-N-methylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[methyl(N-methylglycyl)amino]phenyl}-7-oxo-3-(trifluoromethyl)-4,5,6,7-tetrahydro-1H-pyrazolo[3,4-c]pyridin-1-yl]benzamide;

3-[6-{4-[(N-ethyl-N-propylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[(N-isopropylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[(N-butyl-N-methylglycyl)(methyl)amino]phenyl}-7-oxo-3-(trifluoromethyl)-4,5,6,7-tetrahydro-1H-pyrazolo[3,4-c]pyridin-1-yl]benzamide;

3-[6-{4-[[N-(2-hydroxyethyl)glycyl](methyl)amino]phenyl}-7-oxo-3-(trifluoromethyl)-4,5,6,7-tetrahydro-1H-pyrazolo[3,4-c]pyridin-1-yl]benzamide;

$N^1$-{4-[3-methoxy-1-(4-methoxyphenyl)-7-oxo-1,4,5,7-tetrahydro-6H-pyrazolo[3,4-c]pyridin-6-yl]phenyl}-$N^1$,$N^2$,$N^2$-trimethylglycinamide;

$N^2$-ethyl-$N^1$-{4-[3-methoxy-1-(4-methoxyphenyl)-7-oxo-1,4,5,7-tetrahydro-6H-pyrazolo[3,4-c]pyridin-6-yl]phenyl}-$N^1$,$N^2$-dimethylglycinamide;

$N^2$-isopropyl-$N^1$-{4-[3-methoxy-1-(4-methoxyphenyl)-7-oxo-1,4,5,7-tetrahydro-6H-pyrazolo[3,4-c]pyridin-6-yl]phenyl}-$N^1$-methylglycinamide;

$N^2$-butyl-$N^1$-{4-[3-methoxy-1-(4-methoxyphenyl)-7-oxo-1,4,5,7-tetrahydro-6H-pyrazolo[3,4-c]pyridin-6-yl]phenyl}-$N^1$,$N^2$-dimethylglycinamide;

$N^1$-{4-[1-(4-methoxyphenyl)-7-oxo-3-(trifluoromethyl)-1,4,5,7-tetrahydro-6H-pyrazolo[3,4-c]pyridin-6-yl]phenyl}-$N^1$,$N^2$,$N^2$-trimethylglycinamide;

$N^2$-(tert-butyl)-$N^1$-{4-[1-(4-methoxyphenyl)-7-oxo-3-(trifluoromethyl)-1,4,5,7-tetrahydro-6H-pyrazolo[3,4-c]pyridin-6-yl]phenyl}-$N^1$-methylglycinamide;

$N^2$-cyclobutyl-$N^1$-{4-[1-(4-methoxyphenyl)-7-oxo-3-(trifluoromethyl)-1,4,5,7-tetrahydro-6H-pyrazolo[3,4-c]pyridin-6-yl]phenyl}-$N^1$-methylglycinamide;

$N^2$-(cyclopropylmethyl)-$N^1$-{4-[1-(4-methoxyphenyl)-7-oxo-3-(trifluoromethyl)-1,4,5,7-tetrahydro-6H-pyrazolo[3,4-c]pyridin-6-yl]phenyl}-$N^1$-methylglycinamide;

$N^2$-cyclopentyl-$N^1$-{4-[1-(4-methoxyphenyl)-7-oxo-3-(trifluoromethyl)-1,4,5,7-tetrahydro-6H-pyrazolo[3,4-c]pyridin-6-yl]phenyl}-$N^1$-methylglycinamide;

$N^2$-((R)-2-hydroxyl-1-methylethyl)-$N^1$-{4-[1-(4-methoxyphenyl)-7-oxo-3-(trifluoromethyl)-1,4,5,7-tetrahydro-6H-pyrazolo[3,4-c]pyridin-6-yl]phenyl}-$N^1$-methylglycinamide;

6-{4-[(N,N-dimethylglycyl)(methyl)amino]phenyl}-1-(4-methoxyphenyl)-7-oxo-4,5,6,7-tetrahydro-1H-pyrazolo[3,4-c]pyridine-3-carboxamide;

$N^1$-{4-[1-(4-methoxyphenyl)-3-(methylsulfonyl)-7-oxo-1,4,5,7-tetrahydro-6H-pyrazolo[3,4-c]pyridin-6-yl]phenyl}-$N^1$,$N^2$,$N^2$-trimethylgycinamide;

$N^1$-{4-[1-(4-methoxyphenyl)-3-(methylsulfonyl)-7-oxo-1,4,5,7-tetrahydro-6H-pyrazolo[3,4-c]pyridin-6-yl]phenyl}-$N^1$,$N^2$-dimethylgycinamide;

3-[6-[4-(ethyl{N-[(1S)-1-phenylpropyl]glycyl}amino)phenyl]-7-oxo-3-(trifluoromethyl)-4,5,6,7-tetrahydro-1H-pyrazolo[3,4-c]pyridin-1-yl]benzamide;

3-[6-{4-[[N-(1,3-dimethylbutyl)glycyl](ethyl)amino]phenyl}-7-oxo-3-(trifluoromethyl)-4,5,6,7-tetrahydro-1H-pyrazolo[3,4-c]pyridin-1-yl]benzamide;

2-Dimethylamino-N-{4-[1-(4-methoxy-phenyl)-3-(4-methyl-oxazol-2-yl)-7-oxo-1,4,5,7-tetrahydro-pyrazolo[3,4-c]pyridin-6-yl]-phenyl}-N-methyl-acetamide;

6-[4-(2-hydroxy-2-methyl-propionylamino)-phenyl]-1-(4-methoxy-phenyl)-7-oxo-4,5,6,7-tetrahydro-1H-pyrazolo[3,4-c]pyridine-3-carboxylic acid amide;

3-[6-{4-[[(3-hydroxy-1-pyrrolidinyl)acetyl](methyl)amino]phenyl}-7-oxo-3-(trifluoromethyl)-4,5,6,7-tetrahydro-1H-pyrazolo[3,4-c]pyridin-1-yl]benzamide;

3-[6-{4-[methyl(1-pyrrolidinylacetyl)amino]phenyl}-7-oxo-3-(trifluoromethyl)-4,5,6,7-tetrahydro-1H-pyrazolo[3,4-c]pyridin-1-yl]benzamide;

3-[6-{4-[[(4-hydroxy-1-piperidinyl)acetyl](methyl)amino]phenyl}-7-oxo-3-(trifluoromethyl)-4,5,6,7-tetrahydro-1H-pyrazolo[3,4-c]pyridin-1-yl]benzamide;

3-[7-oxo-6-{4-[propyl(1-pyrrolidinylacetyl)amino]phenyl}-3-(trifluoromethyl)-4,5,6,7-tetrahydro-1H-pyrazolo[3,4-c]pyridin-1-yl]benzamide;

3-[6-{4-[ethyl(1-pyrrolidinylacetyl)amino]phenyl}-7-oxo-3-(trifluoromethyl)-4,5,6,7-tetrahydro-1H-pyrazolo[3,4-c]pyridin-1-yl]benzamide;

N-{4-[3-methoxy-1-(4-methoxyphenyl)-7-oxo-1,4,5,7-tetrahydro-6H-pyrazolo[3,4-c]pyridin-6-yl]phenyl}-N-methyl-2-(1-pyrrolidinyl)acetamide;

2-(3-hydroxy-1-pyrrolidinyl)-N-{4-[3-methoxy-1-(4-methoxyphenyl)-7-oxo-1,4,5,7-tetrahydro-6H-pyrazolo[3,4-c]pyridin-6-yl]phenyl}-N-methylacetamide;

N-{4-[1-(4-methoxyphenyl)-7-oxo-3-(trifluoromethyl)-1,4,5,7-tetrahydro-6H-pyrazolo[3,4-c]pyridin-6-yl]phenyl}-N-methyl-2-(1-pyrrolidinyl)acetamide;

1-(4-methoxyphenyl)-6-{4-[methyl(1-pyrrolidinylacetyl)amino]phenyl}-7-oxo-4,5,6,7-tetrahydro-1H-pyrazolo[3,4-c]pyridine-3-carboxamide;

$N^1$-{4-[1-(4-methoxyphenyl)-3-(methylsulfonyl)-7-oxo-1,4,5,7-tetrahydro-6H-pyrazolo[3,4-c]pyridin-6-yl]phenyl}-N-methyl-2-(1-pyrrolidinyl)acetamide;

3-[6-[4-(ethyl{[3-(methylsulfonyl)-1-pyrrolidinyl]acetyl}amino)phenyl]-7-oxo-3-(trifluoromethyl)-4,5,6,7-tetrahydro-1H-pyrazolo[3,4-c]pyridin-1-yl]benzamide;

3-[6-[4-[{[3-(cyclohexylmethyl)-1-piperidinyl]acetyl}(ethyl)amino]phenyl]-7-oxo-3-(trifluoromethyl)-4,5,6,7-tetrahydro-1H-pyrazolo[3,4-c]pyridin-1-yl]benzamide;

N-{4-[1-(3-amino-1,2-benzisoxazol-5-yl)-3-methoxy-7-oxo-1,4,5,7-tetrahydro-6H-pyrazolo[3,4-c]pyridin-6-yl]phenyl}-N-methyl-2-(1-pyrrolidinyl)acetamide;

N-{4-[1-(4-methoxyphenyl)-3-(methylsulfonyl)-7-oxo-1,4,5,7-tetrahydro-6H-pyrazolo[3,4-c]pyridin-6-yl]phenyl}-N-methyl-2-(2-methyl-1H-imidazol-1-yl)acetamide;

N-{4-[1-(4-methoxyphenyl)-3-(trifluoromethyl)-7-oxo-1,4,5,7-tetrahydro-6H-pyrazolo[3,4-c]pyridin-6-yl]phenyl}-N-methyl-2-(2-methyl-1H-imidazol-1-yl)acetamide;

1-(3-Chloro-phenyl)-6-{4-[methyl-(2-pyrrolidin-1-yl-acetyl)-amino]-phenyl}-7-oxo-4,5,6,7-tetrahydro-1H-pyrazolo[3,4-c]pyridine-3-carboxylic acid amide;

N-{4-[1-(4-Methoxy-phenyl)-3-(4-methyl-oxazol-2-yl)-7-oxo-1,4,5,7-tetrahydro-pyrazolo[3,4-c]pyridin-6-yl]-phenyl}-N-methyl-2-pyrrolidin-1-yl-acetamide;

N-{4-[1-(4-Methoxy-phenyl)-3-(4-methyl-oxazol-2-yl)-7-oxo-1,4,5,7-tetrahydro-pyrazolo[3,4-c]pyridin-6-yl]-phenyl}-N-methyl-3-pyrrolidin-1-yl-propionamide;

or a pharmaceutically acceptable salt form thereof.

8. A pharmaceutical composition, comprising: a pharmaceutically acceptable carrier and a therapeutically effective amount of a compound of claim 1, 2, 3, 4, 5, 6, or 7 or a pharmaceutically acceptable salt form thereof.

9. A method for treating a thromboembolic disorder, comprising: administering to a patient in need thereof a therapeutically effective amount of a compound of claim 1, 2, 3, 4, 5, 6, or 7 or a pharmaceutically acceptable salt form thereof.

10. A method according to claim 9, wherein the thromboembolic disorder is selected from the group consisting of arterial cardiovascular thromboembolic disorders, venous cardiovascular thromboembolic disorders, and thromboembolic disorders in the chambers of the heart.

11. A method according to claim 9, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

* * * * *